United States Patent
Adachi et al.

(10) Patent No.: US 8,044,042 B2
(45) Date of Patent: Oct. 25, 2011

(54) THIENOTRIAZOLODIAZEPINE COMPOUND AND MEDICINAL USE THEREOF

(75) Inventors: Kunitomo Adachi, Osaka (JP); Hidemasa Hikawa, Osaka (JP); Maiko Hamada, Osaka (JP); Jun-ichi Endoh, Osaka (JP); Seigo Ishibuchi, Osaka (JP); Naoto Fujie, Osaka (JP); Minoru Tanaka, Osaka (JP); Kunio Sugahara, Osaka (JP); Kouichi Oshita, Osaka (JP); Meguru Murata, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 856 days.

(21) Appl. No.: 11/916,015

(22) PCT Filed: May 30, 2006

(86) PCT No.: PCT/JP2006/310709
§ 371 (c)(1), (2), (4) Date: Dec. 28, 2007

(87) PCT Pub. No.: WO2006/129623
PCT Pub. Date: Dec. 7, 2006

(65) Prior Publication Data
US 2010/0041643 A1 Feb. 18, 2010

(30) Foreign Application Priority Data
May 30, 2005 (JP) ................... 2005-157825

(51) Int. Cl.
| A61P 1/04 | (2006.01) |
| A61P 3/10 | (2006.01) |
| A61P 13/12 | (2006.01) |
| A61P 17/00 | (2006.01) |
| A61P 19/02 | (2006.01) |
| A61P 25/00 | (2006.01) |
| A61P 27/14 | (2006.01) |
| A61P 29/00 | (2006.01) |
| A61P 37/00 | (2006.01) |
| A61P 43/00 | (2006.01) |
| A61K 31/551 | (2006.01) |
| C07D 495/14 | (2006.01) |

(52) U.S. Cl. ......... 514/219; 514/220; 540/555; 540/560
(58) Field of Classification Search ................. 514/219, 514/220; 540/555, 560
See application file for complete search history.

(56) References Cited

FOREIGN PATENT DOCUMENTS

| CA | 2020806 A1 | 1/1991 |
| EP | 0 407 955 A1 | 7/1990 |
| EP | 0 989 131 A1 | 3/2000 |
| JP | 03-215489 A | 9/1991 |
| WO | WO 98/11111 A1 | 3/1998 |

OTHER PUBLICATIONS

Sharpe et al., T-Cell Costimulation—Biology, Therapeutic Potential, and Challenges, The New England Journal of Medcine, vol. 355, pp. 973-975, Sep. 7, 2006.*
Alimardanov et al., *Advanced Synthesis & Catalysis*, 346: 1812-1817 (2004).
Citterio et al., *J. Org. Chem.*, 56: 5335-5341 (1991).
Dai et al., *Advanced Synthesis & Catalysis*, 346: 1669-1673 (2004).
Najera et al., *Advanced Synthesis & Catalysis*, 346: 1798-1811 (2004).
Rahman et al. *Organic Letters*, 5(16): 2887-2890 (2003).

* cited by examiner

*Primary Examiner* — Brenda Coleman
(74) *Attorney, Agent, or Firm* — Leydig, Voit & Mayer, Ltd.

(57) ABSTRACT

A thienotriazolodiazepine compound of the following formula (I)

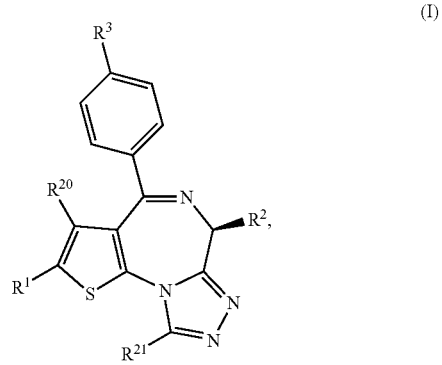

(I)

a pharmaceutical agent containing the compound as an active ingredient, and a production intermediate and a production method of the thienotriazolodiazepine compound.
Since this compound has an inhibitory action on costimulatory signal from CD28 on T cell, it is useful for the prophylaxis or suppression of rejection reaction in transplantation of organ or bone marrow and the like, and the prophylaxis or treatment of autoimmune diseases or allergic diseases.

31 Claims, No Drawings

THIENOTRIAZOLODIAZEPINE COMPOUND AND MEDICINAL USE THEREOF

CROSS-REFERENCE TO A RELATED APPLICATION

This patent application is the U.S. national phase application of International Patent Application No. PCT/JP2006/310709, filed May 30, 2006.

TECHNICAL FIELD

The present invention relates to a thienotriazolodiazepine compound, a pharmaceutical agent comprising this as an active ingredient, and a production intermediate for and a production method of the thienotriazolodiazepine compound.

BACKGROUND ART

When an antigen is presented by a major histocompatibility complex (MHC) on an antigen-presenting cell such as dendritic cell, macrophage, B cell and the like, T cells recognize the antigen via a T cell receptor (TcR/CD3 complex) and are activated. However, an antigen specific signal (first signal) from the T cell receptor alone is not sufficient for the normal activation of T cells, and a second signal called costimulatory signal is essential. Solely with the stimulation by the first signal via TcR, sufficient activation of T cells does not occur, and moreover, T cells fall into the condition called antigen specific T cell unresponsiveness in which T cell cannot respond to the antigen stimulation after the second. As a most important molecule (costimulatory molecule) for transmitting the second signal, CD28 on the T cell is known (*Cell*, 71, 1065-1068, 1992. *Immunology Today*, 15, 321-331, 1994). CD28 binds with B7-1 (CD80)/B7-2 (CD86) expressed on an antigen-presenting cell and inserts the second signal into T cells. In fact, stimulation of mouse T cells only with an anti-CD3 antibody does not induce growth of T cells and interleukin (IL)-2 production. However, by the addition of an anti-CD28 antibody in addition to the anti-CD3 antibody, the growth and IL-2 production are drastically enhanced. Therefore, creation of a drug inhibiting the costimulatory signal enables induction of antigen specific immunological tolerance, which possibly leads to the provision of a basic therapeutic drug for various autoimmune diseases.

As a molecule binding with CD80/CD86 like CD28, CTLA-4 is known to be present (*Immunity*, 1, 405-413, 1994. *Biochem. J.*, 318, 361-377, 1996). While CD28 is constantly expressed in T cell, but CTLA-4 is belatedly expressed after the activation. It has been clarified that the signal from this molecule suppressively acts on the signal from CD28, and regulates the signal from CD28. A fusion protein (CTLA-4-Ig) of an extracellular region of CTLA-4 and immunoglobulin constant region inhibits binding of CD28 and CD80/CD86. The inhibitory action on the CD28 signal has been evaluated using CTLA-4-Ig or an antibody to CD80/CD86 in various mouse disease models. As a result, it has been reported that the inhibition of the CD28 signal shows a striking effect on transplantation (organ transplantation, transplantation of pancreatic islet cell/neuron or bone marrow and the like), autoimmune disease model (collagen induced arthritis, lupus nephritis) and allergic disease model (asthma, dermatitis) (*J. Exp. Med.*, 178, 1801-1806, 1993. *J. Exp. Med.*, 181, 1869-1874, 1995. *Nature*, 381, 434-438, 1996. *J. Immunol.*, 154, 1481-1490, 1995. *Igakuno Ayumi*, 193, 787-792, 2000.)

Incidentally, a thienotriazolodiazepine compound is disclosed in WO 94/06801 and WO 94/06802 as a compound having a CCK antagonistic action or gastrin antagonistic action. In addition, WO 93/07129 discloses a compound useful as a therapeutic drug for osteoporosis, WO 93/12117, WO 94/06802, WO 94/22872 and WO 98/11111 disclose a compound having a cell adhesion inhibitory action, WO 97/47622 discloses a compound having a cytokine production suppressive action, and JP-A-1-156982, JP-A-2-243691, JP-A-2-256681, JP-A-2-256682 and JP-A-3-215489 disclose a compound having a platelet-activating factor (PAF) inhibitory activity. However, these publications do not describe or suggest inhibition of costimulatory signal from CD28.

Non-patent reference 1: *Cell*, 71, 1065-1068, 1992

Non-patent reference 2: *Immunology Today*, 15, 321-331, 1994

Non-patent reference 3: *Immunity*, 1, 405-413, 1994

Non-patent reference 4: *Biochem. J.*, 318, 361-377, 1996

Non-patent reference 5: *J. Exp. Med.*, 178, 1801-1806, 1993

Non-patent reference 6: *J. Exp. Med.*, 181, 1869-1874, 1995

Non-patent reference 7: *Nature*, 381, 434-438, 1996

Non-patent reference 8: *J. Immunol.*, 154, 1481-1490, 1995

Non-patent reference 9: *Igakuno Ayumi*, 193, 787-792, 2000

Patent reference 1: WO 94/06801

Patent reference 2: WO 94/06802

Patent reference 3: WO 93/07129

Patent reference 4: WO 93/12117

Patent reference 5: WO 94/22872

Patent reference 6: WO 98/11111

Patent reference 7: WO 97/47622

Patent reference 8: JP-A-1-156982

Patent reference 9: JP-A-2-243691

Patent reference 10: JP-A-2-256681

Patent reference 11: JP-A-2-256682

Patent reference 12: JP-A-3-215489

DISCLOSURE OF THE INVENTION

Problems to be Solved by the Invention

The problem of the present invention is to provide a novel thienotriazolodiazepine compound having a costimulatory signal from CD28 on T cell inhibitory action, a pharmaceutical agent comprising this as an active ingredient, and a production intermediate for and a production method of the thienotriazolodiazepine compound.

Means of Solving the Problems

The present inventors have conducted intensive studies in view of the above-mentioned problems and found that a thienotriazolodiazepine compound of the following formula (I) has an inhibitory action on the costimulatory signal from CD28, which resulted in the completion of the present invention. The gist of the present invention is as follows.

(1) A thienotriazolodiazepine compound represented by the formula (I)

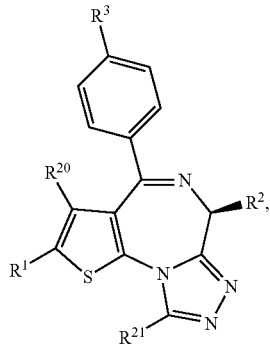

wherein
$R^1$ is hydrogen atom, halogen atom, $C_{1-6}$ alkyl optionally substituted by halogen atom or hydroxyl group, or —$(CH_2)_k$ $OR^a$ (k is an integer of 1 to 4, and $R^a$ is $C_{1-6}$ alkyl optionally having substituent(s)),
$R^{20}$ is $C_{1-6}$ alkyl, or
$R^1$ and $R^{20}$ in combination form trimethylene or tetramethylene,
$R^2$ is hydrogen atom, or the following formula (a)

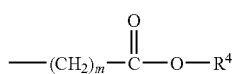

wherein $R^4$ is $C_{1-6}$ alkyl optionally having substituent(s), and m is an integer of 1 to 4,
$R^{21}$ is methyl or hydroxymethyl, and
$R^3$ is
when $R^2$ is a hydrogen atom, then $C_{6-12}$ aryl optionally having one or more substituents selected from halogen atom, cyano, acetyl, hydroxymethyl, hydroxyethyl, methoxy and hydroxyl group; pyridyl, thienyl, thiazolyl, pyrimidinyl, or pyrazolyl, each of which optionally has one or more substituents selected from acetyl, hydroxymethyl, hydroxyethyl, cyano, amino, methyl and halogen atom; or —$NR^5$—$(CH_2)_n$—$R^6$ ($R^5$ is hydrogen atom or methyl, n is an integer of 0 to 3, and $R^6$ is $C_{6-12}$ aryl optionally having one or more substituents selected from halogen atom, hydroxyl group, methoxy, methylenedioxy and cyano; or pyridyl, thiazolyl, isoxazolyl, pyrazolyl, tetrahydrofuranyl or tetrahydropyranyl, each of which optionally has substituents one or more selected from methyl optionally substituted by halogen atom, cyano, halogen atom and methoxy), and
when $R^2$ is the formula (a), then $C_{6-12}$ aryl optionally having substituent(s), heteroaryl having 5 to 12 ring-constituting atoms and optionally having substituent(s), arylcarbonyl alkyl (the aryl moiety has 6 to 12 carbon atoms, and the alkyl moiety has 1 to 6 carbon atoms) optionally having substituent(s) on the ring, —$NR^{5a}$—$(CH_2)_o$—$R^{6a}$ ($R^{5a}$ is hydrogen atom or $C_{1-6}$ alkyl optionally having substituent(s), o is an integer of 0 to 4, and $R^{6a}$ is $C_{6-12}$ aryl optionally having substituent(s), $C_{7-13}$ arylcarbonyl optionally having substituent(s), $C_{6-12}$ aryloxy optionally having substituent(s) or heteroaryl having 5 to 12 ring-constituting atoms and optionally having substituent(s)), or a group selected by following

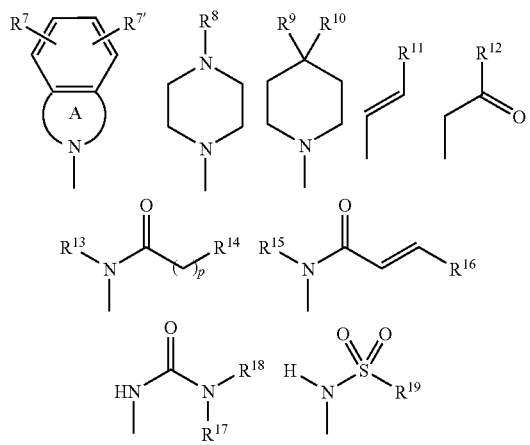

wherein
$R^7$ and $R^{7'}$ are the same or different and each is hydrogen atom, $C_{1-6}$ alkyl optionally having substituent(s) or $C_{1-6}$ alkoxy optionally having substituent(s),
ring A is cyclic amine having 4 or 5 carbon atoms, which is condensed with aromatic ring,
$R^8$ is $C_{6-12}$ aryl optionally having substituent(s), heteroaryl having 5 to 12 ring-constituting atoms and optionally having substituent(s), $C_{7-18}$ aralkyl optionally having substituent(s), $C_{7-13}$ arylcarbonyl optionally having substituent(s) or heteroarylcarbonyl having 5 to 12 ring-constituting atoms and optionally having substituent(s),
$R^9$ is hydrogen atom, hydroxyl group or cyano group,
$R^{10}$ is $C_{1-6}$ alkyl optionally having substituent(s), $C_{6-12}$ aryl optionally having substituent(s) or heteroaryl having 5 to 12 ring-constituting atoms and optionally having substituent(s),
$R^{11}$ is $C_{6-12}$ aryl optionally having substituent(s), heteroaryl having 5 to 12 ring-constituting atoms and optionally having substituent(s) or anilinocarbonyl optionally having substituent(s),
$R^{12}$ is heteroaryl having 5 to 12 ring-constituting atoms and optionally having substituent(s),
$R^{13}$ is hydrogen atom or $C_{1-6}$ alkyl optionally having substituent(s),
p is an integer of 0 to 2,
$R^{14}$ is $C_{6-12}$ aryl optionally having substituent(s) or heteroaryl having 5 to 12 ring-constituting atoms and optionally having substituent(s),
$R^{15}$ is hydrogen atom or $C_{1-6}$ alkyl optionally having substituent(s),
$R^{16}$ is $C_{6-12}$ aryl optionally having substituent(s) or heteroaryl having 5 to 12 ring-constituting atoms and optionally having substituent(s),
$R^{17}$ is hydrogen atom or $C_{1-6}$ alkyl optionally having substituent(s),
$R^{18}$ is $C_{6-12}$ aryl optionally having substituent(s) or $C_{7-18}$ aralkyl, and
$R^{19}$ is $C_{6-12}$ aryl optionally having substituent(s) or heteroaryl having 5 to 12 ring-constituting atoms and optionally having substituent(s),
or a pharmaceutically acceptable salt thereof, or a hydrate or solvate thereof.
(2) The compound of the above-mentioned (1), wherein $R^{20}$ is methyl, or a pharmaceutically acceptable salt thereof, or a hydrate or solvate thereof.

(3) The compound of the above-mentioned (1) or (2), wherein $R^{21}$ is methyl, or a pharmaceutically acceptable salt thereof, or a hydrate or solvate thereof.

(4) The compound of any of the above-mentioned (1) to (3), wherein $R^1$ is hydrogen atom, halogen atom, methyl, hydroxymethyl, —$CH_2OCH_3$ or —$CH_2OCH_2CH_3$, or a pharmaceutically acceptable salt thereof, or a hydrate or solvate thereof.

(5) The compound of any of the above-mentioned (1) to (3), wherein $R^1$ is methyl, hydroxymethyl or —$(CH_2)_kOR^a$ (k is an integer of 1 to 4, and $R^a$ is $C_{1-6}$ alkyl optionally having substituent(s)), or a pharmaceutically acceptable salt thereof, or a hydrate or solvate thereof.

(6) The compound of the above-mentioned (1), wherein $R^1$ is methyl, hydroxymethyl or —$(CH_2)_kOR^a$ (k is an integer of 1 to 4, and $R^a$ is $C_{1-6}$ alkyl optionally having substituent(s)), and
$R^{20}$ and $R^{21}$ are each methyl,
or a pharmaceutically acceptable salt thereof, or a hydrate or solvate thereof.

(7) The compound of any of the above-mentioned (1) to (6), wherein $R^1$ is methyl, hydroxymethyl, —$CH_2OCH_3$ or —$CH_2OCH_2CH_3$, or a pharmaceutically acceptable salt thereof, or a hydrate or solvate thereof.

(8) The compound of any of the above-mentioned (1) to (7), wherein $R^1$ is methyl, hydroxymethyl or —$CH_2OCH_3$, or a pharmaceutically acceptable salt thereof, or a hydrate or solvate thereof.

(9) The compound of any of the above-mentioned (1) to (8), wherein $R^1$ is methyl or hydroxymethyl, or a pharmaceutically acceptable salt thereof, or a hydrate or solvate thereof.

(10) The compound of the above-mentioned (1) or (3), wherein $R^1$ and $R^{20}$ in combination form trimethylene, or a pharmaceutically acceptable salt thereof, or a hydrate or solvate thereof.

(11) The compound of any of the above-mentioned (1) to (10), wherein $R^2$ is hydrogen atom, or

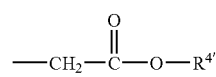

wherein
$R^{4'}$ is methyl, ethyl, hydroxyethyl, methoxyethyl, morpholinoethyl or dimethylaminoethyl,
or a pharmaceutically acceptable salt thereof, or a hydrate or solvate thereof.

(12) The compound of any of the above-mentioned (1) to (11), wherein $R^2$ is hydrogen atom, or

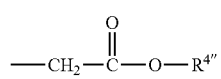

wherein
$R^{4''}$ is methyl or ethyl,
or a pharmaceutically acceptable salt thereof, or a hydrate or solvate thereof.

(13) The compound of any of the above-mentioned (1) to (12), wherein
$R^2$ is hydrogen atom, and
$R^3$ is thiazolyl, phenyl substituted by cyano, pyridyl substituted by cyano, or —NH—$(CH_2)_n$—$R^{6'}$ (n is an integer of 0 to 2, and $R^{6'}$ is phenyl optionally having one or more substituents selected from halogen atom and cyano, or pyridyl optionally having one or more substituents selected from halogen atom and cyano),
or a pharmaceutically acceptable salt thereof, or a hydrate or solvate thereof.

(14) The compound of any of the above-mentioned (1) to (13), wherein $R^2$ is hydrogen atom, and $R^3$ is phenyl substituted by cyano, or a pharmaceutically acceptable salt thereof, or a hydrate or solvate thereof.

(15) The compound of any of the above-mentioned (1) to (11), wherein
$R^2$ is the formula (a), and
$R^3$ is phenyl substituted by one or more selected from hydroxyl group, cyano, ethoxy substituted by morpholino, methylsulfonyl, piperazyl substituted by methyl, methylcarbonyl, methylenedioxy, methoxy and morpholino; thienyl substituted by cyano; pyrazyl; pyridyl substituted by cyano or methylcarbonyl; pyrimidinyl; —$NR^{5a'}$—$(CH_2)_o$—$R^{6a'}$ (wherein $R^{5a'}$ is hydrogen atom or methyl, o is an integer of 0 to 2, and $R^{6a'}$ is phenyl optionally substituted by cyano or halogen atom, or pyrazolyl substituted by methyl or ethyl);

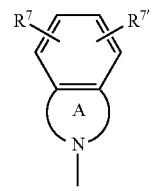

wherein $R^7$ and $R^{7'}$ are each hydrogen atom, and ring A is piperidine or pyrrolidine, each of which is condensed with aromatic ring;

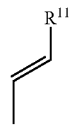

wherein $R^{11}$ is phenyl substituted by halogen atom; or

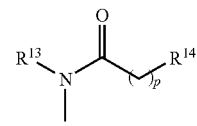

wherein $R^{13}$ is hydrogen atom, p is 2, and $R^{14}$ is phenyl,
or a pharmaceutically acceptable salt thereof, or a hydrate or solvate thereof.

(16) The compound of any of the above-mentioned (1) to (12) and (15), wherein
$R^2$ is the formula (a),
$R^3$ is phenyl substituted by cyano, phenyl substituted by methoxy, —$NR^{5a''}$—$(CH_2)_o$—$R^{6a''}$ ($R^{5a''}$ is hydrogen atom or methyl, o is 0 or 1, and $R^{6a''}$ is phenyl optionally substituted by halogen atom), or

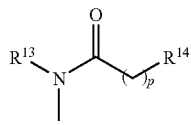

wherein R¹³ is hydrogen atom, p is 2, and R¹⁴ is phenyl, or a pharmaceutically acceptable salt thereof, or a hydrate or solvate thereof.

(17) 4-(3'-Cyanobiphenyl-4-yl)-2,3,9-trimethyl-6H-thieno[3,2-f][1,2,4]triazolo[4,3-a][1,4]diazepine or a pharmaceutically acceptable salt thereof, or a hydrate or solvate thereof.

(18) Ethyl (S)-(4-{4-[(4-fluorophenyl)methylamino]phenyl}-2,3,9-trimethyl-6H-thieno[3,2-f][1,2,4]triazolo[4,3-a][1,4]diazepin-6-yl)acetate or a pharmaceutically acceptable salt thereof, or a hydrate or solvate thereof.

(19) Methyl (S)-{2-hydroxymethyl-4-(4'-methoxybiphenyl-4-yl)-3,9-dimethyl-6H-thieno[3,2-f][1,2,4]triazolo[4,3-a][1,4]diazepin-6-yl}acetate or a pharmaceutically acceptable salt thereof, or a hydrate or solvate thereof.

(20) Methyl (S)-{4-(3'-cyanobiphenyl-4-yl)-2,3,9-trimethyl-6H-thieno[3,2-f][1,2,4]triazolo[4,3-a][1,4]diazepin-6-yl}acetate or a pharmaceutically acceptable salt thereof, or a hydrate or solvate thereof.

(21) Methyl (S)-{2,3,9-trimethyl-4-(4-phenylaminophenyl)-6H-thieno[3,2-f][1,2,4]triazolo[4,3-a][1,4]diazepin-6-yl}acetate or a pharmaceutically acceptable salt thereof, or a hydrate or solvate thereof.

(22) Methyl (S)-{4-(4-benzylaminophenyl)-2,3,9-trimethyl-6H-thieno[3,2-f][1,2,4]triazolo[4,3-a][1,4]diazepin-6-yl}acetate or a pharmaceutically acceptable salt thereof, or a hydrate or solvate thereof.

(23) Methyl (S)-{2,3,9-trimethyl-4-[4-(3-phenylpropionylamino)phenyl]-6H-thieno[3,2-f][1,2,4]triazolo[4,3-a][1,4]diazepin-6-yl}acetate or a pharmaceutically acceptable salt thereof, or a hydrate or solvate thereof.

(24) A pharmaceutical composition comprising the compound of any of the above-mentioned (1) to (23) or a pharmaceutically acceptable salt thereof, or a hydrate or solvate thereof, and a pharmaceutically acceptable carrier.

(25) A pharmaceutical agent inhibiting a costimulatory signal from CD28 on T cell, which comprises, as an active ingredient, the compound of any of the above-mentioned (1) to (23) or a pharmaceutically acceptable salt thereof, or a hydrate or solvate thereof.

(26) An agent for inducing immunological tolerance, comprising, as an active ingredient, the compound of any of the above-mentioned (1) to (23) or a pharmaceutically acceptable salt thereof, or a hydrate or solvate thereof.

(27) An agent for the prophylaxis and/or suppression of a rejection reaction in organ or bone marrow transplantation, or an agent for the prophylaxis and/or treatment of autoimmune disease or allergic disease, which comprises, as an active ingredient, the compound of any of the above-mentioned (1) to (23) or a pharmaceutically acceptable salt thereof, or a hydrate or solvate thereof.

(28) The agent of the above-mentioned (27), wherein the rejection reaction in organ or bone marrow transplantation is a rejection reaction in organ or tissue transplantation or a graft-versus-host (GvH) reaction in bone marrow transplantation.

(29) The agent of the above-mentioned (27), wherein the autoimmune disease is rheumatoid arthritis, systemic lupus erythematosus, multiple sclerosis, psoriasis, inflammatory bowel disease, Type I diabetes mellitus, lupus nephritis or encephalomyelitis.

(30) The agent of the above-mentioned (27), wherein the allergic disease is asthma, allergic rhinitis, pollinosis, atopic dermatitis, urticaria, contact dermatitis or allergic conjunctivitis.

(31) A thienotriazolodiazepine compound represented by the formula (II)

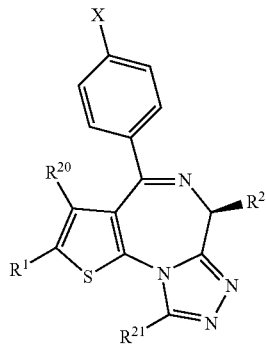

(II)

wherein X is a reactive group, and R¹, R²⁰, R² and R²¹ are as defined above (1), or a salt thereof.

(32) The compound of the above-mentioned (31), wherein R¹ is methyl, hydroxymethyl or —(CH₂)$_k$OR$^a$ (k is an integer of 1 to 4, and R$^a$ is $C_{1-6}$ alkyl optionally having substituent(s)), and R²⁰ and R²¹ are each methyl, or a salt thereof.

(33) The compound of the above-mentioned (31) or (32), wherein X is halogen atom, methylsulfonyloxy optionally substituted by p-toluenesulfonyloxy or halogen atom, or a salt thereof.

(34) A production method of the compound of the above-mentioned (1), which is represented by the formula (I), comprising reacting the compound of any of the above-mentioned (31) to (33) or a salt thereof with a compound represented by R³'—H wherein R³' is, when R² is hydrogen, then —NR⁵—(CH₂)$_n$—R⁶ (R⁵ is hydrogen atom or methyl, n is an integer of 0 to 3, and R⁶ is $C_{6-12}$ aryl optionally having one or more substituents selected from halogen atom, hydroxyl group, methoxy, methylenedioxy and cyano; or pyridyl, thiazolyl, isoxazolyl, pyrazolyl, tetrahydrofuranyl or tetrahydropyranyl, each of which optionally has one or more substituents selected from methyl optionally substituted by halogen atom, cyano, halogen atom and methoxy, and when R² is the formula (a), then —NR$^{5a}$—(CH₂)$_o$—R$^{6a}$ (wherein R$^{5a}$ is hydrogen atom or $C_{1-6}$ alkyl optionally having substituent(s), o is an integer of 0 to 4, and R$^{6a}$ is $C_{6-12}$ aryl optionally having substituent(s), $C_{7-13}$ arylcarbonyl optionally having substituent(s), $C_{6-12}$ aryloxy optionally having substituent(s) or heteroaryl having 5 to 12 ring-constituting atoms and optionally having substituent(s)), or a group selected by following

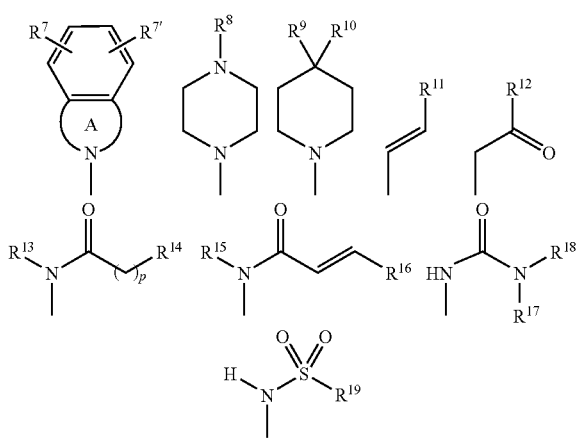

wherein
R⁷ and R⁷' are the same or different and each is hydrogen atom, $C_{1-6}$ alkyl optionally having substituent(s) or $C_{1-6}$ alkoxy optionally having substituent(s),
ring A is cyclic amine having 4 or 5 carbon atoms, which is condensed with aromatic ring,
$R^8$ is $C_{6-12}$ aryl optionally having substituent(s), heteroaryl having 5 to 12 ring-constituting atoms and optionally having substituent(s), $C_{7-18}$ aralkyl optionally having substituent(s), $C_{7-13}$ arylcarbonyl optionally having substituent(s) or heteroarylcarbonyl having 5 to 12 ring-constituting atoms and optionally having substituent(s),
$R^9$ is hydrogen atom, hydroxyl group or cyano group,
$R^{10}$ is $C_{1-6}$ alkyl optionally having substituent(s), $C_{6-12}$ aryl optionally having substituent(s) or heteroaryl having 5 to 12 ring-constituting atoms and optionally having substituent(s),
$R^{11}$ is $C_{6-12}$ aryl optionally having substituent(s), heteroaryl having 5 to 12 ring-constituting atoms and optionally having substituent(s) or anilinocarbonyl optionally having substituent(s),
$R^{12}$ is heteroaryl having 5 to 12 ring-constituting atoms and optionally having substituent(s),
$R^{13}$ is hydrogen atom or $C_{1-6}$ alkyl optionally having substituent(s),
p is an integer of 0 to 2,
$R^{14}$ is $C_{6-12}$ aryl optionally having substituent(s) or heteroaryl having 5 to 12 ring-constituting atoms and optionally having substituent(s),
$R^{15}$ is hydrogen atom or $C_{1-6}$ alkyl optionally having substituent(s),
$R^{16}$ is $C_{6-12}$ aryl optionally having substituent(s) or heteroaryl having 5 to 12 ring-constituting atoms and optionally having substituent(s),
$R^{17}$ is hydrogen atom or $C_{1-6}$ alkyl optionally having substituent(s),
$R^{18}$ is $C_{6-12}$ aryl optionally having substituent(s) or $C_{7-18}$ aralkyl, and
$R^{19}$ is $C_{6-12}$ aryl optionally having substituent(s) or heteroaryl having 5 to 12 ring-constituting atoms and optionally having substituent(s), or
a boronic acid represented by $R^{3''}$—B$(OH)_2$
wherein
$R^{3''}$ is,
when $R^2$ is hydrogen, then $C_{6-12}$ aryl optionally having one or more substituents selected from halogen atom, cyano, acetyl, hydroxymethyl, hydroxyethyl, methoxy and hydroxyl group; or pyridyl, thienyl, thiazolyl, pyrimidinyl or pyrazolyl, each of which optionally has one or more substituents selected from acetyl, hydroxymethyl, hydroxyethyl, cyano, amino, methyl and halogen atom,
when $R^2$ is the formula (a), then $C_{6-12}$ aryl optionally having substituent(s), heteroaryl having 5 to 12 ring-constituting atoms and optionally having substituent(s), or arylcarbonylalkyl (wherein the aryl moiety has 6 to 12 carbon atoms, and the alkyl moiety has 1 to 6 carbon atoms) optionally having substituent(s) on the ring,
or an ester thereof.

(35) The production method of the above-mentioned (34), wherein, in the compound represented by the formula (I) in the above-mentioned (1),
$R^1$ is methyl, hydroxymethyl or —$(CH_2)_kOR^a$ (wherein k is an integer of 1 to 4, and $R^a$ is $C_{1-6}$ alkyl optionally having substituent(s)), and
$R^{20}$ and $R^{21}$ are each methyl.
(36) The production method of the above-mentioned (34) or (35), wherein the reaction is carried out using a palladium catalyst.
(37) A production method of a compound represented by the following formula (II')

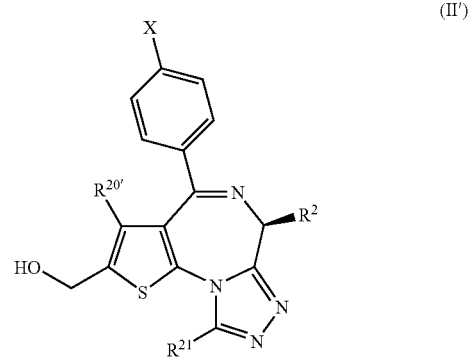

wherein
X is reactive group,
$R^{20'}$ is $C_{1-6}$ alkyl, and
$R^2$ and $R^{21}$ are as defined in (1),
which comprises reacting a compound represented by the following formula (III)

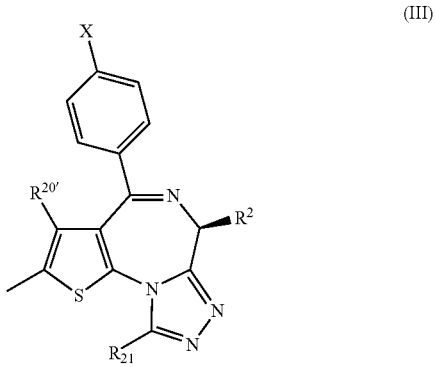

wherein
X is reactive group,
$R^{20'}$ is $C_{1-6}$ alkyl, and
$R^2$ and $R^{21}$ are as defined in (1), with a mixture of acetic acid, acetic anhydride and concentrated sulfuric acid in the presence of manganese acetate (III), and subjecting the resulting compound to hydrolysis.

(38) The production method of the above-mentioned (37), wherein $R^{20'}$ and $R^{21}$ are each methyl.

(39) The production method of the above-mentioned (37) or (38), wherein the hydrolysis is carried out using a base.

(40) The production method of the above-mentioned (39), wherein the base is potassium carbonate, sodium carbonate, potassium hydroxide and/or sodium hydroxide.

(41) The production method of any of the above-mentioned (37) to (40), which further comprises reduction after the hydrolysis.

(42) The production method of the above-mentioned (41), wherein the reduction is carried out using sodium borohydride as a reducing agent.

EFFECT OF THE INVENTION

Since the compound of the present invention inhibits costimulatory signal from CD28 on T cell, it is effective for the prophylaxis or suppression of, for example, a rejection reaction in transplantation of organ or bone marrow and the like, and the prophylaxis or treatment of autoimmune diseases (rheumatoid arthritis, systemic lupus erythematosus, multiple sclerosis, psoriasis, inflammatory bowel disease (e.g., Crohn's disease and ulcerative colitis), Type I diabetes mellitus, lupus nephritis, encephalomyelitis and the like), or allergic diseases (asthma, allergic rhinitis, pollinosis, atopic dermatitis, urticaria, contact dermatitis, allergic conjunctivitis and the like). Moreover, the compound of the present invention is expected to induce antigen specific immunological tolerance.

BEST MODE FOR EMBODYING THE INVENTION

The terms and symbols used in the present specification are defined as follows.

The halogen atom means a fluorine atom, a chlorine atom, a bromine atom, an iodine atom or the like.

The $C_{1-6}$ alkyl means a straight chain or branched chain alkyl, and examples thereof include methyl, ethyl, n-propyl, isopropyl, n-butyl, isobutyl, secondary butyl, tertiary butyl (hereinafter "tertiary" is to be indicated as t- or tert-), pentyl, isopentyl, neopentyl, tertiary pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl and the like. Preferable examples of $C_{1-6}$ alkyl include $C_{1-4}$ alkyl and the like from the aforementioned specific examples.

The $C_{6-12}$ aryl means monocyclic-bicyclic aryl or the like, and examples thereof include phenyl, naphthyl and the like.

The heteroaryl having 5 to 12 ring-constituting atoms means 5-7-membered aromatic heterocycle (mono-cyclic) group containing, as a ring-constituting atoms besides carbon atom, 1 to 3 kinds of 1 to 4 hetero atoms selected from nitrogen atom, sulfur atom and oxygen atom, and examples thereof include furyl, thienyl, pyrrolyl, thiazolyl, pyrazolyl, oxazolyl, isoxazolyl, isothiazolyl, imidazolyl, oxadiazolyl, triazolyl, thiadiazolyl, tetrazolyl, pyridyl, pyrimidinyl, pyrazinyl, pyridazinyl, triazinyl, azepinyl, diazepinyl and the like. In addition, the heteroaryl encompasses a group derived from aromatic (bi- or more-cyclic) heterocycle wherein 5- to 7-membered aromatic heterocycle containing, as a ring atoms besides carbon atom, 1 to 3 kinds of 1 to 4 hetero atoms selected from nitrogen atom, sulfur atom and oxygen atom is fused with benzene ring or the above-mentioned aromatic heterocycle (mono-cyclic) group, and examples thereof include indolyl, isoindolyl, benzo[b]furyl, benzo[b]thienyl, benzoimidazolyl, benzoxazolyl, benzisoxazolyl, benzothiazolyl, benzisothiazolyl, quinolyl, isoquinolyl and the like. Moreover, these heteroaryls may be partially or completely hydrogenated. The hydrogenated position is not particularly limited. Examples of the partially or completely hydrogenated heteroaryl include tetrahydrobenzoimidazolyl, tetrahydroquinolyl, tetrahydroisoquinolyl, morpholinyl and the like.

Preferable examples the heteroaryl having 5 to 12 ring-constituting atoms include monocyclic group having 5 or 6 ring-constituting atoms and containing, as a ring atoms besides carbon atom, 1 to 3 kinds of 1 or 2 hetero atoms selected from nitrogen atom, sulfur atom and oxygen atom, and more preferable examples thereof include furyl, thienyl, pyridyl, thiazolyl, pyrazolyl, pyrazinyl, pyrimidinyl, morpholinyl and the like.

The arylcarbonylalkyl means $C_{1-6}$ alkyl to which $C_{6-12}$ aryl is bonded via carbonyl, and the $C_{1-6}$ alkyl and $C_{6-12}$ aryl are as mentioned above. Specific examples of arylcarbonylalkyl include phenylcarbonylmethyl, phenylcarbonylethyl, naphthylcarbonylmethyl, naphthylcarbonylethyl and the like, and preferable examples include phenylcarbonylmethyl, phenylcarbonylethyl and the like.

The $C_{7-13}$ arylcarbonyl means monocyclic or bicyclic $C_{7-13}$ arylcarbonyl, and examples thereof include phenylcarbonyl, naphthylcarbonyl and the like.

The $C_{6-12}$ aryloxy means monocyclic or bicyclic $C_{6-12}$ aryloxy, and examples thereof include phenyloxy, naphthyloxy and the like.

The $C_{1-6}$ alkoxy means straight chain or branched chain alkoxy having 1 to 6 carbon atoms, and examples thereof include methoxy, ethoxy, n-propoxy, isopropoxy, n-butoxy, isobutoxy, secondary butoxy, tertiary butoxy, pentoxy, isopentoxy, neopentoxy, tertiary pentoxy, 1-methylbutoxy, 2-methylbutoxy, 1,2-dimethylpropoxy, 1-ethylpropoxy, hexyloxy, isohexyloxy, 1-methylpentoxy, 2-methylpentoxy, 3-methylpentoxy, 1,1-dimethylbutoxy, 1,2-dimethylbutoxy, 2,2-dimethylbutoxy, 1-ethylbutoxy, 1,1,2-trimethylpropoxy, 1,2,2-trimethylpropoxy, 1-ethyl-2-methylpropoxy, 1-ethyl-1-methylpropoxy and the like. Preferable examples of the $C_{1-6}$ alkoxy include $C_{1-4}$ alkoxy and the like from the aforementioned examples.

Example of the cyclic amine having 4 or 5 carbon atoms include pyrrole, pyrroline, pyrrolidine, pyridine, dihydropyridine, tetrahydropyridine, piperidine and the like.

The $C_{7-18}$ aralkyl means $C_{1-6}$ alkyl substituted by $C_{6-12}$ aryl, and the $C_{6-12}$ aryl and $C_{1-6}$ alkyl are as mentioned above. Specific examples of the $C_{7-18}$ aralkyl include benzyl, phenethyl, naphthylmethyl, naphthylethyl and the like.

The heteroarylcarbonyl having 5 to 12 ring-constituting atoms means carbonyl to which the aforementioned heteroaryl having 5 to 12 ring-constituting atoms is bonded. Specific examples include furylcarbonyl, thienylcarbonyl, pyridylcarbonyl, thiazolylcarbonyl, pyrazolylcarbonyl, pyrazinylcarbonyl, pyrimidinylcarbonyl, morpholinylcarbonyl and the like.

The $C_{2-7}$ alkoxycarbonyl means carbonyl to which the aforementioned $C_{1-6}$ alkoxy is bonded. Specific examples include methoxycarbonyl, ethoxycarbonyl, n-propoxycarbonyl, isopropoxycarbonyl, n-butoxycarbonyl, isobutoxycarbonyl, secondary butoxycarbonyl, tertiary butoxycarbonyl, n-pentoxycarbonyl, n-hexoxycarbonyl and the like.

The $C_{2-7}$ alkylcarbonyl means carbonyl to which the aforementioned $C_{1-6}$ alkyl is bonded. Specific examples include methylcarbonyl (acetyl), ethylcarbonyl, n-propylcarbonyl, isopropylcarbonyl, n-butylcarbonyl, isobutylcarbonyl, secondary butylcarbonyl, tertiary butylcarbonyl, n-pentylcarbonyl, n-hexylcarbonyl and the like.

Example of the substituent of the "optionally having substituent(s)" when the substituent is not particularly defined include halogen atom; hydroxyl group; cyano; nitro; $C_{1-6}$ alkyl optionally substituted by halogen atom, hydroxyl group, morpholino, $C_{2-7}$ alkoxycarbonyl or $C_{1-6}$ alkoxy; $C_{1-6}$ alkoxy optionally substituted by morpholino, pyridyl, hydroxyl group, cyano, halogen atom, amino optionally substituted by $C_{1-6}$ alkyl, $C_{2-7}$ alkylcarbonyl, $C_{3-6}$ cycloalkyl, $C_{2-7}$ alkoxycarbonyl or $C_{1-6}$ alkoxy; heteroaryl having 5 to 12 ring-constituting atoms; heteroaryloxy having 5 to 12 ring-constituting atoms; heteroarylcarbonyl having 5 to 12 ring-constituting atoms, $C_{2-7}$ alkylcarbonyl or amino optionally substituted by one or more $C_{1-6}$ alkyl; methylenedioxy; ethylenedioxy; $C_{1-6}$ alkylthio; $C_{1-6}$ alkylsulfonyl; $C_{2-7}$ alkylcarbonyl; $C_{2-7}$ alkoxycarbonyl; $C_{4-7}$ cycloalkylcarbonyl; aminocarbonyl; $C_{2-6}$ alkynyloxy; $C_{2-6}$ alkenyl optionally substituted by hydroxyl group; $C_{2-6}$ alkenyloxy; sulfonyloxy optionally substituted by $C_{1-6}$ alkyl optionally substituted by halogen atom; piperazinyl optionally substituted by $C_{1-6}$ alkyl and the like, with preference given to $C_{2-7}$ alkylcarbonyl, $C_{1-6}$ alkylsulfonyl, $C_{1-6}$ alkoxy optionally substituted by morpholino, cyano, piperazinyl optionally substituted by $C_{1-6}$ alkyl, methylenedioxy, morpholino, hydroxyl group, halogen atom, $C_{1-6}$ alkyl and the like, with more preference given to $C_{1-6}$ alkoxy, cyano, halogen atom and the like.

Examples of the $C_{3-6}$ cycloalkyl include cyclopropyl, cyclobutyl, cyclopentyl, cyclohexyl and the like.

The heteroaryl having 5 to 12 ring-constituting atoms moiety of the heteroaryloxy having 5 to 12 ring-constituting atoms is as mentioned above.

The $C_{1-6}$ alkylthio means a group wherein the oxygen atom of the aforementioned $C_{1-6}$ alkoxy is replaced by sulfur atom, and examples thereof include methylthio, ethylthio, n-propylthio, isopropylthio, n-butylthio, isobutylthio, secondary butylthio, tertiary butylthio, n-pentylthio, n-hexylthio and the like.

The $C_{1-6}$ alkylsulfonyl means sulfonyl to which aforementioned $C_{1-6}$ alkyl is bonded, and examples thereof include methylsulfonyl, ethylsulfonyl, n-propylsulfonyl, isopropylsulfonyl, n-butylsulfonyl, isobutylsulfonyl, secondary butylsulfonyl, tertiary butylsulfonyl, n-pentylsulfonyl, n-hexylsulfonyl and the like.

The $C_{4-7}$ cycloalkylcarbonyl means carbonyl to which aforementioned $C_{3-6}$ cycloalkyl is bonded, and examples thereof include cyclopropylcarbonyl, cyclobutylcarbonyl, cyclopentylcarbonyl, cyclohexylcarbonyl and the like.

The $C_{2-6}$ alkynyloxy means straight chain or branched chain alkynyloxy having 2 to 6 carbon atoms, and examples thereof include ethynyloxy, propynyloxy, butynyloxy, pentynyloxy, hexynyloxy and the like.

The $C_{2-6}$ alkenyl means straight chain or branched chain alkenyl having 2 to 6 carbon atoms, and examples thereof include ethenyl, propenyl, butenyl, pentenyl, hexenyl and the like.

The $C_{2-6}$ alkenyloxy means straight chain or branched chain alkenyl having 2 to 6 carbon atoms, and examples thereof include ethenyloxy, propenyloxy, butenyloxy, pentenyloxy, hexenyloxy and the like.

The other substituent is as mentioned above.

Preferable examples of k in —$(CH_2)_kOR^a$ for $R^1$ include 1, 2 and 3, with more preference given to 1 and 2, with further preference given to 1. Preferable examples of $R^a$ include $C_{1-4}$ alkyl optionally having substituent(s), with more preference given to $C_{1-4}$ alkyl. Specific examples of the $C_{1-4}$ alkyl for $R^a$ include methyl, ethyl, n-propyl, isopropyl and the like, with more preference given to methyl, ethyl and the like, with further preference given to methyl.

Preferable examples of $R^1$ include hydrogen atom, chlorine atom, bromine atom, methyl, hydroxymethyl, methoxymethyl, ethoxymethyl and the like, with more preference given to methyl, hydroxymethyl, methoxymethyl and the like.

Preferable examples of $R^{20}$ include $C_{1-4}$ alkyl, with more preference given to methyl.

Preferable examples also include a compound wherein $R^1$ and $R^{20}$ in combination form trimethylene.

Preferable examples of $R^4$ in

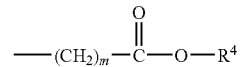

wherein $R^4$ is $C_{1-6}$ alkyl optionally having substituent(s), and m is an integer of 1 to 4, for $R^2$, include $C_{1-4}$ alkyl optionally having substituent(s), with more preference given to $C_{1-2}$ alkyl optionally having substituent(s), with further preference given to $C_{1-2}$ alkyl. Specific examples the substituent which the alkyl optionally has, include hydroxyl group, $C_{1-6}$ alkoxy, heteroaryl having 5 to 12 ring-constituting atoms, amino optionally substituted by $C_{1-6}$ alkyl and the like, with more preference given to hydroxyl group, methoxy, morpholino, dimethylamino and the like.

Preferable examples of m include 1 to 3, with more preference given to 1 or 2, with further preference given to 1.

Preferable examples of $R^2$ include hydrogen atom, methoxycarbonylmethyl, ethoxycarbonylmethyl,

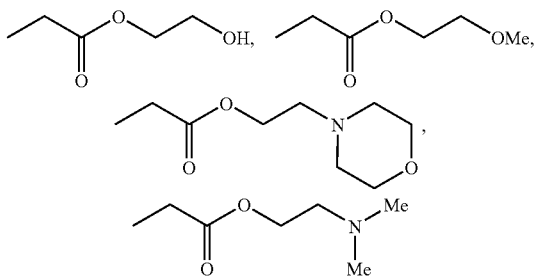

and the like, with more preference given to hydrogen atom, methoxycarbonylmethyl, ethoxycarbonylmethyl and the like, with further preference given to methoxycarbonylmethyl.

Preferable examples of $R^{21}$ include methyl.

Preferable examples of $R^3$ when $R^2$ is hydrogen atom include phenyl having one or more substituents selected from halogen atom, cyano, acetyl, hydroxymethyl, hydroxyethyl, methoxy and hydroxyl group; pyridyl, thienyl, thiazolyl, pyrimidinyl or pyrazolyl, each of which optionally has one or more substituents selected from acetyl, hydroxymethyl, hydroxyethyl, cyano, amino, methyl and halogen atom; and —$NR^5$—$(CH_2)_n$—$R^6$ ($R^5$ is hydrogen atom or methyl, n is an integer of 0 to 2, and $R^6$ is phenyl optionally having one or more substituents selected from halogen atom, hydroxyl group, methoxy, methylenedioxy and cyano; or pyridyl, tetrahydrofuranyl or tetrahydropyranyl, each of which optionally has one or more substituents selected from cyano, methyl optionally substituted by halogen atom, halogen atom and methoxy) and the like. More preferable examples of $R^3$ when $R^2$ is hydrogen atom include phenyl optionally substituted by cyano, pyridyl optionally substituted by cyano, thiazolyl optionally substituted by cyano; and —$NR^5$—$(CH_2)_n$—$R^6$ ($R^5$ is hydrogen atom, n is an integer of 0 to 2, and $R^6$ is phenyl optionally having one or more substituents selected from halogen atom and cyano; or pyridyl optionally having one or more substituents selected from cyano and halogen atom) and the like. Further preferable examples of $R^3$ when $R^2$ is hydrogen atom include thiazolyl, phenyl substituted by cyano, pyridyl substituted by cyano, and —$NR^5$—$(CH_2)_n$—$R^6$ ($R^5$ is hydrogen atom, n is an integer of 0 to 2, and $R^6$ is phenyl, phenyl substituted by fluorine atom, phenyl substituted by cyano, pyridyl substituted by cyano, pyridyl substituted by fluorine or pyridyl) and the like. Particularly preferable examples of $R^3$ when $R^2$ is hydrogen atom include phenyl substituted by cyano.

$R^3$ is explained as follows, when $R^2$ is not hydrogen atom.

Preferable examples of the $C_{6-12}$ aryl optionally having substituent(s) include phenyl optionally having substituent(s), naphthyl optionally having substituent(s) and the like, with more preference given to naphthyl, phenyl having substituents and the like, with further preference given to phenyl having substituents. Preferable examples of the substituents which these optionally has, include amino optionally having substituent(s), $C_{2-6}$ alkynyloxy optionally having substituent(s), $C_{1-6}$ alkyl optionally having substituent(s), $C_{2-7}$ alkylcarbonyl optionally having substituent(s), $C_{1-6}$ alkylsulfonyl optionally having substituent(s), $C_{1-6}$ alkylthio optionally having substituent(s), $C_{2-6}$ alkenyl optionally having substituent(s), $C_{2-6}$ alkenyloxy optionally having substituent(s), $C_{1-6}$ alkoxy optionally having substituent(s), cyano, $C_{4-7}$ cycloalkylcarbonyl optionally having substituent(s), sulfonyloxy optionally having substituent(s), halogen atom, heteroaryl having 5 to 12 ring-constituting atoms and optionally having substituent(s), heteroaryloxy having 5 to 12 ring-constituting atoms and optionally having substituent(s), methylenedioxy, hydroxyl group and the like, with more preference given to $C_{2-7}$ alkylcarbonyl, $C_{1-6}$ alkylsulfonyl, $C_{1-6}$ alkoxy optionally having substituent(s), cyano, heteroaryl having 5 to 12 ring-constituting atoms and optionally having substituent(s), heteroaryloxy having 5 to 12 ring-constituting atoms and optionally having substituent(s), hydroxyl group and the like, with further preference given to $C_{1-6}$ alkoxy, cyano and the like. Specific examples thereof include amino, methylcarbonylamino, ethylcarbonylaminomethylsulfonylamino, dimethylsulfonylamino, dimethylamino, pyridylcarbonylamino, propynyloxy, methyl, hydroxymethyl, methoxymethyl, morpholinomethyl, methylcarbonyl, ethylcarbonyl, methylsulfonyl, methylthio, butenyl substituted by methyl and hydroxyl group, propenyloxy, methoxy, ethoxy, n-propoxy, n-butoxy, methoxycarbonylmethoxy, cyanomethoxy, methoxymethoxy, trifluoromethoxy, t-butylcarbonylmethoxy, cyclopropylmethoxy, pyridylmethoxy, methoxyethoxy, ethoxyethoxy, morpholinoethoxy, hydroxypropoxy, cyanopropoxy, dimethylaminopropoxy, cyano, cyclopropylcarbonyl, trifluoromethylsulfonyloxy, fluorine, methylpiperazinyl, morpholino, pyridyloxy, methylenedioxy, hydroxyl group and the like, with more preference given to methylcarbonyl, methylsulfonyl, morpholinoethoxy, methoxy, cyano, methylpiperazinyl, methylenedioxy, morpholino, hydroxyl group and the like, with further preference given to methoxy and cyano.

Specific examples of the heteroaryl having 5 to 12 ring-constituting atoms and optionally having substituent(s) include heteroaryl having 5 or 6 ring-constituting atoms, containing 1 or 2 atoms selected from nitrogen atom, sulfur atom and oxygen atom, and optionally having substituent(s), with preference given to thiazolyl, thienyl, pyrazinyl, pyrazolyl, pyridyl, pyrimidinyl and furyl, each of which optionally has substituent(s) and the like, with more preference given to pyrazinyl, thienyl, pyridyl and pyrimidinyl, each of which optionally has substituent(s). Preferable examples of the substituents which these optionally has, include halogen atom, $C_{1-6}$ alkyl optionally having substituent(s), $C_{2-7}$ alkylcarbonyl optionally having substituent(s), cyano, amino optionally having substituent(s), aminocarbonyl optionally having substituent(s), $C_{1-6}$ alkylsulfonyl optionally having substituent(s) and the like, with preference given to halogen atom, $C_{1-4}$ alkyl optionally having substituent(s), $C_{2-5}$ alkylcarbonyl, cyano, amino optionally substituted by one or more $C_{1-4}$ alkyl, aminocarbonyl optionally substituted by one or more $C_{1-4}$ alkyl, $C_{1-4}$ alkylsulfonyl optionally having substituent(s), with more preference given to halogen atom, $C_{1-4}$ alkyl optionally substituted by hydroxyl group or halogen atom, $C_{1-4}$ alkylcarbonyl, cyano, amino optionally substituted by one $C_{1-4}$ alkyl, aminocarbonyl, $C_{1-4}$ alkylsulfonyl and the like, with further preference given to cyano, methylcarbonyl and the like. Specific examples of the heteroaryl having 5 to 12 ring-constituting atoms and optionally having substituent(s) include thiazole, thiazole substituted by halogen atom, thienyl, thienyl substituted by $C_{1-6}$ alkyl substituted by hydroxyl group, thienyl substituted by $C_{2-7}$ alkylcarbonyl, thienyl substituted by cyano, pyrazinyl, pyrazinyl substituted by amino substituted by one $C_{1-6}$ alkyl, pyrazinyl substituted by cyano, pyrazinyl substituted by halogen atom, pyrazolyl, pyridyl, pyridyl substituted by amino, pyridyl substituted by aminocarbonyl, pyridyl substituted by $C_{2-7}$ alkylcarbonyl, pyridyl substituted by cyano, pyrimidinyl, pyrimidinyl substituted by $C_{1-6}$ alkyl substituted by halogen atom, pyrimidinyl substituted by $C_{1-6}$ alkylsulfonyl, pyrimidinyl substituted by cyano, pyrimidinyl substituted by halogen atom, furyl and the like. Preferable examples of the halogen atom in this paragraph include fluorine atom, chlorine atom and the like.

Examples of the arylcarbonylalkyl (the aryl moiety has 6 to 12 carbon atoms, and the alkyl moiety has 1 to 6 carbon atoms) optionally having substituent(s) on the ring include arylcarbonylalkyl wherein the aryl moiety is phenyl, naphthyl or the like, preferably phenyl, and the alkyl moiety has 1 to 6, preferably 1 to 4, more preferably 1 or 2, carbon atoms. Examples of the substituents which these optionally has, include halogen atom, $C_{1-6}$ alkyl, $C_{1-6}$ alkoxy, hydroxyl group and the like, with preference given to halogen atom, $C_{1-6}$ alkoxy and the like, with more preference given to halogen atom, $C_{1-4}$ alkoxy and the like, with further preference given to fluorine atom, methoxy and the like. Specific examples of the arylcarbonylalkyl (the aryl moiety has 6 to 12 carbon atoms, and the alkyl moiety has 1 to 6 carbon atoms) optionally having substituent(s) on the ring include phenylcarbonylmethyl optionally substituted by halogen atom or $C_{1-6}$ alkoxy, phenylcarbonylethyl optionally substituted by halogen atom or $C_{1-6}$ alkoxy and the like, with preference given to phenylcarbonylethyl, phenylcarbonylethyl substituted by halogen atom, methoxycarbonylmethyl and the like. Preferable examples of the halogen atom in this paragraph include fluorine atom.

Preferable examples of $R^{5a}$ in —$NR^{5a}$—$(CH_2)_o$—$R^{6a}$ include hydrogen atom, $C_{1-6}$ alkyl and the like, with more preference given to hydrogen atom, $C_{1-4}$ alkyl and the like, with more preference given to hydrogen atom, methyl, ethyl and the like, with further preference given to hydrogen atom, methyl and the like. Preferable examples of o include 0 to 3, with more preference given to 0 to 2, with further preference given to 0 or 1. Preferable examples of $R^{6a}$ include $C_{6-12}$ aryl optionally having substituent(s), and heteroaryl having 5 to 12 ring-constituting atoms and optionally having substituent(s). Specific examples of the $C_{6-12}$ aryl optionally having substituent(s) for $R^{6a}$ include, phenyl optionally having substituent(s), naphthyl optionally having substituent(s) and the like, with preference given to phenyl optionally having substituent(s). Specific examples of the $C_{7-13}$ arylcarbonyl optionally having substituent(s) for $R^{6a}$ include phenylcarbonyl optionally having substituent(s), naphthylcarbonyl optionally having substituent(s) and the like, with preference given to phenylcarbonyl optionally having substituent(s), with more preference given to phenylcarbonyl having substituents, with further preference given to phenylcarbonyl substituted by halogen atom. Preferable examples of the halogen atom include fluorine atom, chlorine atom and the like, with more preference given to fluorine atom. Specific examples of the $C_{6-12}$ aryloxy optionally having substituent(s) for $R^{6a}$ include phenyloxy optionally having substituent(s), naphthyloxy optionally having substituent(s) and the like, with preference given to phenyloxy optionally having substituent(s), with more preference given to phenyloxy. Preferable examples of the heteroaryl having 5 to 12 ring-constituting atoms and optionally having substituent(s) for $R^{6a}$ include heteroaryl having 5 or 6 ring-constituting atoms, containing 1 or 2 atoms selected from nitrogen atom, oxygen atom and sulfur atom, and optionally having substituent(s), with more preference given to imidazolyl optionally having substituent(s), thiazolyl optionally having substituent(s), pyrazolyl optionally having substituent(s), pyridyl optionally having substituent(s), furyl optionally having substituent(s) and the like, with further preference given to pyrazolyl optionally having substituent(s). Preferable examples of the substituents which these optionally has, include amino optionally substituted by $C_{2-7}$ alkylcarbonyl, $C_{1-6}$ alkyl optionally substituted by $C_{2-7}$ alkoxycarbonyl or halogen atom, $C_{1-6}$ alkylsulfonyl, $C_{1-6}$ alkoxy, $C_{2-7}$ alkoxycarbonyl, cyano, nitro, halogen atom, methylenedioxy and the like, with preference given to amino substituted by $C_{2-5}$ alkylcarbonyl (particularly, methylcarbonylamino), $C_{1-4}$ alkyl optionally substituted by $C_{2-5}$ alkoxycarbonyl or halogen atom (particularly, ethoxycarbonylmethyl, trifluoromethyl, methyl, t-butyl, ethyl etc.), $C_{1-4}$ alkylsulfonyl (particularly, methylsulfonyl), $C_{1-4}$ alkoxy (particularly, methoxy), $C_{2-5}$ alkoxycarbonyl (particularly, methoxycarbonyl), cyano, nitro, halogen (particularly, fluorine atom, chlorine atom etc.), methylenedioxy and the like, with more preference given to cyano, fluorine atom, methyl, ethyl and the like, with further preference given to fluorine atom. Specific preferable examples of $R^{6a}$ include cyanophenyl, phenyl substituted by halogen atom (particularly, fluorophenyl), phenyl, pyrazolyl substituted by alkyl (particularly, methylpyrazolyl, ethylpyrazolyl etc.), with more preference given to fluorophenyl, phenyl and the like.

Preferable examples of $R^7$ and $R^{7'}$ include hydrogen atom, $C_{1-6}$ alkoxy and the like, with more preference given to hydrogen atom, $C_{1-4}$ alkoxy and the like, with further preference given to hydrogen atom, methoxy and the like. Preferable examples of the ring A include saturated cyclic amine having 4 or 5 carbon atoms, with more preference given to tetrahydropyridine, pyrrolidine and the like. Specific preferable examples of

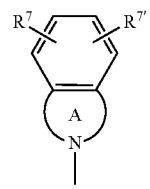

include

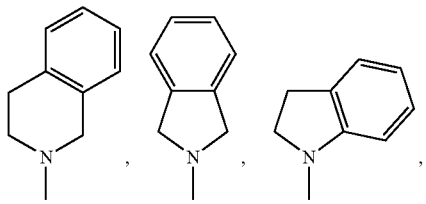

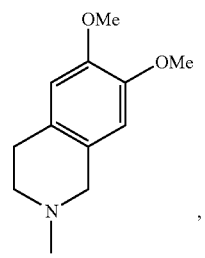

with more preference given to

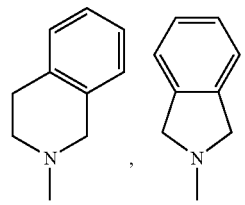

Preferable examples of $R^8$ include phenyl optionally having substituent(s), naphthyl optionally having substituent(s), pyridyl optionally having substituent(s), benzyl optionally having substituent(s), phenethyl optionally having substituent(s), naphthylmethyl optionally having substituent(s), naphthylethyl optionally having substituent(s), phenylcarbonyl optionally having substituent(s), naphthylcarbonyl optionally having substituent(s), pyridylcarbonyl optionally having substituent(s) and the like, with more preference given to phenyl, pyridyl, benzyl, methoxyphenyl, pyridylcarbonyl and the like.

Preferable examples of $R^9$ include hydrogen atom, hydroxyl group and cyano group. Preferable examples of $R^{10}$ include $C_{1-6}$ alkyl optionally having substituent(s), $C_{6-12}$ aryl optionally having substituent(s) and the like, with more preference given to $C_{1-4}$ alkyl optionally having substituent(s), phenyl optionally having substituent(s) and the like, with further preference given to phenyl, phenylmethyl and hydroxy(diphenyl)methyl.

Specific preferable examples of

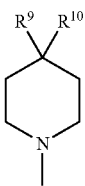

include

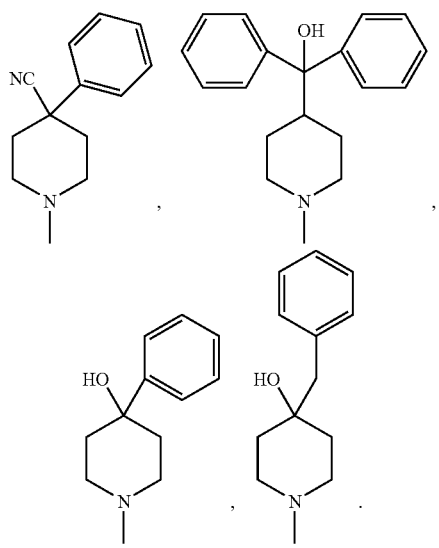

Preferable examples of $R^{11}$ include phenyl optionally having substituent(s), thiazolyl optionally having substituent(s), anilinocarbonyl optionally having substituent(s) and the like, with more preference given to phenyl optionally having substituent(s), with further preference given to phenyl substituted by halogen atom (particularly, fluorine atom). Preferable examples of the substituents which these optionally has, include $C_{1-6}$ alkyl optionally substituted by hydroxyl group, $C_{1-6}$ alkoxy, cyano, halogen atom, hydroxyl group and the like, with preference given to $C_{1-4}$ alkyl optionally substituted by hydroxyl group, $C_{1-4}$ alkoxy, cyano, halogen atom, hydroxyl group and the like, with more preference given to methyl, hydroxymethyl, methoxy, cyano, fluorine atom, hydroxyl group and the like, with further preference given to fluorine atom. Specific preferable examples of $R^{11}$ include phenyl, phenyl substituted by methyl, phenyl substituted by hydroxymethyl, phenyl substituted by methoxy, phenyl substituted by cyano, phenyl substituted by halogen atom, phenyl substituted by hydroxyl group, thiazolyl substituted by methyl, anilinocarbonyl, cyanoanilinocarbonyl and the like, with more preference given to phenyl substituted by fluorine atom.

Preferable examples of $R^{12}$ include pyridyl optionally having substituent(s), with more preference given to pyridyl.

Preferable examples of $R^{13}$ include hydrogen atom, $C_{1-4}$ alkyl optionally having substituent(s) and the like, with more preference given to hydrogen atom, methyl and the like, with further preference given to hydrogen atom. Preferable examples of the p include 2. Preferable examples of $R^{14}$ include phenyl optionally having substituent(s), pyridyl optionally having substituent(s) and the like, with more preference given to phenyl optionally having substituent(s), with further preference given to phenyl. Preferable examples of the substituents which these optionally has, include $C_{1-6}$ alkyl optionally substituted by halogen atom, $C_{2-7}$ alkylcarbonyloxy, $C_{1-6}$ alkoxy, cyano, halogen atom and the like, with preference given to $C_{1-4}$ alkyl substituted by halogen atom, $C_{2-5}$ alkylcarbonyloxy, $C_{1-4}$ alkoxy, cyano, halogen atom and the like, with more preference given to trifluoromethyl, methylcarbonyloxy, methoxy, cyano, fluorine atom, bromine atom and the like.

Specific preferable examples of

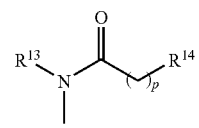

include

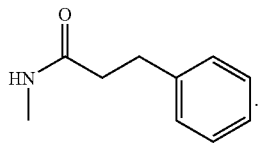

Preferable examples of $R^{15}$ include hydrogen atom, $C_{1-4}$ alkyl optionally having substituent(s) and the like, with more preference given to hydrogen atom, $C_{1-4}$ alkyl and the like, with further preference given to hydrogen atom, methyl and the like. Preferable examples of $R^{16}$ include phenyl optionally having substituent(s), pyridyl optionally having substituent(s) and the like, with more preference given to phenyl, pyridyl and the like.

Preferable examples of $R^{17}$ include hydrogen atom, $C_{1-4}$ alkyl optionally having substituent(s) and the like, with more preference given to hydrogen atom, $C_{1-4}$ alkyl and the like, with further preference given to hydrogen atom, methyl and the like. Preferable examples of $R^{18}$ include phenyl optionally having substituent(s), benzyl optionally having substituent(s) and the like, with more preference given to phenyl, benzyl and the like.

Preferable examples of $R^{19}$ include phenyl optionally having substituent(s), thienyl optionally having substituent(s) and the like, with more preference given to phenyl having substituents, thienyl optionally having substituent(s) and the like. Examples of the substituents which these optionally has, include halogen atom, $C_{1-6}$ alkyl optionally substituted by halogen atom, $C_{1-6}$ alkoxy and the like, with preference given to halogen atom, $C_{1-4}$ alkyl optionally substituted by halogen atom, $C_{1-4}$ alkoxy and the like, with more preference given to halogen atom, $C_{1-4}$ alkyl substituted by halogen atom, $C_{1-4}$ alkoxy and the like, with more preference given to fluorine atom, chlorine atom, trifluoromethyl, methoxy.

Examples of the pharmaceutically acceptable salt of the compound of the present invention include salts with inorganic acids, salts with organic acids, salts with inorganic bases and salts with organic bases. In addition, the compound of the present invention also encompasses hydrates and solvates. They can be obtained by a well-known method.

The reactive group in the formulas (II), (II') and (III) may be any as long as it can react with $R^3$—H and $R^3$—B(OH)$_2$ easily and can be substituted for $R^3$, and examples thereof include halogen atom, p-toluenesulfonyloxy or methylsulfonyloxy optionally substituted by a halogen atom and the like.

Examples of the palladium catalyst include palladium acetate (II), palladium chloride (II), tris(dibenzylideneacetone)dipalladium (0), chloroform adduct thereof and the like, as well as tetrakis(triphenylphosphine)palladium (0), [1,1-bis(diphenylphosphino)ferrocene]dichloropalladium (II), dichlorobis(triphenylphosphine)palladium (II), dichlorobis(tricyclohexylphosphine)palladium (II), bis(tri-tert-butylphosphine)palladium (0) and the like wherein a palladium catalyst and a phosphine ligand form a complex.

BEST MODE FOR EMBODYING THE INVENTION

The starting material of the compound of the present invention can be produced according to Starting Material Preparation Example 1 or 4 of WO 98/11111 and the like.

The compound of the present invention (I) can be produced according to the following methods.

Method 1: The production method described here is suitable for producing, from compounds represented by the formula (I), a compound wherein $R^1$ is hydrogen atom, $C_{1-6}$ alkyl optionally substituted by halogen atom or optionally substituted by hydroxyl group or —$(CH_2)_k OR^a$ (wherein k is an integer of 1-4, $R^a$ is $C_{1-6}$ alkyl optionally having substituent(s), $R^2$ is the following group

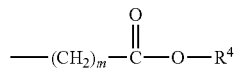

wherein $R^4$ is $C_{1-6}$ alkyl optionally having substituent(s), and m is an integer of 1-4,
$R^3$ is $C_{6-12}$ aryl optionally having substituent(s), heteroaryl optionally having substituent(s) wherein the ring has 5-12 constituent atoms, arylcarbonylalkyl optionally having substituent(s) on the ring (aryl moiety has 6 to 12 carbon atoms, alkyl moiety has 1 to 6 carbon atoms), —$NR^{5a}$—$(CH_2)_o$—$R^{6a}$ (wherein $R^{5a}$ is hydrogen atom or $C_{1-6}$ alkyl optionally having substituent(s), o is an integer of 0-4, $R^{6a}$ is $C_{6-12}$ aryl optionally having substituent(s), $C_{7-13}$ arylcarbonyl optionally having substituent(s), $C_{6-12}$ aryloxy optionally having substituent(s) or heteroaryl optionally having substituent(s) wherein the ring has 5-12 constituent atoms), or the following group

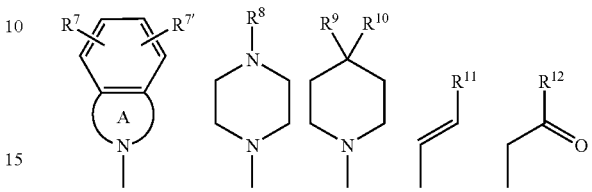

wherein $R^7$ and $R^{7'}$ are the same or different and each is hydrogen atom, $C_{1-6}$ alkyl optionally having substituent(s) or $C_{1-6}$ alkoxy optionally having substituent(s), ring A is cyclic amine having 4 or 5 carbon atoms, which is condensed with aromatic ring, $R^8$ is $C_{6-12}$ aryl optionally having substituent(s), heteroaryl optionally having substituent(s) wherein the ring has 5-12 constituent atoms, $C_{7-18}$ aralkyl optionally having substituent(s), $C_{7-13}$ arylcarbonyl optionally having substituent(s) or heteroaryl-carbonyl wherein a ring optionally having substituents has 5-12 constituent atoms, $R^9$ is hydrogen atom, hydroxyl group or cyano group, $R^{10}$ is $C_{1-6}$ alkyl optionally having substituent(s), $C_{6-12}$ aryl optionally having substituent(s) or heteroaryl optionally having substituent(s) wherein the ring has 5-12 constituent atoms, $R^{11}$ is $C_{6-12}$ aryl optionally having substituent(s), heteroaryl optionally having substituent(s) wherein the ring has 5-12 constituent atoms or optionally having substituent(s) anilinocarbonyl, and $R^{12}$ is heteroaryl optionally having substituent(s) wherein the ring has 5-12 constituent atoms), i.e., a compound represented by the following the formula (I-a). The method thereof includes a route performing 1) Step 2 (coupling reaction) via Step 1 (esterification), or 2) Step 4 (esterification) via Step 3 (coupling reaction).

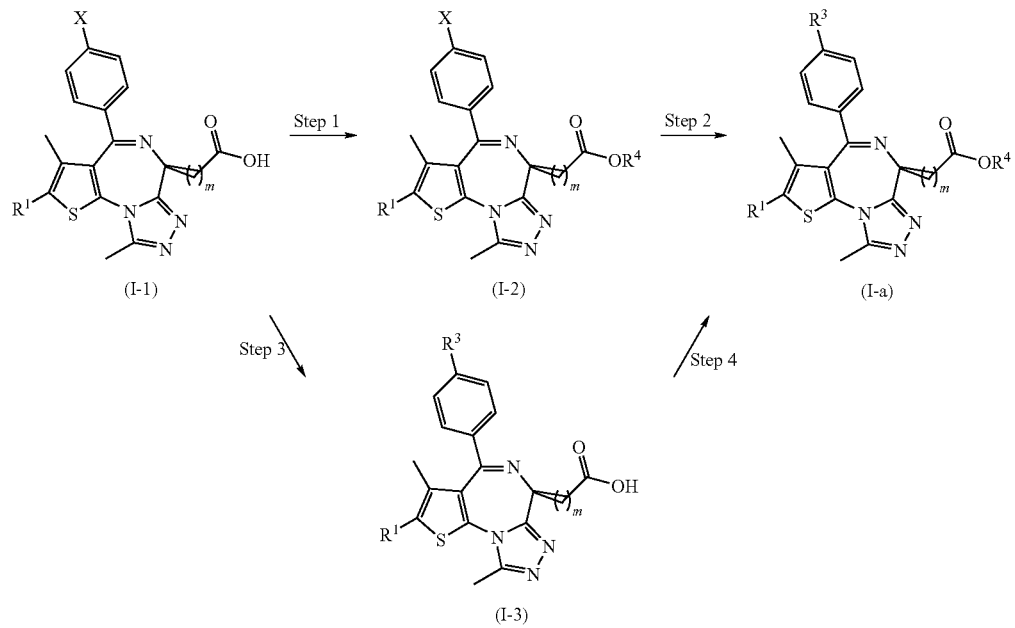

wherein each symbol is as defined above.

Step 1

A compound represented by the formula (I-1) is reacted in the presence of sulfuric acid, hydrochloric acid, thionyl chloride in alcohol such as methanol, ethanol and the like, at 0° C.—heating under reflux to give the corresponding compound represented by the formula (I-2). Alternatively, a condensation agent may be used instead of an acid.

Step 2

A compound represented by the formula (I-2) and an amine represented by $R^3$—H
wherein $R^3$ is as defined above, olefin, alcohol or methylketone derivative, aryl boronic acid derivative represented by $R^3$—B(OH)$_2$ or ester thereof
wherein $R^3$ is as defined above, are subjected to a coupling reaction to give a compound represented by the formula (I-a). The reaction preferably proceeds in the presence of a palladium catalyst, a phosphine ligand and a base, in a suitable solvent at 0° C.—under heating, particularly from room temperature to the boiling point. The palladium catalyst includes, for example, palladium acetate (II), palladium chloride (II), tris(dibenzylideneacetone)dipalladium (0), chloroform adduct thereof and the like. Examples of the phosphine ligand include triphenylphosphine, tri-ortho-tolylphosphine, 2-(dicyclohexylphosphino)biphenyl, 2-(di-tert-butylphosphino) biphenyl, 2-dicyclohexylphosphino-2,6-dimethoxybiphenyl, 2-dicyclohexylphosphino-2,4,6-triisopropylbiphenyl, 2-(dicyclohexylphosphino)-2-(N,N-dimethylamino)biphenyl, 2-(di-tert-butylphosphino)-1,1-binaphthyl, tri-tert-butylphosphine, tri-tert-butylphosphoniumtetrafluoroborate and the like. A reagent wherein a palladium catalyst and a phosphine ligand form a complex may be used and, for example, tetrakis(triphenylphosphine)palladium (0), [1,1-bis (diphenylphosphino)ferrocene]dichloropalladium (II), dichlorobis(triphenylphosphine)palladium (II), dichlorobis (tricyclohexylphosphine)palladium (II), bis(tri-tert-butylphosphine)palladium (0) and the like can be mentioned. Examples of the base include tert-butoxy sodium, tripotassium phosphate, cesium carbonate, potassium carbonate, sodium hydrogencarbonate, triethylamine, diisopropylethylamine, dicyclohexylethylamine, potassium fluoride, cesium fluoride and the like. Examples of the solvent include ether type solvents such as tetrahydrofuran, dimethoxyethane, dioxane and the like, alcohol type solvents such as methanol, ethanol, propanol, butanol and the like, N,N-dimethylformamide, or a mixed solvent of these organic solvents and water and the like.

When $R^3$ is $C_{6-12}$ aryl, heteroaryl wherein the ring has 5-12 constituent atoms or olefin, a compound represented by the formula (I-a) can be obtained by a coupling reaction of an organic metal salt for $R^3$ (e.g., tin, zinc, etc.), or an alkyl metal derivative for $R^3$ (e.g., alkylaluminum derivative, alkyltin derivative, alkylborane derivative, etc.) and the like and a compound represented by the formula (I-2).

Moreover, the 6-position ester group of the obtained compound represented by the formula (I-a) may be hydrolyzed and then condensed again with different alcohol. For the reaction, the method of Step 1 can be performed.

Step 3

A compound represented by the formula (I-3) can be obtained by applying the method of Step 2 to a compound represented by the formula (I-1).

Step 4

A compound represented by the formula (I-a) can be obtained by applying the method of Step 1 to a compound represented by the formula (I-3).

Method 2:

The production method described here is suitable for producing, from compounds represented by the formula (I), a compound wherein $R^1$ is the same as in Method 1 and $R^2$ is hydrogen atom, i.e., a compound represented by the following formula (I-b).

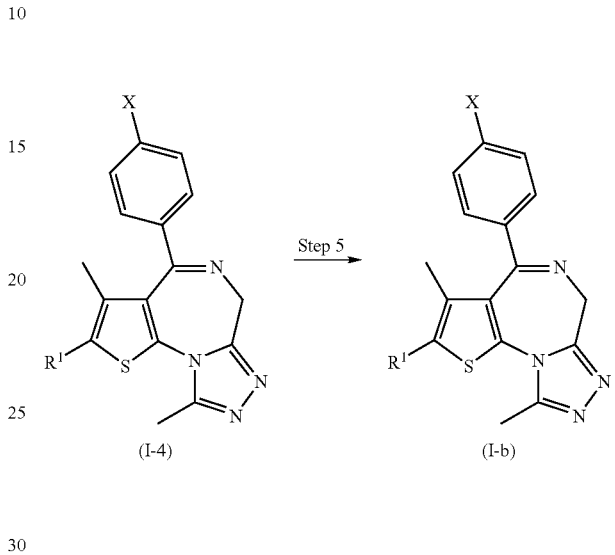

wherein each symbol is as defined above.

Step 5

A compound represented by the formula (I-b) can be obtained by applying the method of Step 2 to a compound represented by the formula (I-4).

Method 3:

The production method described here is suitable for producing, from compounds represented by the formula (I), a compound wherein $R^1$ is the same as in Method 1, and $R^3$ is $C_{6-12}$ aryl optionally having substituent(s) or heteroaryl wherein the ring has 5-12 constituent atoms, i.e., a compound represented by the following formula (I-c).

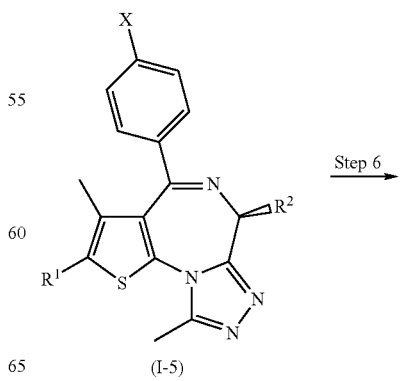

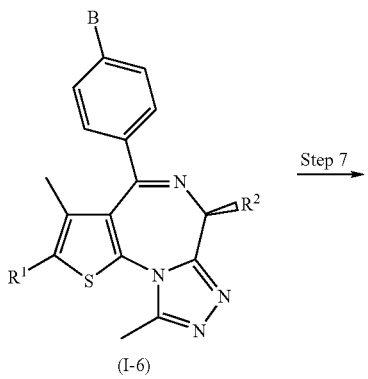

(I-6)

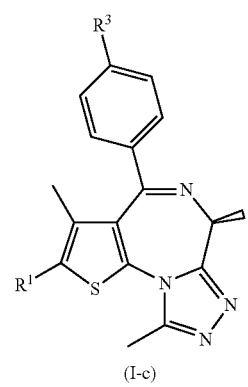

(I-c)

wherein X, R¹, R² and R³ are as defined above, and B is boronic acid or boronic ester optionally having substituent(s). The method thereof includes a route performing Step 7 (coupling reaction) via Step 6 (conversion to boronic acid or ester thereof).

Step 6

A compound represented by the formula (I-5) is reacted with a boronic acid derivative (e.g., bispinacolatodiboron, bisneopentylglycolatodiboron etc.) to give a compound represented by the formula (I-6). The reaction preferably proceeds in the presence of a palladium catalyst, a phosphine ligand and a base in a suitable solvent at 0° C.—under heating, particularly from room temperature to the boiling point. As the palladium catalyst, phosphine ligand, base and solvent, those recited in Step 2 can be used.

Step 7

A compound represented by the formula (I-6) is reacted with R³—X (R³ is $C_{6-12}$ aryl optionally having substituent(s) or heteroaryl wherein the ring has 5-12 constituent atoms, and X is halogen where halogen is preferably iodine, bromine or chlorine) to give a compound represented by the formula (I-c). The reaction preferably proceeds in the presence of a palladium catalyst, a phosphine ligand and a base, in a suitable solvent at 0° C.—under heating, particularly from room temperature to the boiling point. As the palladium catalyst, phosphine ligand, base and solvent, those recited in Step 2 can be used.

Method 4:

The production method described here is suitable for producing, from compounds represented by the formula (I), a compound wherein R¹ is the same as in Method 1, and R³ is —NR⁵—(CH₂)ₙ—R⁶ (wherein R⁵ is hydrogen atom or methyl, n is an integer of 0-3, R⁶ is $C_{6-12}$ aryl optionally having one or more substituents selected from halogen atom, hydroxyl group, methoxy, methylenedioxy and cyano; or pyridyl, thiazolyl, isoxazolyl, pyrazolyl, tetrahydrofuranyl or tetrahydropyranyl optionally having one or more substituents selected from methyl optionally substituted by halogen atom, cyano, halogen atom and methoxy) or —NR⁵ᵃ—(CH₂)ₒ—R⁶ᵃ (wherein R⁵ᵃ is hydrogen atom or $C_{1-6}$ alkyl optionally having substituent(s), o is an integer of 0-4, R⁶ᵃ is $C_{6-12}$ aryl optionally having substituent(s) or heteroaryl wherein the ring has 5-12 constituent atoms), i.e., a compound represented by the following formula (I-d). In the explanation of the following formulas and from Step 8 to Step 14, —NR⁵ᵃ—(CH₂)ₙ—R⁶ᵃ is shown as a representative example, where R⁵ᵃ, o and R⁶ᵃ are to be appropriately replaced by R⁵, n and R⁶.

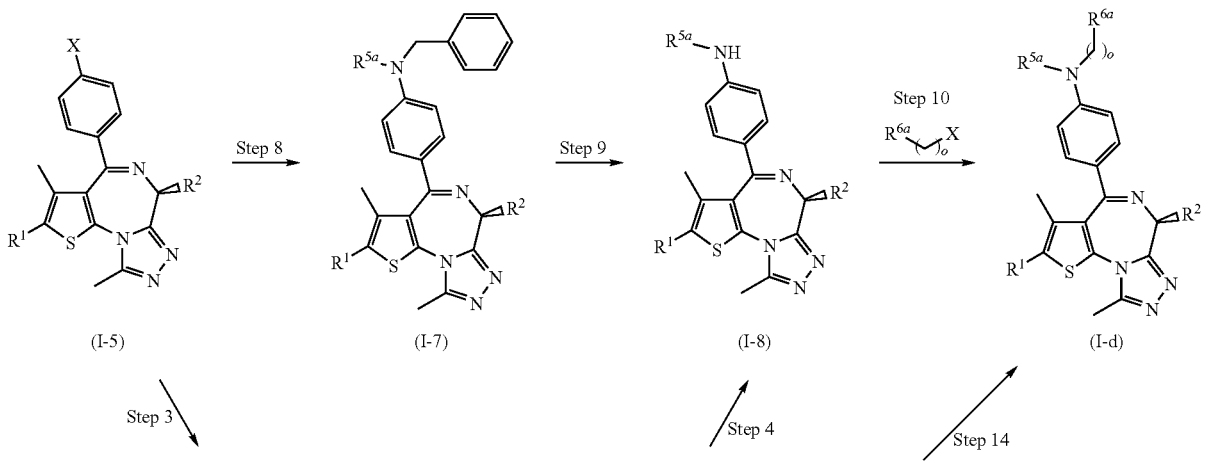

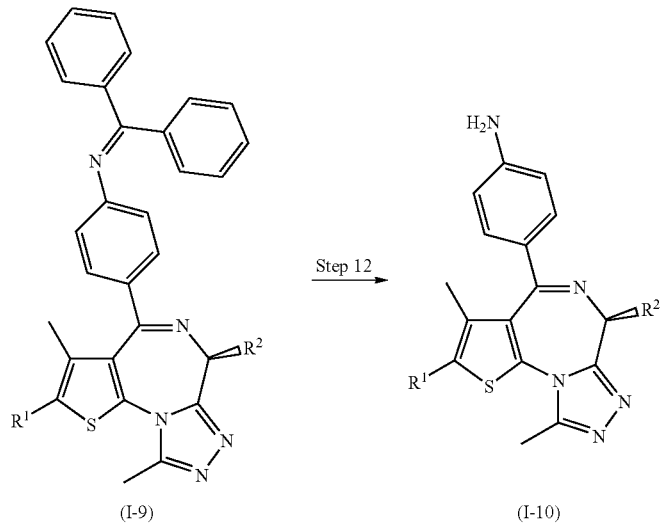

(I-9)  (I-10)

wherein each symbol is as defined above.

The method thereof includes a route performing 1) Step 10 (coupling reaction) via Step 8 (coupling reaction with benzylamine) and Step 9 (debenzylation), or 2) Step 14 via Step 11 (coupling reaction with benzophenoneimine) and Step 12 (deprotection).

Step 8

A compound represented by the formula (I-5) is reacted with $R^{5a}NHCH_2Ph$
wherein $R^{5a}$ is as defined above, to give a compound represented by formula (I-7). The reaction preferably proceeds in the presence of a palladium catalyst, a phosphine ligand and a base in a suitable solvent at 0° C.—under heating, particularly from room temperature to the boiling point. As the palladium catalyst, phosphine ligand, base and solvent, those recited in Step 2 can be used.

Step 9

A compound represented by the formula (I-7) is debenzylated to give a compound represented by the formula (I-8). The reaction preferably proceeds in the presence of a palladium catalyst, in a suitable solvent at 0° C.—under heating, particularly from room temperature to 60° C. As the palladium catalyst, for example, palladium carbon, palladium black and the like can be mentioned. As the solvent, for example, alcohol, acetic acid and the like can be mentioned. In some cases, addition of a strong acid promotes the reaction.

Step 10

When $R^3$ is $—NR^{5a}—(CH_2)_o—R^{6a}$
wherein other than o are as defined above, o is 0, a compound represented by the formula (I-8) is reacted with arylhalide, heteroaryl halide (halogen is preferably iodine, bromine, chlorine) to give a compound represented by the formula (I-d). The reaction preferably proceeds in the presence of a palladium catalyst, a phosphine ligand and a base in a suitable solvent at 0° C.—under heating, particularly from room temperature to the boiling point. As the palladium catalyst, phosphine ligand, base and solvent, those recited in Step 2 can be used.

When $R^3$ is $—NR^{5a}—(CH_2)_o—R^{6a}$
wherein other than o are as defined above, o is an integer of 1-4, aralkyl halide (halogen is preferably iodine, bromine, chlorine) is reacted to give a compound represented by the formula (I-d). The reaction proceeds in the presence of a base in a suitable solvent at 0° C.—under heating. As the base, for example, potassium carbonate, cesium carbonate, triethylamine, diisopropylethylamine, sodium hydride and the like can be mentioned. As the solvent, for example, acetone, tetrahydrofuran, dimethylformamide and the like can be mentioned.

Step 11

A compound represented by the formula (I-5) is reacted with benzophenoneimine to give a compound represented by the formula (I-9). The reaction preferably proceeds in the presence of a palladium catalyst, a phosphine ligand and a base in a suitable solvent at 0° C.—under heating, particularly from room temperature to the boiling point. As the palladium catalyst, phosphine ligand, base and solvent, those recited in Step 2 can be used.

Step 12

A compound represented by the formula (I-9) is reacted in a suitable solvent by addition of a strong acid at room temperature to give a compound represented by the formula (I-10). As the solvent, for example, tetrahydrofuran and the like can be mentioned.

Step 13

A compound represented by the formula (I-10) is reacted with $R^{5a}$—X wherein $R^{5a}$ is as defined above and X is halogen, preferably, iodine, bromine, chlorine) to give a compound represented by the formula (I-8). The reaction proceeds in the presence of a base, in a suitable solvent at 0° C.—under heating. As the base, for example, potassium carbonate, cesium carbonate, triethylamine, diisopropylethylamine and the like can be mentioned. As the solvent, for example, acetone, tetrahydrofuran, dimethylformamide and the like can be mentioned. Alternatively, a compound represented by the formula (I-10) is reacted with alkylaldehyde to give a compound represented by the formula (I-8). The reaction proceeds in the presence of palladium carbon, in a suitable solvent at 0° C.—under heating. As the solvent, for example, alcohol, acetic acid and the like can be mentioned. In some cases, addition of a strong acid promotes the reaction. Similarly, a reductive amination reaction using sodium triacetoxyborohydride and the like may be performed.

Step 14

A compound represented by the formula (I-10) is reacted with aralkylhalide (halogen is preferably iodine, bromine, chlorine) to give a compound represented by the formula (I-d). The reaction proceeds in the presence of a base in a suitable solvent at 0° C.—under heating. As the base, for example, potassium carbonate, cesium carbonate, triethylamine, diisopropylethylamine and the like can be mentioned. As the solvent, for example, acetone, tetrahydrofuran, dimethylformamide and the like can be mentioned.

Method 5:

The production method described here is suitable for producing, from compounds represented by the formula (I), a compound wherein $R^1$ is the same as in Method 1 or $C_{6-12}$ aryl optionally having one or more substituents selected from halogen atom, cyano, acetyl, hydroxymethyl, hydroxyethyl, methoxy and hydroxyl group; pyridyl, thienyl, thiazolyl, pyrimidinyl, or pyrazolyl optionally having one or more substituents selected from acetyl, hydroxymethyl, hydroxyethyl, cyano, amino, methyl and halogen atom; —$NR^5$—$(CH_2)_n$—$R^6$ (wherein $R^5$ is hydrogen atom or methyl, n is an integer of 0-3, $R^6$ is $C_{6-12}$ aryl optionally having one or more substituents selected from halogen atom, hydroxyl group, methoxy, methylenedioxy and cyano; or pyridyl, thiazolyl, isoxazolyl, pyrazolyl, tetrahydrofuranyl or tetrahydropyranyl optionally having one or more substituents selected from methyl optionally substituted by halogen atom, cyano, halogen atom and methoxy), i.e., a compound represented by the following formula (I-e).

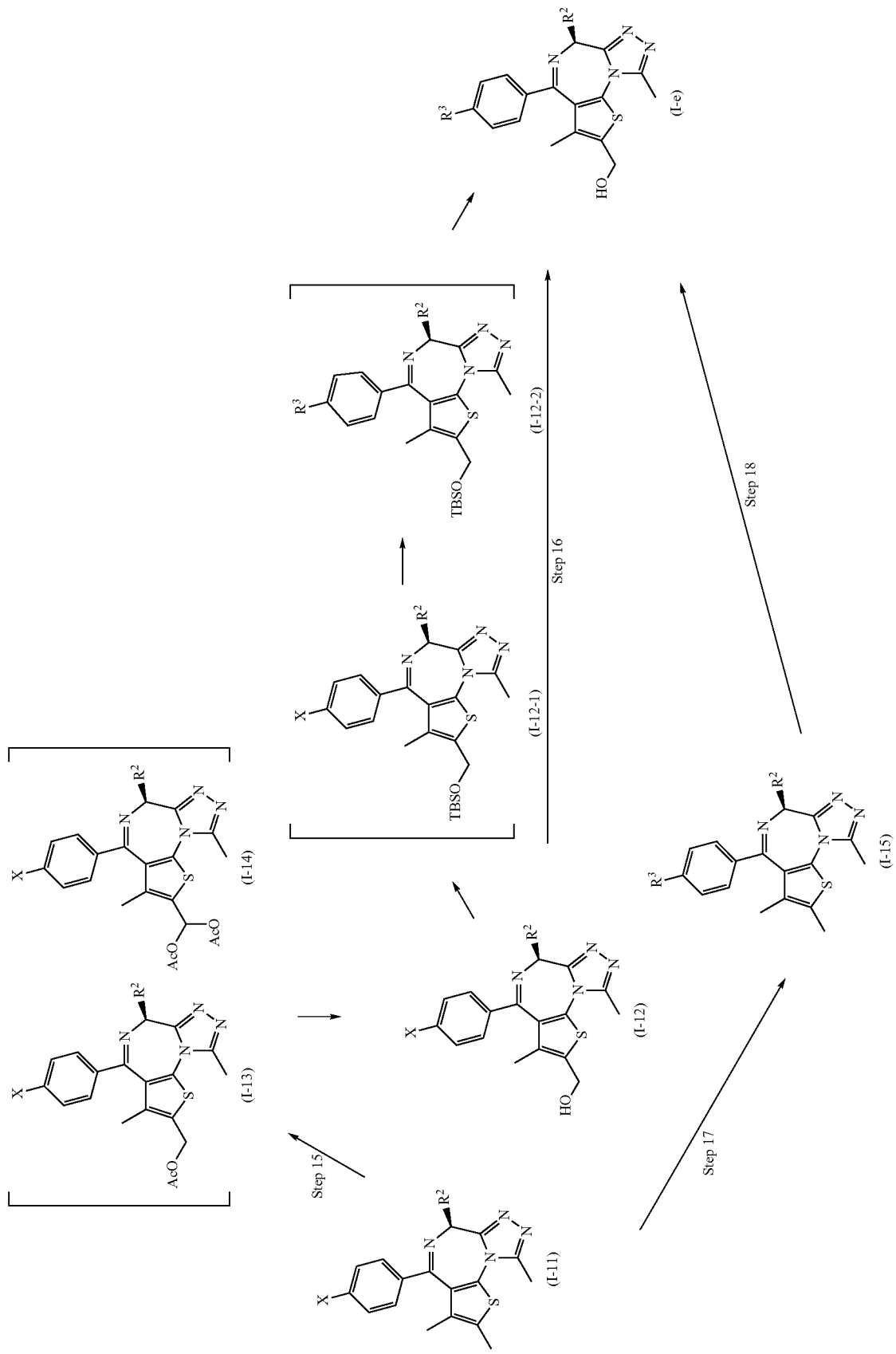
wherein each symbol is as defined above.

The method thereof includes a route performing 1) Step 16 (coupling reaction) via Step 15 (oxidation reaction), or 2) Step 18 (oxidation reaction) via Step 17 (coupling reaction).

Step 15

A compound represented by the formula (I-11) is reacted in the presence of manganese acetate (III), in a mixture of acetic acid, acetic anhydride and concentrated sulfuric acid at room temperature to give a mixture of the compounds represented by the formulas (I-13) and (I-14). This is reacted using a base in a suitable solvent at 0° C.—room temperature and, where necessary, a reducing agent is added to give a compound represented by the formula (I-12). As the base, for example, potassium carbonate, sodium carbonate, potassium hydroxide, sodium hydroxide and the like can be mentioned. As the solvent, for example, alcohol, aqueous alcohol, water and the like can be mentioned. As the reducing agent, sodium borohydride, lithium borohydride, lithium aluminum halide and the like can be mentioned, and sodium borohydride is a preferable example.

Step 16

1) Method with Protection of Hydroxyl Group

The hydroxyl group of a compound represented by the formula (I-12) is protected with a tert-butyldimethylsilyl (TBS) group to give a compound represented by the formula (I-12-1). For the reaction, imidazol and tert-butyldimethylsilylchloride are added to dimethylformamide and the mixture is stirred at room temperature. By the reaction of the obtained compound represented by the formula (I-12-1) with boronic acid ($R^3$—$B(OH)_2$) or an ester thereof (e.g., (4,4,5,5-tetramethyl-1,3,2-dioxaborolan-2-yl)benzene etc., hereinafter the same), or a compound such as $R^3$—H (wherein each symbol is as defined above) and the like, a compound represented by the formula (I-12-2) is obtained. The reaction preferably proceeds in the presence of a palladium catalyst, a phosphine ligand and a base in a suitable solvent at 0° C.—under heating, particularly from room temperature to the boiling point. As the palladium catalyst, phosphine ligand, base and solvent, those recited in Step 2 can be used. The obtained compound represented by the formula (I-12-2) is treated with tetra-n-butylammoniumfluoride in tetrahydrofuran at 0° C.—room temperature to give a compound represented by the formula (I-e).

2) Method without Protection of Hydroxyl Group

A compound represented by the formula (I-12) is reacted with boronic acid ($R^3$—$B(OH)_2$) or an ester thereof, or a compound such as $R^3$—H (wherein each symbol is as defined above) and the like to give a compound represented by the formula (I-e). The reaction preferably proceeds in the presence of a palladium catalyst, a phosphine ligand and a base in a suitable solvent at 0° C.—under heating, particularly from room temperature to the boiling point. As the palladium catalyst, phosphine ligand, base and solvent, those recited in Step 2 can be used.

Step 17

A compound represented by the formula (I-11) is reacted with boronic acid ($R^3$—$B(OH)_2$) or an ester thereof, or a compound such as $R^3$—H (wherein each symbol is as defined above) and the like to give a compound represented by the formula (I-15). The reaction preferably proceeds in the presence of a palladium catalyst, a phosphine ligand and a base in a suitable solvent at 0° C.—under heating, particularly from room temperature to the boiling point. As the palladium catalyst, phosphine ligand, base and solvent, those recited in Step 2 can be used.

Step 18

A compound represented by the formula (I-e) can be obtained by applying the method of Step 15 to a compound represented by the formula (I-15).

Method 6:

The production method described here is suitable for producing, from compounds represented by the formula (I), a compound wherein $R^2$ is

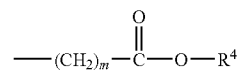

wherein $R^4$ is $C_{1-6}$ alkyl optionally having substituent(s), m is an integer of 1-4, $R^3$ is a group selected from the following

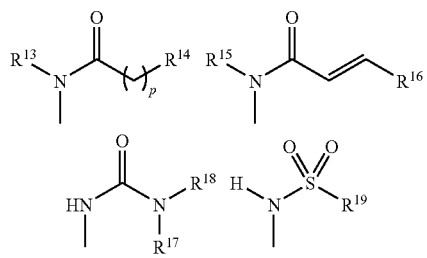

wherein each symbol is as defined above, i.e., compounds represented by the following formulas (I-f), (I-g), (I-h) and (I-i).

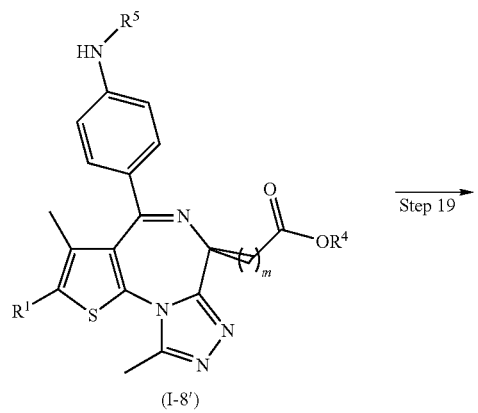

(I-8')

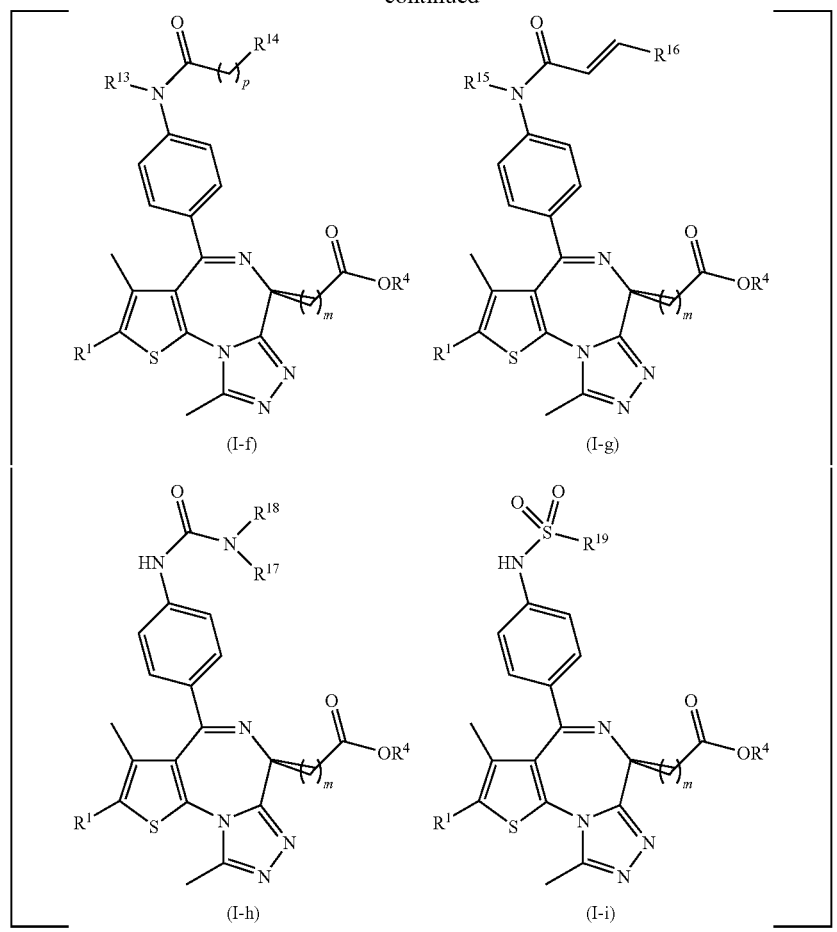

wherein each symbol is as defined above.

Step 19

1) A compound represented by the formula (I-8') is reacted with acid chloride represented by $R^{14}$—$(CH_2)_p$—COCl, $R^{16}$—CH=CH—COCl, $R^{17}R^{18}$N—COCl or $R^{19}$—$SO_2$Cl (wherein each symbol is as defined above) to give the corresponding compound represented by the formula (I-f), (I-g), (I-h) or (I-i). The reaction preferably proceeds in the presence of a suitable base in a suitable solvent at 0° C.—under heating, particularly at room temperature. As the base, for example, pyridine, triethylamine, sodium hydrogencarbonate and the like can be mentioned. As the solvent, for example, methylene chloride and the like can be mentioned.

2) A compound represented by the formula (I-8') is reacted with carboxylic acid represented by $R^{14}$—$(CH_2)_p$—$CO_2H$, $R^{16}$—CH=CH—$CO_2H$ or $R^{17}R^{18}N$—$CO_2H$ (wherein each symbol is as defined above) to give a compound represented by the formula (I-f) or (I-g). The reaction preferably proceeds using a condensation agent in the presence of a suitable base in a suitable solvent at 0° C.—under heating, particularly at room temperature. As the condensation agent, for example, 1-ethyl-3-(3-dimethylaminopropyl)carbodiimide hydrochloride (WSC.HCl), 2-chloro-1-methylpyridinium iodide and the like can be mentioned. As the base, for example, pyridine, triethylamine, sodium hydrogencarbonate and the like can be mentioned. As the solvent, for example, methylene chloride and the like can be mentioned.

Method 7:

The production method described here is suitable for producing, from compounds represented by the formula (I), a compound wherein $R^{21}$ is hydroxymethyl group, i.e., a compound represented by the following formula (I-j).

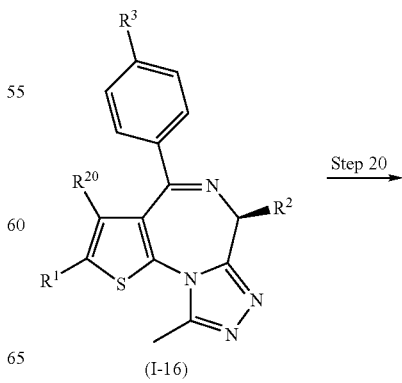

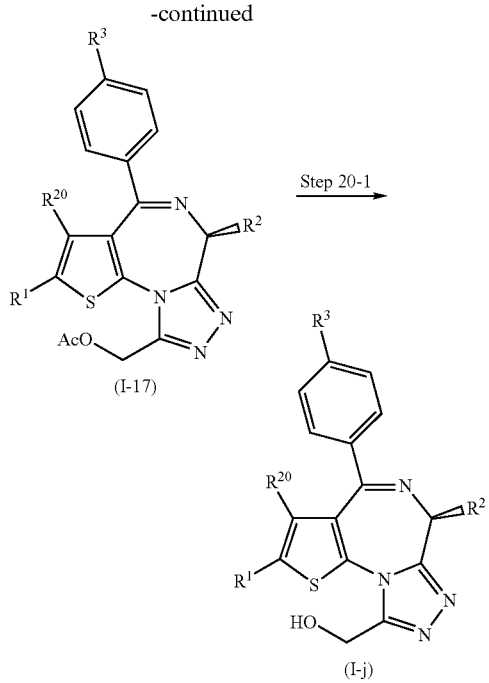

(I-17)

(I-j)

wherein each symbol is as defined above.

As the method therefor, step 20-1 (hydrolysis) via step 20 (oxidation reaction) can be mentioned.

Step 20

A compound represented by the formula (I-16) is heated in the presence of lead tetraacetate in acetic acid to give a compound represented by the formula (I-17).

Step 20-1

A compound represented by the formula (I-17) is reacted using a base in a suitable solvent at 0° C.—room temperature to give a compound represented by the formula (I-j). As the base, for example, potassium carbonate, sodium carbonate and the like can be mentioned. As the solvent, for example, alcohol and the like can be mentioned.

Method 8:

The production method described here is suitable for producing, from compounds represented by the formula (I), a compound wherein $R^1$ is hydrogen or halogen and $R^{21}$ is methyl, i.e., a compound represented by the following formula (I-k) or (I-l).

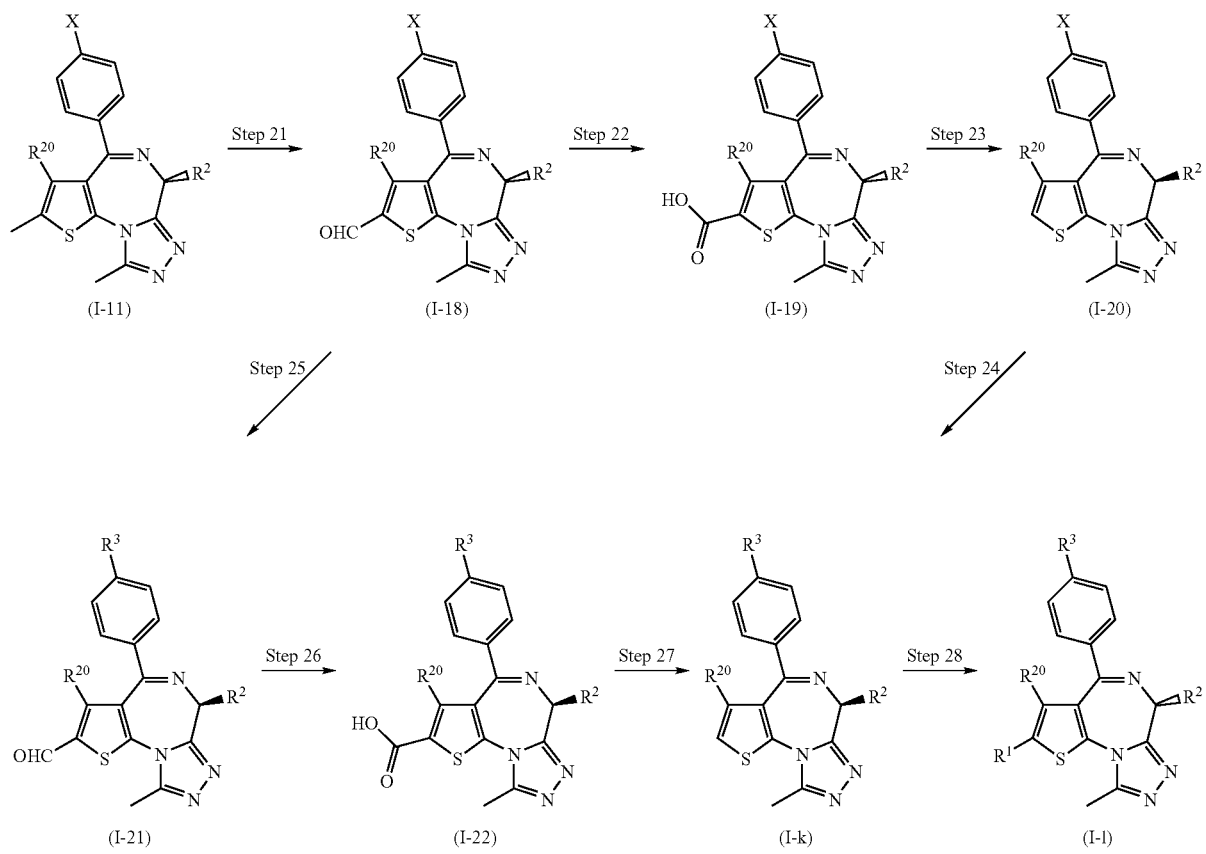

wherein each symbol is as defined above.

The method thereof includes a route performing 1) Step 28 (halogenated) via Steps 21 and 22 (oxidation reaction), Step 23 (decarboxylation) and Step 24 (coupling reaction), or 2) Step 28 (halogenated) via Step 21 (oxidation reaction), Step 25 (coupling reaction), Step 26 (oxidation reaction) and Step 27 (decarboxylation).

Step 21

A compound represented by the formula (I-11) is reacted in the presence of manganese acetate (III) in a mixture of acetic acid, acetic anhydride and concentrated sulfuric acid at room temperature, and then reacted using a base in a suitable solvent at 0° C.—room temperature to give a compound represented by the formula (I-18). As the base, for example, potassium carbonate, sodium carbonate, sodium methoxide and the like can be mentioned. As the solvent, for example, alcohol, aqueous alcohol, water and the like can be mentioned.

Step 22

A compound represented by the formula (I-18) is dissolved in a mixture of acetonitrile and aqueous sodium dihydrogen phosphate, 35% hydrogen peroxide solution and aqueous sodium chlorite are added dropwise thereto in this order at 0° C.—room temperature and the mixture is reacted to give a compound represented by the formula (I-19).

Step 23

A compound represented by the formula (I-19) is reacted in the presence of copper in quinoline at 150° C. to give a compound represented by the formula (I-20).

Step 24

A compound represented by the formula (I-20) is reacted using Method 1, 2, 3, 4 or 6 described above to give a compound represented by the formula (I-k).

Step 25

A compound represented by the formula (I-18) is reacted using Method 1, 2, 3, 4 or 6 described above to give a compound represented by the formula (I-21).

Step 26

A compound represented by the formula (I-21) is dissolved in a mixture of acetonitrile and aqueous sodium dihydrogen phosphate, 35% hydrogen peroxide solution and aqueous sodium chlorite are added dropwise thereto in this order at 0° C.—room temperature and the mixture is reacted to give a compound represented by the formula (I-22).

Step 27

A compound represented by the formula (I-22) is reacted in the presence of copper in quinoline at 150° C. to give a compound represented by the formula (I-k).

Step 28

A compound represented by the formula (I-k) is reacted with sulfuryl chloride, N-bromosuccinimide and the like in a mixture of acetic acid or acetic acid and chloroform at room temperature—50° C. to give a compound represented by the formula (I-l).

Method 9:

The production method described here is suitable for producing, from compounds represented by the formula (I), a production starting material of a compound wherein $R^1$ and $R^{20}$ in combination show trimethylene or tetramethylene, i.e., compounds represented by the following formulas (I-4a) and (I-1a). The formulas (I-4a) and (I-1a) obtained by the following method can be converted to various compounds by a method according to Method 1, 2, 3, 4, 6 or 7.

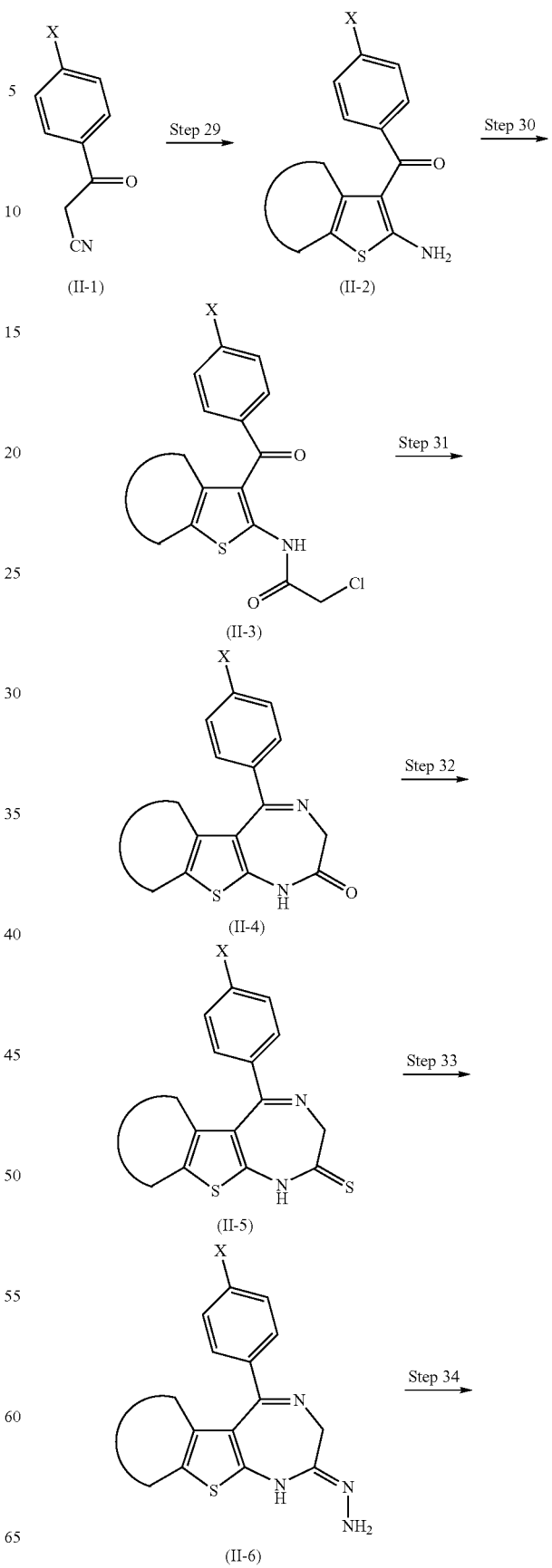

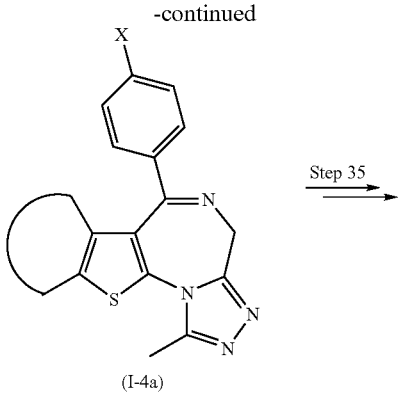

wherein each symbol is as defined above.

Step 29

A compound represented by the formula (II-1), a base, cyclic ketone (cyclopentanone, cyclohexanone and the like) and sulfur are heated under reflux in alcohol to give a compound represented by the formula (II-2).

Step 30

A compound represented by the formula (II-2) is dissolved in a solvent such as chloroform and the like, chloroacetyl chloride is added, and the mixture is reacted at room temperature to give a compound represented by the formula (II-3).

Step 31

A compound represented by the formula (II-3) is dissolved in tetrahydrofuran, sodium iodide is added, the mixture is heated under reflux, the reaction mixture is cooled to −50° C., liquid ammonia is added thereto, and the mixture is reacted at room temperature to give a compound represented by the formula (II-4).

Step 32

A compound represented by the formula (II-4) is dissolved in chloroform, diphosphorus pentasulfide is added, and the mixture is heated under reflux to give a compound represented by the formula (II-5).

Step 33

A compound represented by the formula (II-5) is suspended in methanol, 100% hydrazine-hydrate is added, and the mixture is reacted at room temperature to give a compound represented by the formula (II-6).

Step 34

A compound represented by the formula (II-6) is suspended in toluene, triethyl orthoacetate is added, and the mixture is stirred with heating to give a compound represented by the formula (I-4a).

Step 35

A compound represented by the formula (I-4a) is treated according to the method described in WO98/11111, Starting Material Preparation Examples 2, 3 and 4 to give a compound represented by the formula (I-1a).

Furthermore, the compounds represented by the formula (I) obtained in the above-mentioned Methods 1-8 are subjected to a known method such as oxidation, reduction, alkylation and the like to convert substituents to give various derivatives.

The compound of the present invention obtained in this way can be isolated and purified by a method known in the field of organic synthetic chemistry such as recrystallization, column chromatography and the like. When the obtained product is a racemate, for example, it can be resolved into a desired optically active form by fractional crystallization with a salt of optically active acid or base, or by passing a column packed with an optically active carrier. They can also be produced using an optically active starting compound and the like.

Since the compound of the present invention is suggested to be capable of inhibiting the costimulatory signal from CD28 on T cell and inducing antigen specific immunological tolerance, it can be used for the prophylaxis and/or suppression of acute rejection and chronic rejection that occur upon homogeneous or heterogeneous transplantation of mammalian (e.g., human, canine, feline, bovine, equine, swine, monkey, mouse and the like) organs (liver, heart, kidney etc.), bone marrow and the like. In addition, it can be used for the prophylaxis and/or suppression of various autoimmune diseases, various allergic diseases, lupus nephritis and the like. That is, the compound of the present invention can be used as a prophylactic agent and/or suppressive agent of resistance reaction and rejection reaction in organ or tissue transplantation (e.g., transplantation of heart, kidney, liver, lung, bone marrow, cornea, pancreas, small intestine, four limbs, muscles, nerves, fatty marrow, duodenum, skin, pancreatic islet cell and the like, including heterogenous transplantation), as well as graft-versus-host (GvH) reaction in bone marrow transplantation. Furthermore, the compound can also be used as a prophylactic agent and/or suppressive agent of, for example, autoimmune diseases such as rheumatoid arthritis, systemic lupus erythematosus, multiple sclerosis, psoriasis, inflammatory bowel disease (e.g., Crohn's disease and ulcerative colitis), Type I diabetes mellitus, encephalomyelitis and the like; and, for example, allergic diseases such as asthma (bronchial asthma, pediatric asthma, endogenous asthma, exogenous asthma, dust asthma), allergic rhinitis, pollinosis, atopic dermatitis, urticaria, contact dermatitis, allergic conjunctivitis and the like.

When the compound of the present invention is used as a pharmaceutical agent, it can be administered orally or parenterally in the form of a pharmaceutical composition or preparation (e.g., tablet, liquid etc.) obtained by mixing the compound of the present invention with a pharmaceutically acceptable carrier (excipient, binder, disintegrant etc.). The pharmaceutical composition can be formulated according to a conventional method.

The dose is determined in consideration of the age, body weight, general condition, sex, meal, administration time, administration method, clearance rate, combination of drugs, and the level of disease state for which the patient is undergoing the treatment, and other factors. The compound of the present invention is low toxic and can be used safely. While the daily dose thereof varies depending on the condition and body weight of patient, kind of the compound, administration route and the like, for example, it is 0.01-1000 mg/kg body weight/day for oral route, which is administered in one to several portions a day, and about 0.01-100 mg/kg body weight/day for parenteral route, which is preferably administered in one to several portions a day.

EXAMPLES

While the present invention is explained in detail in the following by referring to Starting Material Synthetic Examples, Examples and Experimental Examples, the present invention is not limited in any way by these Examples. In the following Examples and Starting Material Synthetic Examples, the starting material A is 4-(4-chlorophenyl)-2,3,9-trimethyl-6H-thieno[3,2-f][1,2,4]triazolo[4,3-a][1,4]diazepine, and the starting material B is (S)-4-(4-chlorophenyl)-2,3,9-trimethyl-6H-thieno[3,2-f][1,2,4]triazolo[4,3-a][1,4]diazepin-6-acetic acid. These starting materials A and B are the compounds described in Starting Material Preparation Examples 1 and 4 of WO 98/11111. In addition, "the compounds described in Examples or Starting Material Synthetic Examples" mean the title compound of each Example or Starting Material Synthetic Example and, for example, "the compound described in Example 1" means the title compound of Example 1.

Example 1

Methyl (S)-{4-(4-chlorophenyl)-2,3,9-trimethyl-6H-thieno[3,2-f][1,2,4]triazolo[4,3-a][1,4]diazepin-6-yl}acetate To a suspension of starting material B (300 g) in methanol (1.5 L) was added dropwise (10-25° C.) thionyl chloride (320 g) over 1 hr under ice-cooling, and the mixture was stirred at room temperature for 4 hr. After completion of the reaction, the solvent was evaporated under reduced pressure. The residue was partitioned by adding chloroform (1.5 L) and water (1 L) and the mixture was further extracted with chloroform (500 mL). The organic layer was washed with saturated aqueous sodium hydrogencarbonate (500 mL) and dried over anhydrous sodium sulfate. The solvent was evaporated under reduced pressure (azeotroped twice with methanol) and the residue was washed with methanol/water (300 mL/300 mL) to give the title compound (250 g).
$^1$H-NMR (400 MHz, DMSO-$d_6$) δ: 1.62 (3H, s), 2.41 (3H, s), 2.61 (3H, s), 3.41 (1H, dd, J=16.4, 6.8 Hz), 3.49 (1H, dd, J=16.4, 6.8 Hz), 3.67 (3H, s), 4.51 (1H, t, J=7.2 Hz), 7.43 (2H, d, J=8.4 Hz), 7.48 (2H, d, J=8.4 Hz).

Starting Material Synthetic Example 1

Step 6 methyl (S)-{4-[4-(5,5-dimethyl[1,3,2]dioxaborinan-2-yl)phenyl]-2,3,9-trimethyl-6H-thieno[3,2-f][1,2,4]triazolo[4,3-a][1,4]diazepin-6-yl}acetate A mixture of the compound described in Example 1 (12.4 g), dichlorobis(tricyclohexylphosphine)palladium (1.1 g), bis(neopentylglycolato)diboron (8.1 g) and potassium acetate (4.42 g) in dioxane was stirred at 100° C. for 5 hr. After cooling, the mixture was partitioned by adding water and chloroform. The chloroform layer was washed with saturated brine, and dried over anhydrous sodium sulfate. The solvent was evaporated and the residue was purified by column chromatography (chloroform:methanol=100:1) to give the title compound (14.8 g).

$^1$H-NMR (400 MHz, DMSO-$d_6$) δ: 0.95 (6H, s), 1.59 (3H, s), 2.33 (3H, s), 2.61 (3H, s), 3.3-3.6 (2H, m), 3.67 (3H, s), 3.76 (4H, s), 4.50 (1H, t, J=7.2 Hz), 7.39 (2H, d, J=8.0 Hz), 7.72 (2H, d, J=8.0 Hz)
MS (ESI) m/z: 425 (M+H-68)$^+$ (hydrolysis of boronic ester).

Starting Material Synthetic Example 2

Step 6 ethyl (S)-{4-[4-(5,5-dimethyl[1,3,2]dioxaborinane-2-yl)phenyl]-2,3,9-trimethyl-6H-thieno[3,2-f][1,2,4]triazolo[4,3-a][1,4]diazepin-6-yl}acetate The title compound (30 g) was obtained by treating the compound (26 g) described in the below-mentioned Example 62, instead of the compound described in Example 1, in the same manner as in Starting Material Synthetic Example 1.
$^1$H-NMR (400 MHz, DMSO-$d_6$) δ: 0.85 (6H, s), 1.22 (3H, t, J=7.2 Hz), 1.59 (3H, s), 2.41 (3H, s), 2.61 (3H, s), 3.3-3.5 (2H, m), 3.76 (4H, s), 4.1-4.4 (2H, m), 4.49 (1H, t, J=7.6 Hz), 7.39 (2H, d, J=8.0 Hz), 7.72 (2H, d, J=8.0 Hz)
MS (ESI) m/z: 439 (M+H-68)$^+$ (hydrolysis of boronic ester).

Starting Material Synthetic Example 3

Step 15

4-(4-chlorophenyl)-2-hydroxymethyl-3,9-dimethyl-6H-thieno[3,2-f][1,2,4]triazolo[4,3-a][1,4]diazepine To a mixture of acetic acid (103 mL) and acetic anhydride (61 mL) was added dropwise concentrated sulfuric acid (16 mL). Starting material A (10 g) was added, and manganese acetate (III).dihydrate (16 g) was further added. The mixture was stirred at room temperature for 8 hr and left standing for 2 days. The reaction mixture was poured into ice water, and extracted twice with ethyl acetate (500 mL). The organic layer was washed three times with 3M aqueous sodium hydroxide solution (600 mL) and twice with saturated brine (500 mL). The residue was dried over anhydrous sodium sulfate, and the solvent was evaporated to give an oil (9.9 g).
To a suspension of the obtained oil (9.9 g) in methanol (100 mL) was added 28% sodium methoxide methanol solution (15 mL), and the mixture was stirred at room temperature for 3 hr. After completion of the reaction, the reaction mixture was poured into water (500 mL) and extracted twice with ethyl acetate (300 mL). The organic layer was washed with saturated brine (500 mL), and dried over anhydrous sodium sulfate. The solvent was evaporated and the residue was purified by column chromatography (chloroform:methanol=9:1) to give the title compound (3.8 g).
$^1$H-NMR (300 MHz, CDCl$_3$) δ: 1.75 (3H, s), 2.38 (1H, t, J=5.3 Hz), 2.71 (3H, s), 4.11 (1H, d, J=12.9 Hz), 4.87 (2H, d, J=4.5 Hz), 5.51 (1H, d, J=12.9 Hz), 7.35 (2H, d, J=8.7 Hz), 7.44 (2H, d, J=8.7 Hz)
MS (ESI) m/z: 359 (M+H)$^+$.

Starting Material Synthetic Example 4

Steps 11 and 12

Methyl (S)-{4-(4-aminophenyl)-2,3,9-trimethyl-6H-thieno[3,2-f][1,2,4]triazolo[4,3-a][1,4]diazepin-6-yl}acetate To a mixture of the compound described in Example 1 (12.4 g), tris(dibenzylideneacetone)dipalladium (0)chloroform adduct (776 mg), 2-(dicyclohexylphosphino)biphenyl (1.1 g) and tripotassium phosphate (8.9 g) were successively added dimethoxyethane (60 mL) and benzophenoneimine (6.6 mL), and the mixture was heated under reflux for 6 hr. After cooling, water was added, and the mixture was extracted with ethyl acetate. The organic layer was washed with saturated brine, and dried over anhydrous sodium sulfate. The solvent was evaporated and the residue was dissolved in tetrahydrofuran (60 mL). 1M aqueous hydrochloric acid solution (240 mL) was added, and the mixture was stirred at room temperature for 30 min. After completion of the reaction, the mixture was basified with aqueous sodium hydroxide solution and extracted with ethyl acetate. The organic layer was washed with saturated brine, and dried over anhydrous sodium sulfate. The solvent was evaporated and the residue was purified by column chromatography (chloroform:methanol=100:1) and recrystallized from hexane-ethyl acetate to give the title compound (2.26 g).

$^1$H-NMR (270 MHz, DMSO-$d_6$) δ: 1.73 (3H, s), 2.42 (3H, s), 2.58 (3H, s), 3.3-3.5 (2H, m), 3.65 (3H, s), 4.37 (1H, t, J=7.6 Hz), 5.62 (2H, s), 6.51 (2H, d, J=8.6 Hz), 7.11 (2H, d, J=8.6 Hz)

MS (ESI) m/z: 396 (M+H)$^+$.

Starting Material Synthetic Example 5

Step 16

Methyl (S)-{4-(4-chlorophenyl)-2-(tert-butyldimethylsilyloxymethyl)-3,9-dimethyl-6H-thieno[3,2-f][1,2,4]triazolo[4,3-a][1,4]diazepin-6-yl}acetate A mixture of the compound described in the below-mentioned Example 231 (3.8 g) and imidazol (1.2 g) was dissolved in dimethylformamide (30 mL), tert-butyldimethylsilylchloride (2.0 g) was added, and the mixture was stirred at room temperature for 24 hr. After completion of the reaction, the reaction mixture was poured into ice water (300 mL) and extracted with ethyl acetate (300 mL). The organic layer was washed with saturated brine, and dried over anhydrous sodium sulfate. The solvent was evaporated and the residue was purified by column chromatography (hexane:ethyl acetate=1:1) to give the title compound (3.7 g).

$^1$H-NMR (300 MHz, CDCl$_3$) δ: 0.16 (3H, s), 0.17 (3H, s), 0.97 (9H, s), 1.69 (3H, s), 2.70 (3H, s), 3.64 (2H, m), 3.78 (3H, s), 4.62 (1H, t, J=7.2 Hz), 4.83 (2H, s), 7.33 (2H, d, J=8.7 Hz), 7.40 (2H, d, J=8.7 Hz)

MS (ESI) m/z: 545 (M+H)$^+$.

Starting Material Synthetic Example 6

Step 16

4-(4-chlorophenyl)-2-(tert-butyldimethylsilyloxymethyl)-3,9-dimethyl-6H-thieno[3,2-f][1,2,4]triazolo[4,3-a][1,4]diazepine The title compound (3.6 g) was obtained by a treatment in the same manner as in Starting Material Synthetic Example 5 and using the compound (3.5 g) described in Starting Material Synthetic Example 3 instead of the compound described in Example 231.

$^1$H-NMR (300 MHz, CDCl$_3$) δ: 0.155 and 0.168 (6H, 2s), 0.965 (9H, s), 1.68 (3H, s), 2.71 (3H, s), 4.11 (1H, d, J=12.6 Hz), 4.84 (2H, s), 5.51 (1H, d, J=12.6 Hz), 7.34 (2H, d, J=8.7 Hz), 7.45 (2H, d, J=8.7 Hz)

MS (ESI) m/z: 473 (M)$^+$.

Starting Material Synthetic Example 7

Step 6

4-[4-(5,5-dimethyl-[1,3,2]dioxaborinan-2-yl)phenyl]-2,3,9-trimethyl-6H-thieno[3,2-f][1,2,4]triazolo[4,3-a][1,4]diazepine The title compound (8.4 g) was obtained by treating starting material A (6.9 g), instead of the compound described in Example 1, in the same manner as in Starting Material Synthetic Example 1.

$^1$H-NMR (400 MHz, DMSO-$d_6$) δ: 0.96 (6H, s), 1.57 (3H, s), 2.39 (3H, s), 2.60 (3H, s), 3.76 (4H, s), 4.15 (1H, d, J=12.6 Hz), 5.25 (1H, d, J=12.6 Hz), 7.43 (2H, d, J=7.8 Hz), 7.72 (2H, d, J=7.8 Hz)

MS (ESI) m/z: 353 (M+H-68)$^+$ (hydrolysis of boronic ester).

Starting Material Synthetic Example 8

Steps 8 and 9 methyl (S)-{4-(4-methylaminophenyl)-2,3,9-trimethyl-6H-thieno[3,2-f][1,2,4]triazolo[4,3-a][1,4]diazepin-6-yl}acetate To a mixture of the compound described in Example 1 (10 g), palladium acetate (270 mg), 2-(dicyclohexylphosphino)biphenyl (840 mg) and tripotassium phosphate (7.2 g) were successively added dimethoxyethane (50 mL) and N-methylbenzylamine (4.7 mL), and the mixture was heated under reflux for 14 hr. After cooling, water was added, and the mixture was extracted with ethyl acetate. The mixture was washed with water and saturated brine. The mixture was dried over anhydrous sodium sulfate, and the solvent was evaporated. The residue was purified by column chromatography (chloroform:methanol=100:1) to give a compound (8 g). The obtained compound (8 g) was dissolved in methanol (40 mL), and concentrated hydrochloric acid (800 µL) and palladium carbon (1.6 g) were successively added. The mixture was vigorously stirred at 60° C. for 4 hr under a hydrogen stream. After cooling, palladium carbon was filtered off through celite, and the filtrate was concentrated. To the residue was added aqueous potassium carbonate solution. The mixture was extracted with ethyl acetate and washed with water and saturated brine, and dried over anhydrous sodium sulfate. The solvent was evaporated and the residue was recrystallized from hexane-ethyl acetate to give the title compound (6.3 g).

$^1$H-NMR (300 MHz, DMSO-$d_6$) δ: 1.70 (3H, s), 2.40 (3H, s), 2.56 (3H, s), 2.66 (3H, d, J=4.8 Hz), 3.32 (1H, dd, J=16.5, 7.5 Hz), 3.42 (1H, dd, J=16.5, 6.9 Hz), 3.63 (3H, s), 4.36 (2H, t, J=7.2 Hz), 6.18 (1H, q, J=4.8 Hz), 6.47 (2H, d, J=8.7 Hz), 7.15 (2H, d, J=8.7 Hz)

MS (ESI) m/z: 410 (M+H)$^+$.

Starting Material Synthetic Example 9

Steps 8 and 9

4-(4-aminophenyl)-2,3,9-trimethyl-6H-thieno[3,2-f][1,2,4]triazolo[4,3-a][1,4]diazepine To a mixture of starting material A (10 g), palladium acetate (328 mg), 2-(dicyclohexylphosphino)biphenyl (1 g)

and tripotassium phosphate (8.7 g) were successively added dimethoxyethane (58 mL) and benzylamine (4.8 mL), and the mixture was heated under reflux for 8 hr. After cooling, water was added, and the mixture was extracted with ethyl acetate. The organic layer was washed with saturated brine, and dried over anhydrous sodium sulfate. The solvent was evaporated and the residue was recrystallized from ethyl acetate to give 4-(4-benzylaminophenyl)-2,3,9-trimethyl-6H-thieno[3,2-f][1,2,4]triazolo[4,3-a][1,4]diazepine (6.2 g). The obtained compound (6.2 g) was dissolved in ethanol (30 mL), concentrated hydrochloric acid (10 mL), palladium carbon (620 mg) were successively added, and the mixture was vigorously stirred under a hydrogen stream at 80° C. for 7 hr. After cooling, palladium carbon was filtered off through celite, and the filtrate was concentrated. Aqueous sodium hydroxide solution was added to the residue, and the mixture was extracted with ethyl acetate, the organic layer was washed with water and saturated brine, and dried over anhydrous sodium sulfate. The solvent was evaporated and the residue was recrystallized from ethyl acetate to give the title compound (2.8 g).

$^1$H-NMR (270 MHz, DMSO-$d_6$) δ: 1.71 (3H, s), 2.40 (3H, s), 2.57 (3H, s), 4.00 (1H, d, J=12.7 Hz), 5.09 (1H, d, J=12.7 Hz), 5.59 (2H, s), 6.51 (2H, d, J=8.6 Hz), 7.15 (2H, d, J=8.6 Hz)

MS (ESI) m/z: 324 (M+H)$^+$.

Starting Material Synthetic Example 10

Steps 8 and 9

4-(4-methylaminophenyl)-2,3,9-trimethyl-6H-thieno[3,2-f][1,2,4]triazolo[4,3-a][1,4]diazepine To a mixture of starting material A (5 g), palladium acetate (164 mg), 2-(dicyclohexylphosphino)biphenyl (512 mg) and tripotassium phosphate (6.2 g) were successively added dimethoxyethane (29 mL) and N-methylbenzylamine (2.4 mL), and the mixture was heated under reflux for 8 hr. After cooling, water was added, and the mixture was extracted with ethyl acetate. The organic layer was washed with saturated brine and dried over anhydrous sodium sulfate. The solvent was evaporated and the residue was purified by column chromatography (chloroform:methanol=100:1) and recrystallized from ethyl acetate to give a compound (5.6 g). The obtained compound (5.6 g) was dissolved in ethanol (25 mL) and acetic acid (25 mL), and palladium carbon (1.7 g) was added under a hydrogen stream. The mixture was stirred at room temperature for 7 hr, and vigorously stirred at 50° C. for 24 hr. After cooling, palladium carbon was filtered off through celite, and the filtrate was concentrated. To the residue was added aqueous sodium hydroxide solution. The mixture was extracted with chloroform, and the organic layer was washed with water and saturated brine, and dried over anhydrous sodium sulfate. The solvent was evaporated and the residue was purified by column chromatography (chloroform:methanol=100:1) and recrystallized from ethyl acetate to give the title compound (1.4 g).

$^1$H-NMR (400 MHz, DMSO-$d_6$) δ: 1.71 (3H, s), 2.40 (3H, s), 2.58 (3H, s), 2.69 (3H, d, J=4.9 Hz), 4.00 (1H, d, J=12.6 Hz), 5.10 (1H, d, J=12.6 Hz), 6.19 (1H, m), 6.50 (2H, d, J=8.2 Hz), 7.22 (2H, d, J=8.2 Hz)

MS (ESI) m/z: 338 (M+H)$^+$.

Example 2

Methyl (S)-{2,3,9-trimethyl-4-(4'-methylthiobiphenyl-4-yl)-6H-thieno[3,2-f][1,2,4]triazolo[4,3-a][1,4]diazepin-6-yl}acetate To a mixture of the compound described in Example 1 (415 mg), palladium acetate (11 mg), 2-(di-tert-butylphosphino)biphenyl (30 mg), potassium fluoride (174 mg) and 4-methylthiophenylboronic acid (252 mg) was added tetrahydrofuran (3 mL), and the mixture was heated under reflux for 8 hr. After cooling, water was added, and the mixture was extracted with ethyl acetate. The organic layer was washed with saturated brine, and dried over anhydrous sodium sulfate. The solvent was evaporated and the residue was purified by column chromatography (chloroform:methanol=100:1) to give the title compound (503 mg).

$^1$H-NMR (270 MHz, DMSO-$d_6$) δ: 1.69 (3H, s), 2.43 (3H, s), 2.62 (3H, s), 3.30 (3H, s), 3.3-3.6 (2H, m), 3.68 (3H, s), 4.51 (1H, d, J=7.3 Hz), 7.35 (2H, d, J=8.6 Hz), 7.48 (2H, d, J=8.6 Hz), 7.66 (2H, d, J=8.4 Hz), 7.72 (2H, d, J=8.4 Hz)

MS (ESI) m/z: 503 (M+H)$^+$.

Example 3

Methyl (S)-{4-(4'-methylsulfonylbiphenyl-4-yl)-2,3,9-trimethyl-6H-thieno[3,2-f][1,2,4]triazolo[4,3-a][1,4]diazepin-6-yl}acetate The compound described in Example 2 (395 mg) was dissolved in a mixture of methanol (40 mL) and water (4 mL), sodium hydrogencarbonate (198 mg) and oxone (966 mg) were successively added thereto, and the mixture was stirred at room temperature for 3 hr. After completion of the reaction, water was added, and the mixture was extracted with ethyl acetate. The organic layer was washed with saturated brine, and dried over anhydrous sodium sulfate. The solvent was evaporated and the residue was purified by column chromatography (chloroform:methanol=100:1) to give the title compound (289 mg).

$^1$H-NMR (270 MHz, DMSO-$d_6$) δ: 1.69 (3H, s), 2.44 (3H, s), 2.63 (3H, s), 3.26 (3H, s), 3.3-3.6 (2H, m), 3.69 (3H, s), 4.54 (1H, d, J=7.6 Hz), 7.55 (2H, d, J=8.4 Hz), 7.83 (2H, d, J=8.4 Hz), 7.97 (2H, d, J=8.6 Hz), 8.02 (2H, d, J=8.6 Hz)

MS (ESI) m/z: 535 (M+H)$^+$.

Example 4

Methyl (S)-{4-(3'-hydroxybiphenyl-4-yl)-2,3,9-trimethyl-6H-thieno[3,2-f][1,2,4]triazolo[4,3-a][1,4]diazepin-6-yl}acetate The title compound (215 mg) was obtained from the compound (210 mg) described in Example 1 by a treatment in the same manner as in Example 2 and using 3-hydroxyphenylboronic acid (138 mg) instead of 4-methylthiophenylboronic acid.

$^1$H-NMR (270 MHz, DMSO-$d_6$) δ: 1.69 (3H, s), 2.43 (3H, s), 2.62 (3H, s), 3.3-3.6 (2H, m), 3.68 (3H, s), 4.52 (1H, t, J=7.6 Hz), 6.79 (1H, dd, J=7.8, 1.6 Hz), 7.0-7.2 (2H, m), 7.2-7.4 (1H, m), 7.48 (2H, d, J=8.4 Hz), 7.66 (2H, d, J=8.4 Hz), 9.57 (1H, brs)

MS (ESI) m/z: 473 (M+H)$^+$.

Example 5

Methyl (S)-{4-(4'-methoxybiphenyl-4-yl)-2,3,9-trimethyl-6H-thieno[3,2-f][1,2,4]triazolo[4,3-a][1,4]diazepin-6-yl}acetate To a mixture of the compound described in Example 1 (415 mg), palladium acetate (11 mg), 2-(di-tert-butylphosphino)biphenyl (30 mg), potassium fluoride (174 mg) and 4-methoxyphenylboronic acid (228 mg) was added tetrahydrofuran (3 mL), and the mixture was heated under reflux for 8 hr. After cooling, water was added, and the mixture was extracted with ethyl acetate. The organic layer was washed with saturated brine, and dried over anhydrous sodium sulfate. The solvent was evaporated and the residue was purified by column chromatography (chloroform:methanol=100:1) to give the title compound (463 mg).

$^1$H-NMR (270 MHz, DMSO-$d_6$) δ: 1.69 (3H, s), 2.43 (3H, s), 2.62 (3H, s), 3.3-3.6 (2H, m), 3.68 (3H, s), 3.80 (3H, s), 4.51 (1H, d, J=7.6 Hz), 7.03 (2H, d, J=8.6 Hz), 7.47 (2H, d, J=8.6 Hz), 7.65 (2H, d, J=8.0 Hz), 7.68 (2H, d, J=8.0 Hz)

MS (ESI) m/z: 487 (M+H)$^+$.

Example 6

Methyl (S)-{4-(4'-dimethylaminobiphenyl-4-yl)-2,3,9-trimethyl-6H-thieno[3,2-f][1,2,4]triazolo[4,3-a][1,4]diazepin-6-yl}acetate The title compound (223 mg) was obtained from the compound (210 mg) described in Example 1 by a treatment in the same manner as in Example 2 and using 4-dimethylaminophenylboronic acid (165 mg) instead of 4-methylthiophenylboronic acid.

$^1$H-NMR (270 MHz, DMSO-$d_6$) δ: 1.70 (3H, s), 2.43 (3H, s), 2.61 (3H, s), 2.95 (6H, s), 3.30-3.60 (2H, m), 3.68 (3H, s), 4.49 (1H, t, J=7.6 Hz), 6.80 (2H, d, J=8.9 Hz), 7.43 (2H, d, J=8.6 Hz), 7.56 (2H, d, J=8.9 Hz), 7.65 (2H, d, J=8.6 Hz)

MS (ESI) m/z: 487 (M+H)$^+$.

Example 7

Methyl (S)-{4-(3'-acetylaminobiphenyl-4-yl)-2,3,9-trimethyl-6H-thieno[3,2-f][1,2,4]triazolo[4,3-a][1,4]diazepin-6-yl}acetate The title compound (487 mg) was obtained from the compound (1.7 g) described in Example 1 by a treatment in the same manner as in Example 2 and using 3-acetamidephenylboronic acid (859 mg) instead of 4-methylthiophenylboronic acid.

$^1$H-NMR (400 MHz, DMSO-$d_6$) δ: 1.69 (3H, s), 2.06 (3H, s), 2.44 (3H, s), 2.62 (3H, s), 3.44 (1H, dd, J=16.4, 6.8 Hz), 3.51 (1H, dd, J=16.4, 6.8 Hz), 3.68 (3H, s), 4.52 (1H, t, J=6.8 Hz), 7.32-7.43 (2H, m), 7.51 (2H, d, J=8.0 Hz), 7.59 (1H, d, J=8.0 Hz), 7.66 (2H, d, J=8.0 Hz), 7.91 (1H, s), 10.1 (1H, brs)

MS (ESI) m/z: 514 (M+H)$^+$.

Example 8

Methyl (S)-{4-(3'-cyanobiphenyl-4-yl)-2,3,9-trimethyl-6H-thieno[3,2-f][1,2,4]triazolo[4,3-a][1,4]diazepin-6-yl}acetate The title compound (274 mg) was obtained from the compound (249 mg) described in Example 1 by a treatment in the same manner as in Example 2 and using 3-cyanophenylboronic acid (132 mg) instead of 4-methylthiophenylboronic acid (Method A).

$^1$H-NMR (270 MHz, DMSO-$d_6$) δ: 1.67 (3H, s), 2.44 (3H, s), 2.63 (3H, s), 3.45-3.51 (2H, m), 3.69 (3H, s), 4.53 (1H, d, J=7.0 Hz), 7.53 (2H, d, J=8.2 Hz), 7.69 (1H, t, J=7.8 Hz), 7.82 (2H, d, J=8.2 Hz), 7.86 (1H, d, J=7.8 Hz), 8.06 (1H, d, J=7.8 Hz), 8.21 (1H, s)

To a mixture of the compound described in Example 1 (41 g), palladium acetate (90 mg), 2-dicyclohexylphosphino-2,6-dimethoxybiphenyl (164 mg), 3-cyanophenylboronic acid (22 g) and tripotassium phosphate (64 g) were added tetrahydrofuran (200 mL) and water (6.5 mL), and the mixture was heated under reflux for 4 hr. Furthermore, palladium acetate (90 mg), 2-dicyclohexylphosphino-2,6-dimethoxybiphenyl (164 mg) and 3-cyanophenylboronic acid (2.2 g) were added. The mixture was heated under reflux for 4 hr and purified according to a conventional method to give the title compound (13 g). (METHOD B)

$^1$H-NMR (400 MHz, DMSO-$d_6$) δ: 1.67 (3H, s), 2.44 (3H, s), 2.62 (3H, s), 3.45 (1H, dd, J=16.5, 6.8 Hz), 3.51 (1H, dd, J=16.5, 6.8 Hz), 3.68 (3H, s), 4.53 (1H, d, J=7.0 Hz), 7.53 (2H, d, J=8.2 Hz), 7.69 (1H, t, J=7.8 Hz), 7.82 (2H, d, J=8.2 Hz), 7.86 (1H, d, J=7.8 Hz), 8.06 (1H, d, J=7.8 Hz), 8.20 (1H, s)

Since the compounds obtained by METHOD A and METHOD B showed identical $^1$H-NMR, they were confirmed to be the same compounds.

MS (ESI) m/z: 482 (M+H)$^+$.

Example 9

Methyl (S)-{2,3,9-trimethyl-4-[4-(naphthalen-2-yl)phenyl]-6H-thieno[3,2-f][1,2,4]triazolo[4,3-a][1,4]diazepin-6-yl}acetate The title compound (241 mg) was obtained from the compound (210 mg) described in Example 1 by a treatment in the same manner as in Example 2 and using 2-naphthaleneboronic acid (129 mg) instead of 4-methylthiophenylboronic acid.

$^1$H-NMR (270 MHz, DMSO-$d_6$) δ: 1.70 (3H, s), 2.44 (3H, s), 2.63 (3H, s), 3.3-3.6 (2H, m), 3.69 (3H, s), 4.54 (1H, t, J=7.3 Hz), 7.4-7.7 (4H, m), 7.8-8.1 (6H, m), 8.28 (1H, brs)

MS (ESI) m/z: 507 (M+H)$^+$.

Example 10

Methyl (S)-{4-(4'-hydroxymethylbiphenyl-4-yl)-2,3,9-trimethyl-6H-thieno[3,2-f][1,2,4]triazolo[4,3-a][1,4]diazepin-6-yl}acetate The title compound (159 mg) was obtained from the compound (210 mg) described in Example 1 by a treatment in the same manner as in Example 2 and using 4-hydroxymethylphenylboronic acid (4.2 g) instead of 4-methylthiophenylboronic acid.

$^1$H-NMR (400 MHz, DMSO-$d_6$) δ: 1.69 (3H, s), 2.43 (3H, s), 2.62 (3H, s), 3.43 (1H, dd, J=16.6, 6.8 Hz), 3.50 (1H, dd, J=16.6, 6.8 Hz), 3.68 (3H, s), 4.4-4.6 (3H, m), 5.22 (1H, m), 7.42 (2H, d, J=8.0 Hz), 7.49 (2H, d, J=8.0 Hz), 7.67 (2H, d, J=8.0 Hz), 7.73 (2H, d, J=8.0 Hz)

MS (ESI) m/z: 487 (M+H)$^+$.

Example 11

Methyl (S)-{4-(2',4'-difluorobiphenyl-4-yl)-2,3,9-trimethyl-6H-thieno[3,2-f][1,2,4]triazolo[4,3-a][1,4]diazepin-6-yl}acetate The title compound (127 mg) was obtained from the compound (210 mg) described in Example 1 by a treatment in the same manner as in Example 2 and using 2,4-difluorophenylboronic acid (118 mg) instead of 4-methylthiophenylboronic acid.

$^1$H-NMR (270 MHz, DMSO-$d_6$) δ: 1.69 (3H, s), 2.43 (3H, s), 2.62 (3H, s), 3.3-3.6 (2H, m), 3.68 (3H, s), 4.53 (1H, d, J=7.6 Hz), 7.21 (1H, t-like), 7.3-7.7 (6H, m)

MS (ESI) m/z: 493 (M+H)$^+$.

Example 12

Methyl (S)-{4-(3'-cyano-4'-fluorobiphenyl-4-yl)-2,3,9-trimethyl-6H-thieno[3,2-f][1,2,4]triazolo[4,3-a][1,4]diazepin-6-yl}acetate The title compound (242 mg) was obtained from the compound (210 mg) described in Example 1 by a treatment in the same manner as in Example 2 and using 3-cyano-4-fluorophenylboronic acid (124 mg) instead of 4-methylthiophenylboronic acid.

$^1$H-NMR (270 MHz, DMSO-$d_6$) δ: 1.66 (3H, s), 2.43 (3H, s), 2.62 (3H, s), 3.3-3.6 (2H, m), 3.68 (3H, s), 4.52 (1H, d, J=7.6 Hz), 7.52 (2H, d, J=8.4 Hz), 7.64 (1H, t, J=8.9 Hz), 7.81 (2H, d, J=8.4 Hz), 8.1-8.2 (1H, m), 8.2-8.4 (1H, m)

MS (ESI) m/z: 500 (M+H)$^+$.

Example 13

Methyl (S)-{4-(3'-methoxybiphenyl-4-yl)-2,3,9-trimethyl-6H-thieno[3,2-f][1,2,4]triazolo[4,3-a][1,4]diazepin-6-yl}acetate The title compound (207 mg) was obtained from the compound (210 mg) described in Example 1 by a treatment in the same manner as in Example 2 and using 3-methoxyphenylboronic acid (114 mg) instead of 4-methylthiophenylboronic acid.

$^1$H-NMR (270 MHz, DMSO-$d_6$) δ: 1.69 (3H, s), 2.43 (3H, s), 2.62 (3H, s), 3.30-3.60 (2H, m), 3.68 (3H, s), 3.82 (3H, s), 4.52 (1H, d, J=7.3 Hz), 6.97 (1H, dd, J=8.1, 2.4 Hz), 7.2-7.3 (2H, m), 7.30-7.49 (1H, m), 7.49 (2H, d, J=8.1 Hz), 7.74 (2H, d, j=8.1 Hz)

MS (ESI) m/z: 487 (M+H)$^+$.

Example 14

Methyl (S)-{4-(3'-acetylbiphenyl-4-yl)-2,3,9-trimethyl-6H-thieno[3,2-f][1,2,4]triazolo[4,3-a][1,4]diazepin-6-yl}acetate The title compound (1.4 g) was obtained from the compound (1.7 g) described in Example 1 by a treatment in the same manner as in Example 2 and using 3-acetylphenylboronic acid (787 mg) instead of 4-methylthiophenylboronic acid.

$^1$H-NMR (400 MHz, DMSO-$d_6$) δ: 1.69 (3H, s), 2.44 (3H, s), 2.63 (3H, s), 2.66 (3H, s), 3.45 (1H, dd, J=16.4, 6.8 Hz), 3.51 (1H, dd, J=16.4, 6.8 Hz), 3.69 (3H, s), 4.53 (1H, d, J=6.8 Hz), 7.54 (2H, d, J=8.0 Hz), 7.65 (1H, t, J=7.6 Hz), 7.81 (2H, d, J=8.0 Hz), 7.96-8.00 (2H, m), 8.21 (1H, s)

MS (ESI) m/z: 490 (M+H)$^+$.

Example 15

Methyl (S)-{4-(3'-hydroxymethyl-4'-methoxybiphenyl-4-yl)-2,3,9-trimethyl-6H-thieno[3,2-f][1,2,4]triazolo[4,3-a][1,4]diazepin-6-yl}acetate To a mixture of the compound described in Example 1 (415 mg), palladium acetate (11 mg), 2-(di-tert-butylphosphino)biphenyl (30 mg), potassium fluoride (174 mg) and 3-formyl-4-methoxyphenylboronic acid (270 mg) was added tetrahydrofuran (3 mL), and the mixture was heated under reflux for 8 hr. After cooling, water was added, the mixture was extracted with ethyl acetate. The organic layer was washed with saturated brine, and dried over anhydrous sodium sulfate. The solvent was evaporated and the residue was dissolved in methanol (6 mL). Sodium borohydride (38 mg) was added, and the mixture was stirred at room temperature for 3 hr. After completion of the reaction, water was added and extracted with chloroform. The organic layer was washed with saturated brine, and dried over anhydrous sodium sulfate. The solvent was evaporated and the residue was purified by column chromatography (chloroform:methanol=100:1) to give the title compound (76 mg).

$^1$H-NMR (270 MHz, DMSO-$d_6$) δ: 1.69 (3H, s), 2.44 (3H, s), 2.62 (3H, s), 3.3-3.6 (2H, m), 3.68 (3H, s), 3.82 (3H, s), 4.4-4.6 (3H, m), 5.09 (1H, d, J=5.4 Hz), 7.03 (1H, d, J=8.6 Hz), 7.48 (2H, d, J=8.4 Hz), 7.57 (1H, dd, J=8.6, 1.9 Hz), 7.6-7.8 (3H, m)

MS (ESI) m/z: 517 (M+H)$^+$.

Example 16

Methyl (S)-{4-(4'-cyanobiphenyl-4-yl)-2,3,9-trimethyl-6H-thieno[3,2-f][1,2,4]triazolo[4,3-a][1,4]diazepin-6-yl}acetate The title compound (480 mg) was obtained from the compound (830 mg) described in Example 1 by a treatment in the same manner as in Example 2 and using 4-cyanophenylboronic acid (441 mg) instead of 4-methylthiophenylboronic acid.

$^1$H-NMR (400 MHz, DMSO-$d_6$) δ: 1.67 (3H, s), 2.43 (3H, s), 2.62 (3H, s), 3.3-3.6 (2H, m), 3.68 (3H, s), 4.53 (1H, t, J=7.6 Hz), 7.54 (2H, d, J=8.4 Hz), 7.83 (2H, d, J=8.4 Hz), 7.92 (2H, d, J=8.8 Hz), 7.96 (2H, d, J=8.8 Hz)

MS (ESI) m/z: 482 (M+H)$^+$.

Example 17

Methyl (S)-{4-(2'-hydroxymethylbiphenyl-4-yl)-2,3,9-trimethyl-6H-thieno[3,2-f][1,2,4]triazolo[4,3-a][1,4]diazepin-6-yl}acetate The title compound (144 mg) was obtained from the compound (210 mg) described in Example 1 by a treatment in the same manner as in Example 15 and using 2-formylphenylboronic acid (112 mg) instead of 3-formyl-4-methoxyphenylboronic acid.

$^1$H-NMR (400 MHz, DMSO-$d_6$) δ: 1.70 (3H, s), 2.44 (3H, s), 2.62 (3H, s), 3.3-3.6 (2H, m), 3.68 (3H, s), 4.37 (2H, d, J=5.1 Hz), 4.53 (1H, t, J=7.6 Hz), 5.13 (1H, t, J=5.1 Hz), 7.21 (1H, d, J=8.4 Hz), 7.23-7.49 (6H, m), 7.57 (1H, d, J=7.4 Hz)

MS (ESI) m/z: 487 (M+H)$^+$.

Example 18

Methyl (S)-{4-(3'-hydroxymethylbiphenyl-4-yl)-2,3,9-trimethyl-6H-thieno[3,2-f][1,2,4]triazolo[4,3-a][1,4]diazepin-6-yl}acetate The title compound (191 mg) was obtained from the compound (210 mg) described in Example 1 by a treatment in the same manner as in Example 2 and using 3-hydroxymethylphenylboronic acid (114 mg) instead of 4-methylthiophenylboronic acid.

$^1$H-NMR (400 MHz, DMSO-$d_6$) δ: 1.69 (3H, s), 2.44 (3H, s), 2.62 (3H, s), 3.3-3.6 (2H, m), 3.68 (3H, s), 4.52 (1H, t, J=7.2 Hz), 4.57 (2H, d, J=5.6 Hz), 5.22 (1H, t, J=6.0 Hz), 7.34 (1H, d, J=7.6 Hz), 7.43 (1H, d, J=7.6 Hz), 7.51 (2H, d, J=8.4 Hz), 7.56 (1H, d, J=7.6 Hz), 7.63 (1H, s), 7.71 (2H, d, J=8.4 Hz)

MS (ESI) m/z: 487 (M+H)$^+$.

Example 19

Methyl (S)-{4-(3'-methoxycarbonylmethoxybiphenyl-4-yl)-2,3,9-trimethyl-6H-thieno[3,2-f][1,2,4]triazolo[4,3-a][1,4]diazepin-6-yl}acetate To a mixture of the compound described in Example 4 (236 mg) and cesium carbonate (407 mg) were successively added dimethylformamide (2 mL) and methyl bromoacetate (80 μL), and the mixture was stirred at 110° C. for 6 hr. After cooling, water was added, and extracted with chloroform. The organic layer was washed with water and purified by column chromatography (chloroform:methanol=100:1) to give the title compound (129 mg).

$^1$H-NMR (400 MHz, DMSO-$d_6$) δ: 1.69 (3H, s), 2.43 (3H, s), 2.62 (3H, s), 3.44 (1H, dd, J=16.4, 6.4 Hz), 3.50 (1H, dd, J=16.4, 6.4 Hz), 3.68 (3H, s), 3.71 (3H, s), 4.52 (1H, t, J=6.4 Hz), 4.88 (2H, s), 6.96 (1H, dd, J=8.0, 2.0 Hz), 7.23 (1H, d, J=2.0 Hz), 7.30 (1H, d, J=8.0 Hz), 7.39 (1H, t, J=8.0 Hz), 7.49 (2H, d, J=8.4 Hz), 7.73 (2H, d, J=8.4 Hz)

MS (ESI) m/z: 535 (M+H)$^+$.

Example 20

Methyl (S)-{4-[3'-(2-methoxyethoxy)biphenyl-4-yl]-2,3,9-trimethyl-6H-thieno[3,2-f][1,2,4]triazolo[4,3-a][1,4]diazepin-6-yl}acetate The title compound (163 mg) was obtained from the compound (236 mg) described in Example 4 by a treatment in the same manner as in Example 19 and using methoxyethyl bromide (80 μL) instead of methyl bromoacetate.

$^1$H-NMR (400 MHz, DMSO-$d_6$) δ: 1.69 (3H, s), 2.43 (3H, s), 2.62 (3H, s), 3.32 (3H, s), 3.3-3.6 (2H, m), 3.68 (3H, s), 3.6-3.7 (2H, m), 4.17 (2H, t, J=4.8 Hz), 4.52 (1H, t, J=6.8 Hz), 6.97 (1H, dd, J=8.0, 2.0 Hz), 7.23 (1H, s), 7.26 (1H, d, J=8.0 Hz), 7.38 (1H, t, J=8.0 Hz), 7.48 (2H, d, J=8.0 Hz), 7.73 (2H, d, J=8.0 Hz)

MS (ESI) m/z: 531 (M+H)$^+$.

Example 21

Methyl (S)-{4-(3'-cyanomethoxybiphenyl-4-yl)-2,3,9-trimethyl-6H-thieno[3,2-f][1,2,4]triazolo[4,3-a][1,4]diazepin-6-yl}acetate The title compound (42 mg) was obtained from the compound (236 mg) described in Example 4 by a treatment in the same manner as in Example 19 and using cyanomethylbromide (50 μL) instead of methyl bromoacetate.

$^1$H-NMR (400 MHz, DMSO-$d_6$) δ: 1.69 (3H, s), 2.44 (3H, s), 2.62 (3H, s), 3.3-3.6 (2H, m), 3.68 (3H, s), 4.52 (1H, t, J=7.2 Hz), 5.26 (2H, s), 7.10 (1H, dd, J=8.0, 2.0 Hz), 7.37-7.53 (5H, m), 7.76 (2H, d, J=8.4 Hz)

MS (ESI) m/z: 512 (M+H)$^+$.

Example 22

Methyl (S)-{4-(4'-methoxymethylbiphenyl-4-yl)-2,3,9-trimethyl-6H-thieno[3,2-f][1,2,4]triazolo[4,3-a][1,4]diazepin-6-yl}acetate The compound described in Example 10 (243 mg) was dissolved in dimethylformamide (2 mL), and sodium hydride (23 mg) was added under ice-cooling. The mixture was stirred for 1 hr. Methyl iodide (50 μL) was added thereto, and the mixture was stirred at room temperature for 6 hr. After completion of the reaction, water was added, and the mixture was extracted with chloroform. The organic layer was washed with saturated brine, and dried over anhydrous sodium sulfate. The solvent was evaporated and the residue was purified by column chromatography (chloroform:methanol=100:1) and recrystallized from hexane-ethyl acetate to give the title compound (38 mg).

$^1$H-NMR (400 MHz, DMSO-$d_6$) δ: 1.69 (3H, s), 2.43 (3H, s), 2.62 (3H, s), 3.31 (3H, s), 3.3-3.6 (2H, m), 3.68 (3H, s), 4.46 (2H, s), 4.52 (1H, t, J=7.2 Hz), 7.41 (2H, d, J=8.4 Hz), 7.50 (2H, d, J=8.4 Hz), 7.69 (2H, d, J=8.4 Hz), 7.73 (2H, d, J=8.4 Hz)

MS (ESI) m/z: 501 (M+H)$^+$.

Example 23

Methyl (S)-{4-(2'-fluorobiphenyl-4-yl)-2,3,9-trimethyl-6H-thieno[3,2-f][1,2,4]triazolo[4,3-a][1,4]diazepin-6-yl}acetate The title compound (375 mg) was obtained from the compound (750 mg) described in Example 1 by a treatment in the same manner as in Example 2 and using 2-fluorophenylboronic acid (312 mg) instead of 4-methylthiophenylboronic acid.

$^1$H-NMR (400 MHz, CDCl$_3$) δ: 1.76 (3H, s), 2.43 (3H, s), 2.69 (3H, s), 3.62-3.68 (2H, m), 3.79 (3H, s), 4.66 (1H, t, J=6.8 Hz), 7.13-7.18 (1H, m), 7.20-7.24 (1H, m), 7.31-7.35 (1H, m), 7.40-7.45 (1H, m), 7.52-7.58 (4H, m)

MS (ESI) m/z: 475 (M+H)$^+$.

Example 24

Methyl (S)-{4-(2'-cyanobiphenyl-4-yl)-2,3,9-trimethyl-6H-thieno[3,2-f][1,2,4]triazolo[4,3-a][1,4]diazepin-6-yl}acetate To a mixture of the compound described in Example 1 (630 mg), palladium acetate (18 mg), 2-(di-tert-butylphosphino)biphenyl (45 mg), cesium fluoride (684 mg) and 2-formylphenylboronic acid (336 mg) was added tetrahydrofuran (4.5 mL), and the mixture was heated under reflux for 8 hr. After cooling, water was added, and the mixture was extracted with ethyl acetate. The organic layer was washed with saturated brine and dried over anhydrous sodium sulfate. The solvent was evaporated and the residue was purified by column chromatography (chloroform:methanol=100:1) to give methyl (S)-{4-(2'-formylbiphenyl-4-yl)-2,3,9-trimethyl-6H-thieno[3,2-f][1,2,4]triazolo[4,3-a][1,4]diazepin-6-yl}acetate (722 mg). The obtained compound (300 mg) was dissolved in methylene chloride (3 mL), and triethylamine (90 μL) and hydroxylamine hydrochloride (43 mg) were successively added. The mixture was stirred at room temperature for 24 hr. After completion of the reaction, 2-chloro-1,3-dimethyl-2-imidazolium tetrafluoroborate (172 mg), triethylamine (175 μL) were successively added, and the mixture was stirred at room temperature for 3 hr. After completion of the reaction, water was added, and the mixture was extracted with ethyl acetate. The organic layer was washed successively with 1M hydrochloric acid aqueous solution, saturated aqueous sodium hydrogencarbonate and saturated brine, and dried over anhydrous sodium sulfate. The solvent was evaporated and the residue was purified by column chromatography (chloroform:methanol=100:1) to give the title compound (27 mg).

$^1$H-NMR (400 MHz, DMSO-$d_6$) δ: 1.69 (3H, s), 2.44 (3H, s), 2.63 (3H, s), 3.3-3.6 (2H, m), 3.69 (3H, s), 4.54 (1H, t, J=6.8 Hz), 7.5-7.7 (6H, m), 7.82 (1H, d, J=8.0 Hz), 7.98 (1H, d, J=8.0 Hz)

MS (ESI) m/z: 482 (M+H)$^+$.

Example 25

Methyl (S)-{4-(3'-cyano-4'-methoxybiphenyl-4-yl)-2,3,9-trimethyl-6H-thieno[3,2-f][1,2,4]triazolo[4,3-a][1,4]diazepin-6-yl}acetate The title compound (124 mg) was obtained from the compound (630 mg) described in Example 1 by a treatment in the same manner as in Example 24 and using 3-formyl-4-methoxyphenylboronic acid (405 mg) instead of 2-formylphenylboronic acid.

$^1$H-NMR (400 MHz, DMSO-$d_6$) δ: 1.67 (3H, s), 2.43 (3H, s), 2.62 (3H, s), 3.3-3.6 (2H, m), 3.68 (3H, s), 3.97 (3H, s), 4.51 (1H, t, J=7.6 Hz), 7.36 (1H, d, J=8.4 Hz), 7.48 (2H, d, J=8.4 Hz), 7.77 (2H, d, J=8.4 Hz), 8.04 (1H, dd, J=8.4, 2.0 Hz), 8.12 (1H, d, J=2.0 Hz)

MS (ESI) m/z: 512 (M+H)$^+$.

Example 26

Methyl (S)-{4-(5'-cyano-2'-methoxybiphenyl-4-yl)-2,3,9-trimethyl-6H-thieno[3,2-f][1,2,4]triazolo[4,3-a][1,4]diazepin-6-yl}acetate The title compound (2.7 g) was obtained from the compound (12.5 g) described in Example 1 by a treatment in the same manner as in Example 24 and using 3-formyl-6-methoxyphenylboronic acid (8.1 g) instead of 2-formylphenylboronic acid.

$^1$H-NMR (400 MHz, DMSO-$d_6$) δ: 1.70 (3H, s), 2.44 (3H, s), 2.62 (3H, s), 3.43 (1H, dd, J=16.8, 6.8 Hz), 3.50 (1H, dd, J=16.8 6.8 Hz), 3.68 (3H, s), 3.85 (3H, s), 4.52 (1H, t, J=6.8 Hz), 7.31 (1H, d, J=8.4 Hz), 7.47 (2H, d, J=8.4 Hz), 7.57 (2H, d, J=8.4 Hz), 7.77 (1H, d, J=2.4 Hz), 7.87 (1H, d, J=8.4, 2.4 Hz)

MS (ESI) m/z: 512 (M+H)$^+$.

Example 27

Methyl (S)-{4-(3'-butoxybiphenyl-4-yl)-2,3,9-trimethyl-6H-thieno[3,2-f][1,2,4]triazolo[4,3-a][1,4]diazepin-6-yl}acetate The title compound (3.5 g) was obtained from the compound (3.3 g) described in Example 1 by a treatment in the same manner as in Example 2 and using 3-butoxyphenylboronic acid (2.3 g) instead of 4-methylthiophenylboronic acid.

$^1$H-NMR (400 MHz, DMSO-$d_6$) δ: 0.94 (3H, t, J=7.6 Hz), 1.4-1.5 (2H, m), 1.6-1.8 (5H, m), 2.43 (3H, s), 2.62 (3H, s), 3.44 (1H, dd, J=16.4, 6.8 Hz), 3.51 (1H, dd, J=16.4 6.8 Hz), 3.68 (3H, s), 4.03 (2H, t, J=6.4 Hz), 4.52 (1H, t, J=6.8 Hz), 6.95 (1H, dd, J=8.4, 2.0 Hz), 7.20 (1H, s), 7.24 (1H, d, J=7.6 Hz), 7.37 (1H, t, J=8.0 Hz), 7.48 (2H, d, J=8.0 Hz), 7.73 (2H, d, J=8.0 Hz)

MS (ESI) m/z: 529 (M+H)$^+$.

Example 28

Methyl (S)-{2,3,9-trimethyl-4-(3'-trifluoromethoxybiphenyl-4-yl)-6H-thieno[3,2-f][1,2,4]triazolo[4,3-a][1,4]diazepin-6-yl}acetate The title compound (725 mg) was obtained from the compound (830 mg) described in Example 1 by a treatment in the same manner as in Example 2 and using 3-trifluoromethoxyphenylboronic acid (618 mg) instead of 4-methylthiophenylboronic acid.

$^1$H-NMR (400 MHz, DMSO-$d_6$) δ: 1.68 (3H, s), 2.44 (3H, s), 2.62 (3H, s), 3.44 (1H, dd, J=16.8, 7.2 Hz), 3.51 (1H, dd, J=16.8 7.2 Hz), 3.68 (3H, s), 4.53 (1H, t, J=7.2 Hz), 7.41 (1H, d, J=8.8 Hz), 7.52 (2H, d, J=8.4 Hz), 7.62 (1H, t, J=8.0 Hz), 7.69 (1H, s), 7.7-7.8 (3H, m)

MS (ESI) m/z: 541 (M+H)$^+$.

Example 29

Methyl (S)-{4-(3'-methylsulfonylbiphenyl-4-yl)-2,3,9-trimethyl-6H-thieno[3,2-f][1,2,4]triazolo[4,3-a][1,4]diazepin-6-yl}acetate A mixture of the compound described in Example 1 (1.66 g), palladium acetate (44 mg), 2-(di-tert-butylphosphino)biphenyl (120 mg), cesium fluoride (1.82 g) and 3-methylthiophenylboronic acid (1 g) was heated under reflux for 8 hr in tetrahydrofuran (10 mL). After cooling, water was added, and the mixture was extracted with chloroform. The organic layer was washed with saturated brine and dried over anhydrous sodium sulfate. The solvent was evaporated and the residue was purified by column chromatography (chloroform:methanol=100:1) to give methyl (S)-{4-(3'-methylthiobiphenyl-4-yl)-2,3,9-trimethyl-6H-thieno[3,2-f][1,2,4]triazolo[4,3-a][1,4]diazepin-6-yl}acetate (2 g). The obtained compound (2 g) was dissolved in a mixture of methanol (40 mL) and water (4 mL). Sodium bicarbonate (1 g) and oxone (4.9 g) were successively added thereto, and the mixture was stirred at room temperature for 3 hr. After completion of the reaction, water was added, and the mixture was extracted with ethyl acetate. The organic layer was washed with saturated brine, and dried over anhydrous sodium sulfate. The solvent was evaporated and the residue was purified by column chromatography (chloroform:methanol=100:1) to give the title compound (2 g).

$^1$H-NMR (400 MHz, DMSO-$d_6$) δ: 1.68 (3H, s), 2.44 (3H, s), 2.63 (3H, s), 3.31 (3H, s), 3.45 (1H, dd, J=16.8, 7.2 Hz), 3.52 (1H, dd, J=16.8 7.2 Hz), 3.69 (3H, s), 4.53 (1H, t, J=7.2 Hz), 7.56 (2H, d, J=8.0 Hz), 7.77 (1H, t, J=8.0 Hz), 7.84 (2H, t, J=8.0 Hz), 7.95 (1H, d, J=8.0 Hz), 8.07 (1H, d, J=8.0 Hz), 8.19 (1H, s)

MS (ESI) m/z: 535 (M+H)$^+$.

Example 30

Methyl (S)-{4-(3'-methoxymethylbiphenyl-4-yl)-2,3, 9-trimethyl-6H-thieno[3,2-f][1,2,4]triazolo[4,3-a][1, 4]diazepin-6-yl}acetate The compound described in Example 18 (2 g) was dissolved in chloroform (10 mL). Methylsulfonyl chloride (0.15 mL) and triethylamine (0.86 mL) were successively added, and the mixture was stirred at room temperature overnight. Water was added to the reaction mixture, and the mixture was extracted with chloroform. The organic layer was washed twice with water. After drying over anhydrous sodium sulfate, the solvent was evaporated under reduced pressure. The residue was dissolved in methanol (10 mL). Sodium methoxide (28% methanol solution, 2 mL) was added, and the mixture was heated under reflux for 6 hr. Water was added to the reaction mixture, and the mixture was extracted with ethyl acetate. The organic layer was washed twice with water. After drying over anhydrous sodium sulfate, the solvent was evaporated under reduced pressure, and the obtained residue was purified by silica gel column chromatography (chloroform:methanol=100:1) to give the title compound (158 mg).

$^1$H-NMR (400 MHz, CDCl$_3$) δ: 1.74 (3H, s), 2.43 (3H, s), 2.69 (3H, s), 3.43 (3H, s), 3.61-3.71 (2H, m), 3.79 (3H, s), 4.52 (2H, s), 4.66 (1H, t, J=7.2 Hz), 7.34 (1H, d, J=7.6 Hz), 7.41 (1H, dd, J=7.6, 7.2 Hz), 7.51-7.55 (6H, m)

MS (ESI) m/z: 501 (M+H)$^+$.

Example 31

Methyl (S)-{2,3,9-trimethyl-4-(3'-morpholin-4-ylmethylbiphenyl-4-yl)-6H-thieno[3,2-f][1,2,4]triazolo[4,3-a][1,4]diazepin-6-yl}acetate The compound described in Example 18 (650 mg) was dissolved in methylene chloride (60 mL). 1,8-Diazabicyclo[5.4.0]-7-undecene (DBU, 820 µL) and dichloro(tri-o-tolyl)bismuth (3 g) were added, and the mixture was stirred at room temperature for 1 hr. After completion of the reaction, water was added, and the mixture was extracted with chloroform. The organic layer was washed with saturated brine and dried over anhydrous sodium sulfate. The solvent was evaporated and the residue was purified by column chromatography (chloroform:methanol=100:1) to give a compound (485 mg). The obtained compound (485 mg) was dissolved in acetic acid (0.13 mL). Morpholine (0.09 mL), sodium triacetoxyborohydride (318 mg) were successively added, and the mixture was stirred at room temperature for 3 hr. After completion of the reaction, water was added, and the mixture was extracted with chloroform. The organic layer was washed with saturated brine and dried over anhydrous sodium sulfate. The solvent was evaporated and the residue was purified by column chromatography (chloroform:methanol=100:1) to give the title compound (122 mg).

$^1$H-NMR (400 MHz, CDCl$_3$) δ 1.74 (3H, s), 2.43 (3H, s), 2.44-2.54 (4H, m), 2.69 (3H, s), 3.56 (2H, brs), 3.62-3.72 (2H, m), 3.70-3.73 (4H, m), 3.79 (3H, s), 4.66 (1H, t, J=6.4 Hz), 7.33 (1H, d, J=7.6 Hz), 7.40 (1H, t, J=7.6 Hz), 7.49 (1H, d, J=7.6 Hz), 7.52-7.62 (5H, m)

MS (ESI) m/z: 556 (M+H)$^+$.

Example 32

Methyl (S)-{4-(5'-acetyl-2'-methoxybiphenyl-4-yl)-2,3,9-trimethyl-6H-thieno[3,2-f][1,2,4]triazolo[4,3-a][1,4]diazepin-6-yl}acetate To a mixture of the compound described in Example 1 (12.5 g), palladium acetate (360 mg), 2-(di-tert-butylphosphino)biphenyl (900 mg), cesium fluoride (13.7 g) and 5-formyl-2-methoxyphenylboronic acid (8.1 g) was added tetrahydrofuran (90 mL), and the mixture was heated under reflux for 8 hr. Furthermore, palladium acetate (360 mg), 2-(di-tert-butylphosphino)biphenyl (900 mg), potassium fluoride (1.4 g) and 5-formyl-2-methoxyphenylboronic acid (2.1 g) were added, and the mixture was heated under reflux for 8 hr. After cooling, water was added, and the mixture was extracted with ethyl acetate. The organic layer was washed with saturated brine and dried over anhydrous sodium sulfate. The solvent was evaporated and the residue was purified by column chromatography (chloroform:methanol=100:1) to give methyl (S)-{4-(5'-formyl-2'-methoxybiphenyl-4-yl)-2,3,9-trimethyl-6H-thieno[3,2-f][1,2,4]triazolo[4,3-a][1,4]diazepin-6-yl}acetate (9.6 g). The obtained compound (4.7 g) was dissolved in tetrahydrofuran (60 mL). A solution of methyl magnesium bromide in tetrahydrofuran (1.4 M, 6.5 mL) was added dropwise, and the mixture was stirred at 0° C. for 30 min. After completion of the reaction, 1M aqueous hydrochloric acid solution (10 mL) was added, and the mixture was extracted with chloroform. The organic layer was washed with saturated aqueous sodium hydrogencarbonate and saturated brine and dried over anhydrous sodium sulfate. The solvent was evaporated and the residue was purified by column chromatography (chloroform:methanol=100:1) to give methyl (S)-{4-[5'-(1-hydroxyethyl)-2'-methoxybiphenyl-4-yl]-2,3,9-trimethyl-6H-thieno[3,2-f][1,2,4]triazolo[4,3-a][1,4]diazepin-6-yl}acetate (1.8 g). The obtained compound (1 g) was dissolved in methylene chloride (20 mL). 1,8-Diazabicyclo[5.4.0]-7-undecene (DBU) (330 µL) and dichloro(tri-o-tolyl)bismuth (1.2 g) were added, and the mixture was stirred at room temperature for 1 hr. After completion of the reaction, water was added, and the mixture was extracted with chloroform. The organic layer was washed with saturated brine and dried over anhydrous sodium sulfate. The solvent was evaporated and the residue was purified by column chromatography (chloroform:methanol=100:1) to give the title compound (725 mg).

$^1$H-NMR (400 MHz, DMSO-d$_6$) δ: 1.72 (3H, s), 2.44 (3H, s), 2.57 (3H, s), 2.62 (3H, s), 3.44 (1H, dd, J=16.4, 7.2 Hz), 3.50 (1H, dd, J=16.4 7.2 Hz), 3.68 (3H, s), 3.85 (3H, s), 4.52 (1H, t, J=7.2 Hz), 7.24 (1H, d, J=8.8 Hz), 7.48 (2H, d, J=8.4 Hz), 7.57 (2H, d, J=8.4 Hz), 7.86 (1H, d, J=2.4 Hz), 8.01 (1H, dd, J=8.8, 2.4 Hz)

MS (ESI) m/z: 529 (M+H)$^+$.

Example 33

Methyl (S)-{4-(2',5'-dimethoxybiphenyl-4-yl)-2,3,9-trimethyl-6H-thieno[3,2-f][1,2,4]triazolo[4,3-a][1,4]diazepin-6-yl}acetate The title compound (1.2 g) was obtained from the compound (1.2 g) described in Example 1 by a treatment in the same manner as in Example 2 and using 2,5-dimethoxyphenylboronic acid (819 mg) instead of 4-methylthiophenylboronic acid.

$^1$H-NMR (400 MHz, DMSO-d$_6$) δ: 1.72 (3H, s), 2.44 (3H, s), 2.62 (3H, s), 3.43 (1H, dd, J=16.4, 7.2 Hz), 3.50 (1H, dd,

J=16.4 7.2 Hz), 3.68 (6H, s), 3.74 (3H, s), 4.51 (1H, t, J=7.2 Hz), 6.87 (1H, d, J=3.2 Hz), 6.93 (1H, dd, J=8.8, 3.2 Hz), 7.05 (1H, d, J=8.8 Hz), 7.44 (2H, d, J=8.4 Hz), 7.54 (2H, d, J=8.4 Hz)

MS (ESI) m/z: 517 (M+H)+.

Example 34

Methyl (S)-{2,3,9-trimethyl-4-(3'-propionylbiphenyl-4-yl)-6H-thieno[3,2-f][1,2,4]triazolo[4,3-a][1,4]diazepin-6-yl}acetate The title compound (2.7 g) was obtained from the compound (8.4 g) described in Example 1 by a treatment in the same manner as in Example 32 and using 3-formylphenylboronic acid (4.5 g) instead of 3-formyl-6-methoxyphenylboronic acid.

1H-NMR (400 MHz, DMSO-d6) δ: 1.11 (3H, t, J=6.4 Hz), 1.69 (3H, s), 2.44 (3H, s), 2.63 (3H, s), 3.15 (2H, q, J=6.4 Hz), 3.45 (1H, dd, J=16.4, 7.2 Hz), 3.52 (1H, dd, J=16.4 7.2 Hz), 3.69 (3H, s), 4.53 (1H, t, J=7.2 Hz), 7.53 (2H, d, J=8.0 Hz), 7.64 (1H, t, J=8.0 Hz), 7.81 (2H, d, J=8.0 Hz), 7.96 (1H, d, J=8.0 Hz), 7.99 (1H, d, J=8.0 Hz), 8.21 (1H, s)

MS (ESI) m/z: 513 (M+H)+.

Example 35

Methyl (S)-{4-(3'-acetyl-4'-methoxybiphenyl-4-yl)-2,3,9-trimethyl-6H-thieno[3,2-f][1,2,4]triazolo[4,3-a][1,4]diazepin-6-yl}acetate The title compound (550 mg) was obtained from the compound (1.2 g) described in Example 1 by a treatment in the same manner as in Example 32 and using 3-formyl-4-methoxyphenylboronic acid (810 mg) instead of 5-formyl-2-methoxyphenylboronic acid.

1H-NMR (400 MHz, DMSO-d6) δ: 1.68 (3H, s), 2.43 (3H, s), 2.57 (3H, s), 2.62 (3H, s), 3.44 (1H, dd, J=16.4, 7.2 Hz), 3.51 (1H, dd, J=16.4 7.2 Hz), 3.68 (3H, s), 3.94 (3H, s), 4.51 (1H, t, J=7.2 Hz), 7.29 (1H, d, J=8.0 Hz), 7.49 (2H, t, J=8.0 Hz), 7.71 (2H, d, J=8.0 Hz), 7.8-7.9 (2H, m)

MS (ESI) m/z: 529 (M+H)+.

Example 36

Methyl (S)-{4-(2'-acetylbiphenyl-4-yl)-2,3,9-trimethyl-6H-thieno[3,2-f][1,2,4]triazolo[4,3-a][1,4]diazepin-6-yl}acetate The title compound (728 mg) was obtained from the compound (1.2 g) described in Example 1 by a treatment in the same manner as in Example 32 and using 2-formylphenylboronic acid (675 mg) instead of 5-formyl-2-methoxyphenylboronic acid.

1H-NMR (400 MHz, DMSO-d6) δ: 1.67 (3H, s), 2.15 (3H, s), 2.49 (3H, s), 2.62 (3H, s), 3.44 (1H, dd, J=16.4, 7.2 Hz), 3.51 (1H, dd, J=16.4 7.2 Hz), 3.68 (3H, s), 4.52 (1H, t, J=7.2 Hz), 7.35 (2H, d, J=8.0 Hz), 7.4-7.7 (6H, m)

MS (ESI) m/z: 499 (M+H)+.

Example 37

Methyl (S)-(4-{4-benzo[1,3]dioxol-5-ylphenyl}-2,3,9-trimethyl-6H-thieno[3,2-f][1,2,4]triazolo[4,3-a][1,4]diazepin-6-yl)acetate The title compound (1.4 g) was obtained from the compound (1.2 g) described in Example 1 by a treatment in the same manner as in Example 2 and using 3,4-methylenedioxyphenylboronic acid (747 mg) instead of 4-methylthiophenylboronic acid.

1H-NMR (400 MHz, DMSO-d6) δ: 1.69 (3H, s), 2.43 (3H, s), 2.62 (3H, s), 3.43 (1H, dd, J=16.4, 7.2 Hz), 3.51 (1H, dd, J=16.4 7.2 Hz), 3.68 (3H, s), 4.51 (1H, t, J=7.2 Hz), 6.06 (2H, s), 7.00 (1H, d, J=8.0 Hz), 7.19 (1H, dd, J=8.0, 1.6 Hz), 7.28 (1H, d, J=1.6 Hz), 7.45 (2H, d, J=8.0 Hz), 7.66 (2H, d, J=8.0 Hz)

MS (ESI) m/z: 501 (M+H)+.

Example 38

Methyl (S)-{4-(3'-cyclopropanecarbonylbiphenyl-4-yl)-2,3,9-trimethyl-6H-thieno[3,2-f][1,2,4]triazolo[4,3-a][1,4]diazepin-6-yl}acetate The title compound (881 mg) was obtained from intermediate methyl (S)-{4-(3'-formylbiphenyl-4-yl)-2,3,9-trimethyl-6H-thieno[3,2-f][1,2,4]triazolo[4,3-a][1,4]diazepin-6-yl}acetate (1.7 g) obtained in Example 34 by a treatment in the same manner as in Example 34 and using cyclohexylmagnesium bromide (0.5 M tetrahydrofuran solution of 10 mL) instead of ethylmagnesium bromide.

1H-NMR (400 MHz, DMSO-d6) δ: 1.0-1.1 (4H, m), 1.69 (3H, s), 2.44 (3H, s), 2.66 (3H, s), 2.9-3.1 (1H, m), 3.45 (1H, dd, J=16.4, 7.2 Hz), 3.52 (1H, dd, J=16.4 7.2 Hz), 3.69 (3H, s), 4.53 (1H, t, J=7.2 Hz), 7.54 (2H, d, J=8.4 Hz), 7.66 (1H, t, J=8.0 Hz), 7.82 (2H, d, J=8.4 Hz), 7.98 (1H, d, J=8.0 Hz), 8.08 (1H, d, J=8.0 Hz), 8.29 (1H, s)

MS (ESI) m/z: 525 (M+H)+.

Example 39

Methyl (S)-{4-(3'-ethoxybiphenyl-4-yl)-2,3,9-trimethyl-6H-thieno[3,2-f][1,2,4]triazolo[4,3-a][1,4]diazepin-6-yl}acetate The title compound (1.3 g) was obtained from the compound (1.2 g) described in Example 1 by a treatment in the same manner as in Example 2 and using 3-ethoxyphenylboronic acid (747 mg) instead of 4-methylthiophenylboronic acid.

1H-NMR (400 MHz, DMSO-d6) δ: 1.35 (3H, t, J=7.2 Hz), 1.69 (3H, s), 2.43 (3H, s), 2.62 (3H, s), 3.44 (1H, dd, J=16.4, 7.2 Hz), 3.51 (1H, dd, J=16.4 7.2 Hz), 3.68 (3H, s), 4.10 (2H, q, J=7.2 Hz), 4.52 (1H, t, J=7.2 Hz), 6.96 (1H, dd, J=8.0, 2.4 Hz), 7.20 (1H, s), 7.25 (1H, d, J=8.0 Hz), 7.38 (2H, t, J=8.0 Hz), 7.49 (2H, d, J=8.4 Hz), 7.73 (1H, d, J=8.4 Hz)

MS (ESI) m/z: 501 (M+H)+.

Example 40

Methyl (S)-{4-[3'-(3,3-dimethyl-2-oxobutoxy)biphenyl-4-yl]-2,3,9-trimethyl-6H-thieno[3,2-f][1,2,4]triazolo[4,3-a][1,4]diazepin-6-yl}acetate To a mixture of the compound described in Example 4 (236 mg) and cesium carbonate (407 mg) were successively added 2-butanone (5 mL) and 1-chloropinacolone (610 μL), and the mixture was stirred at room temperature for 1 hr. After completion of the reaction, water was added, and the mixture was extracted with chloroform. The organic layer was washed with water and purified by column chromatography (chloroform:methanol=100:1) to give the title compound (270 mg).

1H-NMR (400 MHz, DMSO-d6) δ: 1.18 (9H, s), 1.68 (3H, s), 2.43 (3H, s), 2.62 (3H, s), 3.3-3.6 (2H, m), 3.68 (3H, s), 4.52 (1H, t, J=7.2 Hz), 5.21 (2H, s), 6.91 (1H, d, J=8.0 Hz), 7.15 (1H, s), 7.27 (1H, d, J=8.0 Hz), 7.37 (1H, t, J=8.0 Hz), 7.49 (2H, d, J=8.0 Hz), 7.72 (2H, d, J=8.0 Hz)

MS (ESI) m/z: 571 (M+H)+.

Example 41

Methyl (S)-{2,3,9-trimethyl-4-(3'-trifluoromethylsulfonyloxybiphenyl-4-yl)-6H-thieno[3,2-f][1,2,4]triazolo[4,3-a][1,4]diazepin-6-yl}acetate The compound described in Example 4 (1.9 g) was dissolved in methylene chloride (20 mL). Pyridine (970 µL) was added under ice-cooling, a solution of anhydrous trifluoromethanesulfone acid (1.3 mL) in methylene chloride (20 mL) was added dropwise, and the mixture was stirred at 0° C. for 1 hr. Water was added, and the mixture was extracted with chloroform. The organic layer was washed with saturated brine and dried over anhydrous sodium sulfate. The solvent was evaporated and the residue was purified by column chromatography (chloroform:methanol=100:1) to give the title compound (1.8 g).

1H-NMR (400 MHz, DMSO-$d_6$) δ: 1.68 (3H, s), 2.43 (3H, s), 2.63 (3H, s), 3.44 (1H, dd, J=16.4, 7.2 Hz), 3.51 (1H, dd, J=16.4 7.2 Hz), 3.69 (3H, s), 4.53 (1H, t, J=7.2 Hz), 7.53 (3H, d, J=8.0 Hz), 7.69 (1H, t, J=8.0 Hz), 7.81 (2H, d, J=8.0 Hz), 7.87 (2H, d, J=8.0 Hz)

MS (ESI) m/z: 605 (M+H)+.

Example 42

Methyl (S)-{4-(3'-aminobiphenyl-4-yl)-2,3,9-trimethyl-6H-thieno[3,2-f][1,2,4]triazolo[4,3-a][1,4]diazepin-6-yl}acetate The compound described in Example 7 (6 g) was dissolved in methanol (5 mL). 5M aqueous hydrochloric acid solution (5 mL) was added, and the mixture was stirred at 100° C. for 3 hr. After cooling, the mixture was neutralized with aqueous alkali, and the mixture was extracted with chloroform. The organic layer was washed with saturated brine and dried over anhydrous sodium sulfate. The solvent was evaporated and the residue was purified by column chromatography (chloroform:methanol=100:1) to give the title compound (1 g).

1H-NMR (400 MHz, DMSO-$d_6$) δ: 1.68 (3H, s), 2.43 (3H, s), 2.62 (3H, s), 3.43 (1H, dd, J=16.4, 7.2 Hz), 3.51 (1H, dd, J=16.4 7.2 Hz), 3.68 (3H, s), 4.51 (1H, t, J=7.2 Hz), 5.20 (2H, s), 6.58 (1H, dd, J=8.0, 1.6 Hz), 6.80 (1H, d, J=8.0 Hz), 6.85 (1H, s), 7.11 (1H, t, J=8.0 Hz), 7.47 (2H, d, J=8.4 Hz), 7.60 (2H, d, J=8.4 Hz)

MS (ESI) m/z: 472 (M+H)+.

Example 43

Methyl (S)-{2,3,9-trimethyl-4-(3'-propionylaminobiphenyl-4-yl)-6H-thieno[3,2-f][1,2,4]triazolo[4,3-a][1,4]diazepin-6-yl}acetate The compound described in Example 42 (471 mg) was dissolved in methylene chloride (5 mL). Pyridine (490 µL), dimethylaminopyridine (10 mg) and anhydrous propionic acid (390 µL) were successively added, and the mixture was stirred at room temperature for 24 hr. After completion of the reaction, water was added, and the mixture was extracted with chloroform. The organic layer was washed with saturated brine and dried over anhydrous sodium sulfate. The solvent was evaporated and the residue was purified by column chromatography (chloroform:methanol=100:1) and recrystallized from hexane-ethyl acetate to give the title compound (508 mg).

1H-NMR (400 MHz, DMSO-$d_6$) δ: 1.09 (3H, t, J=7.2 Hz), 1.69 (3H, s), 2.34 (2H, q, J=7.2 Hz), 2.44 (3H, s), 2.62 (3H, s), 3.3-3.6 (2H, m), 3.69 (3H, s), 4.52 (1H, t, J=7.2 Hz), 7.3-7.5 (2H, m), 7.51 (2H, d, J=8.0 Hz), 7.61 (1H, d, J=8.0 Hz), 7.66 (2H, d, J=8.0 Hz), 7.94 (1H, s), 9.99 (1H, s)

MS (ESI) m/z: 528 (M+H)+.

Example 44

Methyl (S)-{(3'-dimethylsulfonylaminobiphenyl-4-yl)-2,3,9-trimethyl-4-6H-thieno[3,2-f][1,2,4]triazolo[4,3-a][1,4]diazepin-6-yl}acetate The title compound (129 mg) was obtained from the compound (159 mg) described in Example 42 by a treatment in the same manner as in Example 43 and using methylsulfonylchloride (120 µL) instead of anhydrous propionic acid.

1H-NMR (400 MHz, DMSO-$d_6$) δ: 1.68 (3H, s), 2.43 (3H, s), 2.63 (3H, s), 3.3-3.6 (2H, m), 3.58 (6H, s), 3.68 (3H, s), 4.53 (1H, t, J=7.2 Hz), 7.53 (2H, d, J=8.0 Hz), 7.55 (2H, d, J=8.0 Hz), 7.60 (1H, t, J=8.0 Hz), 7.8-7.9 (4H, m)

MS (ESI) m/z: 628 (M+H)+.

Example 45

Methyl (S)-{4-[3'-(3-hydroxy-3-methylbut-1-enyl)biphenyl-4-yl]-2,3,9-trimethyl-6H-thieno[3,2-f][1,2,4]triazolo[4,3-a][1,4]diazepin-6-yl}acetate To a mixture of the compound described in Example 41 (300 mg), tris(dibenzylideneacetone)dipalladium (0) chloroform adduct (26 mg) and tri-tert-butylphosphonium tetrafluoroborate (29 mg) were successively added dioxane (1 mL), dicyclohexylmethylamine (210 µL) and 2-methyl-3-butene-2-ol (160 µL), and the mixture was heated under reflux for 8 hr. After cooling, water was added, and the mixture was extracted with chloroform. The organic layer was washed with saturated brine and dried over anhydrous sodium sulfate. The solvent was evaporated and the residue was purified by column chromatography (chloroform:methanol=100:1) and recrystallized from hexane-ethyl acetate to give the title compound (157 mg).

1H-NMR (400 MHz, DMSO-$d_6$) δ: 1.29 (6H, s), 1.69 (3H, s), 2.44 (3H, s), 2.62 (3H, s), 3.3-3.6 (2H, m), 3.68 (3H, s), 4.52 (1H, t, J=7.2 Hz), 4.74 (1H, s), 6.52 (1H, d, J=16.0 Hz), 6.59 (1H, d, J=16.0 Hz), 7.4-7.6 (5H, m), 7.71 (1H, s), 7.76 (2H, d, J=8.4 Hz)

MS (ESI) m/z: 541 (M+H)+.

Example 46

Methyl (S)-{2,3,9-trimethyl-4-[3'-(4-methylpiperazin-1-yl)biphenyl-4-yl]-6H-thieno[3,2-f][1,2,4]triazolo[4,3-a][1,4]diazepin-6-yl}acetate To a mixture of the compound described in Example 41 (300 mg), palladium acetate (6 mg), 2-(dicyclohexylphosphino)biphenyl (18 mg) and tripotassium phosphate (149 mg) were successively added dimethoxyethane (2 mL) and N-methylpiperazine (90 µL), and the mixture was heated under reflux for 8 hr. After cooling, water was added, and the mixture was extracted with chloroform. The organic layer was washed with saturated brine and dried over anhydrous sodium sulfate. The solvent was evaporated and the residue was purified by column chromatography (chloroform:methanol=100:1) and recrystallized from hexane-ethyl acetate to give the title compound (155 mg).

1H-NMR (400 MHz, DMSO-$d_6$) δ: 1.69 (3H, s), 2.23 (3H, s), 2.44 (3H, s), 2.44-2.50 (4H, m), 2.62 (3H, s), 3.19-3.22 (4H, m), 3.3-3.6 (2H, m), 3.68 (3H, s), 4.51 (1H, t, J=7.2 Hz), 6.97 (1H, d, J=8.0 Hz), 7.07 (1H, d, J=8.0 Hz), 7.17 (1H, s), 7.30 (1H, t, J=8.0 Hz), 7.47 (2H, d, J=8.0 Hz), 7.71 (2H, d, J=8.0 Hz)

MS (ESI) m/z: 555 (M+H)+.

Example 47

Methyl (S)-{4-(3'-cyclopropylmethoxybiphenyl-4-yl)-2,3,9-trimethyl-6H-thieno[3,2-f][1,2,4]triazolo[4,3-a][1,4]diazepin-6-yl}acetate To a mixture of the compound described in Example 4 (473 mg) and cesium carbonate (977 mg) were successively added 2-butanone (5 mL) and cyclopropylmethyl bromide (200 μL), and the mixture was heated under reflux for 3 hr. After cooling, water was added, and the mixture was extracted with chloroform. The organic layer was washed with water and saturated brine and dried over anhydrous sodium sulfate. The solvent was evaporated and the residue was purified by column chromatography (chloroform:methanol=100:1) to give the title compound (358 mg).

1H-NMR (400 MHz, DMSO-$d_6$) δ: 0.3-0.4 (2H, m), 0.5-0.7 (2H, m), 1.68 (3H, s), 2.44 (3H, s), 2.62 (3H, s), 3.44 (1H, dd, J=16.4, 7.2 Hz), 3.51 (1H, dd, J=16.4 7.2 Hz), 3.68 (3H, s), 3.89 (1H, d, J=7.2 Hz), 4.52 (1H, t, J=7.2 Hz), 6.95 (1H, dd, J=8.0, 1.6 Hz), 7.21 (1H, s), 7.25 (1H, d, J=8.0 Hz), 7.37 (1H, t, J=8.0 Hz), 7.48 (2H, d, J=8.0 Hz), 7.74 (2H, d, J=8.0 Hz)

MS (ESI) m/z: 527 (M+H)+.

Example 48

Methyl (S)-{2,3,9-trimethyl-4-(3'-morpholin-4-ylbiphenyl-4-yl)-6H-thieno[3,2-f][1,2,4]triazolo[4,3-a][1,4]diazepin-6-yl}acetate The title compound (172 mg) was obtained from the compound (300 mg) described in Example 41 by a treatment in the same manner as in Example 46 and using morpholine (70 μL) instead of N-methylpiperazine.

1H-NMR (400 MHz, DMSO-$d_6$) δ: 1.69 (3H, s), 2.43 (3H, s), 2.62 (3H, s), 3.1-3.2 (4H, m), 3.44 (1H, dd, J=16.4, 7.2 Hz), 3.51 (1H, dd, J=16.4 7.2 Hz), 3.75 (3H, s), 3.7-3.8 (4H, m), 4.51 (1H, t, J=7.2 Hz), 6.98 (1H, d, J=8.0 Hz), 7.11 (1H, d, J=8.0 Hz), 7.19 (1H, s), 7.30 (1H, t, J=8.0 Hz), 7.47 (2H, d, J=8.0 Hz), 7.71 (2H, d, J=8.0 Hz)

MS (ESI) m/z: 542 (M+H)+.

Example 49

Methyl (S)-{4-(3'-fluorobiphenyl-4-yl)-2,3,9-trimethyl-6H-thieno[3,2-f][1,2,4]triazolo[4,3-a][1,4]diazepin-6-yl}acetate The title compound (460 mg) was obtained from the compound (630 mg) described in Example 1 by a treatment in the same manner as in Example 2 and using 3-fluorophenylboronic acid (315 mg) instead of 4-methylthiophenylboronic acid.

1H-NMR (400 MHz, DMSO-$d_6$) δ: 1.68 (3H, s), 2.43 (3H, s), 2.63 (3H, s), 3.45 (1H, dd, J=16.4, 7.2 Hz), 3.52 (1H, dd, J=16.4 7.2 Hz), 3.69 (3H, s), 4.53 (1H, t, J=7.2 Hz), 7.24 (1H, d, J=8.0 Hz), 7.5-7.7 (5H, m), 7.78 (2H, d, J=8.0 Hz)

MS (ESI) m/z: 475 (M+H)+.

Example 50

Methyl (S)-{4-(3'-allyloxybiphenyl-4-yl)-2,3,9-trimethyl-6H-thieno[3,2-f][1,2,4]triazolo[4,3-a][1,4]diazepin-6-yl}acetate The title compound (210 mg) was obtained from the compound (415 mg) described in Example 4 by a treatment in the same manner as in Example 47 and using ally chloride (250 μL) instead of cyclopropylmethyl bromide.

1H-NMR (400 MHz, DMSO-$d_6$) δ: 1.69 (3H, s), 2.44 (3H, s), 2.62 (3H, s), 3.3-3.6 (2H, m), 3.68 (3H, s), 4.52 (1H, t, J=7.2 Hz), 4.65 (2H, t, J=5.2 Hz), 5.28 (1H, d, J=9.6 Hz), 5.42 (1H, dd, J=17.2, 1.2 Hz), 6.0-6.1 (1H, m), 6.99 (1H, dd, J=8.0, 2.0 Hz), 7.2-7.3 (2H, m), 7.39 (1H, t, J=8.0 Hz), 7.49 (2H, d, J=8.4 Hz), 7.74 (2H, d, J=8.4 Hz)

MS (ESI) m/z: 513 (M+H)+.

Example 51

Methyl (S)-{2,3,9-trimethyl-4-(3'-prop-2-ynyloxybiphenyl-4-yl)-6H-thieno[3,2-f][1,2,4]triazolo[4,3-a][1,4]diazepin-6-yl}acetate The title compound (303 mg) was obtained from the compound (473 mg) described in Example 4 by a treatment in the same manner as in Example 47 and using propargyl bromide (240 μL) instead of cyclopropylmethyl bromide.

1H-NMR (400 MHz, DMSO-$d_6$) δ: 1.69 (3H, s), 2.44 (3H, s), 2.62 (3H, s), 3.44 (1H, dd, J=16.4, 7.2 Hz), 3.50 (1H, dd, J=16.4 7.2 Hz), 3.68 (3H, s), 4.52 (1H, t, J=7.2 Hz), 4.89 (2H, s), 7.02 (1H, dd, J=8.0, 2.0 Hz), 7.25-7.35 (2H, m), 7.42 (1H, t, J=8.0 Hz), 7.50 (2H, d, J=8.4 Hz), 7.74 (2H, d, J=8.4 Hz)

MS (ESI) m/z: 511 (M+H)+.

Example 52

Methyl (S)-{4-[3'-(3-hydroxypropoxy)biphenyl-4-yl]-2,3,9-trimethyl-6H-thieno[3,2-f][1,2,4]triazolo[4,3-a][1,4]diazepin-6-yl}acetate To a mixture of the compound described in Example 4 (473 mg) and cesium carbonate (977 mg) were successively added 2-butanone (3 mL) and (3-bromopropoxy)-tert-butyldimethylsilane (470 μL), and the mixture was heated under reflux for 3 hr. After cooling, water was added, and the mixture was extracted with chloroform. The organic layer was washed with water and saturated brine and dried over anhydrous sodium sulfate. The solvent was evaporated and the residue was dissolved in tetrahydrofuran (3 mL). A solution (1 M, 2 mL) of tetra-n-butylammonium fluoride in tetrahydrofuran was added, and the mixture was stirred at room temperature for 24 hr. After completion of the reaction, water was added, and the mixture was extracted with chloroform. The organic layer was washed with water and saturated brine and dried over anhydrous sodium sulfate. The solvent was evaporated and the residue was purified by column chromatography (chloroform:methanol=100:1) and recrystallized from hexane-ethyl acetate to give the title compound (267 mg).

1H-NMR (400 MHz, DMSO-$d_6$) δ: 1.69 (3H, s), 1.8-1.9 (2H, m), 2.44 (3H, s), 2.62 (3H, s), 3.3-3.6 (4H, m), 3.68 (3H, s), 4.0-4.2 (2H, m), 4.52 (1H, t, J=7.2 Hz), 4.57 (1H, t, J=5.2

Hz), 6.97 (1H, dd, J=8.0, 2.0 Hz), 7.21 (1H, s), 7.25 (1H, d, J=8.0 Hz), 7.38 (1H, t, J=8.0 Hz), 7.48 (2H, d, J=8.0 Hz), 7.73 (2H, d, J=8.0 Hz)
MS (ESI) m/z: 531 (M+H)+.

Example 53

Methyl (S)-{4-[3'-(2-ethoxyethoxy)biphenyl-4-yl]-2,3,9-trimethyl-6H-thieno[3,2-f][1,2,4]triazolo[4,3-a][1,4]diazepin-6-yl}acetate The title compound (425 mg) was obtained from the compound (473 mg) described in Example 4 by a treatment in the same manner as in Example 47 and using ethoxyethyl bromide (230 μL) instead of cyclopropylmethyl bromide.
1H-NMR (400 MHz, DMSO-$d_6$) δ: 1.13 (3H, t, J=7.2 Hz), 1.69 (3H, s), 2.43 (3H, s), 2.62 (3H, s), 3.3-3.6 (4H, m), 3.68 (3H, s), 3.7-3.8 (2H, m), 4.1-4.2 (2H, m), 4.52 (1H, t, J=7.2 Hz), 6.97 (1H, d, J=8.0 Hz), 7.24 (1H, s), 7.26 (1H, d, J=8.0 Hz), 7.38 (1H, t, J=8.0 Hz), 7.48 (2H, d, J=8.0 Hz), 7.74 (2H, d, J=8.0 Hz)
MS (ESI) m/z: 545 (M+H)+.

Example 54

Methyl (S)-{2,3,9-trimethyl-4-[3'-(2-morpholin-4-ylethoxy)biphenyl-4-yl]-6H-thieno[3,2-f][1,2,4]triazolo[4,3-a][1,4]diazepin-6-yl}acetate The title compound (332 mg) was obtained from the compound (473 mg) described in Example 4 by a treatment in the same manner as in Example 47 and using N-(2-chloroethyl) morpholine hydrochloride (372 mg) instead of cyclopropylmethyl bromide.
1H-NMR (400 MHz, DMSO-$d_6$) δ: 1.69 (3H, s), 2.43 (3H, s), 2.62 (3H, s), 2.71 (2H, t, J=6.0 Hz), 3.44 (1H, dd, J=16.4, 7.2 Hz), 3.50 (1H, dd, J=16.4 7.2 Hz), 3.5-36 (4H, m), 3.68 (3H, s), 4.16 (2H, t, J=6.0 Hz), 4.52 (1H, t, J=7.2 Hz), 6.97 (1H, dd, J=8.0, 2.0 Hz), 7.23 (1H, s), 7.26 (1H, d, J=8.0 Hz), 7.38 (1H, t, J=8.0 Hz), 7.48 (2H, d, J=8.0 Hz), 7.74 (2H, d, J=8.0 Hz)
MS (ESI) m/z: 586 (M+H)+.

Example 55

Methyl (S)-{4-[3'-(3-cyanopropoxy)biphenyl-4-yl]-2,3,9-trimethyl-6H-thieno[3,2-f][1,2,4]triazolo[4,3-a][1,4]diazepin-6-yl}acetate The title compound (238 mg) was obtained from the compound (473 mg) described in Example 4 by a treatment in the same manner as in Example 47 and using cyanopropyl bromide (200 μL) instead of cyclopropylmethyl bromide.
1H-NMR (400 MHz, DMSO-$d_6$) δ: 1.69 (3H, s), 2.0-2.1 (2H, m), 2.43 (3H, s), 2.62 (3H, s), 2.67 (2H, t, J=6.0 Hz), 3.44 (1H, dd, J=16.4, 7.2 Hz), 3.50 (1H, dd, J=16.4 7.2 Hz), 3.68 (3H, s), 4.12 (2H, t, J=6.0 Hz), 4.52 (1H, t, J=7.2 Hz), 6.99 (1H, dd, J=8.0, 2.0 Hz), 7.24 (1H, s), 7.28 (1H, d, J=8.0 Hz), 7.40 (1H, t, J=8.0 Hz), 7.49 (2H, d, J=8.0 Hz), 7.73 (2H, d, J=8.0 Hz)
MS (ESI) m/z: 540 (M+H)+.

Example 56

Methyl (S)-{4-(3'-cyano-4'-hydroxybiphenyl-4-yl)-2,3,9-trimethyl-6H-thieno[3,2-f][1,2,4]triazolo[4,3-a][1,4]diazepin-6-yl}acetate To a mixture of the compound described in Starting Material Synthetic Example 1 (2 g), dichlorobis(triphenylphosphine)palladium (II) (140 mg), sodium carbonate (2.5 g) and 4-bromo-2-cyanophenol (1.6 g) were added tetrahydrofuran (12 mL) and water (12 mL), and the mixture was stirred at 100° C. for 3 hr. After cooling, water was added, and the mixture was extracted with chloroform. The organic layer was washed with saturated brine and dried over anhydrous sodium sulfate. The solvent was evaporated and the residue was purified by column chromatography (chloroform:methanol=100:1) to give the title compound (1.5 g).
1H-NMR (400 MHz, DMSO-$d_6$) δ: 1.67 (3H, s), 2.43 (3H, s), 2.67 (3H, s), 3.44 (1H, dd, J=16.4, 7.2 Hz), 3.50 (1H, dd, J=16.4 7.2 Hz), 3.68 (3H, s), 4.51 (1H, t, J=7.2 Hz), 7.11 (1H, d, J=8.8 Hz), 7.47 (2H, d, J=8.4 Hz), 7.72 (2H, d, J=8.4 Hz), 7.86 (1H, dd, J=8.8, 2.0 Hz), 7.97 (1H, d, J=2.0 Hz), 11.3 (1H, brs)
MS (ESI) m/z: 498 (M+H)+.

Example 57

Methyl (S)-{4-(5'-cyano-2'-hydroxybiphenyl-4-yl)-2,3,9-trimethyl-6H-thieno[3,2-f][1,2,4]triazolo[4,3-a][1,4]diazepin-6-yl}acetate The title compound (159 mg) was obtained from the compound (210 mg) described in Starting Material Synthetic Example 1 by a treatment in the same manner as in Example 56 and using 2-bromo-4-cyanophenol (1.6 g) instead of 4-bromo-2-cyanophenol.
1H-NMR (400 MHz, DMSO-$d_6$) δ: 1.70 (3H, s), 2.44 (3H, s), 2.62 (3H, s), 3.44 (1H, dd, J=16.4, 7.2 Hz), 3.50 (1H, dd, J=16.4 7.2 Hz), 3.68 (3H, s), 4.52 (1H, t, J=7.2 Hz), 7.03 (1H, d, J=8.4 Hz), 7.45 (2H, d, J=8.4 Hz), 7.60 (1H, d, J=8.4 Hz), 7.65 (2H, d, J=8.4 Hz), 7.71 (1H, d, J=1.6 Hz)
MS (ESI) m/z: 498 (M+H)+.

Example 58

Methyl (S)-{2,3,9-trimethyl-4-[3'-(pyridin-4-ylmethoxy)biphenyl-4-yl]-6H-thieno[3,2-f][1,2,4]triazolo[4,3-a][1,4]diazepin-6-yl}acetate The title compound (805 mg) was obtained from the compound (945 mg) described in Example 4 by a treatment in the same manner as in Example 47 and using 4-(chloromethyl) pyridine hydrochloride (492 mg) instead of cyclopropylmethyl bromide.
1H-NMR (400 MHz, DMSO-$d_6$) δ: 1.68 (3H, s), 2.43 (3H, s), 2.62 (3H, s), 3.44 (1H, dd, J=16.4, 7.2 Hz), 3.50 (1H, dd, J=16.4 7.2 Hz), 3.68 (3H, s), 4.52 (1H, t, J=7.6 Hz), 5.28 (2H, s), 7.05 (1H, dd, J=8.0, 2.0 Hz), 7.2-7.6 (7H, m), 7.73 (2H, d, J=8.4 Hz), 8.58 (2H, d, J=8.0 Hz)
MS (ESI) m/z: 564 (M+H)+.

Example 59

Methyl (S)-(4-{3'-cyano-4'-[(pyridine-4-carbonyl)amino]biphenyl-4-yl}-2,3,9-trimethyl-6H-thieno[3,2-f][1,2,4]triazolo[4,3-a][1,4]diazepin-6-yl)acetate To a mixture of the compound described in Starting Material Synthetic Example 1 (7.4 g), dichlorobis(triphenylphosphine)palladium (II) (526 mg), sodium carbonate (9.5 g) and 4-bromo-2-cyanoaniline (3 g) were added tetrahydrofuran (45 mL) and water (45 mL), and the mixture was stirred at 100° C. for 3 hr. After cooling, water was added, and the mixture was extracted with chloroform. The organic layer was washed with saturated brine and dried over anhydrous sodium sulfate. The solvent was evaporated and the residue was purified by column chromatography (chloroform:methanol=100:1) to give methyl (S)-{4-(4'-amino-3'-cyanobiphenyl-4-yl)-2,3,9-trimethyl-6H-thieno[3,2-f][1,2,4]triazolo[4,3-a][1,4]diazepin-6-yl}acetate (7.4 g). The obtained compound (500 mg) was dissolved in methylene chloride (5 mL). Triethylamine (1 mL) and isonicotinoylchloride hydrochloride (428 mg) were successively added, and the mixture was stirred at room temperature for 24 hr. After completion of the reaction, water was added, and the mixture was extracted with chloroform. The organic layer was washed with saturated brine and dried over anhydrous sodium sulfate. The solvent was evaporated and the residue was purified by column chromatography (chloroform:methanol=100:1) to give the title compound (223 mg).

$^1$H-NMR (400 MHz, DMSO-d$_6$) δ: 1.69 (3H, s), 2.44 (3H, s), 2.63 (3H, s), 3.44 (1H, dd, J=16.4, 7.2 Hz), 3.50 (1H, dd, J=16.4 7.2 Hz), 3.68 (3H, s), 4.53 (1H, t, J=7.2 Hz), 7.54 (2H, d, J=8.0 Hz), 7.73 (1H, d, J=8.4 Hz), 7.85 (2H, d, J=8.0 Hz), 7.91 (2H, d, J=8.0 Hz), 8.11 (1H, dd, J=8.4, 2.0 Hz), 8.27 (1H, d, J=2.0 Hz), 8.84 (2H, d, J=6.0 Hz), 11.0 (1H, s)

MS (ESI) m/z: 602 (M+H)$^+$.

Example 60

Methyl (S)-{4-[3'-(3-dimethylaminopropoxy)biphenyl-4-yl]-2,3,9-trimethyl-6H-thieno[3,2-f][1,2,4]triazolo[4,3-a][1,4]diazepin-6-yl}acetate The title compound (344 mg) was obtained from the compound (473 mg) described in Example 4 by a treatment in the same manner as in Example 47 and using dimethylaminopropyl chloride (316 mg) instead of cyclopropylmethyl bromide.

$^1$H-NMR (400 MHz, DMSO-d$_6$) δ: 1.69 (3H, s), 1.8-1.9 (2H, m), 2.14 (6H, s), 2.3-2.4 (2H, m), 2.44 (3H, s), 2.62 (3H, s), 3.44 (1H, dd, J=16.4, 7.2 Hz), 3.50 (1H, dd, J=16.4 7.2 Hz), 3.68 (3H, s), 4.07 (2H, t, J=6.4 Hz), 4.52 (1H, t, J=7.2 Hz), 6.96 (1H, dd, J=8.0, 2.0 Hz), 7.20 (1H, d, J=2.0 Hz), 7.24 (1H, d, J=8.0 Hz), 7.38 (2H, d, J=8.0 Hz), 7.73 (2H, d, J=8.0 Hz)

MS (ESI) m/z: 558 (M+H)$^+$.

Example 61

Methyl (S)-{4-biphenyl-2,3,9-trimethyl-6H-thieno[3,2-f][1,2,4]triazolo[4,3-a][1,4]diazepin-6-yl}acetate The title compound (340 mg) was obtained from the compound (415 mg) described in Example 1 by a treatment in the same manner as in Example 2 and using phenylboronic acid (183 mg) instead of 4-methylthiophenylboronic acid.

$^1$H-NMR (300 MHz, DMSO-d$_6$) δ: 1.67 (3H, s), 2.42 (3H, s), 2.60 (3H, s), 3.4-3.6 (2H, m), 3.67 (3H, s), 4.50 (1H, t, J=7.2 Hz), 7.3-7.6 (5H, m), 7.68 (2H, d, J=7.8 Hz), 7.73 (2H, d, J=7.8 Hz)

MS (ESI) m/z: 457 (M+H)$^+$.

Example 62

Ethyl (S)-{4-(4-chlorophenyl)-2,3,9-trimethyl-6H-thieno[3,2-f][1,2,4]triazolo[4,3-a][1,4]diazepin-6-yl}acetate To a solution of starting material B (70 g) in ethanol (500 mL) was added concentrated sulfuric acid (4 mL), and the mixture was heated under reflux for 9 hr. After cooling, the solvent was evaporated under reduced pressure. Aqueous potassium carbonate solution was added, and the mixture was extracted with chloroform. The organic layer was washed with water and saturated brine and dried over anhydrous sodium sulfate. The solvent was evaporated and the residue was recrystallized from ethyl acetate to give the title compound (45 g).

$^1$H-NMR (300 MHz, DMSO-d$_6$) δ: 1.19 (3H, t, J=7.1 Hz), 1.60 (3H, s), 2.39 (3H, s), 2.58 (3H, s), 3.3-3.5 (2H, m), 4.0-4.3 (2H, m), 4.47 (1H, dd, J=7.8, 6.8 Hz), 7.41 (2H, d, J=7.0 Hz), 7.47 (2H, d, J=7.0 Hz)

MS (ESI) m/z: 429 (M+H)$^+$.

Example 63

Ethyl (S)-{4-(3'-acetylbiphenyl-4-yl)-2,3,9-trimethyl-6H-thieno[3,2-f][1,2,4]triazolo[4,3-a][1,4]diazepin-6-yl}acetate A mixture of the compound described in Example 62 (1.3 g), palladium acetate (33 mg), 2-(di-tert-butylphosphino)biphenyl (30 mg), cesium fluoride (90 mg) and 3-acetylphenylboronic acid (738 mg) was heated under reflux for 8 hr in tetrahydrofuran (9 mL). After cooling, water was added, and the mixture was extracted with chloroform. The organic layer was washed with saturated brine and dried over anhydrous sodium sulfate. The solvent was evaporated and the residue was purified by column chromatography (chloroform:methanol=100:1) to give the title compound (1.3 g).

$^1$H-NMR (400 MHz, DMSO-d$_6$) δ: 1.23 (3H, t, J=7.2 Hz), 1.69 (3H, s), 2.44 (3H, s), 2.63 (3H, s), 2.66 (3H, s), 3.4-3.6 (2H, m), 4.1-4.3 (2H, m), 4.52 (1H, d, J=7.6 Hz), 7.54 (2H, d, J=8.0 Hz), 7.64 (1H, t, J=8.0 Hz), 7.80 (2H, d, J=8.4 Hz), 7.9-8.0 (2H, m), 8.21 (1H, d, J=1.6 Hz)

MS (ESI) m/z: 513 (M+H)$^+$.

Example 64

Ethyl (S)-{4-(4'-methoxybiphenyl-4-yl)-2,3,9-trimethyl-6H-thieno[3,2-f][1,2,4]triazolo[4,3-a][1,4]diazepin-6-yl}acetate The compound described in Example 5 (1.4 g) was dissolved in methanol (12 mL). 4M aqueous sodium hydroxide solution (2.1 mL) was added, and the mixture was stirred at room temperature for 3 hr. After completion of the reaction, 1 M aqueous hydrochloric acid (9 mL) was added, and the mixture was extracted with chloroform. The organic layer was washed with saturated brine and dried over anhydrous sodium sulfate. The solvent was evaporated and the residue was dissolved in ethanol (10 mL). Concentrated sulfuric acid (100 μL) was added, and the mixture was heated under reflux for 8 hr. After cooling, the solvent was evaporated, and aqueous potassium carbonate solution was added. The mixture was extracted with ethyl acetate. The organic layer was washed with saturated brine and dried over anhydrous sodium sulfate. The solvent was evaporated and the residue was purified by column chromatography (chloroform:methanol=100:1) to give the title compound (977 mg).

$^1$H-NMR (400 MHz, DMSO-d$_6$) δ: 1.23 (3H, t, J=7.2 Hz), 1.69 (3H, s), 2.43 (3H, s), 2.62 (3H, s), 3.4-3.5 (2H, m), 3.80 (3H, s), 4.1-4.2 (2H, m), 4.52 (1H, dd, J=8.0, 6.8 Hz), 7.04 (2H, d, J=8.8 Hz), 7.46 (2H, d, J=8.4 Hz), 7.4-7.6 (4H, m)

MS (ESI) m/z: 501 (M+H)$^+$.

Example 65

Ethyl (S)-{4-(3'-cyanobiphenyl-4-yl)-2,3,9-trimethyl-6H-thieno[3,2-f][1,2,4]triazolo[4,3-a][1,4]diazepin-6-yl}acetate The title compound (1 g) was obtained from the compound (1.3 g) described in Example 62 by a treatment in the same manner as in Example 63 and using 3-cyanophenylboronic acid (661 mg) instead of 3-acetylphenylboronic acid.

$^1$H-NMR (400 MHz, DMSO-$d_6$) δ: 1.23 (3H, t, J=7.2 Hz), 1.67 (3H, s), 2.44 (3H, s), 2.63 (3H, s), 3.4-3.5 (2H, m), 4.1-4.2 (2H, m), 4.52 (1H, dd, J=8.0, 6.8 Hz), 7.53 (2H, d, J=8.4 Hz), 7.69 (1H, t, J=8.0 Hz), 7.3-7.4 (3H, m), 8.07 (1H, d, J=8.0 Hz), 8.22 (1H, s)

MS (ESI) m/z: 496 (M+H)$^+$.

Example 66

Ethyl (S)-{4-(3'-methoxybiphenyl-4-yl)-2,3,9-trimethyl-6H-thieno[3,2-f][1,2,4]triazolo[4,3-a][1,4]diazepin-6-yl}acetate The title compound (1.2 mg) was obtained from the compound (1.3 g) described in Example 62 by a treatment in the same manner as in Example 63 and using 3-methoxyphenylboronic acid (684 mg) instead of 3-acetylphenylboronic acid.

$^1$H-NMR (400 MHz, DMSO-$d_6$) δ: 1.23 (3H, t, J=7.2 Hz), 1.69 (3H, s), 2.44 (3H, s), 2.62 (3H, s), 3.3-3.5 (2H, m), 3.82 (3H, s), 4.1-4.2 (2H, m), 4.51 (1H, t, J=7.6 Hz), 6.97 (1H, dd, J=8.0, 2.0 Hz), 7.22 (1H, d, J=2.0 Hz), 7.27 (1H, d, J=8.0 Hz), 7.39 (1H, t, J=8.0 Hz), 7.49 (2H, d, J=8.0 Hz), 7.74 (2H, d, J=8.0 Hz)

MS (ESI) m/z: 501 (M+H)$^+$.

Example 67

Ethyl (S)-{4-(4'-hydroxy-3'-methoxybiphenyl-4-yl)-2,3,9-trimethyl-6H-thieno[3,2-f][1,2,4]triazolo[4,3-a][1,4]diazepin-6-yl}acetate To a mixture of the compound described in Starting Material Synthetic Example 2 (1.5 g), dichlorobis(triphenylphosphine)palladium (II) (106 mg), sodium carbonate (1.9 g) and 4-bromo-2-methoxy-phenol (1.2 g) were added tetrahydrofuran (9 mL) and water (9 mL), and the mixture was stirred at 100° C. for 3 hr. After cooling, the mixture was acidified with hydrochloric acid and extracted with chloroform. The organic layer was washed with saturated brine and dried over anhydrous sodium sulfate. The solvent was evaporated and the residue was purified by column chromatography (chloroform:methanol=100:1) to give the title compound (1.1 g).

$^1$H-NMR (400 MHz, DMSO-$d_6$) δ: 1.23 (3H, t, J=7.2 Hz), 1.69 (3H, s), 2.44 (3H, s), 2.62 (3H, s), 3.3-3.5 (2H, m), 3.85 (3H, s), 4.1-4.2 (2H, m), 4.50 (1H, t, J=7.6 Hz), 6.86 (1H, d, J=8.4 Hz), 7.13 (1H, dd, J=8.0, 2.0 Hz), 7.23 (1H, d, J=1.2 Hz), 7.44 (2H, d, J=8.4 Hz), 7.68 (2H, d, J=8.4 Hz), 9.19 (1H, s)

MS (ESI) m/z: 517 (M+H)$^+$.

Example 68

Ethyl (S)-{4-(3'-cyano-4'-methylsulfonylaminobiphenyl-4-yl)-2,3,9-trimethyl-6H-thieno[3,2-f][1,2,4]triazolo[4,3-a][1,4]diazepin-6-yl}acetate Methyl (S)-{4-(4'-amino-3'-cyanobiphenyl-4-yl)-2,3,9-trimethyl-6H-thieno[3,2-f][1,2,4]triazolo[4,3-a][1,4]diazepin-6-yl}acetate (2 g) synthesized as an intermediate in Example 59 was dissolved in methylene chloride (8 mL). Triethylamine (3.4 mL) and methylsulfonylchloride (920 μL) were successively added, and the mixture was stirred at room temperature for 24 hr. After completion of the reaction, water was added, and the mixture was extracted with chloroform. The organic layer was washed with saturated brine and dried over anhydrous sodium sulfate. The solvent was evaporated and the residue was purified by column chromatography (chloroform:methanol=100:1) to give methyl (S)-{4-(3'-cyano-4',4'-dimethylsulfonylaminobiphenyl-4-yl)-2,3,9-trimethyl-6H-thieno[3,2-f][1,2,4]triazolo[4,3-a][1,4]diazepin-6-yl}acetate (892 mg). The obtained compound (653 mg) was dissolved in methanol (4 mL). 1 M aqueous sodium hydroxide solution (4 mL) was added, and the mixture was stirred at room temperature for 3 hr. After completion of the reaction, the mixture was acidified with aqueous 1 M hydrochloric acid and extracted with chloroform. The organic layer was washed with saturated brine and dried over anhydrous sodium sulfate. The solvent was evaporated and the residue was dissolved in ethanol (10 mL). Concentrated sulfuric acid (50 μL) was added, and the mixture was heated under reflux for 8 hr. After cooling, aqueous potassium carbonate solution was added, and the mixture was extracted with chloroform. The organic layer was washed with saturated brine and dried over anhydrous sodium sulfate. The solvent was evaporated and the residue was purified by column chromatography (chloroform:methanol=100:1) to give the title compound (465 mg).

$^1$H-NMR (400 MHz, DMSO-$d_6$) δ: 1.23 (3H, t, J=7.2 Hz), 1.69 (3H, s), 2.44 (3H, s), 2.62 (3H, s), 2.69 (3H, s), 3.3-3.5 (2H, m), 4.1-4.2 (2H, m), 4.48 (1H, t, J=7.2 Hz), 6.86 (1H, d, J=8.4 Hz), 7.3-7.5 (3H, m), 7.6-7.8 (4H, m)

MS (ESI) m/z: 589 (M+H)$^+$.

Example 69

Ethyl (S)-{4-[3'-cyano-4'-(pyrimidin-2-yloxy)biphenyl-4-yl]-2,3,9-trimethyl-6H-thieno[3,2-f][1,2,4]triazolo[4,3-a][1,4]diazepin-6-yl}acetate Ethyl (S)-{4-(4'-hydroxy-3'-cyanobiphenyl-4-yl)-2,3,9-trimethyl-6H-thieno[3,2-f][1,2,4]triazolo[4,3-a][1,4]diazepin-6-yl}acetate (1.1 g) was obtained from the compound (1.5 g) described in Starting Material Synthetic Example 2 by a treatment in the same manner as in Example 67 and using 4-bromo-2-cyanophenol (1.2 g) instead of 4-bromo-2-methoxyphenol. To a mixture of the obtained compound (512 mg) and cesium carbonate (2 g) were added 2-butanone (4 mL) and 2-chloropyrimidine (458 mg), and the mixture was heated under reflux for 8 hr. After cooling, water was added, and the mixture was extracted with chloroform. The organic layer was washed with saturated brine and dried over anhydrous sodium sulfate. The solvent was evaporated and the residue was purified by column chromatography (chloroform:methanol=100:1) and recrystallized from hexane-ethyl acetate to give the title compound (294 mg).

$^1$H-NMR (400 MHz, DMSO-$d_6$) δ: 1.23 (3H, t, J=7.2 Hz), 1.69 (3H, s), 2.44 (3H, s), 2.63 (3H, s), 3.3-3.5 (2H, m), 4.1-4.2 (2H, m), 4.52 (1H, t, J=6.8 Hz), 7.39 (1H, d, J=4.8 Hz), 7.53 (2H, d, J=8.0 Hz), 7.62 (1H, d, J=8.8 Hz), 7.85 (2H, d, J=8.4 Hz), 8.13 (1H, dd, J=8.4, 2.0 Hz), 8.31 (1H, d, J=2.0 Hz), 8.73 (2H, d, J=8.0 Hz)

MS (ESI) m/z: 590 (M+H)$^+$.

Example 70

Ethyl (S)-{4-[3'-methoxy-4'-(pyridin-4-ylmethoxy) biphenyl-4-yl]-2,3,9-trimethyl-6H-thieno[3,2-f][1,2,4]triazolo[4,3-a][1,4]diazepin-6-yl}acetate To a mixture of the compound described in Example 67 (750 mg) and cesium carbonate (1.4 g) were successively added 2-butanone (5 mL) and 4-(chloromethyl)pyridine (357 mg), and the mixture was heated under reflux for 5 hr. After cooling, water was added, and the mixture was extracted with chloroform. The organic layer was washed with saturated brine and dried over anhydrous sodium sulfate. The solvent was evaporated and the residue was purified by column chromatography (chloroform:methanol=100:1) to give the title compound (676 mg).
$^1$H-NMR (400 MHz, DMSO-$d_6$) δ: 1.23 (3H, t, J=7.2 Hz), 1.69 (3H, s), 2.44 (3H, s), 2.63 (3H, s), 3.3-3.5 (2H, m), 3.90 (3H, s), 4.1-4.2 (2H, m), 4.50 (1H, t, J=7.2 Hz), 5.22 (2H, s), 7.02 (1H, d, J=8.4 Hz), 7.21 (1H, dd, J=8.4, 2.0 Hz), 7.31 (1H, d, J=2.0 Hz), 7.4-7.5 (4H, m), 7.71 (2H, d, J=8.4 Hz), 8.59 (2H, d, J=5.6 Hz)
MS (ESI) m/z: 608 (M+H)$^+$.

Example 71

Methyl (S)-{4-(4-thiophen-2-ylphenyl)-2,3,9-trimethyl-6H-thieno[3,2-f][1,2,4]triazolo[4,3-a][1,4]diazepin-6-yl}acetate The title compound (120 mg) was obtained from the compound (249 mg) described in Example 1 by a treatment in the same manner as in Example 2 and using 2-thiopheneboronic acid (230 mg) instead of 4-methylthiophenylboronic acid.
$^1$H-NMR (270 MHz, DMSO-$d_6$) δ: 1.68 (3H, s), 2.43 (3H, s), 2.62 (3H, s), 3.3-3.6 (2H, m), 3.68 (3H, s), 4.50 (1H, t, J=7.6 Hz), 7.17 (1H, t, J=5.1 Hz), 7.44 (2H, d, J=8.4 Hz), 7.60-7.63 (2H, m), 7.72 (2H, d, J=8.4 Hz)
MS (ESI) m/z: 463 (M+H)$^+$.

Example 72

Methyl (S)-{4-(4-thiophen-3-ylphenyl)-2,3,9-trimethyl-6H-thieno[3,2-f][1,2,4]triazolo[4,3-a][1,4]diazepin-6-yl}acetate The title compound (292 mg) was obtained from the compound (415 mg) described in Example 1 by a treatment in the same manner as in Example 2 and using 3-thiopheneboronic acid (192 mg) instead of 4-methylthiophenylboronic acid.
$^1$H-NMR (270 MHz, DMSO-$d_6$) δ: 1.67 (3H, s), 2.43 (3H, s), 2.62 (3H, s), 3.3-3.6 (2H, m), 3.68 (3H, s), 4.51 (1H, t, J=7.3 Hz), 7.45 (1H, d, J=8.4 Hz), 7.58-7.62 (1H, m), 7.44 (1H, dd, J=5.1, 3.0 Hz), 7.77 (2H, d, J=8.4 Hz), 7.97 (2H, dd, J=3.0, 1.4 Hz)
MS (ESI) m/z: 463 (M+H)$^+$.

Example 73

Methyl (S)-{4-(4-furan-3-ylphenyl)-2,3,9-trimethyl-6H-thieno[3,2-f][1,2,4]triazolo[4,3-a][1,4]diazepin-6-yl}acetate The title compound (180 mg) was obtained from the compound (210 mg) described in Example 1 by a treatment in the same manner as in Example 2 and using 3-furanboronic acid (168 mg) instead of 4-methylthiophenylboronic acid.
$^1$H-NMR (270 MHz, DMSO-$d_6$) δ: 1.66 (3H, s), 2.42 (3H, s), 2.62 (3H, s), 3.30-3.60 (2H, m), 3.68 (3H, s), 4.49 (1H, d, J=7.6 Hz), 6.99 (1H, d, J=1.9 Hz), 7.42 (2H, d, J=8.4 Hz), 7.66 (2H, d, J=8.4 Hz), 7.77 (1H, d, J=1.9 Hz), 8.26 (1H, s)
MS (ESI) m/z: 447 (M+H)$^+$.

Example 74

Methyl (S)-{4-[4-(5-acetylthiophen-2-yl)phenyl]-2,3,9-trimethyl-6H-thieno[3,2-f][1,2,4]triazolo[4,3-a][1,4]diazepin-6-yl}acetate The title compound (486 mg) was obtained from the compound (415 mg) described in Example 1 by a treatment in the same manner as in Example 2 and using 5-acetyl-2-thiopheneboronic acid (510 mg) instead of 4-methylthiophenylboronic acid.
$^1$H-NMR (270 MHz, DMSO-$d_6$) δ: 1.67 (3H, s), 2.43 (3H, s), 2.55 (3H, s), 2.62 (3H, s), 3.30-3.60 (2H, m), 3.68 (3H, s), 4.52 (1H, d, J=7.6 Hz), 7.49 (2H, d, J=8.6 Hz), 7.73 (1H, d, J=3.8 Hz), 7.84 (2H, d, J=8.6 Hz), 7.97 (1H, d, J=3.8 Hz)
MS (ESI) m/z: 505 (M+H)$^+$.

Example 75

Methyl (S)-{4-[4-(3-hydroxymethylthiophen-2-yl)phenyl]-2,3,9-trimethyl-6H-thieno[3,2-f][1,2,4]triazolo[4,3-a][1,4]diazepin-6-yl}acetate The title compound (50 mg) was obtained from the compound (415 mg) described in Example 1 by a treatment in the same manner as in Example 15 and using 3-formyl-2-thiopheneboronic acid (468 mg) instead of 3-formyl-4-methoxyphenylboronic acid.
$^1$H-NMR (270 MHz, DMSO-$d_6$) δ: 1.69 (3H, s), 2.44 (3H, s), 2.62 (3H, s), 3.30-3.60 (2H, m), 3.68 (3H, s), 4.45 (2H, d, J=5.1 Hz), 4.52 (1H, t, J=7.3 Hz), 5.25 (1H, t, J=5.1 Hz), 7.20 (1H, d, J=5.1 Hz), 7.4-7.6 (5H, m)
MS (ESI) m/z: 493 (M+H)$^+$.

Example 76

Methyl (S)-{4-[4-(5-hydroxymethylthiophen-2-yl)phenyl]-2,3,9-trimethyl-6H-thieno[3,2-f][1,2,4]triazolo[4,3-a][1,4]diazepin-6-yl}acetate The title compound (159 mg) was obtained from the compound (415 mg) described in Example 1 by a treatment in the same manner as in Example 15 and using 5-formyl-2-thiopheneboronic acid (468 mg) instead of 3-formyl-4-methoxyphenylboronic acid.
$^1$H-NMR (270 MHz, DMSO-$d_6$) δ: 1.69 (3H, s), 2.43 (3H, s), 2.61 (3H, s), 3.30-3.60 (2H, m), 3.68 (3H, s), 4.50 (1H, t, J=7.3 Hz), 4.64 (2H, d, J=5.4 Hz), 5.54 (1H, t, J=5.4 Hz), 6.98 (1H, d, J=3.8 Hz), 7.3-7.5 (3H, m), 7.67 (2H, d, J=8.1 Hz)
MS (ESI) m/z: 493 (M+H)$^+$.

Example 77

Methyl (S)-{4-[4-(5-cyanothiophen-2-yl)phenyl]-2,3,9-trimethyl-6H-thieno[3,2-f][1,2,4]triazolo[4,3-a][1,4]diazepin-6-yl}acetate The compound described in Example 76 (1.5 g) was dissolved in toluene (30 mL), 1,8-diazabicyclo[5.4.0]-7-undecene (DBU, 500 µL) and dichloro(tri-o-tolyl)bismuth (1.8 g) were successively added, and the mixture was stirred at room temperature for 30 min. After completion of the reaction, water was added, and the mixture was extracted with chloroform. The organic layer was washed with saturated brine and dried over anhydrous sodium sulfate. The solvent was evaporated and the residue was purified by column chromatography (chloroform:methanol=100:1). The obtained compound (881 mg) was dissolved in methylene chloride (18 mL). Triethylamine (250 µL) and hydroxylamine hydrochloride (125 mg) were successively added, and the mixture was stirred at room temperature for 24 hr. To the reaction mixture were successively added 2-chloro-1,3-dimethyl-2-imidazolium tetrafluoroborate (502 mg) and triethylamine (500 µL), and the mixture was stirred at room temperature for 3 hr. After completion of the reaction, water was added, and the mixture was extracted with chloroform. The organic layer was washed successively with 1 M aqueous hydrochloric acid solution, saturated aqueous sodium hydrogencarbonate and saturated brine and dried over anhydrous sodium sulfate. The solvent was evaporated and the residue was purified by column chromatography (chloroform:methanol=100:1) to give the title compound (505 mg).

$^1$H-NMR (400 MHz, DMSO-$d_6$) δ: 1.66 (3H, s), 2.43 (3H, s), 2.62 (3H, s), 3.44 (1H, dd, J=16.8, 6.8 Hz), 3.50 (1H, dd, J=16.8 6.8 Hz), 3.68 (3H, s), 4.52 (1H, t, J=6.8 Hz), 7.51 (2H, d, J=8.0 Hz), 7.77 (1H, d, J=4.0 Hz), 7.83 (2H, d, J=8.4 Hz), 8.02 (1H, d, J=4.0 Hz)

MS (ESI) m/z: 488 (M+H)$^+$.

Example 78

Methyl (S)-{4-[4-(2-acetylthiophen-3-yl)phenyl]-2,3,9-trimethyl-6H-thieno[3,2-f][1,2,4]triazolo[4,3-a][1,4]diazepin-6-yl}acetate A mixture of the compound described in Example 1 (2.1 g), palladium acetate (55 mg), 2-(di-tert-butylphosphino)biphenyl (150 mg), potassium fluoride (1.74 g) and 2-formyl-3-thiopheneboronic acid (2.3 g) was heated under reflux for 8 hr in tetrahydrofuran (15 mL). After cooling, water was added, and the mixture was extracted with chloroform. The organic layer was washed with saturated brine and dried over anhydrous sodium sulfate. The solvent was evaporated and the residue was purified by column chromatography (chloroform:methanol=100:1) to give methyl (S)-{4-[4-(2-formylthiophen-3-yl)phenyl]-2,3,9-trimethyl-6H-thieno[3,2-f][1,2,4]triazolo[4,3-a][1,4]diazepin-6-yl}acetate (2.5 g). The obtained compound (1.2 g) was dissolved in tetrahydrofuran (16 mL). A solution of methyl magnesium bromide (1.4 M, 2.7 mL) in tetrahydrofuran was added dropwise under ice-cooling, and the mixture was stirred at 0° C. for 30 min. After completion of the reaction, 1 M aqueous hydrochloric acid solution (4 mL) was added, and the mixture was extracted with chloroform. The organic layer was washed with saturated aqueous sodium hydrogencarbonate and saturated brine, and dried over anhydrous sodium sulfate. The solvent was evaporated and the residue was purified by column chromatography (chloroform:methanol=100:1) to give methyl (S)-(4-{4-[2-(1-hydroxyethyl)thiophen-3-yl]phenyl}-2,3,9-trimethyl-6H-thieno[3,2-f][1,2,4]triazolo[4,3-a][1,4]diazepin-6-yl)acetate (1.8 g). The obtained compound (1.1 g) was dissolved in methylene chloride (20 mL). 1,8-Diazabicyclo[5.4.0]-7-undecene (DBU, 360 µL) and dichloro(tri-o-tolyl)bismuth (1.3 g) were added, and the mixture was stirred at room temperature for 1 hr. After completion of the reaction, water was added, and the mixture was extracted with chloroform. The organic layer was washed with saturated brine and dried over anhydrous sodium sulfate. The solvent was evaporated and the residue was purified by column chromatography (chloroform:methanol=100:1) to give the title compound (886 mg).

$^1$H-NMR (400 MHz, DMSO-$d_6$) δ: 1.67 (3H, s), 2.11 (3H, s), 2.43 (3H, s), 2.62 (3H, s), 3.4-3.6 (2H, m), 3.68 (3H, s), 4.53 (1H, t, J=6.8 Hz), 7.19 (1H, d, J=4.8 Hz), 7.49 (4H, s), 7.97 (1H, d, J=4.8 Hz)

MS (ESI) m/z: 505 (M+H)$^+$.

Example 79

Methyl (S)-{4-[4-(2-cyanothiophen-3-yl)phenyl]-2,3,9-trimethyl-6H-thieno[3,2-f][1,2,4]triazolo[4,3-a][1,4]diazepin-6-yl}acetate The title compound (680 mg) was obtained from the compound (1 g) described in Example 1 by a treatment in the same manner as in Example 25 and using 2-formyl-3-phenylboronic acid (1.2 g) instead of 3-formyl-4-methoxyphenylboronic acid.

$^1$H-NMR (400 MHz, DMSO-$d_6$) δ: 1.68 (3H, s), 2.43 (3H, s), 2.62 (3H, s), 3.44 (1H, dd, J=16.4, 7.2 Hz), 3.51 (1H, dd, J=16.4 7.2 Hz), 3.68 (3H, s), 4.54 (1H, t, J=7.2 Hz), 7.5-7.7 (3H, m), 7.81 (2H, d, J=8.4 Hz), 8.16 (1H, d, J=4.8 Hz)

MS (ESI) m/z: 488 (M+H)$^+$.

Example 80

Methyl (S)-{4-[4-(5-cyanopyridin-3-yl)phenyl]-2,3,9-trimethyl-6H-thieno[3,2-f][1,2,4]triazolo[4,3-a][1,4]diazepin-6-yl}acetate To a mixture of the compound described in Starting Material Synthetic Example 1 (4.9 g), dichlorobis(triphenylphosphine)palladium (II) (702 mg) and 3-bromo-5-cyanopyridine (6.8 g) were added tetrahydrofuran, (30 mL) and 2M aqueous sodium carbonate solution (30 mL), and the mixture was stirred at 100° C. for 6 hr. After cooling, water was added, and the mixture was extracted with chloroform. The organic layer was washed with saturated brine and dried over anhydrous sodium sulfate. The solvent was evaporated and the residue was purified by column chromatography (chloroform:methanol=100:1) and recrystallized from hexane-ethyl acetate to give the title compound (1.8 g).

$^1$H-NMR (400 MHz, DMSO-$d_6$) δ: 1.67 (3H, s), 2.44 (3H, s), 2.63 (3H, s), 3.45 (1H, dd, J=16.4, 6.8 Hz), 3.52 (1H, dd, J=16.4, 6.8 Hz), 3.69 (3H, s), 4.54 (1H, t, J=7.2 Hz), 7.55 (2H, t, J=8.0 Hz), 7.90 (2H, d, J=8.0 Hz), 8.70 (1H, t, J=1.6 Hz), 9.03 (1H, d, J=1.6 Hz), 9.23 (1H, d, J=1.6 Hz)

MS (ESI) m/z: 482 (M+H)$^+$.

Example 81

Methyl (S)-{2,3,9-trimethyl-4-(4-thiazole-2-ylphenyl)-6H-thieno[3,2-f][1,2,4]triazolo[4,3-a][1,4]diazepin-6-yl}acetate The title compound (93 mg) was obtained from the compound (492 mg) described in Starting Material Synthetic Example 1 by an operation in the same manner as in Example 80 and using 2-bromothiazole (180 µL) instead of 3-bromo-5-cyanopyridine.

$^1$H-NMR (400 MHz, DMSO-$d_6$) δ: 1.67 (3H, s), 2.43 (3H, s), 2.62 (3H, s), 3.41-3.54 (2H, m), 3.68 (3H, s), 4.53 (1H, t,

J=7.2 Hz), 7.54 (2H, d, J=8.4 Hz), 7.85 (1H, d, J=3.2 Hz), 7.97 (1H, d, J=3.2 Hz), 8.01 (2H, d, J=8.4 Hz)
MS (ESI) m/z: 464 (M+H)$^+$.

Example 82

Methyl (S)-{2,3,9-trimethyl-4-[4-(1-methyl-1H-pyrazol-4-yl)phenyl]-6H-thieno[3,2-f][1,2,4]triazolo[4,3-a][1,4]diazepin-6-yl}acetate The title compound (55 mg) was obtained from the compound (492 mg) described in Starting Material Synthetic Example 1 by an operation in the same manner as in Example 80 and using 1-methyl-4-iodo-1H-pyrazole (416 mg) instead of 3-bromo-5-cyanopyridine.
$^1$H-NMR (400 MHz, DMSO-d$_6$) δ: 1.67 (3H, s), 2.43 (3H, s), 2.61 (3H, s), 3.15 (3H, s), 3.39-3.52 (2H, m), 3.67 (3H, s), 4.48 (1H, t, J=7.2 Hz), 7.39 (2H, d, J=8.0 Hz), 7.59 (2H, d, J=8.0 Hz), 7.90 (1H, s), 8.19 (1H, s)
MS (ESI) m/z: 461 (M+H)$^+$.

Example 83

Methyl (S)-{4-[4-(5-bromothiazole-2-yl)phenyl]-2,3,9-trimethyl-6H-thieno[3,2-f][1,2,4]triazolo[4,3-a][1,4]diazepin-6-yl}acetate The title compound (183 mg) was obtained from the compound (1.5 g) described in Starting Material Synthetic Example 1 by an operation in the same manner as in Example 80 and using 2,5-dibromothiazole (1.5 g) instead of 3-bromo-5-cyanopyridine.
$^1$H-NMR (400 MHz, DMSO-d$_6$) δ: 1.66 (3H, s), 2.43 (3H, s), 2.62 (3H, s), 3.41-3.54 (2H, m), 3.68 (3H, s), 4.53 (1H, t, J=7.2 Hz), 7.54 (2H, d, J=8.0 Hz), 7.95 (2H, d, J=8.0 Hz), 8.04 (1H, s)
MS (ESI) m/z: 542 (M+H)$^+$.

Example 84

Methyl (S)-{4-[4-(4-cyanopyridin-2-yl)phenyl]-2,3,9-trimethyl-6H-thieno[3,2-f][1,2,4]triazolo[4,3-a][1,4]diazepin-6-yl}acetate The title compound (660 mg) was obtained from the compound (985 mg) described in Starting Material Synthetic Example 1 by an operation in the same manner as in Example 80 and using 2-chloro-4-cyanopyridine (1.1 g) instead of 3-bromo-5-cyanopyridine.
$^1$H-NMR (400 MHz, DMSO-d$_6$) δ: 1.66 (3H, s), 2.43 (3H, s), 2.63 (3H, s), 3.45 (1H, dd, J=16.4, 6.8 Hz), 3.52 (1H, dd, J=16.4, 6.8 Hz), 3.69 (3H, s), 4.54 (1H, t, J=7.6 Hz), 7.56 (2H, t, J=8.4 Hz), 7.84 (1H, d, J=5.6 Hz), 8.22 (2H, d, J=8.4 Hz), 8.53 (1H, s), 8.93 (1H, d, J=5.6 Hz)
MS (ESI) m/z: 483 (M+H)$^+$.

Example 85

Methyl (S)-{4-[4-(2-cyanopyridin-4-yl)phenyl]-2,3,9-trimethyl-6H-thieno[3,2-f][1,2,4]triazolo[4,3-a][1,4]diazepin-6-yl}acetate The title compound (1.9 g) was obtained from the compound (5.9 g) described in Starting Material Synthetic Example 1 by an operation in the same manner as in Example 80 and using 4-chloro-2-cyanopyridine (5.8 g) instead of 3-bromo-5-cyanopyridine.
$^1$H-NMR (400 MHz, DMSO-d$_6$) δ: 1.65 (3H, s), 2.43 (3H, s), 2.63 (3H, s), 3.45 (1H, dd, J=16.4, 6.8 Hz), 3.52 (1H, dd, J=16.4, 6.8 Hz), 3.69 (3H, s), 4.54 (1H, t, J=7.6 Hz), 7.57 (2H, t, J=8.0 Hz), 7.98 (2H, d, J=8.0 Hz), 8.11 (1H, dd, J=5.6, 1.6 Hz), 8.47 (1H, s), 8.82 (1H, d, J=5.6 Hz)
MS (ESI) m/z: 483 (M+H)$^+$.

Example 86

Methyl (S)-{4-[4-(6-chloropyrazin-2-yl)phenyl]-2,3,9-trimethyl-6H-thieno[3,2-f][1,2,4]triazolo[4,3-a][1,4]diazepin-6-yl}acetate The title compound (1.3 g) was obtained from the compound (2 g) described in Starting Material Synthetic Example 1 by an operation in the same manner as in Example 80 and using 2,6-dichloropyrazine (1.2 g) instead of 3-bromo-5-cyanopyridine.
$^1$H-NMR (400 MHz, DMSO-d$_6$) δ: 1.65 (3H, s), 2.43 (3H, s), 2.63 (3H, s), 3.45 (1H, dd, J=16.4, 6.8 Hz), 3.52 (1H, dd, J=16.4, 6.8 Hz), 3.69 (3H, s), 4.55 (1H, t, J=7.6 Hz), 7.58 (2H, d, J=8.4 Hz), 8.18 (2H, d, J=8.4 Hz), 8.78 (1H, s), 9.31 (1H, s)
MS (ESI) m/z: 492 (M+H)$^+$.

Example 87

Methyl (S)-{4-[4-(6-cyanopyridin-2-yl)phenyl]-2,3,9-trimethyl-6H-thieno[3,2-f][1,2,4]triazolo[4,3-a][1,4]diazepin-6-yl}acetate To a mixture of the compound described in Starting Material Synthetic Example 1 (985 mg), dichlorobis(triphenylphosphine)palladium (II) (70 mg), sodium carbonate (1.3 g) and 2-bromo-6-formylpyridine (1.5 g) were added tetrahydrofuran (6 mL) and water (6 mL), and the mixture was stirred at 100° C. for 3 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give methyl (S)-{4-[4-(6-formylpyridin-2-yl)phenyl]-2,3,9-trimethyl-6H-thieno[3,2-f][1,2,4]triazolo[4,3-a][1,4]diazepin-6-yl}acetate (860 mg). The obtained compound (860 mg) was dissolved in methylene chloride (5 mL). Triethylamine (305 μL) and hydroxylamine hydrochloride (153 mg) were successively added, and the mixture was stirred at room temperature for 24 hr. After completion of the reaction, 2-chloro-1,3-dimethyl-2-imidazolium tetrafluoroborate (613 mg) and triethylamine (610 μL) were successively added, and the mixture was stirred at room temperature for 3 hr. After completion of the reaction, water was added, and the mixture was extracted with chloroform. The organic layer was washed with saturated brine, dried over anhydrous sodium sulfate, and the solvent was evaporated. The residue was purified by column chromatography (chloroform:methanol=100:1) and recrystallized from hexane-ethyl acetate to give the title compound (483 mg).
$^1$H-NMR (400 MHz, DMSO-d$_6$) δ: 1.66 (3H, s), 2.43 (3H, s), 2.63 (3H, s), 3.45 (1H, dd, J=16.4, 6.8 Hz), 3.52 (1H, dd, J=16.4, 6.8 Hz), 3.69 (3H, s), 4.55 (1H, t, J=7.6 Hz), 7.57 (2H, d, J=8.0 Hz), 8.03 (1H, d, J=8.0 Hz), 8.1-8.2 (3H, m), 8.35 (1H, d, J=8.0 Hz)
MS (ESI) m/z: 483 (M+H)$^+$.

Example 88

Methyl (S)-{4-[4-(6-cyanopyrazin-2-yl)phenyl]-2,3,9-trimethyl-6H-thieno[3,2-f][1,2,4]triazolo[4,3-a][1,4]diazepin-6-yl}acetate To a mixture of the compound described in Example 86 (942 mg), zinc cyanide (135 mg), tris(dibenzylideneacetone)dipalladium (0) chloroform adduct (98 mg), diphenylphosphinoferrocene (105 mg) and zinc (15 mg) was added dimethylacetamide (6 mL), and the mixture was stirred at 130° C. for 6 hr. After cooling, aqueous potassium carbonate solution was added, and the mixture was extracted with ethyl acetate. The organic layer was washed with water and saturated brine, dried over anhydrous sodium sulfate, and the solvent was evaporated. The residue was purified by column chromatography (chloroform:methanol=100:1) and recrystallized from hexane-ethyl acetate to give the title compound (490 mg).

$^1$H-NMR (400 MHz, DMSO-$d_6$) δ: 1.65 (3H, s), 2.43 (3H, s), 2.63 (3H, s), 3.45 (1H, dd, J=16.4, 6.8 Hz), 3.52 (1H, dd, J=16.4, 6.8 Hz), 3.69 (3H, s), 4.55 (1H, t, J=7.6 Hz), 7.61 (2H, d, J=8.0 Hz), 8.23 (2H, d, J=8.0 Hz), 9.20 (1H, s), 9.61 (1H, s)

MS (ESI) m/z: 483 (M+H)$^+$.

Example 89

Methyl (S)-{2,3,9-trimethyl-4-[4-(4-trifluoromethylpyrimidin-2-yl)phenyl]-6H-thieno[3,2-f][1,2,4]triazolo[4,3-a][1,4]diazepin-6-yl}acetate The title compound (333 mg) was obtained from the compound (985 mg) described in Starting Material Synthetic Example 1 by an operation in the same manner as in Example 80 and using 2-chloro-4-trifluoromethylpyrimidine (480 µL) instead of 3-bromo-5-cyanopyridine.

$^1$H-NMR (400 MHz, DMSO-$d_6$) δ: 1.65 (3H, s), 2.43 (3H, s), 2.63 (3H, s), 3.45 (1H, dd, J=16.4, 6.8 Hz), 3.52 (1H, dd, J=16.4, 6.8 Hz), 3.69 (3H, s), 4.55 (1H, t, J=7.6 Hz), 7.63 (2H, d, J=8.0 Hz), 7.99 (1H, d, J=5.0 Hz), 8.45 (2H, d, J=8.0 Hz), 9.30 (1H, d, J=5.0 Hz)

MS (ESI) m/z: 527 (M+H)$^+$.

Example 90

Methyl (S)-{4-[4-(6-chloropyrimidin-4-yl)phenyl]-2,3,9-trimethyl-6H-thieno[3,2-f][1,2,4]triazolo[4,3-a][1,4]diazepin-6-yl}acetate The title compound (1.4 g) was obtained from the compound (2 g) described in Starting Material Synthetic Example 1 by an operation in the same manner as in Example 80 and using 4,6-dichloropyrimidine (1.2 g) instead of 3-bromo-5-cyanopyridine.

$^1$H-NMR (400 MHz, DMSO-$d_6$) δ: 1.64 (3H, s), 2.43 (3H, s), 2.63 (3H, s), 3.45 (1H, dd, J=16.4, 6.8 Hz), 3.52 (1H, dd, J=16.4, 6.8 Hz), 3.69 (3H, s), 4.55 (1H, t, J=7.6 Hz), 7.59 (2H, d, J=8.4 Hz), 8.31 (2H, d, J=8.4 Hz), 8.36 (1H, s), 9.12 (1H, s)

MS (ESI) m/z: 493 (M+H)$^+$.

Example 91

Methyl (S)-{4-[4-(6-cyanopyrimidin-4-yl)phenyl]-2,3,9-trimethyl-6H-thieno[3,2-f][1,2,4]triazolo[4,3-a][1,4]diazepin-6-yl}acetate The title compound (166 mg) was obtained by an operation in the same manner as in Example 88 and using the compound (942 mg) described in Example 90 instead of the compound described in Example 86.

$^1$H-NMR (400 MHz, DMSO-$d_6$) δ: 1.64 (3H, s), 2.43 (3H, s), 2.63 (3H, s), 3.45 (1H, dd, J=16.4, 6.8 Hz), 3.52 (1H, dd, J=16.4, 6.8 Hz), 3.69 (3H, s), 4.55 (1H, t, J=7.6 Hz), 7.62 (2H, d, J=8.4 Hz), 8.34 (2H, d, J=8.4 Hz), 8.83 (1H, s), 9.45 (1H, s)

MS (ESI) m/z: 483 (M+H)$^+$.

Example 92

Methyl (S)-{2,3,9-trimethyl-4-[4-(pyrimidin-5-yl)phenyl]-6H-thieno[3,2-f][1,2,4]triazolo[4,3-a][1,4]diazepin-6-yl}acetate The title compound (155 mg) was obtained from the compound (492 mg) described in Starting Material Synthetic Example 1 by an operation in the same manner as in Example 80 and using 5-bromopyrimidine (477 mg) instead of 3-bromo-5-cyanopyridine.

$^1$H-NMR (400 MHz, DMSO-$d_6$) δ: 1.67 (3H, s), 2.44 (3H, s), 2.63 (3H, s), 3.45-3.50 (2H, m), 3.69 (3H, s), 4.54 (1H, t, J=7.0 Hz), 7.56 (2H, d, J=8.0 Hz), 7.90 (2H, d, J=8.0 Hz), 9.19 (2H, s), 9.21 (1H, s)

MS (ESI) m/z: 459 (M+H)$^+$.

Example 93

Methyl (S)-{4-[4-(2-methylsulfonylpyrimidin-4-yl)phenyl]-2,3,9-trimethyl-6H-thieno[3,2-f][1,2,4]triazolo[4,3-a][1,4]diazepin-6-yl}acetate The intermediate of methyl (S)-{4-[4-(2-methylthiopyrimidin-4-yl)phenyl]-2,3,9-trimethyl-6H-thieno[3,2-f][1,2,4]triazolo[4,3-a][1,4]diazepin-6-yl}acetate (1.3 g) was obtained by an operation in the same manner as in Example 80 and using 4-chloro-2-(methylthio)pyrimidine (930 µL) instead of 3-bromo-5-cyanopyridine, and the title compound (1.3 g) was obtained by an operation in the same manner as in Example 3 and using the obtained compound.

$^1$H-NMR (400 MHz, DMSO-$d_6$) δ: 1.65 (3H, s), 2.43 (3H, s), 2.63 (3H, s), 3.45 (1H, dd, J=16.4, 6.8 Hz), 3.49 (3H, s), 3.52 (1H, dd, J=16.4, 6.8 Hz), 3.69 (3H, s), 4.56 (1H, t, J=7.6 Hz), 7.63 (2H, d, J=8.4 Hz), 8.31 (1H, s), 8.35 (2H, d, J=8.4 Hz), 8.43 (1H, d, J=5.6 Hz)

MS (ESI) m/z: 537 (M+H)$^+$.

Example 94

Methyl (S)-{4-[4-(2-cyanopyrimidin-4-yl)phenyl]-2,3,9-trimethyl-6H-thieno[3,2-f][1,2,4]triazolo[4,3-a][1,4]diazepin-6-yl}acetate To a mixture of the compound described in Example 93 (900 mg) and sodium cyanide (124 mg) was added dimethyl sulfoxide (6 mL), and the mixture was stirred at 100° C. for 3 hr. After cooling, aqueous potassium carbonate solution was added, and the mixture was extracted with chloroform. The organic layer was washed with water and saturated brine, dried over anhydrous sodium sulfate, and the solvent was evaporated. The residue was purified by column chromatography (chloroform:methanol=100:1) to give the title compound (335 mg).

$^1$H-NMR (400 MHz, DMSO-d$_6$) δ: 1.64 (3H, s), 2.43 (3H, s), 2.63 (3H, s), 3.45 (1H, dd, J=16.4, 6.8 Hz), 3.52 (1H, dd, J=16.4, 6.8 Hz), 3.69 (3H, s), 4.55 (1H, t, J=7.6 Hz), 7.63 (2H, d, J=8.4 Hz), 8.31 (2H, d, J=8.4 Hz), 8.46 (1H, d, J=5.6 Hz), 9.09 (1H, d, J=5.6 Hz)

MS (ESI) m/z: 484 (M+H)$^+$.

Example 95

Methyl (S)-{2,3,9-trimethyl-4-[4-(1H-pyrazol-4-yl)phenyl]-6H-thieno[3,2-f][1,2,4]triazolo[4,3-a][1,4]diazepin-6-yl}acetate To a mixture of the compound described in Starting Material Synthetic Example 1 (420 mg), tetrakistriphenylphosphine palladium (58 mg) and 4-iodo-1-trityl-1H-pyrazole (654 mg) were added tetrahydrofuran (1.5 mL) and 2 M aqueous sodium carbonate solution (1.5 mL), and the mixture was stirred at 100° C. for 4 hr. After cooling, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) to give compound (729 mg). The obtained compound (729 mg) was dissolved in methanol (3 mL). Trifluoroacetic acid (154 μL) was added, and the mixture was stirred at room temperature for 2 days. After completion of the reaction, the mixture was neutralized with aqueous sodium hydroxide solution and extracted with ethyl acetate. The organic layer was washed with saturated brine, dried over anhydrous sodium sulfate, and the solvent was evaporated. The residue was purified by column chromatography (chloroform:methanol=100:1) to give the title compound (162 mg).

$^1$H-NMR (400 MHz, DMSO-d$_6$) δ: 2.67 (3H, s), 2.43 (3H, s), 2.62 (3H, s), 3.39-3.52 (2H, m), 3.68 (3H, s), 4.49 (1H, t, J=7.2 Hz), 7.39 (2H, d, J=8.2 Hz), 7.65 (2H, d, J=8.2 Hz), 8.11 (2H, brs)

MS (ESI) m/z: 447 (M+H)$^+$.

Example 96

Ethyl (S)-{2,3,9-trimethyl-4-[4-(pyridin-3-yl)phenyl]-6H-thieno[3,2-f][1,2,4]triazolo[4,3-a][1,4]diazepin-6-yl}acetate To a mixture of the compound described in Starting Material Synthetic Example 2 (1.5 g) and dichlorobis(triphenylphosphine)palladium (II) (105 mg) were successively added tetrahydrofuran (7.5 mL), 2 M aqueous sodium carbonate solution (7.5 mL) and 3-bromopyridine (590 μL), and the mixture was stirred at 100° C. for 3 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (287 mg).

$^1$H-NMR (400 MHz, DMSO-d$_6$) δ: 1.1-1.4 (3H, m), 1.69 (3H, s), 2.44 (3H, s), 2.62 (3H, s), 3.3-3.5 (2H, m), 4.0-4.2 (2H, m), 4.52 (1H, t, J=7.2 Hz), 7.4-7.6 (3H, m), 7.81 (2H, d, J=8.4 Hz), 8.12 (1H, d, J=8.0 Hz), 8.60 (1H, d, J=4.4 Hz), 8.93 (1H, d, J=1.6 Hz)

MS (ESI) m/z: 471 (M+H)$^+$.

Example 97

Ethyl (S)-{2,3,9-trimethyl-4-(4-pyrimidin-5-ylphenyl)-6H-thieno[3,2-f][1,2,4]triazolo[4,3-a][1,4]diazepin-6-yl}acetate The title compound (354 mg) was obtained from the compound (1 g) described in Starting Material Synthetic Example 2 by an operation in the same manner as in Example 96 and using 5-bromopyrimidine (636 mg) instead of 3-bromopyridine.

$^1$H-NMR (400 MHz, DMSO-d$_6$) δ: 1.1-1.4 (3H, m), 1.67 (3H, s), 2.44 (3H, s), 2.63 (3H, s), 3.3-3.6 (2H, m), 4.0-4.3 (2H, m), 4.53 (1H, t, J=7.6 Hz), 7.56 (2H, d, J=8.0 Hz), 7.89 (2H, d, J=8.0 Hz), 9.19 (2H, s), 9.21 (1H, s)

MS (ESI) m/z: 473 (M+H)$^+$.

Example 98

Ethyl (S)-{4-[4-(5-cyanopyridin-2-yl)phenyl]-2,3,9-trimethyl-6H-thieno[3,2-f][1,2,4]triazolo[4,3-a][1,4]diazepin-6-yl}acetate The title compound (284 mg) was obtained from the compound (506 mg) described in Starting Material Synthetic Example 2 by an operation in the same manner as in Example 96 and using 2-chloro-5-cyanopyridine (831 mg) instead of 3-bromopyridine.

$^1$H-NMR (400 MHz, DMSO-d$_6$) δ: 1.23 (3H, t, J=7.6 Hz), 1.66 (3H, s), 2.43 (3H, s), 2.62 (3H, s), 3.3-3.6 (2H, m), 4.0-4.3 (2H, m), 4.53 (1H, t, J=7.6 Hz), 7.58 (2H, d, J=8.0 Hz), 8.23 (2H, d, J=8.0 Hz), 8.25 (1H, d, J=8.0 Hz), 8.42 (1H, d, J=8.0, 1.2 Hz), 9.11 (1H, d, J=1.2 Hz),

MS (ESI) m/z: 497 (M+H)$^+$.

Example 99

Ethyl (S)-{4-[4-(5-carbamoylpyridin-3-yl)phenyl]-2,3,9-trimethyl-6H-thieno[3,2-f][1,2,4]triazolo[4,3-a][1,4]diazepin-6-yl}acetate The title compound (449 mg) was obtained from the compound (2.1 g) described in Starting Material Synthetic Example 2 by an operation in the same manner as in Example 96 and using 5-bromonicotinamide (201 mg) instead of 3-bromopyridine.

$^1$H-NMR (400 MHz, DMSO-d$_6$) δ: 1.23 (3H, t, J=7.2 Hz), 1.68 (3H, s), 2.44 (3H, s), 2.63 (3H, s), 3.3-3.6 (2H, m), 4.0-4.3 (2H, m), 4.53 (1H, t, J=7.6 Hz), 7.56 (2H, d, J=8.4 Hz), 7.67 (1H, s), 7.88 (2H, d, J=8.4 Hz), 8.26 (1H, s), 8.49 (1H, t, J=2.0 Hz), 9.02 (1H, d, J=2.0 Hz), 9.06 (1H, d, J=2.0 Hz)

MS (ESI) m/z: 515 (M+H)$^+$.

Example 100

Ethyl (S)-{4-[4-(4-carbamoylpyridin-2-yl)phenyl]-2,3,9-trimethyl-6H-thieno[3,2-f][1,2,4]triazolo[4,3-a][1,4]diazepin-6-yl}acetate The title compound (126 mg) was obtained from the compound (1.5 g) described in Starting Material Synthetic Example 2 by an operation in the same manner as in Example 96 and using 2-chloroisonicotinamide (620 mg) instead of 3-bromopyridine.

¹H-NMR (400 MHz, DMSO-d₆) δ: 1.24 (3H, t, J=7.2 Hz), 1.67 (3H, s), 2.43 (3H, s), 2.63 (3H, s), 3.3-3.6 (2H, m), 4.0-4.3 (2H, m), 4.53 (1H, t, J=7.6 Hz), 7.56 (2H, d, J=8.0 Hz), 7.7-7.8 (2H, m), 8.19 (2H, d, J=8.0 Hz), 8.3-8.4 (2H, m), 8.81 (1H, d, J=4.8 Hz)

MS (ESI) m/z: 515 (M+H)⁺.

Example 101

Ethyl (S)-{4-[4-(4-cyanopyridin-2-yl)phenyl]-2,3,9-trimethyl-6H-thieno[3,2-f][1,2,4]triazolo[4,3-a]-[1,4]diazepin-6-yl}acetate The title compound (347 mg) was obtained from the compound (500 mg) described in Starting Material Synthetic Example 2 by an operation in the same manner as in Example 96 and using 2-chloro-4-cyanopyridine (831 mg) instead of 3-bromopyridine.

¹H-NMR (400 MHz, DMSO-d₆) δ: 1.25 (3H, t, J=7.2 Hz), 1.66 (3H, s), 2.43 (3H, s), 2.63 (3H, s), 3.3-3.6 (2H, m), 4.0-4.3 (2H, m), 4.53 (1H, t, J=7.6 Hz), 7.56 (2H, d, J=8.0 Hz), 7.85 (1H, d, J=5.2 Hz), 8.22 (2H, d, J=8.0 Hz), 8.53 (1H, s), 8.93 (1H, d, J=5.2 Hz)

MS (ESI) m/z: 497 (M+H)⁺.

Example 102

Ethyl (S)-{4-[4-(6-aminopyridin-2-yl)phenyl]-2,3,9-trimethyl-6H-thieno[3,2-f][1,2,4]triazolo[4,3-a][1,4]diazepin-6-yl}acetate The title compound (343 mg) was obtained from the compound (506 mg) described in Starting Material Synthetic Example 2 by an operation in the same manner as in Example 96 and using 2-amino-6-bromopyridine (1 g) instead of 3-bromopyridine.

¹H-NMR (400 MHz, DMSO-d₆) δ: 1.23 (3H, t, J=7.2 Hz), 1.66 (3H, s), 2.43 (3H, s), 2.62 (3H, s), 3.3-3.6 (2H, m), 4.0-4.3 (2H, m), 4.51 (1H, t, J=7.6 Hz), 6.03 (2H, brs), 6.45 (1H, d, J=8.0 Hz), 7.09 (1H, d, J=8.0 Hz), 7.47 (3H, m), 8.00 (2H, d, J=8.0 Hz)

MS (ESI) m/z: 486 (M+H)⁺.

Example 103

Ethyl (S)-{4-[4-(6-methoxypyridin-2-yl)phenyl]-2,3,9-trimethyl-6H-thieno[3,2-f][1,2,4]triazolo[4,3-a][1,4]diazepin-6-yl}acetate The title compound (2.8 g) was obtained from the compound (6.1 g) described in Starting Material Synthetic Example 2 by an operation in the same manner as in Example 96 and using 2-bromo-6-methoxypyridine (8.8 mL) instead of 3-bromopyridine.

¹H-NMR (300 MHz, DMSO-d₆) δ: 1.23 (3H, t, J=7.5 Hz), 1.67 (3H, s), 2.43 (3H, s), 2.63 (3H, s), 3.3-3.6 (2H, m), 3.95 (3H, s), 4.0-4.3 (2H, m), 4.54 (1H, t, J=7.6 Hz), 6.82 (1H, d, J=8.1 Hz), 7.52 (2H, d, J=8.4 Hz), 7.61 (1H, d, J=8.1 Hz), 7.80 (1H, d, J=8.1 Hz), 8.15 (2H, d, J=8.4 Hz)

MS (ESI) m/z: 502 (M+H)⁺.

Example 104

Ethyl (S)-{2,3,9-trimethyl-4-(4-pyrazin-2-ylphenyl)-6H-thieno[3,2-f][1,2,4]triazolo[4,3-a][1,4]diazepin-6-yl}acetate The title compound (292 mg) was obtained from the compound (500 mg) described in Starting Material Synthetic Example 2 by an operation in the same manner as in Example 96 and using chloropyrazine (530 μL) instead of 3-bromopyridine.

¹H-NMR (400 MHz, DMSO-d₆) δ: 1.2-1.3 (3H, m), 1.67 (3H, s), 2.43 (3H, s), 2.63 (3H, s), 3.3-3.6 (2H, m), 4.0-4.3 (2H, m), 4.54 (1H, t, J=7.6 Hz), 7.58 (2H, d, J=8.4 Hz), 8.20 (2H, d, J=8.4 Hz), 8.65 (1H, d, J=1.6 Hz), 8.75 (1H, s), 9.30 (1H, s)

MS (ESI) m/z: 472 (M+H)⁺.

Example 105

Ethyl (S)-{4-[4-(6-cyanopyridin-2-yl)phenyl]-2,3,9-trimethyl-6H-thieno[3,2-f][1,2,4]triazolo[4,3-a][1,4]diazepin-6-yl}acetate Ethyl (S)-{4-[4-(6-formylpyridin-2-yl)phenyl]-2,3,9-trimethyl-6H-thieno[3,2-f][1,2,4]triazolo[4,3-a][1,4]diazepin-6-yl}acetate (1.4 g) was obtained from the compound (1.5 g) described in Starting Material Synthetic Example 2 by an operation in the same manner as in Example 96 and using 2-bromo-6-formylpyridine (3.3 g) instead of 3-bromopyridine. The obtained compound (1.4 g) was dissolved in methylene chloride (10 mL), triethylamine (590 μL) and hydroxylamine hydrochloride (292 mg) were added, and the mixture was stirred at room temperature for 24 hr. After completion of the reaction, water was added, and the mixture was extracted with methylene chloride. To the extract were added 2-chloro-1,3-dimethyl-2-imidazolium tetrafluoroborate (780 mg) and triethylamine (780 μL), and the mixture was stirred at room temperature for 24 hr. After completion of the reaction, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give an amorphous form. The obtained amorphous form was dissolved in ethyl acetate, a solution of p-toluenesulfonic acid-monohydrate (540 mg) in ethyl acetate was added to give an oil. The supernatant was removed and hexane was added. The oil was crystallized to give the title compound (1.2 g).

¹H-NMR (400 MHz, DMSO-d₆) δ: 1.24 (3H, t, J=7.2 Hz), 1.66 (3H, s), 2.29 (3H×1.7, s), 2.44 (3H, s), 2.63 (1H×1.7, s), 2.68 (3H, s), 3.3-3.6 (2H, m), 4.0-4.3 (2H, m), 4.60 (1H, t, J=7.6 Hz), 7.12 (2H×1.7, d, J=7.6 Hz), 7.49 (2H×1.7, d, J=7.6 Hz), 7.61 (2H, d, J=8.4 Hz), 8.03 (1H, d, J=8.0 Hz), 8.1-8.2 (3H, m), 8.35 (1H, d, J=8.0 Hz)

MS (ESI) m/z: 496 (M+H)⁺.

Example 106

Ethyl (S)-{4-[4-(5-acetylpyridin-3-yl)phenyl]-2,3,9-trimethyl-6H-thieno[3,2-f][1,2,4]triazolo[4,3-a][1,4]diazepin-6-yl}acetate The title compound was obtained from the compound (750 mg) described in Starting Material Synthetic Example 2 by an operation in the same manner as in Example 96 and using 3-acetyl-5-bromopyridine (1.2 g) instead of 3-bromopyridine.

¹H-NMR (400 MHz, DMSO-d₆) δ: 1.23 (3H, t, J=7.2 Hz), 1.68 (3H, s), 2.44 (3H, s), 2.69 (3H, s), 2.71 (3H, s), 3.3-3.6 (2H, m), 4.0-4.3 (2H, m), 4.53 (1H, t, J=7.6 Hz), 7.56 (2H, d, J=8.0 Hz), 7.90 (2H, d, J=8.0 Hz), 8.51 (1H, s), 9.12 (1H, d, J=1.6 Hz), 9.15 (1H, d, J=1.6 Hz)

MS (ESI) m/z: 514 (M+H)⁺.

Example 107

Ethyl (S)-[2,3,9-trimethyl-4-(4-pyrimidin-2-ylphenyl)-6H-thieno[3,2-f][1,2,4]triazolo[4,3-a][1,4]diazepin-6-yl]acetate The title compound was obtained from the compound (750 mg) described in Starting Material Synthetic Example 2 by an operation in the same manner as in Example 96 and using 2-chloropyrimidine (687 mg) instead of 3-bromopyridine.

$^1$H-NMR (400 MHz, DMSO-$d_6$) δ: 1.23 (3H, t, J=7.2 Hz), 1.66 (3H, s), 2.43 (3H, s), 2.63 (3H, s), 3.3-3.6 (2H, m), 4.0-4.3 (2H, m), 4.53 (1H, t, J=7.6 Hz), 7.48 (1H, t, J=5.2 Hz), 7.57 (2H, d, J=8.0 Hz), 8.43 (2H, d, J=8.0 Hz), 8.93 (2H, d, J=5.2 Hz)

MS (ESI) m/z: 473 (M+H)$^+$.

Example 108

Ethyl (S)-{4-[4-(2-fluoropyridin-5-yl)phenyl]-2,3,9-trimethyl-6H-thieno[3,2-f][1,2,4]triazolo[4,3-a][1,4]diazepin-6-yl}acetate The title compound (368 mg) was obtained from the compound (750 mg) described in Starting Material Synthetic Example 2 by an operation in the same manner as in Example 96 and using 5-bromo-2-fluoropyridine (1.1 g) instead of 3-bromopyridine.

$^1$H-NMR (400 MHz, DMSO-$d_6$) δ: 1.23 (3H, t, J=7.2 Hz), 1.68 (3H, s), 2.43 (3H, s), 2.62 (3H, s), 3.3-3.6 (2H, m), 4.0-4.3 (2H, m), 4.52 (1H, t, J=7.6 Hz), 7.30 (1H, dd, J=8.4, 2.8 Hz), 7.90 (2H, d, J=8.4 Hz), 7.80 (2H, d, J=8.4 Hz), 8.33 (1H, dt, J=8.4, 2.8 Hz), 8.60 (1H, s)

MS (ESI) m/z: 490 (M+H)$^+$.

Example 109

Ethyl (S)-{2,3,9-trimethyl-4-(4-pyridin-2-ylphenyl)-6H-thieno[3,2-f][1,2,4]triazolo[4,3-a][1,4]diazepin-6-yl}acetate The title compound was obtained from the compound (750 mg) described in Starting Material Synthetic Example 2 by an operation in the same manner as in Example 96 and using 2-chloropyridine (560 μL) instead of 3-bromopyridine.

$^1$H-NMR (400 MHz, DMSO-$d_6$) δ: 1.23 (3H, t, J=7.2 Hz), 1.67 (3H, s), 2.43 (3H, s), 2.63 (3H, s), 3.3-3.6 (2H, m), 4.0-4.3 (2H, m), 4.52 (1H, t, J=7.6 Hz), 7.39 (1H, dd, J=7.6, 5.2 Hz), 7.53 (2H, d, J=8.4 Hz), 7.9-8.0 (1H, m), 8.01 (1H, d, J=8.0 Hz), 8.15 (2H, d, J=8.4 Hz), 8.68 (1H, d, J=5.2 Hz)

MS (ESI) m/z: 472 (M+H)$^+$.

Example 110

Ethyl (S)-{4-[4-(5-cyanopyridin-3-yl)phenyl]-2,3,9-trimethyl-6H-thieno[3,2-f][1,2,4]triazolo[4,3-a][1,4]diazepin-6-yl}acetate The title compound (636 mg) was obtained from the compound (1 g) described in Starting Material Synthetic Example 2 by an operation in the same manner as in Example 96 and using 3-bromo-5-cyanopyridine (684 mg) instead of 3-bromopyridine.

$^1$H-NMR (400 MHz, DMSO-$d_6$) δ: 1.23 (3H, t, J=7.2 Hz), 1.67 (3H, s), 2.44 (3H, s), 2.62 (3H, s), 3.3-3.6 (2H, m), 4.0-4.3 (2H, m), 4.53 (1H, t, J=7.6 Hz), 7.55 (2H, d, J=8.0 Hz), 7.91 (2H, d, J=8.0 Hz), 8.70 (1H, d, J=1.6 Hz), 9.03 (1H, d, J=1.6 Hz), 9.23 (1H, d, J=1.6 Hz)

MS (ESI) m/z: 497 (M+H)$^+$.

Example 111

Ethyl (S)-{4-[4-(6-chloropyrimidin-4-yl)phenyl]-2,3,9-trimethyl-6H-thieno[3,2-f][1,2,4]triazolo[4,3-a][1,4]diazepin-6-yl}acetate The title compound (2.1 g) was obtained from the compound (3 g) described in Starting Material Synthetic Example 2 by an operation in the same manner as in Example 96 and using 4,6-dichloropyrimidine (1.79 g) instead of 3-bromopyridine.

$^1$H-NMR (400 MHz, DMSO-$d_6$) δ: 1.23 (3H, t, J=7.2 Hz), 1.67 (3H, s), 2.44 (3H, s), 2.62 (3H, s), 3.3-3.6 (2H, m), 4.0-4.3 (2H, m), 4.53 (1H, t, J=7.6 Hz), 7.58 (2H, d, J=8.4 Hz), 8.31 (2H, d, J=8.4 Hz), 8.36 (1H, s), 9.12 (1H, s)

MS (ESI) m/z: 507 (M+H)$^+$.

Example 112

Ethyl (S)-{4-[4-(6-chloropyrazin-2-yl)phenyl]-2,3,9-trimethyl-6H-thieno[3,2-f][1,2,4]triazolo[4,3-a][1,4]diazepin-6-yl}acetate The title compound (1.4 g) was obtained from the compound (2 g) described in Starting Material Synthetic Example 2 by an operation in the same manner as in Example 96 and using 2,6-dichloropyrazine (1.2 g) instead of 3-bromopyridine.

$^1$H-NMR (400 MHz, DMSO-$d_6$) δ: 1.23 (3H, t, J=7.2 Hz), 1.67 (3H, s), 2.44 (3H, s), 2.62 (3H, s), 3.3-3.6 (2H, m), 4.0-4.3 (2H, m), 4.53 (1H, t, J=7.6 Hz), 7.58 (2H, d, J=8.4 Hz), 8.19 (2H, d, J=8.4 Hz), 8.79 (1H, s), 9.32 (1H, s)

MS (ESI) m/z: 506 (M+H)$^+$.

Example 113

Ethyl (S)-{4-[4-(6-cyanopyrazin-2-yl)phenyl]-2,3,9-trimethyl-6H-thieno[3,2-f][1,2,4]triazolo[4,3-a][1,4]diazepin-6-yl}acetate The title compound (259 mg) was obtained by an operation in the same manner as in Example 88 and using the compound (963 mg) described in Example 112 instead of the compound described in Example 86.

$^1$H-NMR (400 MHz, DMSO-$d_6$) δ: 1.24 (3H, t, J=7.2 Hz), 1.65 (3H, s), 2.45 (3H, s), 2.63 (3H, s), 3.3-3.6 (2H, m), 4.0-4.3 (2H, m), 4.54 (1H, t, J=7.6 Hz), 7.61 (2H, d, J=8.4 Hz), 8.24 (2H, d, J=8.4 Hz), 9.20 (1H, s), 9.61 (1H, s)

MS (ESI) m/z: 498 (M+H)$^+$.

Example 114

Ethyl (S)-{2,3,9-trimethyl-4-(4-thiazole-2-ylphenyl)-6H-thieno[3,2-f][1,2,4]triazolo[4,3-a][1,4]diazepin-6-yl}acetate The title compound (215 mg) was obtained from the compound (1 g) described in Starting Material Synthetic Example 2 by an operation in the same manner as in Example 96 and using 2-bromothiazole (900 μL) instead of 3-bromopyridine.

$^1$H-NMR (400 MHz, DMSO-$d_6$) δ: 1.38 (3H, d, J=7.2 Hz), 1.67 (3H, s), 2.43 (3H, s), 2.63 (3H, s), 3.46 (2H, t, J=7.3 Hz), 4.11-4.21 (2H, m), 4.54 (1H, t, J=7.3 Hz), 7.55 (2H, d, J=8.2 Hz), 7.85 (1H, d, J=3.2 Hz), 7.97 (1H, d, J=3.2 Hz), 8.01 (2H, d, J=8.2 Hz)
MS (ESI) m/z: 478 (M+H)$^+$.

Example 115

Ethyl (S)-{4-[4-(6-cyanopyrimidin-4-yl)phenyl]-2,3,9-trimethyl-6H-thieno[3,2-f][1,2,4]triazolo[4,3-a][1,4]diazepin-6-yl}acetate The title compound (397 mg) was obtained by an operation in the same manner as in Example 88 and using the compound (820 mg) described in Example 111 instead of the compound described in Example 86.
$^1$H-NMR (400 MHz, DMSO-d$_6$) δ: 1.23 (3H, t, J=7.2 Hz), 1.64 (3H, s), 2.43 (3H, s), 2.63 (3H, s), 3.3-3.6 (2H, m), 4.0-4.3 (2H, m), 4.54 (1H, t, J=7.6 Hz), 7.62 (2H, d, J=8.4 Hz), 8.35 (2H, d, J=8.4 Hz), 8.83 (1H, s), 9.45 (1H, s)
MS (ESI) m/z: 497 (M+H)$^+$.

Example 116

Ethyl (S)-{4-[4-(2-cyanopyridin-4-yl)phenyl]-2,3,9-trimethyl-6H-thieno[3,2-f][1,2,4]triazolo[4,3-a][1,4]diazepin-6-yl}acetate The title compound (790 mg) was obtained from the compound (1.5 mg) described in Starting Material Synthetic Example 2 by an operation in the same manner as in Example 96 and using 4-chloro-2-cyanopyridine (831 mg) instead of 3-bromopyridine.
$^1$H-NMR (400 MHz, DMSO-d$_6$) δ: 1.23 (3H, t, J=7.2 Hz), 1.65 (3H, s), 2.43 (3H, s), 2.63 (3H, s), 3.3-3.6 (2H, m), 4.0-4.3 (2H, m), 4.53 (1H, t, J=7.6 Hz), 7.57 (2H, d, J=8.4 Hz), 7.98 (2H, d, J=8.4 Hz), 8.11 (1H, dd, J=5.2, 1.6 Hz), 8.47 (1H, d, J=1.6 Hz), 8.82 (1H, d, J=5.2 Hz)
MS (ESI) m/z: 497 (M+H)$^+$.

Example 117

Ethyl (S)-{4-[4-(5-methoxypyridin-3-yl)phenyl]-2,3,9-trimethyl-6H-thieno[3,2-f][1,2,4]triazolo[4,3-a][1,4]diazepin-6-yl}acetate The title compound (414 mg) was obtained from the compound (1.5 g) described in Starting Material Synthetic Example 2 by an operation in the same manner as in Example 96 and using 3-bromo-5-methoxypyridine (1.1 g) instead of 3-bromopyridine.
$^1$H-NMR (400 MHz, DMSO-d$_6$) δ: 1.23 (3H, t, J=7.2 Hz), 1.65 (3H, s), 2.43 (3H, s), 2.63 (3H, s), 3.3-3.6 (2H, m), 4.0-4.3 (2H, m), 4.53 (1H, t, J=7.6 Hz), 7.53 (2H, d, J=8.4 Hz), 7.66 (1H, t, J=1.6 Hz), 7.83 (2H, d, J=8.4 Hz), 8.31 (1H, d, J=1.6 Hz), 8.52 (1H, d, J=1.6 Hz)
MS (ESI) m/z: 501 (M+H)$^+$.

Example 118

Ethyl (S)-{4-[4-(5-bromopyridin-3-yl)phenyl]-2,3,9-trimethyl-6H-thieno[3,2-f][1,2,4]triazolo[4,3-a][1,4]diazepin-6-yl}acetate The title compound (1.6 g) was obtained from the compound (5.5 g) described in Starting Material Synthetic Example 2 by an operation in the same manner as in Example 96 and using 3,5-dibromopyridine (3.7 g) instead of 3-bromopyridine.
$^1$H-NMR (400 MHz, DMSO-d$_6$) δ: 1.23 (3H, t, J=7.2 Hz), 1.67 (3H, s), 2.43 (3H, s), 2.62 (3H, s), 3.3-3.6 (2H, m), 4.0-4.3 (2H, m), 4.52 (1H, t, J=7.6 Hz), 7.53 (2H, d, J=8.4 Hz), 7.86 (2H, d, J=8.4 Hz), 8.11 (1H, t, J=2.2 Hz), 8.72 (1H, d, J=2.0 Hz), 8.94 (1H, d, J=2.0 Hz)
MS (ESI) m/z: 550 (M+H)$^+$.

Example 119

Ethyl (S)-{4-[4-(6-butylaminopyrimidin-4-yl)phenyl]-2,3,9-trimethyl-6H-thieno[3,2-f][1,2,4]triazolo[4,3-a][1,4]diazepin-6-yl}acetate To a mixture of the compound (1.0 g) described in Example 111, palladium acetate (22 mg), 2-(dicyclohexylphosphino)biphenyl (70 mg) and tripotassium phosphate (594 mg) were successively added dimethoxyethane (4 mL) and n-butylamine (300 μL), and the mixture was heated under reflux for 8 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (833 mg).
$^1$H-NMR (400 MHz, DMSO-d$_6$) δ: 0.91 (3H, t, J=7.2 Hz), 1.2-1.6 (9H, m), 1.65 (3H, s), 2.43 (3H, s), 2.62 (3H, s), 3.3-3.6 (2H, m), 4.0-4.3 (2H, m), 4.52 (1H, t, J=7.6 Hz), 6.94 (1H, s), 7.45 (1H, brs), 7.53 (2H, d, J=8.0 Hz), 8.03 (2H, brs), 8.48 (1H, s)
MS (ESI) m/z: 544 (M+H)$^+$.

Example 120

Methyl (S)-{2,3,9-trimethyl-4-(4-phenylaminophenyl)-6H-thieno[3,2-f][1,2,4]triazolo[4,3-a][1,4]diazepin-6-yl}acetate To a mixture of the compound (415 mg) described in Example 1, palladium acetate (11 mg), 2-(dicyclohexylphosphino)biphenyl (36 mg) and tripotassium phosphate (298 mg) were successively added dimethoxyethane (2 mL) and aniline (150 μL), and the mixture was heated under reflux for 8 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (436 mg).
$^1$H-NMR (270 MHz, DMSO-d$_6$) δ: 1.75 (3H, s), 2.43 (3H, s), 2.59 (3H, s), 3.3-3.6 (2H, m), 3.66 (3H, s), 4.43 (1H, t, J=7.3 Hz), 6.90 (1H, t, J=7.3 Hz), 7.03 (2H, d, J=8.6 Hz), 7.12 (2H, d, J=8.6 Hz), 7.25 (2H, d, J=7.6 Hz), 7.28 (2H, d, J=7.6 Hz), 8.56 (1H, s)
MS (ESI) m/z: 472 (M+H)$^+$.

Example 121

Methyl (S)-{4-[4-(4-methoxyphenylamino)phenyl]-2,3,9-trimethyl-6H-thieno[3,2-f][1,2,4]triazolo[4,3-a][1,4]diazepin-6-yl}acetate The title compound (350 mg) was obtained from the compound (415 mg) described in Example 1 by a treatment in the same manner as in Example 120 and using 4-methoxyaniline (161 mg) instead of aniline.

¹H-NMR (270 MHz, DMSO-d₆) δ: 1.74 (3H, s), 2.42 (3H, s), 2.58 (3H, s), 3.3-3.6 (2H, m), 3.65 (3H, s), 3.72 (3H, s), 4.41 (1H, t, J=7.3 Hz), 6.86 (2H, d, J=6.5 Hz), 6.89 (2H, d, J=6.5 Hz), 7.07 (2H, d, J=8.9 Hz), 7.23 (2H, d, J=8.9 Hz), 8.28 (1H, s)
MS (ESI) m/z: 502 (M+H)⁺.

Example 122

Methyl (S)-{2,3,9-trimethyl-4-[4-(4-tolylamino)phenyl]-6H-thieno[3,2-f][1,2,4]triazolo[4,3-a][1,4]diazepin-6-yl}acetate The title compound (385 mg) was obtained from the compound (415 mg) described in Example 1 by a treatment in the same manner as in Example 120 and using 4-toluidine (161 mg) instead of aniline.
¹H-NMR (270 MHz, DMSO-d₆) δ: 1.74 (3H, s), 2.24 (3H, s), 2.43 (3H, s), 2.59 (3H, s), 3.3-3.6 (2H, m), 3.65 (3H, s), 4.42 (1H, t, J=7.6 Hz), 6.8-7.2 (6H, m), 7.26 (2H, d, J=8.4), 8.42 (1H, s)
MS (ESI) m/z: 486 (M+H)⁺.

Example 123

Methyl (S)-{4-[4-(3-cyanophenylamino)phenyl]-2,3,9-trimethyl-6H-thieno[3,2-f][1,2,4]triazolo[4,3-a][1,4]diazepin-6-yl}acetate The title compound (2.6 g) was obtained from the compound (4.2 g) described in Example 1 by a treatment in the same manner as in Example 120 and using 3-cyanoaniline (1.8 g) instead of aniline.
¹H-NMR (400 MHz, DMSO-d₆) δ: 1.74 (3H, s), 2.44 (3H, s), 2.60 (3H, s), 3.3-3.6 (2H, m), 3.67 (3H, s), 4.46 (1H, t, J=7.2 Hz), 7.12 (2H, d, J=8.4 Hz), 7.28-7.30 (1H, m), 7.34 (1H, d, J=5.4 Hz), 7.4-7.5 (4H, m), 8.91 (1H, s)
MS (ESI) m/z: 497 (M+H)⁺.

Example 124

Methyl (S)-{4-[4-(4-fluorophenylamino)phenyl]-2,3,9-trimethyl-6H-thieno[3,2-f][1,2,4]triazolo[4,3-a][1,4]diazepin-6-yl}acetate The title compound was obtained by a treatment in the same manner as in Example 120 and using 4-fluoroaniline instead of aniline.
¹H-NMR (300 MHz, DMSO-d₆) δ: 1.72 (3H, s), 2.40 (3H, s), 2.57 (3H, s), 3.3-3.6 (2H, m), 3.63 (3H, s), 4.40 (1H, t, J=6.8 Hz), 6.94 (2H, d, J=8.8 Hz), 7.0-7.2 (4H, m), 7.24 (2H, d, J=8.6 Hz), 8.46 (1H, s)
MS (ESI) m/z: 490 (M+H)⁺.

Example 125

Methyl (S)-{4-[4-(4-trifluoromethylphenylamino)phenyl]-2,3,9-trimethyl-6H-thieno[3,2-f][1,2,4]triazolo[4,3-a][1,4]diazepin-6-yl}acetate The title compound (330 mg) was obtained from the compound (415 mg) described in Example 1 by a treatment in the same manner as in Example 120 and using 4-trifluoromethylaniline (180 μL) instead of aniline.
¹H-NMR (270 MHz, DMSO-d₆) δ: 1.74 (3H, s), 2.39 (3H, s), 2.60 (3H, s), 3.3-3.6 (2H, m), 3.67 (3H, s), 4.45 (1H, t, J=7.3 Hz), 7.17 (2H, d, J=8.6 Hz), 7.22 (2H, d, J=8.6 Hz), 7.36 (2H, d, J=8.4 Hz), 7.56 (2H, d, J=8.4 Hz), 9.02 (1H, s)
MS (ESI) m/z: 540 (M+H)⁺.

Example 126

Methyl (S)-{4-[4-(3-acetylaminophenylamino)phenyl]-2,3,9-trimethyl-6H-thieno[3,2-f][1,2,4]triazolo[4,3-a][1,4]diazepin-6-yl}acetate The title compound (490 mg) was obtained from the compound (415 mg) described in Example 1 by a treatment in the same manner as in Example 120 and using 3-aminoacetoanilide (225 mg) instead of aniline.
¹H-NMR (270 MHz, DMSO-d₆) δ: 1.75 (3H, s), 2.02 (3H, s), 2.43 (3H, s), 2.59 (3H, s), 3.3-3.6 (2H, m), 3.66 (3H, s), 4.43 (1H, t, J=7.6 Hz), 6.76 (1H, d, J=7.3 Hz), 7.04 (3H, d, J=7.3 Hz), 7.16 (1H, t, J=7.3 Hz), 7.27 (2H, d, J=7.3 Hz), 7.54 (1H, s), 8.58 (1H, s), 9.85 (1H, s)
MS (ESI) m/z: 529 (M+H)⁺.

Example 127

Methyl (S)-{4-[4-(2-methoxyphenylamino)phenyl]-2,3,9-trimethyl-6H-thieno[3,2-f][1,2,4]triazolo[4,3-a][1,4]diazepin-6-yl}acetate The title compound (471 mg) was obtained from the compound (415 mg) described in Example 1 by a treatment in the same manner as in Example 120 and using 2-methoxyaniline (150 μL) instead of aniline.
¹H-NMR (270 MHz, DMSO-d₆) δ: 1.74 (3H, s), 2.42 (3H, s), 2.59 (3H, s), 3.3-3.6 (2H, m), 3.66 (3H, s), 3.79 (3H, s), 4.41 (1H, t, J=7 Hz), 6.8-7.1 (5H, m), 7.23 (3H, d, J=8.4 Hz), 7.83 (1H, s)
MS (ESI) m/z: 502 (M+H)⁺.

Example 128

Methyl (S)-{4-[4-(4-ethoxycarbonylmethylphenylamino)phenyl]-2,3,9-trimethyl-6H-thieno[3,2-f][1,2,4]triazolo[4,3-a][1,4]diazepin-6-yl}acetate The title compound (440 mg) was obtained from the compound (415 mg) described in Example 1 by a treatment in the same manner as in Example 120 and using 4-aminophenylethyl acetate (233 mg) instead of aniline.
¹H-NMR (270 MHz, DMSO-d₆) δ: 1.18 (3H, t, J=7.0 Hz), 1.75 (3H, s), 2.43 (3H, s), 2.59 (3H, s), 3.3-3.6 (2H, m), 3.57 (2H, s), 3.66 (3H, s), 4.04 (2H, dd, J=14.3, 7.0 Hz), 4.24 (1H, t, J=7 Hz), 7.00 (2H, d, J=8.6 Hz), 7.07 (2H, d, J=8.6 Hz), 7.15 (2H, d, J=8.4 Hz), 7.28 (2H, d, J=8.4 Hz), 8.54 (1H, s)
MS (ESI) m/z: 558 (M+H)⁺.

Example 129

Methyl (S)-{4-[4-(4-cyanophenylamino)phenyl]-2,3,9-trimethyl-6H-thieno[3,2-f][1,2,4]triazolo[4,3-a][1,4]diazepin-6-yl}acetate The title compound (39 mg) was obtained from the compound (200 mg) described in Example 1 by a treatment in the same manner as in Example 120 and using 4-cyanoaniline (85 mg) instead of aniline.
¹H-NMR (300 MHz, DMSO-d₆) δ: d 1.70 (s, 3H), 2.41 (s, 3H), 2.58 (s, 3H), 3.33-3.49 (m, 2H), 3.64 (s, 3H), 4.44 (dd, J=7.5 Hz, J=7.5 Hz, 1H), 7.14 (d, J=6.9 Hz, 2H), 7.17 (d, J=6.9 Hz, 2H), 7.36 (d, J=8.7 Hz, 2H), 7.61 (d, J=8.7 Hz, 2H), 9.17 (s, 1H);
MS (ESI) m/z: 497 (M+H).

Example 130

Methyl (S)-{4-[4-(2-cyanophenylamino)phenyl]-2,3,9-trimethyl-6H-thieno[3,2-f][1,2,4]triazolo[4,3-a][1,4]diazepin-6-yl}acetate The title compound (105 mg) was obtained from the compound (200 mg) described in Example 1 by a treatment in the same manner as in Example 120 and using 2-cyanoaniline (85 mg) instead of aniline.
$^1$H-NMR (300 MHz, DMSO-$d_6$) δ: d 1.71 (s, 3H), 2.40 (s, 3H), 2.64 (s, 3H), 3.32-3.49 (m, 2H), 3.64 (s, 3H), 4.42 (dd, J=7.2 Hz, 7.2 Hz, 1H), 7.04-7.71 (m, 8H)
MS (ESI) m/z: 497 (M+H).

Example 131

Methyl (S)-{4-[4-(3-methylphenylamino)phenyl]-2,3,9-trimethyl-6H-thieno[3,2-f][1,2,4]triazolo[4,3-a][1,4]diazepin-6-yl}acetate The title compound (47 mg) was obtained from the compound (200 mg) described in Example 1 by a treatment in the same manner as in Example 120 and using 3-toluidine (78 μL) instead of aniline.
$^1$H-NMR (300 MHz, DMSO-$d_6$) δ: d 1.72 (s, 3H), 2.23 (s, 3H), 2.41 (s, 3H), 2.57 (s, 3H), 3.32-3.52 (m, 2H), 3.64 (s, 3H), 4.40 (dd, J=7.2 Hz, 7.2 Hz, 1H), 6.70 (d, J=7.5 Hz, 1H), 6.89 (d, J=7.5 Hz, 1H), 6.91 (s, 1H), 7.00 (d, J=8.4 Hz, 2H), 7.16 (dd, J=7.5 Hz, 7.5 Hz, 1H), 7.26 (d, J=8.4 Hz, 2H), 8.47 (s, 1H);
MS (ESI) m/z: 486 (M+H).

Example 132

Methyl (S)-{4-[4-(2-methylphenylamino)phenyl]-2,3,9-trimethyl-6H-thieno[3,2-f][1,2,4]triazolo[4,3-a][1,4]diazepin-6-yl}acetate The title compound (21 mg) was obtained from the compound (200 mg) described in Example 1 by a treatment in the same manner as in Example 120 and using 2-toluidine (77 μL) instead of aniline.
$^1$H-NMR (300 MHz, DMSO-$d_6$) δ: d 1.72 (s, 3H), 2.14 (s, 3H), 2.40 (s, 3H), 2.56 (s, 3H), 3.32-3.47 (m, 2H), 3.63 (s, 3H), 4.39 (dd, J=7.2 Hz, 7.2 Hz, 1H), 6.76 (d, J=8.7 Hz, 2H), 6.97 (dd, J=7.5 Hz, 7.5 Hz, 1H), 7.09-7.22 (m, 5H), 7.87 (s, 1H)
MS (ESI) m/z: 486 (M+H).

Example 133

Methyl (S)-{4-[4-(3-methoxyphenylamino)phenyl]-2,3,9-trimethyl-6H-thieno[3,2-f][1,2,4]triazolo[4,3-a][1,4]diazepin-6-yl}acetate The title compound (32 mg) was obtained from the compound (200 mg) described in Example 1 by a treatment in the same manner as in Example 120 and using 3-anisidine (81 μL) instead of aniline.
$^1$H-NMR (300 MHz, DMSO-$d_6$) δ: d 1.72 (s, 3H), 2.41 (s, 3H), 2.57 (S, 3H), 3.32-3.48 (m, 2H), 3.64 (s, 3H), 3.69 (s, 3H), 4.41 (dd, J=7.2 Hz, 7.2 Hz, 1H), 6.46 (d, J=8.4 Hz, 1H), 6.63 (s, 1H), 6.68 (d, J=8.4 Hz, 1H), 7.03 (d, J=8.4 Hz, 2H), 7.14 (dd, J=8.4 Hz, 8.4 Hz, 1H), 7.27 (d, J=8.4 Hz, 2H), 8.55 (s, 1H);
MS (ESI) m/z: 502 (M+H).

Example 134

Methyl (S)-{4-[4-(3-fluorophenylamino)phenyl]-2,3,9-trimethyl-6H-thieno[3,2-f][1,2,4]triazolo[4,3-a][1,4]diazepin-6-yl}acetate The title compound (119 mg) was obtained from the compound (200 mg) described in Example 1 by a treatment in the same manner as in Example 120 and using 3-fluoroaniline (69 μL) instead of aniline.
$^1$H-NMR (300 MHz, DMSO-$d_6$) δ: d 1.72 (s, 3H), 2.41 (s, 3H), 2.57 (s, 3H), 3.32-3.49 (m, 2H), 3.64 (s, 3H), 4.42 (dd, J=7.5 Hz, 7.5 Hz, 1H), 6.46 (dd, J=8.4 Hz, 8.4 Hz, 1H), 6.85 (d, 9.5 Hz, 1H), 6.90 (d, J=8.4 Hz, 1H), 7.07 (d, J=8.7 Hz, 2H), 7.25 (dd, J=15.3 Hz, 8.4 Hz, 1H), 7.30 (d, J=8.7 Hz, 2H), 8.75 (s, 1H);
MS (ESI) m/z: 490 (M+H).

Example 135

Methyl (S)-{4-[4-(3-trifluoromethylphenylamino)phenyl]-2,3,9-trimethyl-6H-thieno[3,2-f][1,2,4]triazolo[4,3-a][1,4]diazepin-6-yl}acetate The title compound (72 mg) was obtained from the compound (200 mg) described in Example 1 by a treatment in the same manner as in Example 120 and using 3-trifluoromethylaniline (90 μL) instead of aniline.
$^1$H-NMR (300 MHz, DMSO-$d_6$) δ: d 1.71 (s, 3H), 2.41 (s, 3H), 2.57 (s, 3H), 3.32-3.49 (m, 2H), 3.64 (s, 3H), 4.42 (dd, J=7.2 Hz, 7.2 Hz, 1H), 7.08 (d, 8.7 Hz, 2H), 7.16 (d, J=7.5 Hz, 1H), 7.33 (d, J=7.33 Hz, 2H), 7.30-7.48 (m, 3H), 8.87 (s, 1H)
MS (ESI) m/z: 540 (M+H)$^+$.

Example 136

Methyl (S)-{4-[4-(3-methylsulfonylphenylamino)phenyl]-2,3,9-trimethyl-6H-thieno[3,2-f][1,2,4]triazolo[4,3-a][1,4]diazepin-6-yl}acetate The title compound (93 mg) was obtained from the compound (830 mg) described in Example 1 by a treatment in the same manner as in Example 120 and using 3-methylsulfonylaniline (377 mg) instead of aniline.
$^1$H-NMR (300 MHz, CDCl$_3$) δ: 1.78 (3H, s), 2.43 (3H, s), 2.70 (3H, s), 3.04 (3H, s), 3.54-3.74 (2H, m), 3.77 (3H, s), 4.61 (1H, t, J=6.9 Hz), 6.39 (1H, s), 7.06 (2H, d, J=9.9 Hz), 7.27-7.45 (5H, m), 7.62 (1H, s)
MS (ESI) m/z: 550 (M+H)$^+$.

Example 137

Methyl (S)-{4-[4-(3-chlorophenylamino)phenyl]-2,3,9-trimethyl-6H-thieno[3,2-f][1,2,4]triazolo[4,3-a][1,4]diazepin-6-yl}acetate The title compound (18 mg) was obtained from the compound (415 mg) described in Example 1 by a treatment in the same manner as in Example 120 and using 3-chloroaniline (130 mg) instead of aniline.

¹H-NMR (300 MHz, CDCl₃) δ: 1.78 (3H, s), 2.42 (3H, s), 2.68 (3H, s), 3.54-3.74 (2H, m), 3.77 (3H, s), 4.60 (1H, t, J=7.2 Hz), 6.88-6.96 (2H, m), 7.00 (2H, d, J=9.6 Hz), 7.10 (1H, t, J=2.4 Hz), 7.16-7.22 (1H, m), 7.34-7.41 (3H, m)

MS (ESI) m/z: 506 (M+H)⁺.

Example 138

Methyl (S)-{4-[4-(2,4,6-trifluorophenylamino)phenyl]-2,3,9-trimethyl-6H-thieno[3,2-f][1,2,4]triazolo[4,3-a][1,4]diazepin-6-yl}acetate The title compound (270 mg) was obtained from the compound (415 mg) described in Example 1 by a treatment in the same manner as in Example 120 and using 2,4,6-trifluoroaniline (206 mg) instead of aniline.

¹H-NMR (400 MHz, DMSO-d₆) δ: 1.71 (3H, s), 2.41 (3H, s), 2.58 (3H, s), 3.41 (2H, m), 3.65 (3H, s), 4.41 (1H, t, J=7.2 Hz), 6.62 (2H, d, J=8.2 Hz), 7.24 (2H, d, J=8.2 Hz), 7.29 (2H, t, J=8.6 Hz), 8.14 (1H, s)

MS (ESI) m/z: 526 (M+H)⁺.

Example 139

Ethyl (S)-{4-[4-(4-fluorophenylamino)phenyl]-2,3,9-trimethyl-6H-thieno[3,2-f][1,2,4]triazolo[4,3-a][1,4]diazepin-6-yl}acetate To a mixture of the compound (858 mg) described in Example 62, palladium acetate (22 mg), 2-(dicyclohexylphosphino)biphenyl (72 mg) and tripotassium phosphate (600 mg) were successively added dimethoxyethane (4 mL) and 4-fluoroaniline (290 μL), and the mixture was heated under reflux for 8 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (600 mg).

¹H-NMR (400 MHz, DMSO-d₆) δ: 1.21 (3H, t, J=7.2 Hz), 1.74 (3H, s), 2.43 (3H, s), 2.59 (3H, s), 3.3-3.5 (2H, m), 4.0-4.3 (2H, m), 4.41 (1H, t, J=7.6 Hz), 6.96 (2H, d, J=8.8 Hz), 7.1-7.2 (4H, m), 7.27 (2H, d, J=8.4 Hz), 8.48 (1H, s)

MS (ESI) m/z: 503 (M+H)⁺.

Example 140

Ethyl (S)-{4-[4-(2-cyanophenylamino)phenyl]-2,3,9-trimethyl-6H-thieno[3,2-f][1,2,4]triazolo[4,3-a][1,4]diazepin-6-yl}acetate To a mixture of the compound (5 g) described in Example 1, palladium acetate (135 mg), 2-(dicyclohexylphosphino)biphenyl (423 mg), tripotassium phosphate (3.6 g) and 2-cyanoaniline (2.1 g) was added dimethoxyethane (24 mL), and the mixture was heated under reflux for 7 hr. After cooling, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) to give methyl (S)-{4-[4-(2-cyanophenylamino)phenyl]-2,3,9-trimethyl-6H-thieno[3,2-f][1,2,4]triazolo[4,3-a][1,4]diazepin-6-yl}acetate. The entire amount of the obtained compound was dissolved in ethanol (25 mL). 1 M aqueous sodium hydroxide solution (25 mL) was added, and the mixture was stirred at room temperature for 30 min. After completion of the reaction, water was added, and the mixture was extracted with chloroform. The organic layer was washed with saturated brine, dried over anhydrous sodium sulfate, and the solvent was evaporated. The residue was recrystallized to give (S)-4-[4-(2-cyanophenylamino)phenyl]-2,3,9-trimethyl-6H-thieno[3,2-f][1,2,4]triazolo[4,3-a][1,4]diazepin-6-acetic acid (2.6 g). The obtained compound (410 mg) was dissolved in ethanol (8.5 mL). Thionyl chloride (250 μL) was added dropwise under ice-cooling, and the mixture was stirred at room temperature for 12 hr. After completion of the reaction, water was added, and the mixture was extracted with ethyl acetate. The organic layer was washed with saturated aqueous sodium hydrogencarbonate and saturated brine, dried over anhydrous sodium sulfate, and the solvent was evaporated. The residue was purified by column chromatography (chloroform:methanol=100:1) to give the title compound (360 mg).

¹H-NMR (300 MHz, DMSO-d₆) δ: 1.19 (3H, t, J=7.5 Hz), 1.70 (3H, s), 2.40 (3H, s), 2.57 (3H, s), 3.38 (2H, m), 4.1 (2H, m), 4.42 (1H, t, J=7.5 Hz), 7.05 (2H, d, J=8.1 Hz), 7.0 (1H, m), 7.30 (2H, d, J=8.1 Hz), 7.33 (1H, d, J=7.8 Hz), 7.53 (1H, t, J=7.8 Hz), 7.70 (1H, d, J=7.8 Hz), 8.80 (1H, s)

MS (ESI) m/z: 511 (M+H)⁺.

Example 141

Methyl (S)-{2,3,9-trimethyl-4-[4-(pyridin-2-ylamino)phenyl]-6H-thieno[3,2-f][1,2,4]triazolo[4,3-a][1,4]diazepin-6-yl}acetate To a mixture of the compound (395 mg) described in Starting Material Synthetic Example 4, tris(dibenzylideneacetone)dipalladium (0) (23 mg), 2-(dicyclohexylphosphino)biphenyl (36 mg) and tripotassium phosphate (298 mg) were added dimethoxyethane (2 mL) and 2-bromopyridine (120 μL), and the mixture was heated under reflux for 8 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (132 mg).

¹H-NMR (270 MHz, DMSO-d₆) δ: 1.72 (3H, s), 2.43 (3H, s), 2.60 (3H, s), 3.3-3.6 (2H, m), 3.67 (3H, s), 4.46 (1H, t, J=7.6 Hz), 6.81 (1H, t, J=8.6 Hz), 6.88 (1H, d, J=8.6 Hz), 7.33 (2H, d, J=8.6 Hz), 7.61 (1H, m), 7.73 (2H, d, J=8.6 Hz), 8.17 (1H, d, J=3.2 Hz), 9.39 (1H, s)

MS (ESI) m/z: 473 (M+H)⁺.

Example 142

Methyl (S)-{2,3,9-trimethyl-4-[4-(pyridin-3-ylamino)phenyl]-6H-thieno[3,2-f][1,2,4]triazolo[4,3-a][1,4]diazepin-6-yl}acetate The title compound (1.4 g) was obtained from the compound (4.2 g) described in Example 1 by a treatment in the same manner as in Example 120 and using 3-aminopyridine (1.4 g) instead of aniline.

¹H-NMR (400 MHz, DMSO-d₆) δ: 1.74 (3H, s), 2.43 (3H, s), 2.59 (3H, s), 3.3-3.6 (2H, m), 3.66 (3H, s), 4.44 (1H, t, J=6.8 Hz), 7.07 (2H, d, J=8.4 Hz), 7.3-7.4 (3H, m), 7.53 (1H, d, J=8.8 Hz), 8.10 (1H, d, J=4.4 Hz), 8.39 (1H, d, J=2.8 Hz), 8.73 (1H, s)

MS (ESI) m/z: 473 (M+H)⁺.

Example 143

Methyl (S)-{4-[4-(2-ethyl-2H-pyrazol-3-ylamino)phenyl]-2,3,9-trimethyl-6H-thieno[3,2-f][1,2,4]triazolo[4,3-a][1,4]diazepin-6-yl}acetate The title compound (345 mg) was obtained from the compound (415 mg) described in Example 1 by a treatment in the same manner as in Example 120 and using 5-amino-1-ethylpyrazole (167 mg) instead of aniline.

$^1$H-NMR (270 MHz, DMSO-$d_6$) δ: 1.24 (3H, t, J=7.3 Hz), 1.72 (3H, s), 2.42 (3H, s), 2.58 (3H, s), 3.3-3.6 (2H, m), 3.65 (3H, s), 6.92 (2H, q, J=7.3 Hz), 4.42 (1H, d, J=7 Hz), 6.03 (1H, d, J=1.6 Hz), 6.77 (2H, d, J=8.9 Hz), 7.27 (2H, d, J=8.9 Hz), 7.40 (1H, d, J=1.9 Hz), 8.27 (1H, s)

MS (ESI) m/z: 490 (M+H)$^+$.

Example 144

Methyl (S)-{2,3,9-trimethyl-4-[4-(thiazole-2-ylamino)phenyl]-2,3,9-trimethyl-6H-thieno[3,2-f][1,2,4]triazolo[4,3-a][1,4]diazepin-6-yl}acetate The title compound (43 mg) was obtained from the compound (198 mg) described in Starting Material Synthetic Example 4 by a treatment in the same manner as in Example 141 and using 2-bromothiazole (180 μL) instead of 2-bromopyridine.

$^1$H-NMR (270 MHz, DMSO-$d_6$) δ: 1.69 (3H, s), 2.43 (3H, s), 2.60 (3H, s), 3.3-3.6 (2H, m), 3.67 (3H, s), 4.45 (1H, t, J=7.0 Hz), 6.97 (1H, d, J=3.5 Hz), 7.28 (1H, d, J=3.5 Hz), 7.35 (2H, d, J=8.6 Hz), 7.66 (2H, d, J=8.6 Hz), 10.5 (1H, s)

MS (ESI) m/z: 479 (M+H)$^+$.

Example 145

Methyl (S)-{4-[4-(2,5-dimethyl-2H-pyrazol-3-ylamino)phenyl]-2,3,9-trimethyl-6H-thieno[3,2-f][1,2,4]triazolo[4,3-a][1,4]diazepin-6-yl}acetate The title compound (728 mg) was obtained from the compound (830 mg) described in Example 1 by a treatment in the same manner as in Example 120 and using 5-amino-1,3-dimethylpyrazole (333 mg) instead of aniline.

$^1$H-NMR (400 MHz, DMSO-$d_6$) δ: 1.72 (3H, s), 2.09 (3H, s), 2.42 (3H, s), 2.59 (3H, s), 3.37 (1H, dd, J=16.4, 6.8 Hz), 3.46 (1H, dd, J=16.4, 6.8 Hz), 3.53 (3H, s), 3.65 (3H, s), 4.42 (1H, t, J=6.8 Hz), 5.82 (1H, s), 6.80 (2H, d, J=8.4 Hz), 7.27 (2H, d, J=8.4 Hz), 8.30 (1H, s)

MS (ESI) m/z: 490 (M+H)$^+$.

Example 146

Methyl (S)-{4-[4-(5-tert-butyl-2-methyl-2H-pyrazol-3-ylamino)phenyl]-2,3,9-trimethyl-6H-thieno[3,2-f][1,2,4]triazolo[4,3-a][1,4]diazepin-6-yl}acetate The title compound (932 mg) was obtained from the compound (830 mg) described in Example 1 by a treatment in the same manner as in Example 120 and using 5-amino-3-tert-butyl-1-methylpyrazole (460 mg) instead of aniline.

$^1$H-NMR (400 MHz, DMSO-$d_6$) δ: 1.21 (9H, s), 1.72 (3H, s), 2.42 (3H, s), 2.58 (3H, s), 3.37 (1H, dd, J=16.4, 6.8 Hz), 3.46 (1H, dd, J=16.4, 6.8 Hz), 3.55 (3H, s), 3.66 (3H, s), 4.42 (1H, t, J=6.8 Hz), 5.90 (1H, s), 6.80 (2H, d, J=8.8 Hz), 7.27 (2H, d, J=8.8 Hz), 8.26 (1H, s)

MS (ESI) m/z: 532 (M+H)$^+$.

Example 147

Methyl (S)-{4-[4-(2-cyanopyridin-5-ylamino)phenyl]-2,3,9-trimethyl-6H-thieno[3,2-f][1,2,4]triazolo[4,3-a][1,4]diazepin-6-yl}acetate The title compound (330 mg) was obtained from the compound (830 mg) described in Example 1 by a treatment in the same manner as in Example 120 and using 5-amino-2-cyanopyridine (179 mg) instead of aniline.

$^1$H-NMR (400 MHz, DMSO-$d_6$) δ: 1.72 (3H, s), 2.43 (3H, s), 2.60 (3H, s), 3.40 (1H, dd, J=16.4, 6.8 Hz), 3.48 (1H, dd, J=16.4, 6.8 Hz), 3.67 (3H, s), 4.47 (1H, t, J=6.8 Hz), 7.23 (2H, d, J=8.4 Hz), 7.40 (2H, d, J=8.4 Hz), 7.57 (1H, dd, J=8.4, 2.8 Hz), 7.79 (1H, d, J=8.4 Hz), 8.42 (1H, d, J=2.8 Hz), 9.41 (1H, s),

MS (ESI) m/z: 498 (M+H)$^+$.

Example 148

Methyl (S)-{2,3,9-trimethyl-4-[4-(1,3,5-trimethyl-1H-pyrazol-4-ylamino)phenyl]-6H-thieno[3,2-f][1,2,4]triazolo[4,3-a][1,4]diazepin-6-yl}acetate The title compound (874 mg) was obtained from the compound (830 mg) described in Example 1 by a treatment in the same manner as in Example 120 and using 4-amino-1,3,5-trimethylpyrazole (376 mg) instead of aniline.

$^1$H-NMR (400 MHz, DMSO-$d_6$) δ: 1.74 (3H, s), 1.84 (3H, s), 2.01 (3H, s), 2.41 (3H, s), 2.57 (3H, s), 3.34 (1H, dd, J=16.4, 6.8 Hz), 3.44 (1H, dd, J=16.4, 6.8 Hz), 3.64 (6H, s), 4.38 (1H, t, J=6.8 Hz), 6.43 (2H, d, J=8.8 Hz), 7.16 (2H, d, J=8.8 Hz), 7.42 (1H, s)

MS (ESI) m/z: 504 (M+H)$^+$.

Example 149

Methyl (S)-{4-[4-(2-methoxypyridin-5-ylamino)phenyl]-2,3,9-trimethyl-6H-thieno[3,2-f][1,2,4]triazolo[4,3-a][1,4]diazepin-6-yl}acetate The title compound (738 mg) was obtained from the compound (830 mg) described in Example 1 by a treatment in the same manner as in Example 120 and using 5-amino-2-methoxypyridine (370 μL) instead of aniline.

$^1$H-NMR (400 MHz, DMSO-$d_6$) δ: 1.74 (3H, s), 2.42 (3H, s), 2.59 (3H, s), 3.37 (1H, dd, J=16.4, 6.8 Hz), 3.45 (1H, dd, J=16.4, 6.8 Hz), 3.65 (3H, s), 3.82 (3H, s), 4.41 (1H, t, J=6.8 Hz), 6.79 (1H, d, J=8.8 Hz), 6.85 (2H, d, J=8.8 Hz), 7.25 (2H, d, J=8.8 Hz), 7.54 (1H, d, J=8.8, 2.4 Hz), 8.00 (1H, d, J=2.4 Hz), 8.34 (1H, s)

MS (ESI) m/z: 503 (M+H)$^+$.

Example 150

Methyl (S)-{4-[4-(5-fluoropyridin-2-ylamino)phenyl]-2,3,9-trimethyl-6H-thieno[3,2-f][1,2,4]triazolo[4,3-a][1,4]diazepin-6-yl}acetate The title compound (260 mg) was obtained from the compound (350 mg) described in Starting Material Synthetic Example 4 by a treatment in the same manner as in Example 141 and using 2-chloro-5-fluoropyridine (235 mg) instead of 2-bromopyridine.

¹H-NMR (300 MHz, DMSO-d₆) δ: 1.69 (3H, s), 2.40 (3H, s), 2.58 (3H, s), 3.40 (1H, dd, J=16.5 Hz, 7.8 Hz), 3.46 (1H, dd, J=16.5 Hz, 6.9 Hz), 3.65 (3H, s), 4.43 (1H, t, J=7.2 Hz), 6.90 (1H, dd, J=8.7 Hz, 3.0 Hz), 7.31 (2H, d, J=8.7 Hz), 7.56 (1H, ddd, J=8.7 Hz, 8.7 Hz, 3.0 Hz), 7.66 (2H, d, J=8.7 Hz), 8.13 (1H, d, J=3.0 Hz), 9.42 (1H, s)

MS (ESI) m/z: 491 (M+H)⁺.

Example 151

Ethyl (S)-{4-[4-(2-ethyl-2H-pyrazol-3-ylamino)-phenyl]-2,3,9-trimethyl-6H-thieno[3,2-f][1,2,4]triazolo[4,3-a][1,4]diazepin-6-yl}acetate An intermediate, (S)-4-[4-(2-ethyl-2H-pyrazol-3-ylamino)phenyl]-2,3,9-trimethyl-6H-thieno[3,2-f][1,2,4]triazolo[4,3-a][1,4]diazepin-6-acetic acid (2.5 g), was obtained by a treatment in the same manner as in Example 140 and using the compound (2.8 g) described in Example 143 instead of methyl (S)-{4-[4-(2-cyanophenylamino)phenyl]-2,3,9-trimethyl-6H-thieno[3,2-f][1,2,4]triazolo[4,3-a][1,4]diazepin-6-yl}acetate, which is the intermediate in Example 140. The title compound (300 mg) was obtained by treating this compound (500 mg) in the same manner as in Example 140.

¹H-NMR (300 MHz, DMSO-d₆) δ: 1.18 (3H, t, J=7.2 Hz), 1.22 (3H, t, J=7.2 Hz), 1.69 (3H, s), 2.39 (3H, s), 2.56 (3H, s), 3.3-3.9 (2H, m), 3.93 (2H, q, J=7.2 Hz), 4.0-4.2 (2H, m), 4.38 (1H, t, J=7.8 Hz), 6.01 (1H, d, J=1.5 Hz), 6.75 (2H, d, J=8.1 Hz), 7.24 (2H, d, J=8.1 Hz), 7.38 (1H, d, J=1.5 Hz), 8.26 (1H, s)

MS (ESI) m/z: 504 (M+H)⁺.

Example 152

Ethyl (S)-{2,3,9-trimethyl-4-[4-(pyridin-3-ylamino)phenyl]-6H-thieno[3,2-f][1,2,4]triazolo[4,3-a][1,4]diazepin-6-yl}acetate The title compound (2 g) was obtained from the compound (2.6 g) described in Example 62 by a treatment in the same manner as in Example 139 and using 3-aminopyridine (847 mg) instead of 4-fluoroaniline.

¹H-NMR (400 MHz, DMSO-d₆) δ: 1.21 (3H, t, J=7.2 Hz), 1.74 (3H, s), 2.43 (3H, s), 2.59 (3H, s), 3.3-3.5 (2H, m), 4.0-4.3 (2H, m), 4.43 (1H, dd, J=8.0, 6.8 Hz), 7.07 (2H, d, J=8.8 Hz), 7.27 (1H, dd, J=8.4, 4.8 Hz), 7.32 (2H, d, J=8.4 Hz), 7.5-7.6 (1H, m), 8.0-8.1 (1H, m), 8.39 (1H, d, J=2.8 Hz), 8.70 (1H, s)

MS (ESI) m/z: 487 (M+H)⁺.

Example 153

Ethyl (S)-{2,3,9-trimethyl-4-[4-(1,3,5-trimethyl-1H-pyrazol-4-ylamino)phenyl]-6H-thieno[3,2-f][1,2,4]triazolo[4,3-a][1,4]diazepin-6-yl}acetate The title compound was obtained from the compound (858 mg) described in Example 62 by a treatment in the same manner as in Example 139 and using 4-amino-1,3,5-trimethylpyrazole (376 mg) instead of 4-fluoroaniline.

¹H-NMR (400 MHz, DMSO-d₆) δ: 1.19 (3H, t, J=7.2 Hz), 1.74 (3H, s), 1.89 (3H, s), 2.01 (3H, s), 2.42 (3H, s), 2.57 (3H, s), 3.3-3.5 (2H, m), 3.64 (3H, s), 4.0-4.3 (2H, m), 4.37 (1H, t, J=7.6 Hz), 6.44 (2H, d, J=8.4 Hz), 7.16 (2H, d, J=8.4 Hz), 7.43 (1H, s)

MS (ESI) m/z: 518 (M+H)⁺.

Example 154

Methyl (S)-{2,3,9-trimethyl-4-[4-(methylphenylamino)phenyl]-2,3,9-trimethyl-6H-thieno[3,2-f][1,2,4]triazolo[4,3-a][1,4]diazepin-6-yl}acetate The title compound (138 mg) was obtained from the compound (415 mg) described in Example 1 by a treatment in the same manner as in Example 120 and using N-methylaniline (160 μL) instead of aniline.

¹H-NMR (270 MHz, DMSO-d₆) δ: 1.73 (3H, s), 2.43 (3H, s), 2.59 (3H, s), 3.30 (3H, s), 3.3-3.6 (2H, m), 3.65 (3H, s), 4.4-4.5 (1H, m), 6.83 (2H, d, J=8.9 Hz), 7.0-7.2 (3H, m), 7.27 (2H, d, J=8 Hz), 7.38 (2H, d, J=8 Hz)

MS (ESI) m/z: 486 (M+H)⁺.

Example 155

Methyl (S)-(4-{4-[(4-fluorophenyl)methylamino]phenyl}-2,3,9-trimethyl-6H-thieno[3,2-f][1,2,4]triazolo[4,3-a][1,4]diazepin-6-yl)acetate The title compound (4.3 g) was obtained from the compound (10 g) described in Example 1 by a treatment in the same manner as in Example 120 and using 4-fluoro-N-methylaniline (4.1 mL) instead of aniline.

¹H-NMR (300 MHz, DMSO-d₆) δ: d 1.69 (3H, s), 2.39 (3H, s), 2.56 (3H, s), 3.32 (3H, s), 3.34 (1H, dd, J=16.5 Hz, 7.8 Hz), 3.43 (1H, dd, J=16.5 Hz, 7.2 Hz), 3.62 (3H, s), 4.41 (1H, dd, J=7.8 Hz, 7.2 Hz), 6.72 (2H, d, J=8.4 Hz), 7.19-7.27 (6H, m)

MS (ESI) m/z: 504 (M+H)⁺.

Example 156

Methyl (S)-(4-{4-[(4-methoxyphenyl)methylamino]phenyl}-2,3,9-trimethyl-6H-thieno[3,2-f][1,2,4]triazolo[4,3-a][1,4]diazepin-6-yl)acetate The title compound (1.5 g) was obtained from the compound (5 g) described in Example 1 by a treatment in the same manner as in Example 120 and using 4-methoxy-N-methylaniline (2.5 g) instead of aniline.

¹H-NMR (300 MHz, DMSO-d₆) d 1.70 (s, 3H), 2.39 (s, 3H), 2.56 (s, 3H), 3.20 (s, 3H), 3.32-3.46 (m, 2H), 3.62 (s, 3H), 3.74 (s, 3H), 4.38 (dd, J=7.2 Hz, 7.2 Hz, 1H), 6.62 (d, J=8.4 Hz, 2H), 6.95 (d, J=8.7 Hz, 2H), 7.11 (d, J=8.7 Hz, 2H), 7.19 (d, J=8.4 Hz, 2H);

MS (ESI) m/z: 516 (M+H)⁺.

Example 157

Methyl (S)-(4-{4-[(2,4-difluorophenyl)methylamino]phenyl}-2,3,9-trimethyl-6H-thieno[3,2-f][1,2,4]triazolo[4,3-a][1,4]diazepin-6-yl)acetate The title compound (740 mg) was obtained from the compound (830 mg) described in Example 1 by a treatment in the same manner as in Example 120 and using 2,4-difluoro-N-methylaniline (575 μL) instead of aniline.

¹H-NMR (400 MHz, DMSO-d$_6$) δ: 1.61 (3H, s), 2.41 (3H, s), 2.61 (3H, s), 3.24 (3H, s), 3.3-3.5 (2H, m), 3.64 (3H, s), 4.41 (1H, t, J=7.2 Hz), 6.60 (2H, d, J=8.8 Hz), 7.1-7.3 (3H, m), 7.3-7.5 (2H, m)

MS (ESI) m/z: 522 (M+H)$^+$.

Example 158

Methyl (S)-(4-{4-[(5-cyanopyridin-2-yl)methylamino]phenyl}-2,3,9-trimethyl-6H-thieno[3,2-f][1,2,4]triazolo[4,3-a][1,4]diazepin-6-yl)acetate To a mixture of the compound described in Starting Material Synthetic Example 8 (1 g), palladium acetate (27 mg), 2-(dicyclohexylphosphino)biphenyl (85 mg), potassium phosphate (725 mg) and 6-chloronicotinonitrile (680 mg) was added dimethoxyethane (5 mL), and the mixture was heated under reflux for 9 hr. After cooling, water was added, and the mixture was extracted with ethyl acetate. The organic layer was washed with water and saturated brine, dried over anhydrous sodium sulfate, and the solvent was evaporated. The residue was purified by column chromatography (chloroform:methanol=100:1) to give the title compound (810 mg).

¹H-NMR (300 MHz, DMSO-d$_6$) δ: 1.72 (3H, s), 2.44 (3H, s), 2.61 (3H, s), 3.3-3.5 (2H, m), 3.46 (3H, s), 3.67 (3H, s), 4.52 (1H, t, J=6.9 Hz), 6.57 (1H, d, J=9.0 Hz), 7.40 (2H, d, J=7.8 Hz), 7.51 (2H, d, J=7.8 Hz), 7.78 (1H, d, J=9.0 Hz), 8.58 (1H, s)

MS (ESI) m/z: 512 (M+H)$^+$.

Example 159

Methyl (S)-(4-{4-[(3-cyanophenyl)methylamino]phenyl}-2,3,9-trimethyl-6H-thieno[3,2-f][1,2,4]triazolo[4,3-a][1,4]diazepin-6-yl)acetate The title compound (340 mg) was obtained from the compound (650 mg) described in Starting Material Synthetic Example 8 by a treatment in the same manner as in Example 158 3-bromobenzonitrile (580 mg) instead of 6-chloronicotinonitrile.

¹H-NMR (300 MHz, DMSO-d$_6$) δ: 1.71 (3H, s), 2.40 (3H, s), 2.57 (3H, s), 3.2-3.4 (2H, m), 3.29 (3H, s), 3.64 (3H, s), 4.44 (1H, t, J=7.5 Hz), 7.04 (2H, d, J=8.1 Hz), 7.3-7.5 (6H, m)

MS (ESI) m/z: 511 (M+H)$^+$.

Example 160

Methyl (S)-(4-{4-[(4-nitrophenyl)methylamino]phenyl}-2,3,9-trimethyl-6H-thieno[3,2-f][1,2,4]triazolo[4,3-a][1,4]diazepin-6-yl)acetate The title compound (420 mg) was obtained from the compound (1 g) described in Starting Material Synthetic Example 8 by a treatment in the same manner as in Example 158 and using 4-bromonitrobenzene (740 mg) instead of 6-chloronicotinonitrile.

¹H-NMR (300 MHz, DMSO-d$_6$) δ: 1.71 (3H, s), 2.42 (3H, s), 2.59 (3H, s), 3.39 (3H, s), 3.5 (2H, m), 3.65 (3H, s), 4.49 (1H, t, J=7.2 Hz), 6.86 (2H, d, J=9.6 Hz), 7.33 (2H, d, J=8.7 Hz), 7.48 (2H, d, J=8.7 Hz), 8.03 (2H, d, J=9.6 Hz)

MS (ESI) m/z: 531 (M+H)$^+$.

Example 161

Methyl (S)-(4-{4-[(3-methoxyphenyl)methylamino]phenyl}-2,3,9-trimethyl-6H-thieno[3,2-f][1,2,4]triazolo[4,3-a][1,4]diazepin-6-yl)acetate The title compound (318 mg) was obtained from the compound (415 mg) described in Example 1 by a treatment in the same manner as in Example 120 and using 3-methoxy-N-methylaniline (329 mg) instead of aniline.

¹H-NMR (300 MHz, DMSO-d$_6$) δ: 1.73 (3H, s), 2.42 (3H, s), 2.59 (3H, s), 3.28 (3H, s), 3.34-3.49 (2H, m), 3.65 (3H, s), 3.72 (3H, s), 4.43 (1H, t, J=7.0 Hz), 6.67-6.72 (3H, m), 6.87 (2H, d, J=9.2 Hz), 7.23-7.29 (3H, m)

MS (ESI) m/z: 516 (M+H)$^+$.

Example 162

Ethyl (S)-(4-{4-[(4-methoxyphenyl)methylamino]phenyl}-2,3,9-trimethyl-6H-thieno[3,2-f][1,2,4]triazolo[4,3-a][1,4]diazepin-6-yl)acetate The compound (5 g) described in Example 156 was dissolved in ethanol (25 mL). 2 M aqueous sodium hydroxide solution (30 mL) was added, and the mixture was stirred at 100° C. for 1 hr. After cooling, the mixture was adjusted to pH 4 with 1 M hydrochloric acid. The precipitated crystals were filtered and recrystallized to give (S)-4-{4-[(4-methoxyphenyl)methylamino]phenyl}-2,3,9-trimethyl-6H-thieno[3,2-f][1,2,4]triazolo[4,3-a][1,4]diazepin-6-acetic acid (1.7 g). The obtained compound (1 g) was dissolved in ethanol (10 mL). Concentrated sulfuric acid (200 μL) was added, and the mixture was heated under reflux for 6 hr. After cooling, aqueous potassium carbonate was added, and the mixture was extracted with ethyl acetate. The organic layer was washed with saturated brine, dried over anhydrous sodium sulfate, and the solvent was evaporated. The residue was purified by column chromatography (chloroform:methanol=100:1) to give the title compound (912 mg).

¹H-NMR (400 MHz, DMSO-d$_6$) δ: 1.19 (3H, t, J=7.2 Hz), 1.72 (3H, s), 2.42 (3H, s), 2.58 (3H, s), 3.22 (3H, s), 3.3-3.5 (2H, m), 3.76 (3H, s), 4.1-4.2 (2H, m), 4.39 (1H, dd, J=7.6, 6.4 Hz), 6.35 (2H, d, J=9 Hz), 6.97 (2H, d, J=9 Hz), 7.13 (2H, d, J=8.0 Hz), 7.21 (2H, d, J=8 Hz)

MS (ESI) m/z: 530 (M+H)$^+$.

Example 163

Ethyl (S)-(4-{4-[(4-fluorophenyl)methylamino]phenyl}-2,3,9-trimethyl-6H-thieno[3,2-f][1,2,4]triazolo[4,3-a][1,4]diazepin-6-yl)acetate The title compound (439 mg) was obtained from the compound (1.3 g) described in Example 62 by a treatment in the same manner as in Example 139 and using 4-fluoro-N-methylaniline (510 μL) instead of 4-fluoroaniline.

¹H-NMR (300 MHz, DMSO-d$_6$) δ: 1.17 (3H, t, J=7.2 Hz), 1.69 (3H, s), 2.39 (3H, s), 2.56 (3H, s), 3.23 (3H, s), 3.3 (2H, m), 4.1 (2H, m), 4.38 (1H, t, J=7.5 Hz), 6.72 (2H, d, J=8.7 Hz), 7.16 (4H, d, J=6.6 Hz), 7.22 (2H, d, J=8.7 Hz)

MS (ESI) m/z: 518 (M+H)$^+$.

Example 164

Methyl (S)-{4-[4-(benzylmethylamino)phenyl]-2,3,9-trimethyl-6H-thieno[3,2-f][1,2,4]triazolo[4,3-a][1,4]diazepin-6-yl}acetate To a mixture of the compound (10 g) described in Example 1, palladium acetate (270 mg), 2-(dicyclohexylphosphino)biphenyl (840 mg) and tripotassium phosphate (7.2 g) were added dimethoxyethane (50 mL) and N-methylbenzylamine (4.7 mL), and the mixture was heated under reflux for 14 hr. After cooling, water was added, and the mixture was extracted with ethyl acetate. The organic layer was washed with water and saturated brine, dried over anhydrous sodium sulfate, and the solvent was evaporated. The residue was purified by column chromatography (chloroform:methanol=100:1) to give the title compound (8 g).
$^1$H-NMR (400 MHz, DMSO-$d_6$) δ: 1.72 (3H, s), 2.42 (3H, s), 2.57 (3H, s), 3.05 (3H, s), 3.3-3.6 (2H, m), 3.65 (3H, s), 4.63 (2H, s), 6.71 (2H, d, J=8.8 Hz), 7.2-7.3 (5H, m), 7.35 (2H, d, J=7.2 Hz)
MS (ESI) m/z: 500 (M+H)$^+$.

Example 165

Ethyl (S)-{4-[4-(benzylmethylamino)phenyl]-2,3,9-trimethyl-6H-thieno[3,2-f][1,2,4]triazolo[4,3-a][1,4]diazepin-6-yl}acetate The title compound (415 mg) was obtained by an operation in the same manner as in Example 162 and using the compound (1 g) described in Example 164 instead of the compound described in Example 156.
$^1$H-NMR (400 MHz, DMSO-$d_6$) δ: 1.20 (3H, t, J=7.2 Hz), 1.71 (3H, s), 2.41 (3H, s), 2.57 (3H, s), 3.05 (3H, s), 3.3-3.5 (2H, m), 4.0-4.2 (2H, m), 4.38 (1H, dd, J=8.0, 6.8 Hz), 4.63 (2H, s), 6.70 (2H, d, J=8.8 Hz), 7.1-7.4 (7H, m)
MS (ESI) m/z: 514 (M+H)$^+$.

Example 166

Methyl (S)-{2,3,9-trimethyl-4-[4-(methylpyridin-3-ylmethylamino)phenyl]-6H-thieno[3,2-f][1,2,4]triazolo[4,3-a][1,4]diazepin-6-yl}acetate The title compound (147 mg) was obtained from the compound (415 mg) described in Example 1 by a treatment in the same manner as in Example 164 and using N-methyl-(3-pyridylmethyl)amine (244 mg) instead of N-methylbenzylamine.
$^1$H-NMR (400 MHz, DMSO-$d_6$) δ: 1.71 (3H, s), 2.41 (3H, s), 2.57 (3H, s), 3.06 (3H, s), 3.30-3.46 (2H, m), 3.64 (3H, s), 4.39 (1H, t, J=7.4 Hz), 4.67 (2H, s), 6.73 (2H, d, J=8.8 Hz), 7.23 (2H, d, J=8.0 Hz), 7.30 (1H, m), 7.55 (1H, d, J=8.0 Hz), 8.43 (2H, brs)
MS (ESI) m/z: 501 (M+H)$^+$.

Example 167

Methyl (S)-{4-(4-benzylaminophenyl)-2,3,9-trimethyl-6H-thieno[3,2-f][1,2,4]triazolo[4,3-a][1,4]diazepin-6-yl}acetate The title compound (9 g) was obtained from the compound (12 g) described in Example 1 by a treatment in the same manner as in Example 164 and using benzylamine (4.9 mL) instead of N-methylbenzylamine.
$^1$H-NMR (270 MHz, DMSO-$d_6$) δ: 1.71 (3H, s), 2.41 (3H, s), 2.56 (3H, s), 3.3-3.6 (2H, m), 3.64 (3H, s), 4.29 (2H, d, J=5.9 Hz), 4.37 (1H, t, J=7.6 Hz), 6.55 (2H, d, J=8.4 Hz), 6.80 (1H, m), 7.0-7.4 (7H, m)
MS (ESI) m/z: 486 (M+H)$^+$.

Example 168

Methyl (S)-(2,3,9-trimethyl-4-{4-[(pyridin-3-ylmethyl)amino]phenyl}-6H-thieno[3,2-f][1,2,4]triazolo[4,3-a][1,4]diazepin-6-yl)acetate The title compound (385 mg) was obtained from the compound (415 mg) described in Example 1 by a treatment in the same manner as in Example 164 and using 3-(aminomethyl)pyridine (150 μL) instead of N-methylbenzylamine.
$^1$H-NMR (270 MHz, DMSO-$d_6$) δ: 1.71 (3H, s), 2.41 (3H, s), 2.57 (3H, s), 3.3-3.6 (2H, m), 3.64 (3H, s), 4.3 (3H, m), 6.57 (2H, d, J=8.9 Hz), 6.82 (1H, t-like), 7.14 (2H, d, J=8.9 Hz), 7.32 (1H, dd, J=8, 4 Hz), 7.71 (1H, d, J=8 Hz), 8.43 (1H, d, J=4 Hz), 8.55 (1H, d, J=1.9 Hz)
MS (ESI) m/z: 487 (M+H)$^+$.

Example 169

Methyl (S)-(2,3,9-trimethyl-4-{4-[(pyridin-4-ylmethyl)amino]phenyl}-6H-thieno[3,2-f][1,2,4]triazolo[4,3-a][1,4]diazepin-6-yl)acetate The title compound (162 mg) was obtained from the compound (415 mg) described in Example 1 by a treatment in the same manner as in Example 164 and using 4-aminomethylpyridine (150 μL) instead of N-methylbenzylamine.
$^1$H-NMR (270 MHz, DMSO-$d_6$) δ: 1.70 (3H, s), 2.40 (3H, s), 2.56 (3H, s), 3.3-3.6 (2H, m), 3.64 (3H, s), 4.3-4.5 (3H, m), 6.53 (2H, d, J=8.9 Hz), 6.91 (1H, t-like), 7.13 (1H, d, J=8.9 Hz), 7.29 (2H, d, J=5.7 Hz), 8.46 (2H, d, J=5.7 Hz)
MS (ESI) m/z: 487 (M+H)$^+$.

Example 170

Methyl (S)-{2,3,9-trimethyl-4-[4-(4-trifluoromethylbenzylamino)phenyl]-6H-thieno[3,2-f][1,2,4]triazolo[4,3-a][1,4]diazepin-6-yl}acetate The title compound (200 mg) was obtained from the compound (415 mg) described in Example 1 by a treatment in the same manner as in Example 164 and using 4-trifluoromethylbenzylamine (220 μL) instead of N-methylbenzylamine.
$^1$H-NMR (270 MHz, DMSO-$d_6$) δ: 1.71 (3H, s), 2.41 (3H, s), 2.61 (3H, s), 3.3-3.6 (2H, m), 3.64 (3H, s), 4.3-4.5 (3H, m), 6.53 (2H, d, J=8.9 Hz), 6.91 (1H, t-like), 7.13 (1H, d, J=8.9 Hz), 7.52 (2H, d, J=7.8 Hz), 7.67 (2H, d, J=7.8 Hz)
MS (ESI) m/z: 554 (M+H)$^+$.

Example 171

Methyl (S)-{2,3,9-trimethyl-4-(4-phenethylaminophenyl)-6H-thieno[3,2-f][1,2,4]triazolo[4,3-a][1,4]diazepin-6-yl}acetate The title compound (45 mg) was obtained from the compound (415 mg) described in Example 1 by a treatment in the same manner as in Example 164 and using phenethylamine (190 μL) instead of N-methylbenzylamine.

$^1$H-NMR (270 MHz, DMSO-d$_6$) δ: 1.73 (3H, s), 2.42 (3H, s), 2.58 (3H, s), 2.82 (2H, t, J=7.8 Hz), 3.3-3.6 (4H, m), 3.65 (3H, s), 4.38 (1H, t, J=7 Hz), 6.29 (1H, t-like), 6.55 (1H, d, J=8.9 Hz), 7.0-7.4 (7H, m)
MS (ESI) m/z: 500 (M+H)$^+$.

Example 172

Methyl (S)-{4-[4-(4-methoxybenzylamino)phenyl]-2,3,9-trimethyl-6H-thieno[3,2-f][1,2,4]triazolo[4,3-a][1,4]diazepin-6-yl}acetate The title compound (17 mg) was obtained from the compound (415 mg) described in Example 1 by a treatment in the same manner as in Example 164 and using 4-methoxybenzylamine (200 μL) instead of N-methylbenzylamine.
$^1$H-NMR (270 MHz, DMSO-d$_6$) δ: 1.72 (3H, s), 2.41 (3H, s), 2.57 (3H, s), 3.3-3.6 (2H, m), 3.64 (3H, s), 3.71 (3H, s), 4.20 (2H, d, J=5.7 Hz), 4.37 (1H, t, J=7 Hz), 6.54 (2H, d, J=8.6 Hz), 6.71 (1H, t, J=5.7 Hz), 6.86 (2H, d, J=8.6 Hz), 7.13 (2H, d, J=8.6 Hz), 7.24 (2H, d, J=8.6 Hz),
MS (ESI) m/z: 516 (M+H)$^+$.

Example 173

Methyl (S)-(2,3,9-trimethyl-4-{4-[(thiophen-2-ylmethyl)amino]phenyl}-6H-thieno[3,2-f][1,2,4]triazolo[4,3-a][1,4]diazepin-6-yl)acetate The title compound (45 mg) was obtained from the compound (415 mg) described in Example 1 by a treatment in the same manner as in Example 164 and using thiophene-2-methylamine (155 μL) instead of N-methylbenzylamine.
$^1$H-NMR (270 MHz, DMSO-d$_6$) δ: 1.71 (3H, s), 2.42 (3H, s), 2.58 (3H, s), 3.3-3.6 (2H, m), 3.65 (3H, s), 4.3-4.6 (3H, m), 6.62 (2H, d, J=8.9 Hz), 6.95 (1H, dd, J=4.9, 1.4 Hz), 7.03 (1H, d, J=3.2 Hz), 7.17 (2H, d, J=8.9 Hz), 7.36 (1H, dd, J=4.9, 1.4 Hz)
MS (ESI) m/z: 492 (M+H)$^+$.

Example 174

Methyl (S)-{4-[4-(3-methoxybenzylamino)phenyl]-2,3,9-trimethyl-6H-thieno[3,2-f][1,2,4]triazolo[4,3-a][1,4]diazepin-6-yl}acetate The title compound (339 mg) was obtained from the compound (830 mg) described in Example 1 by a treatment in the same manner as in Example 164 and using 3-methoxybenzylamine (390 μL) instead of N-methylbenzylamine.
$^1$H-NMR (400 MHz, DMSO-d$_6$) δ: 1.71 (3H, s), 2.41 (3H, s), 2.60 (3H, s), 3.3-3.6 (2H, m), 3.64 (3H, s), 3.70 (3H, s), 4.26 (2H, d, J=6.0 Hz), 4.37 (1H, t, J=7.2 Hz), 6.54 (2H, d, J=8.4 Hz), 6.6-6.8 (2H, m), 6.88 (2H, m), 7.14 (2H, d, J=8.4 Hz), 7.21 (1H, t, J=7.6 Hz)
MS (ESI) m/z: 516 (M+H)$^+$.

Example 175

Methyl (S)-{4-[4-(3,4-dimethoxybenzylamino)phenyl]-2,3,9-trimethyl-6H-thieno[3,2-f][1,2,4]triazolo[4,3-a][1,4]diazepin-6-yl}acetate The title compound (820 mg) was obtained from the compound (830 mg) described in Example 1 by a treatment in the same manner as in Example 164 and using 3,4-dimethoxybenzylamine (450 μL) instead of N-methylbenzylamine.
$^1$H-NMR (400 MHz, DMSO-d$_6$) δ: 1.71 (3H, s), 2.41 (3H, s), 2.57 (3H, s), 3.3-3.6 (2H, m), 3.64 (3H, s), 3.70 (6H, s), 4.20 (2H, d, J=6.0 Hz), 4.37 (1H, t, J=7.2 Hz), 6.56 (2H, d, J=8.4 Hz), 6.65 (1H, t-like), 6.8-6.9 (2H, m), 6.93 (1H, d, J=1.2 Hz), 7.13 (2H, d, J=8.4 Hz)
MS (ESI) m/z: 546 (M+H)$^+$.

Example 176

Methyl (S)-{2,3,9-trimethyl-4-[4-(2-methylbenzylamino)phenyl]-6H-thieno[3,2-f][1,2,4]triazolo[4,3-a][1,4]diazepin-6-yl}acetate The title compound (287 mg) was obtained from the compound (830 mg) described in Example 1 by a treatment in the same manner as in Example 164 and using 2-methylbenzylamine (375 μL) instead of N-methylbenzylamine.
$^1$H-NMR (400 MHz, DMSO-d$_6$) δ: 1.73 (3H, s), 2.30 (3H, s), 2.41 (3H, s), 2.57 (3H, s), 3.33 (1H, dd, J=16.4, 6.8 Hz), 3.43 (1H, dd, J=16.4, 6.8 Hz), 3.64 (3H, s), 4.24 (2H, d, J=5.6 Hz), 4.37 (1H, t, J=6.8 Hz), 6.5-6.6 (3H, m), 7.0-7.3 (6H, m)
MS (ESI) m/z: 500 (M+H)$^+$.

Example 177

Methyl (S)-{4-[4-(4-fluorobenzylamino)phenyl]-2,3,9-trimethyl-6H-thieno[3,2-f][1,2,4]triazolo[4,3-a][1,4]diazepin-6-yl}acetate The title compound (339 mg) was obtained from the compound (830 mg) described in Example 1 by a treatment in the same manner as in Example 164 and using 4-fluorobenzylamine (350 μL) instead of N-methylbenzylamine.
$^1$H-NMR (400 MHz, DMSO-d$_6$) δ: 1.71 (3H, s), 2.41 (3H, s), 2.56 (3H, s), 3.33 (1H, dd, J=16.4, 6.8 Hz), 3.42 (1H, dd, J=16.4, 6.8 Hz), 3.64 (3H, s), 4.27 (2H, d, J=6.0 Hz), 4.37 (1H, t, J=6.8 Hz), 6.55 (2H, d, J=8.8 Hz), 6.75 (1H, t, J=6.0 Hz), 7.0-7.2 (4H, m), 7.35 (2H, dd, J=8.8, 5.6 Hz)
MS (ESI) m/z: 504 (M+H)$^+$.

Example 178

Methyl (S)-{4-[4-(4-methoxycarbonylbenzylamino)phenyl]-2,3,9-trimethyl-6H-thieno[3,2-f][1,2,4]triazolo[4,3-a][1,4]diazepin-6-yl}acetate The title compound (126 mg) was obtained from the compound (830 mg) described in Example 1 by a treatment in the same manner as in Example 164 and using 4-methoxycarbonylbenzylamine (1 mL) instead of N-methylbenzylamine.
$^1$H-NMR (400 MHz, DMSO-d$_6$) δ: 1.71 (3H, s), 2.41 (3H, s), 2.56 (3H, s), 3.3-3.5 (2H, m), 3.64 (3H, s), 3.82 (3H, s), 4.3-4.5 (3H, m), 6.54 (2H, d, J=8.0 Hz), 6.86 (1H, brs), 7.13 (2H, d, J=8.0 Hz), 7.45 (2H, d, J=8.0 Hz), 7.89 (2H, d, J=8.0 Hz)
MS (ESI) m/z: 544 (M+H)$^+$.

Example 179

Methyl (S)-{4-[4-(2,4-difluorobenzylamino)phenyl]-2,3,9-trimethyl-6H-thieno[3,2-f][1,2,4]triazolo[4,3-a][1,4]diazepin-6-yl}acetate The title compound (305 mg) was obtained from the compound (830 mg) described in Example 1 by a treatment in the same manner as in Example 164 and using 2,4-difluorobenzylamine (360 μL) instead of N-methylbenzylamine.

¹H-NMR (400 MHz, DMSO-d₆) δ: 1.71 (3H, s), 2.41 (3H, s), 2.57 (3H, s), 3.33 (1H, dd, J=16.4, 6.8 Hz), 3.43 (1H, dd, J=16.4, 6.8 Hz), 3.64 (3H, s), 4.29 (2H, d, J=6.0 Hz), 4.38 (2H, t, J=6.8 Hz), 6.56 (2H, d, J=8.8 Hz), 6.69 (1H, t, J=6.0 Hz), 7.00 (1H, t-like), 7.1-7.3 (3H, m), 7.37 (1H, q, J=7.0 Hz)
MS (ESI) m/z: 522 (M+H)⁺.

Example 180

Methyl (S)-{4-[4-(4-methylbenzylamino)phenyl]-2,3,9-trimethyl-6H-thieno[3,2-f][1,2,4]triazolo[4,3-a][1,4]diazepin-6-yl}acetate The title compound (125 mg) was obtained from the compound (830 mg) described in Example 1 by a treatment in the same manner as in Example 164 and using 4-methylbenzylamine (360 μL) instead of N-methylbenzylamine.
¹H-NMR (400 MHz, DMSO-d₆) δ: 1.71 (3H, s), 2.25 (3H, s), 2.41 (3H, s), 2.57 (3H, s), 3.3-3.5 (2H, m), 3.64 (3H, s), 4.23 (2H, d, J=6.0 Hz), 4.36 (1H, t, J=7.2 Hz), 6.54 (2H, d, J=8.8 Hz), 6.69 (1H, t-like), 7.0-7.1 (4H, m), 7.19 (2H, d, J=8.8 Hz)
MS (ESI) m/z: 500 (M+H)⁺.

Example 181

Methyl (S)-{4-[4-(2-methoxybenzylamino)phenyl]-2,3,9-trimethyl-6H-thieno[3,2-f][1,2,4]triazolo[4,3-a][1,4]diazepin-6-yl}acetate The title compound (147 mg) was obtained from the compound (830 mg) described in Example 1 by a treatment in the same manner as in Example 164 and using 2-methoxybenzylamine (400 μL) instead of N-methylbenzylamine.
¹H-NMR (400 MHz, DMSO-d₆) δ: 1.72 (3H, s), 2.41 (3H, s), 2.56 (3H, s), 3.3-3.5 (2H, m), 3.64 (3H, s), 3.82 (3H, s), 4.23 (2H, d, J=6.0 Hz), 4.37 (1H, t, J=7.2 Hz), 6.5-6.6 (3H, m), 6.85 (1H, t, J=6.0 Hz), 6.98 (2H, d, J=7.6 Hz), 7.1-7.3 (4H, m)
MS (ESI) m/z: 516 (M+H)⁺.

Example 182

Methyl (S)-{4-[4-(2,3-dimethoxybenzylamino)phenyl]-2,3,9-trimethyl-6H-thieno[3,2-f][1,2,4]triazolo[4,3-a][1,4]diazepin-6-yl}acetate The title compound (197 mg) was obtained from the compound (830 mg) described in Example 1 by a treatment in the same manner as in Example 164 and using 2,3-dimethoxybenzylamine (440 μL) instead of N-methylbenzylamine.
¹H-NMR (400 MHz, DMSO-d₆) δ: 1.72 (3H, s), 2.41 (3H, s), 2.56 (3H, s), 3.3-3.5 (2H, m), 3.64 (3H, s), 3.75 (3H, s), 3.79 (3H, s), 4.26 (2H, d, J=6.0 Hz), 4.37 (1H, t, J=7.2 Hz), 6.53 (2H, d, J=8.8 Hz), 6.65 (1H, t, J=6.0 Hz), 6.81 (1H, dd, J=7.2, 1.6 Hz), 6.9-7.0 (2H, m), 7.13 (2H, d, J=8.8 Hz)
MS (ESI) m/z: 546 (M+H)⁺.

Example 183

Methyl (S)-{4-[4-(4-methoxyphenethylamino)phenyl]-2,3,9-trimethyl-6H-thieno[3,2-f][1,2,4]triazolo[4,3-a][1,4]diazepin-6-yl}acetate The title compound (219 mg) was obtained from the compound (830 mg) described in Example 1 by a treatment in the same manner as in Example 164 and using 4-methoxyphenethylamine (440 μL) instead of N-methylbenzylamine.
¹H-NMR (400 MHz, DMSO-d₆) δ: 1.73 (3H, s), 2.42 (3H, s), 2.58 (3H, s), 2.75 (2H, t, J=7.6 Hz), 3.1-3.2 (2H, m), 3.3-3.5 (2H, m), 3.65 (3H, s), 3.71 (3H, s), 4.38 (1H, t, J=7.2 Hz), 6.25 (1H, t, J=5.2 Hz), 6.54 (2H, d, J=8.4 Hz), 6.84 (2H, d, J=8.4 Hz), 7.17 (4H, d, J=8.4 Hz)
MS (ESI) m/z: 530 (M+H)⁺.

Example 184

Methyl (S)-(4-{4-[2-(4-fluorophenyl)ethylamino]phenyl}-2,3,9-trimethyl-6H-thieno[3,2-f][1,2,4]triazolo[4,3-a][1,4]diazepin-6-yl)acetate The title compound (2.2 g) was obtained from the compound (8.3 g) described in Example 1 by a treatment in the same manner as in Example 164 and using 4-fluorophenethylamine (4 mL) instead of N-methylbenzylamine.
¹H-NMR (400 MHz, DMSO-d₆) δ: 1.73 (3H, s), 2.42 (3H, s), 2.58 (3H, s), 2.81 (2H, t, J=7.6 Hz), 3.1-3.5 (4H, m), 3.65 (3H, s), 4.40 (1H, brs), 6.26 (1H, brs), 6.56 (2H, d, J=8.4 Hz), 7.0-7.2 (4H, m), 7.29 (2H, dd, J=8.4, 6.0 Hz)
MS (ESI) m/z: 518 (M+H)⁺.

Example 185

Methyl (S)-(4-{4-[(benzo[1,3]dioxol-5-ylmethyl)amino]phenyl}-2,3,9-trimethyl-6H-thieno[3,2-f][1,2,4]triazolo[4,3-a][1,4]diazepin-6-yl)acetate The title compound (250 mg) was obtained from the compound (830 mg) described in Example 1 by a treatment in the same manner as in Example 164 and using 3,4-methylenedioxybenzylamine (380 μL) instead of N-methylbenzylamine.
¹H-NMR (400 MHz, DMSO-d₆) δ: 1.71 (3H, s), 2.41 (3H, s), 2.57 (3H, s), 3.1-3.5 (2H, m), 3.64 (3H, s), 4.18 (2H, d, J=6.0 Hz), 4.37 (1H, t, J=7.6 Hz), 5.95 (2H, s), 6.54 (2H, d, J=8.8 Hz), 6.73 (1H, t, J=6.0 Hz), 6.79-6.84 (2H, m), 6.87 (1H, s), 7.13 (2H, d, J=8.8 Hz)
MS (ESI) m/z: 530 (M+H)⁺.

Example 186

Methyl (S)-(2,3,9-trimethyl-4-{4-[(naphthalene-1-ylmethyl)amino]phenyl}-6H-thieno[3,2-f][1,2,4]triazolo[4,3-a][1,4]diazepin-6-yl)acetate The title compound (172 mg) was obtained from the compound (830 mg) described in Example 1 by a treatment in the same manner as in Example 164 and using 1-naphthalenemethylamine (440 μL) instead of N-methylbenzylamine.
¹H-NMR (400 MHz, DMSO-d₆) δ: 1.74 (3H, s), 2.41 (3H, s), 2.57 (3H, s), 3.1-3.5 (2H, m), 3.64 (3H, s), 4.38 (1H, t, J=7.2 Hz), 4.74 (2H, d, J=5.6 Hz), 6.62 (2H, d, J=8.8 Hz), 6.82 (1H, t, J=5.6 Hz), 7.16 (2H, d, J=8.0 Hz), 7.4-7.5 (2H, m), 7.5-7.6 (2H, m), 7.83 (1H, d, J=8.0 Hz), 7.95 (1H, d, J=8.0 Hz), 8.23 (1H, d, J=8.0 Hz)
MS (ESI) m/z: 536 (M+H)⁺.

Example 187

Methyl (S)-(4-{4-[3-(4-fluorophenyl)-3-oxopropylamino]phenyl}-2,3,9-trimethyl-6H-thieno[3,2-f][1,2,4]triazolo[4,3-a][1,4]diazepin-6-yl)acetate To a mixture of the compound (200 mg) described in Starting Material Synthetic Example 4, potassium carbonate (140 mg) and 3-chloro-4-fluoropropiophenone (140 mg) was added dimethylformamide (1.7 mL), and the mixture was stirred at 70° C. for 8 hr. After cooling, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) to give the title compound (61 mg).

$^1$H-NMR (300 MHz, DMSO-$d_6$) δ: 1.70 (3H, s), 2.40 (3H, s), 2.55 (3H, s), 3.35 (6H, m), 3.62 (3H, s), 4.45 (1H, t, J=6.9 Hz), 6.21 (1H, m), 6.52 (2H, d, J=8.1 Hz), 7.15 (2H, d, J=7.2 Hz), 7.33 (2H, dd, J=8.1 Hz, 8.1 Hz), 8.02 (2H, m);

MS (ESI) m/z: 546 (M+H)$^+$.

Example 188

Methyl (S)-{2,3,9-trimethyl-4-[4-(3-phenylpropylamino)phenyl]-6H-thieno[3,2-f][1,2,4]triazolo[4,3-a][1,4]diazepin-6-yl}acetate The title compound (10 g) was obtained from the compound (15 g) described in Example 1 by a treatment in the same manner as in Example 164 and using phenylpropylamine (7.8 mL) instead of N-methylbenzylamine.

$^1$H-NMR (400 MHz, DMSO-$d_6$) δ: 1.61 (3H, s), 1.80-1.90 (2H, m), 2.42 (3H, s), 2.58 (3H, s), 2.66 (2H, t, J=7.2 Hz), 3.0-3.1 (2H, m), 3.30-3.50 (2H, m), 3.65 (3H, s), 4.37 (1H, t, J=7.6 Hz), 6.21 (1H, t, J=5.2 Hz), 6.51 (2H, d, J=8.4 Hz), 7.1-7.3 (7H, m)

MS (ESI) m/z: 514 (M+H)$^+$.

Example 189

Ethyl (S)-{2,3,9-trimethyl-4-[4-(2-oxo-2-pyridin-4-ylethyl)phenyl]-6H-thieno[3,2-f][1,2,4]triazolo[4,3-a][1,4]diazepin-6-yl}acetate The title compound (584 mg) was obtained from the compound (1.3 g) described in Example 62 by a treatment in the same manner as in the below-mentioned Example 222 and using 1-pyridin-4-ylethanone (730 μL) instead of 4-methoxyacetophenone.

$^1$H-NMR (400 MHz, DMSO-$d_6$) δ: 1.21 (3H, t, J=7.2 Hz), 1.62 (3H, s), 2.42 (3H, s), 2.60 (3H, s), 3.3-3.5 (2H, m), 4.0-4.3 (2H, m), 4.47 (1H, t, J=7.6 Hz), 4.52 (2H, s), 7.2-7.5 (4H, m), 7.88 (2H, d, J=6.0 Hz), 8.81 (2H, d, J=6.0 Hz)

MS (ESI) m/z: 514 (M+H)$^+$.

Example 190

Methyl (S)-(4-{4-[(furan-2-ylmethyl)amino]phenyl}-2,3,9-trimethyl-6H-thieno[3,2-f][1,2,4]triazolo[4,3-a][1,4]diazepin-6-yl)acetate The title compound (480 mg) was obtained from the compound (1 g) described in Example 1 by a treatment in the same manner as in Example 164 and using furfurylamine (350 μL) instead of N-methylbenzylamine.

$^1$H-NMR (300 MHz, DMSO-$d_6$) δ: 1.70 (3H, s), 2.40 (3H, s), 2.56 (3H, s), 3.4 (2H, m), 3.63 (3H, s), 4.26 (2H, s), 4.42 (1H, brs), 6.27 (1H, s), 6.35 (1H, s), 6.62 (2H, d, J=8.1 Hz), 7.16 (1H, d, J=8.1 Hz), 7.54 (1H, s)

MS (ESI) m/z: 476 (M+H)$^+$.

Example 191

Methyl (S)-(2,3,9-trimethyl-4-{4-[(5-methylfuran-2-ylmethyl)amino]phenyl}-6H-thieno[3,2-f][1,2,4]triazolo[4,3-a][1,4]diazepin-6-yl)acetate The title compound (430 mg) was obtained from the compound (1 g) described in Example 1 by a treatment in the same manner as in Example 164 and using 5-methylfurfurylamine (400 μL) instead of N-methylbenzylamine.

$^1$H-NMR (300 MHz, DMSO-$d_6$) δ: 1.70 (3H, s), 2.18 (3H, s), 2.40 (3H, s), 2.56 (3H, s), 3.36 (1H, m), 3.42 (1H, dd, J=16.5 Hz, 6.6 Hz), 3.63 (3H, s), 4.17 (2H, d, J=5.1 Hz), 4.36 (1H, t, J=7.2 Hz), 5.94 (1H, d, J=2.4 Hz), 6.13 (1H, d, J=2.4 Hz), 6.59 (2H, d, J=8.1 Hz), 7.14 (2H, d, J=8.1 Hz)

MS (ESI) m/z: 490 (M+H)$^+$.

Example 192

Ethyl (S)-(4-{4-[2-(4-fluorophenyl)ethylamino]phenyl}-2,3,9-trimethyl-6H-thieno[3,2-f][1,2,4]triazolo[4,3-a][1,4]diazepin-6-yl)acetate The title compound (257 mg) was obtained from the compound (2.6 g) described in Example 62 by a treatment in the same manner as in Example 139 and using 4-fluorophenethylamine (1.2 mL) instead of 4-fluoroaniline.

$^1$H-NMR (400 MHz, DMSO-$d_6$) δ: 1.20 (3H, t, J=7.2 Hz), 1.72 (3H, s), 2.42 (3H, s), 2.58 (3H, s), 2.81 (2H, t, J=6.8 Hz), 3.2-3.5 (4H, m), 4.0-4.2 (2H, m), 4.37 (1H, t, J=7.2 Hz), 6.23 (1H, t, J=5.2 Hz), 6.54 (2H, d, J=8.8 Hz), 7.09 (2H, t, J=8.8 Hz), 7.16 (2H, d, J=8.8 Hz), 7.29 (2H, dd, J=8.8, 6.0 Hz).

Example 193

Ethyl (S)-{4-(4-benzylaminophenyl)-2,3,9-trimethyl-6H-thieno[3,2-f][1,2,4]triazolo[4,3-a][1,4]diazepin-6-yl}acetate The title compound (1.5 g) was obtained from the compound (6 g) described in Example 62 by a treatment in the same manner as in Example 139 and using benzylamine (2.3 mL) instead of 4-fluoroaniline.

$^1$H-NMR (400 MHz, DMSO-$d_6$) δ: 1.19 (3H, t, J=7.2 Hz), 1.71 (3H, s), 2.41 (3H, s), 2.56 (3H, s), 3.2-3.5 (2H, m), 4.0-4.2 (2H, m), 4.29 (2H, d, J=5.6 Hz), 4.36 (1H, t, J=7.2 Hz), 6.55 (2H, d, J=8.4 Hz), 6.74 (1H, t-like), 7.14 (2H, d, J=8.4 Hz), 7.21 (1H, t-like), 7.2-7.4 (4H, m)

MS (ESI) m/z: 500 (M+H)$^+$.

Example 194

Methyl (S)-(2,3,9-trimethyl-4-{4-[methyl-(2-pyridin-2-yl-ethyl)amino]phenyl}-6H-thieno[3,2-f][1,2,4]triazolo[4,3-a][1,4]diazepin-6-yl)acetate The title compound (3 mg) was obtained from the compound (2 g) described in Example 1 by a treatment in the same manner as in Example 139 and using 2-(2-methylaminoethyl)pyridine (790 mg) instead of 4-fluoroaniline.

1H NMR (400 MHz, CDCl$_3$) δ 1.78 (s, 3H), 2.42 (s, 3H), 2.66 (s, 3H), 2.89 (s, 3H), 3.01 (t, 2H, J=5.4 Hz), 3.54-3.69 (m, 2H), 3.70-3.86 (m, 2H), 3.77 (s, 3H), 4.57 (t, 1H, J=4.8

Hz), 6.63 (d, 2H, J=6.9 Hz), 7.05 (d, 1H, J=5.7 Hz), 7.10-7.14 (m, 1H), 7.33 (d, 2H, J=6.9 Hz), 7.55 (t, 1H, J=6.0, 5.7 Hz), 8.55 (d, 1H, J=3.3 Hz)
MS (ESI) m/z: 515 (M+H)$^+$.

Example 195

Methyl (S)-(2,3,9-trimethyl-4-[4-(4-phenylbutylamino)phenyl]-6H-thieno[3,2-f][1,2,4]triazolo[4,3-a][1,4]diazepin-6-yl)acetate The title compound (4.7 g) was obtained from the compound (5 g) described in Example 1 by a treatment in the same manner as in Example 164 and using 4-phenylbutylamine (2.9 mL) instead of N-methylbenzylamine.
$^1$H-NMR (400 MHz, DMSO-d$_6$) δ: 1.55-1.71 (4H, m), 1.72 (3H, s), 2.36 (3H, s), 2.58 (3H, s), 2.58-2.65 (2H, m), 3.01-3.07 (2H, m), 3.30-3.50 (2H, m), 3.65 (3H, s), 4.37 (1H, t, J=7.2 Hz), 6.14 (1H, t, J=5.2 Hz), 6.50 (2H, t, J=8.8 Hz), 7.1-7.3 (7H, m)
MS (ESI) m/z: 528 (M+H)$^+$.

Example 196

Ethyl (S)-{4-[4-(2-pyridin-3-ylethylamino)phenyl]-2,3,9-trimethyl-6H-thieno[3,2-f][1,2,4]triazolo[4,3-a][1,4]diazepin-6-yl}acetate The title compound (630 mg) was obtained from the compound (858 mg) described in Example 62 by a treatment in the same manner as in Example 139 and using 3-pyridylethylamine (350 μL) instead of 4-fluoroaniline.
$^1$H-NMR (400 MHz, DMSO-d$_6$) δ: 1.20 (3H, t, J=7.2 Hz), 1.72 (3H, s), 2.42 (3H, s), 2.58 (3H, s), 2.84 (2H, t, J=7.2 Hz), 3.2-3.5 (4H, m), 4.0-4.2 (2H, m), 4.37 (1H, t, J=7.6 Hz), 6.28 (1H, t, J=5.2 Hz), 6.56 (2H, d, J=8.4 Hz), 7.17 (2H, d, J=8.4 Hz), 7.30 (1H, dd, J=7.6, 4.8 Hz), 7.68 (1H, d, J=7.6 Hz), 8.41 (1H, dd, J=7.6, 1.2 Hz), 8.47 (1H, d, J=2.0 Hz)
MS (ESI) m/z: 515 (M+H)$^+$.

Example 197

Ethyl (S)-{4-[4-(2-pyridin-2-ylethylamino)phenyl]-2,3,9-trimethyl-6H-thieno[3,2-f][1,2,4]triazolo[4,3-a][1,4]diazepin-6-yl}acetate The title compound (186 mg) was obtained from the compound (858 mg) described in Example 62 by a treatment in the same manner as in Example 139 and using 2-pyridylethylamine (370 μL) instead of 4-fluoroaniline.
$^1$H-NMR (400 MHz, DMSO-d$_6$) δ: 1.20 (3H, t, J=7.2 Hz), 1.73 (3H, s), 2.42 (3H, s), 2.58 (3H, s), 2.97 (2H, t, J=7.6 Hz), 3.3-3.5 (4H, m), 4.0-4.2 (2H, m), 4.37 (1H, t, J=7.6 Hz), 6.26 (1H, t, J=6.8 Hz), 6.56 (2H, d, J=8.8 Hz), 7.17 (2H, d, J=8.8 Hz), 7.21 (1H, dd, J=6.8, 4.8 Hz), 7.29 (1H, d, J=6.8 Hz), 7.6-7.8 (1H, m), 8.50 (1H, d, J=4.8 Hz)
MS (ESI) m/z: 515 (M+H)$^+$.

Example 198

Ethyl (S)-(2,3,9-trimethyl-4-{4-[(pyridin-3-ylmethyl)amino]phenyl}-6H-thieno[3,2-f][1,2,4]triazolo[4,3-a][1,4]diazepin-6-yl)acetate The title compound (122 mg) was obtained from the compound (858 mg) described in Example 62 by a treatment in the same manner as in Example 139 and using 3-pyridylmethylamine (300 μL) instead of 4-fluoroaniline.
$^1$H-NMR (400 MHz, DMSO-d$_6$) δ: 1.19 (3H, t, J=7.2 Hz), 1.70 (3H, s), 2.41 (3H, s), 2.57 (3H, s), 3.3-3.5 (2H, m), 4.0-4.2 (2H, m), 4.3-4.4 (3H, m), 6.58 (2H, t, J=8.4 Hz), 6.79 (1H, t, J=7.6 Hz), 7.15 (2H, d, J=8.4 Hz), 7.32 (1H, dd, J=7.6, 4.8 Hz), 7.70 (1H, d, J=7.6 Hz), 8.43 (1H, dd, J=4.8, 1.2 Hz), 8.55 (1H, d, J=1.2 Hz)
MS (ESI) m/z: 501 (M+H)$^+$.

Example 199

Ethyl (S)-{4-[4-(4-fluorobenzylamino)phenyl]-2,3,9-trimethyl-6H-thieno[3,2-f][1,2,4]triazolo[4,3-a][1,4]diazepin-6-yl}acetate The title compound (567 mg) was obtained from the compound (858 mg) described in Example 62 by a treatment in the same manner as in Example 139 and using 4-fluorobenzylamine (340 μL) instead of 4-fluoroaniline.
$^1$H-NMR (400 MHz, DMSO-d$_6$) δ: 1.19 (3H, t, J=7.2 Hz), 1.71 (3H, s), 2.41 (3H, s), 2.61 (3H, s), 3.3-3.5 (2H, m), 4.0-4.2 (2H, m), 4.27 (2H, d, J=6.0 Hz), 4.36 (1H, t, J=7.6 Hz), 6.55 (2H, d, J=8.4 Hz), 6.76 (1H, t, J=6.0 Hz), 7.0-7.2 (4H, m), 7.35 (2H, dd, J=8.4, 5.6 Hz)
MS (ESI) m/z: 518 (M+H)$^+$.

Example 200

Ethyl (S)-{4-[4-(4-methoxybenzylamino)phenyl]-2,3,9-trimethyl-6H-thieno[3,2-f][1,2,4]triazolo[4,3-a][1,4]diazepin-6-yl}acetate The title compound (319 mg) was obtained from the compound (858 mg) described in Example 62 by a treatment in the same manner as in Example 139 and using 4-methoxybenzylamine (390 μL) instead of 4-fluoroaniline.
$^1$H-NMR (400 MHz, DMSO-d$_6$) δ: 1.19 (3H, t, J=7.2 Hz), 1.71 (3H, s), 2.41 (3H, s), 2.56 (3H, s), 3.3-3.5 (2H, m), 3.71 (3H, s), 4.0-4.2 (2H, m), 4.21 (2H, d, J=6.0 Hz), 4.36 (1H, t, J=7.2 Hz), 6.55 (2H, d, J=8.4 Hz), 6.67 (1H, t-like), 6.86 (2H, d, J=8.4 Hz), 7.13 (2H, d, J=8.4 Hz), 7.24 (2H, d, J=8.4 Hz)
MS (ESI) m/z: 530 (M+H)$^+$.

Example 201

Ethyl (S)-{2,3,9-trimethyl-4-[4-(2-phenoxyethylamino)phenyl]-6H-thieno[3,2-f][1,2,4]triazolo[4,3-a][1,4]diazepin-6-yl}acetate The title compound (540 mg) was obtained from the compound (858 mg) described in Example 62 by a treatment in the same manner as in Example 139 and using 2-phenoxyethylamine (400 μL) instead of 4-fluoroaniline.
$^1$H-NMR (400 MHz, DMSO-d$_6$) δ: 1.20 (3H, t, J=7.2 Hz), 1.73 (3H, s), 2.42 (3H, s), 2.58 (3H, s), 3.3-3.6 (4H, m), 4.0-4.2 (4H, m), 4.37 (1H, t, J=7.2 Hz), 6.37 (1H, t, J=7.2 Hz), 6.62 (2H, d, J=8.0 Hz), 6.8-7.0 (3H, m), 7.18 (2H, d, J=8.0 Hz), 7.27 (2H, dd, J=8.0, 7.2 Hz)
MS (ESI) m/z: 530 (M+H)$^+$.

Example 202

Ethyl (S)-(2,3,9-trimethyl-4-{4-[(pyridin-4-ylmethyl)amino]phenyl}-6H-thieno[3,2-f][1,2,4]triazolo[4,3-a][1,4]diazepin-6-yl)acetate The title compound (517 mg) was obtained from the compound (858 mg) described in Example 62 by a treatment in the same manner as in Example 139 and using 4-pyridylmethylamine (300 μL) instead of 4-fluoroaniline.

$^1$H-NMR (400 MHz, DMSO-$d_6$) δ: 1.19 (3H, t, J=7.2 Hz), 1.70 (3H, s), 2.41 (3H, s), 2.57 (3H, s), 3.3-3.6 (2H, m), 4.0-4.2 (2H, m), 4.3-4.5 (3H, m), 6.55 (2H, d, J=8.4 Hz), 6.99 (1H, brs), 7.16 (2H, d, J=8.4 Hz), 7.44 (2H, d, J=6.0 Hz), 8.54 (2H, d, J=6.0 Hz)

MS (ESI) m/z: 501 (M+H)$^+$.

Example 203

Ethyl (S)-{2,3,9-trimethyl-4-[4-(3-phenylpropylamino)phenyl]-6H-thieno[3,2-f][1,2,4]triazolo[4,3-a][1,4]diazepin-6-yl}acetate The title compound (159 mg) was obtained by a treatment in the same manner as in Example 162 and using the compound (1 g) described in Example 188 instead of the compound described in Example 156.

$^1$H-NMR (400 MHz, DMSO-$d_6$) δ: 1.20 (3H, t, J=7.2 Hz), 1.73 (3H, s), 1.8-1.9 (2H, m), 2.42 (3H, s), 2.58 (3H, s), 2.66 (2H, t, J=8.0 Hz), 3.03 (2H, q, J=6.4 Hz), 3.3-3.5 (2H, m), 4.0-4.2 (2H, m), 4.36 (1H, d, J=7.6, 6.8 Hz), 6.21 (1H, t, J=5.2 Hz), 6.51 (2H, d, J=8.8 Hz), 7.1-7.3 (7H, m)

MS (ESI) m/z: 528 (M+H)$^+$.

Example 204

Ethyl (S)-{4-[4-(3-imidazol-1-ylpropylamino)phenyl]-2,3,9-trimethyl-6H-thieno[3,2-f][1,2,4]triazolo[4,3-a][1,4]diazepin-6-yl}acetate The title compound (175 mg) was obtained from the compound (858 mg) described in Example 62 by a treatment in the same manner as in Example 139 and using N-(3-aminopropyl)imidazol (360 μL) instead of 4-fluoroaniline.

$^1$H-NMR (400 MHz, DMSO-$d_6$) δ: 1.20 (3H, t, J=7.2 Hz), 1.72 (3H, s), 1.9-2.1 (2H, m), 2.42 (3H, s), 2.58 (3H, s), 2.9-3.1 (2H, m), 3.3-3.5 (2H, m), 4.0-4.3 (4H, m), 4.37 (1H, t, J=7.2 Hz), 6.22 (1H, t-like), 6.50 (2H, d, J=8.4 Hz), 6.88 (1H, s), 7.1-7.3 (3H, m), 7.60 (1H, s)

MS (ESI) m/z: 518 (M+H)$^+$.

Example 205

Methyl (S)-{4-[4-(3,4-dihydro-1H-isoquinolin-2-yl)phenyl]-2,3,9-trimethyl-6H-thieno[3,2-f][1,2,4]triazolo[4,3-a][1,4]diazepin-6-yl}acetate The title compound was obtained from the compound (473 mg) described in Example 1 by a treatment in the same manner as in Example 164 and using 1,2,3,4-tetrahydroisoquinoline (570 μL) instead of N-methylbenzylamine.

$^1$H-NMR (400 MHz, DMSO-$d_6$) δ: 1.71 (3H, s), 2.43 (3H, s), 2.59 (3H, s), 2.91 (2H, t, J=6.0 Hz), 3.3-3.6 (2H, m), 3.59 (2H, t, J=6.0 Hz), 3.66 (3H, s), 4.41 (1H, t, J=7.2 Hz), 4.47 (2H, s), 6.95 (2H, d, J=9.2 Hz), 7.1-7.4 (6H, m)

MS (ESI) m/z: 512 (M+H)$^+$.

Example 206

Methyl (S)-{4-[4-(1,3-dihydroisoindol-2-yl)phenyl]-2,3,9-trimethyl-6H-thieno[3,2-f][1,2,4]triazolo[4,3-a][1,4]diazepin-6-yl}acetate The title compound (48 mg) was obtained from the compound (415 mg) described in Example 1 by a treatment in the same manner as in Example 164 and using isoindole (170 μL) instead of N-methylbenzylamine.

$^1$H-NMR (400 MHz, DMSO-$d_6$) δ: 1.74 (3H, s), 2.44 (3H, s), 2.62 (3H, s), 3.3-3.6 (2H, m), 3.67 (3H, s), 4.42 (1H, t, J=6.8 Hz), 4.66 (4H, s), 6.66 (2H, d, J=8.4 Hz), 7.2-7.5 (6H, m)

MS (ESI) m/z: 498 (M+H)$^+$.

Example 207

Methyl (S)-{4-[4-(2,3-dihydroindol-1-yl)phenyl]-2,3,9-trimethyl-6H-thieno[3,2-f][1,2,4]triazolo[4,3-a][1,4]diazepin-6-yl}acetate The title compound (409 mg) was obtained from the compound (415 mg) described in Example 1 by a treatment in the same manner as in Example 164 and using indoline (170 μL) instead of N-methylbenzylamine.

$^1$H-NMR (400 MHz, DMSO-$d_6$) δ: 1.74 (3H, s), 2.44 (3H, s), 2.60 (3H, s), 3.10 (2H, t, J=8.4 Hz), 3.40 (1H, dd, J=16.4, 6.8 Hz), 3.47 (1H, dd, J=16.4, 6.8 Hz), 3.67 (3H, s), 3.9-4.0 (2H, m), 4.46 (1H, t, J=6.8 Hz), 6.78 (1H, t, J=7.6 Hz), 7.07 (1H, t, J=7.6 Hz), 7.1-7.3 (4H, m), 7.40 (2H, d, J=8.4 Hz)

MS (ESI) m/z: 498 (M+H)$^+$.

Example 208

Methyl (S)-{4-[4-(6,7-dimethoxy-3,4-dihydro-1H-isoquinolin-2-yl)phenyl]-2,3,9-trimethyl-6H-thieno[3,2-f][1,2,4]triazolo[4,3-a][1,4]diazepin-6-yl}acetate The title compound (276 mg) was obtained from the compound (415 mg) described in Example 1 by a treatment in the same manner as in Example 164 and using 6,7-dimethoxy-1,2,3,4-tetrahydroisoquinoline (290 mg) instead of N-methylbenzylamine.

$^1$H-NMR (400 MHz, DMSO-$d_6$) δ: 1.71 (3H, s), 2.43 (3H, s), 2.59 (3H, s), 2.81 (2H, t, J=5.6 Hz), 3.37 (1H, dd, J=16.4, 6.8 Hz), 3.46 (1H, dd, J=16.4, 6.8 Hz), 3.56 (2H, t, J=5.6 Hz), 3.66 (3H, s), 3.72 (6H, s), 4.34 (2H, s), 4.41 (1H, d, J=6.8 Hz), 6.76 (1H, s), 6.82 (1H, s), 6.93 (2H, d, J=8.8 Hz), 7.28 (2H, d, J=8.8 Hz)

MS (ESI) m/z: 572 (M+H)$^+$.

Example 209

Ethyl (S)-{4-[4-(1,3-dihydroisoindol-2-yl)phenyl]-2,3,9-trimethyl-6H-thieno[3,2-f][1,2,4]triazolo[4,3-a][1,4]diazepin-6-yl}acetate The title compound (2.8 g) was obtained from the compound (2.6 g) described in Example 62 by a treatment in the same manner as in Example 139 and using isoindoline (1 mL) instead of 4-fluoroaniline.

$^1$H-NMR (400 MHz, DMSO-$d_6$) δ: 1.22 (3H, t, J=7.2 Hz), 1.74 (3H, s), 2.44 (3H, s), 2.61 (3H, s), 3.3-3.5 (2H, m), 4.0-4.2 (2H, m), 4.41 (1H, t, J=7.6 Hz), 4.66 (4H, s), 6.67 (2H, d, J=8.4 Hz), 7.2-7.5 (6H, m)

MS (ESI) m/z: 512 (M+H)$^+$.

Example 210

Methyl (S)-{2,3,9-trimethyl-4-[4-(4-phenylpiperazin-1-yl)phenyl]-6H-thieno[3,2-f][1,2,4]triazolo[4,3-a][1,4]diazepin-6-yl}acetate The title compound (324 mg) was obtained from the compound (415 mg) described in Example 1 by a treatment in the same manner as in Example 164 and using 1-phenylpiperazine (230 µL) instead of N-methylbenzylamine.

$^1$H-NMR (400 MHz, DMSO-$d_6$) δ: 1.70 (3H, s), 2.43 (3H, s), 2.60 (3H, s), 3.25-3.30 (4H, m), 3.35-3.50 (6H, m), 3.66 (3H, s), 4.42 (1H, t, J=7.2 Hz), 6.81 (1H, t, J=7.2 Hz), 6.99 (4H, d, J=8.4 Hz), 7.24 (2H, t, J=7.2 Hz), 7.29 (2H, d, J=8.4 Hz)

MS (ESI) m/z: 541 (M+H)$^+$.

Example 211

Methyl (S)-{4-[4-(4-cyano-4-phenylpiperidin-1-yl)phenyl]-2,3,9-trimethyl-6H-thieno[3,2-f][1,2,4]triazolo[4,3-a][1,4]diazepin-6-yl}acetate The title compound (430 mg) was obtained from the compound (415 mg) described in Example 1 by a treatment in the same manner as in Example 164 and using 4-cyano-4-phenylpiperidine (373 mg) instead of N-methylbenzylamine.

$^1$H-NMR (400 MHz, DMSO-$d_6$) δ: 1.70 (3H, s), 2.0-2.3 (4H, m), 2.43 (3H, s), 2.60 (3H, s), 3.03 (2H, t, J=13 Hz), 3.35-3.50 (2H, m), 3.66 (3H, s), 3.99 (2H, d, J=13 Hz), 4.43 (1H, t, J=7.6 Hz), 7.03 (2H, d, J=8 Hz), 7.30 (2H, d, J=8 Hz), 7.38 (1H, t, J=8 Hz), 7.46 (2H, t, J=8 Hz), 7.56 (2H, d, J=8 Hz)

MS (ESI) m/z: 565 (M+H)$^+$.

Example 212

Methyl (S)-(4-{4-[4-(hydroxydiphenylmethyl)piperidin-1-yl]phenyl}-2,3,9-trimethyl-6H-thieno[3,2-f][1,2,4]triazolo[4,3-a][1,4]diazepin-6-yl)acetate The title compound (173 mg) was obtained from the compound (415 mg) described in Example 1 by a treatment in the same manner as in Example 164 and using α-(4-piperidyl)benzhydrol (401 mg) instead of N-methylbenzylamine.

$^1$H-NMR (400 MHz, DMSO-$d_6$) δ: 1.32-1.36 (2H, m), 1.46-1.60 (2H, m), 1.70 (3H, s), 2.42 (3H, s), 2.58 (3H, s), 2.7-2.8 (3H, m), 3.35-3.50 (2H, m), 3.65 (3H, s), 3.80-3.84 (2H, m), 4.40 (1H, t, J=7.2 Hz), 5.31 (1H, s), 6.85 (2H, d, J=8 Hz), 7.1-7.2 (2H, m), 7.2-7.4 (6H, m), 7.53 (4H, d, J=8 Hz)

MS (ESI) m/z: 646 (M+H)$^+$.

Example 213

Methyl (S)-{2,3,9-trimethyl-4-[4-(4-pyridin-2-ylpiperazin-1-yl)phenyl]-6H-thieno[3,2-f][1,2,4]triazolo[4,3-a][1,4]diazepin-6-yl}acetate The title compound (432 mg) was obtained from the compound (415 mg) described in Example 1 by a treatment in the same manner as in Example 164 and using 1-(2-pyridyl)piperazine (220 µL) instead of N-methylbenzylamine.

$^1$H-NMR (400 MHz, DMSO-$d_6$) δ: 1.70 (3H, s), 2.42 (3H, s), 2.59 (3H, s), 3.35-3.50 (6H, m), 3.6-3.7 (7H, m), 4.42 (1H, t, J=7.2 Hz), 6.66 (1H, dd, J=6.8, 4.4 Hz), 6.88 (1H, d, J=8.8 Hz), 6.97 (2H, d, J=8.8 Hz), 7.29 (2H, d, J=8.8 Hz), 7.5-7.6 (1H, m), 8.13 (1H, dd, J=4.4, 1.6 Hz)

MS (ESI) m/z: 542 (M+H)$^+$.

Example 214

Methyl (S)-{4-[4-(4-benzylpiperazin-1-yl)phenyl]-2,3,9-trimethyl-6H-thieno[3,2-f][1,2,4]triazolo[4,3-a][1,4]diazepin-6-yl}acetate The title compound (419 mg) was obtained from the compound (415 mg) described in Example 1 by a treatment in the same manner as in Example 164 and using N-benzylpiperazine (260 µL) instead of N-methylbenzylamine.

$^1$H-NMR (400 MHz, DMSO-$d_6$) δ: 1.70 (3H, s), 2.42 (3H, s), 2.45-2.55 (4H, m), 2.59 (3H, s), 3.1-3.3 (4H, m), 3.35-3.50 (2H, m), 3.52 (2H, s), 3.65 (3H, s), 4.41 (1H, t, J=7.6 Hz), 6.90 (2H, d, J=9.2 Hz), 7.24-7.28 (3H, m), 7.32-7.34 (4H, m)

MS (ESI) m/z: 555 (M+H)$^+$.

Example 215

Methyl (S)-{4-[4-(4-hydroxy-4-phenylpiperidin-1-yl)phenyl]-2,3,9-trimethyl-6H-thieno[3,2-f][1,2,4]triazolo[4,3-a][1,4]diazepin-6-yl}acetate The title compound (250 mg) was obtained from the compound (415 mg) described in Example 1 by a treatment in the same manner as in Example 164 and using 4-hydroxy-4-phenylpiperidine (266 mg) instead of N-methylbenzylamine.

$^1$H-NMR (400 MHz, DMSO-$d_6$) δ: 1.66-1.73 (5H, m), 1.99-2.03 (2H, m), 2.43 (3H, s), 2.59 (3H, s), 3.20 (2H, t, J=12.4 Hz), 3.35-3.50 (2H, m), 3.66 (3H, s), 3.66-3.72 (2H, d, J=12.4 Hz), 4.42 (1H, t, J=7.2 Hz), 5.07 (1H, s), 6.97 (2H, d, J=9.2 Hz), 7.21 (1H, t, J=7.2 Hz), 7.26-7.34 (4H, m), 7.46 (2H, d, J=7.2 Hz)

MS (ESI) m/z: 556 (M+H)$^+$.

Example 216

Methyl (S)-(4-{4-[4-(2-methoxyphenyl)piperazin-1-yl]phenyl}-2,3,9-trimethyl-6H-thieno[3,2-f][1,2,4]triazolo[4,3-a][1,4]diazepin-6-yl)acetate The title compound (471 mg) was obtained from the compound (415 mg) described in Example 1 by a treatment in the same manner as in Example 164 and using 1-(2-methoxyphenyl)piperazine (288 mg) instead of N-methylbenzylamine.

$^1$H-NMR (400 MHz, DMSO-$d_6$) δ: 1.71 (3H, s), 2.43 (3H, s), 2.60 (3H, s), 3.0-3.1 (4H, m), 3.3-3.5 (6H, m), 3.66 (3H, s), 3.79 (3H, s), 4.42 (1H, t, J=7.6 Hz), 6.8-7.0 (6H, m), 7.29 (2H, d, J=8.8 Hz)

MS (ESI) m/z: 571 (M+H)$^+$.

Example 217

Methyl (S)-{4-[4-(4-benzyl-4-hydroxypiperidin-1-yl)phenyl]-2,3,9-trimethyl-6H-thieno[3,2-f][1,2,4]triazolo[4,3-a][1,4]diazepin-6-yl}acetate The title compound (339 mg) was obtained from the compound (415 mg) described in Example 1 by a treatment in the same manner as in Example 164 and using 4-benzyl-4-hydroxypiperidine (287 mg) instead of N-methylbenzylamine.

$^1$H-NMR (400 MHz, DMSO-$d_6$) δ: 1.3-1.6 (4H, m), 1.69 (3H, s), 2.42 (3H, s), 2.58 (3H, s), 2.69 (2H, s), 3.08 (2H, t, J=10.8 Hz), 3.3-3.6 (4H, m), 3.65 (3H, s), 4.3-4.4 (2H, m), 6.88 (2H, d, J=9.2 Hz), 7.1-7.3 (7H, m)

MS (ESI) m/z: 570 (M+H)$^+$.

Example 218

Methyl (S)-(2,3,9-trimethyl-4-{4-[4-(pyridine-4-carbonyl)piperazin-1-yl]phenyl}-6H-thieno[3,2-f][1,2,4]triazolo[4,3-a][1,4]diazepin-6-yl)acetate To a mixture of the compound (415 mg) described in Example 1, palladium acetate (11 mg), 2-(dicyclohexylphosphino)biphenyl (36 mg), tripotassium phosphate (298 mg)

and 1-(tert-butoxycarbonyl)piperazine (279 mg) was added dimethoxyethane (2 mL), and the mixture was heated under reflux for 16 hr. After cooling, water was added, and the mixture was extracted with ethyl acetate. The organic layer was washed with water and saturated brine, dried over anhydrous sodium sulfate, and the solvent was evaporated. The residue was purified by column chromatography (chloroform:methanol=100:1). The obtained compound was dissolved in methanol (4 mL). Concentrated hydrochloric acid (0.5 mL) was added, and the mixture was heated under reflux for 3 hr. After cooling, aqueous alkali was added, and the mixture was extracted with ethyl acetate. The organic layer was washed with water and saturated brine, dried over anhydrous sodium sulfate, and the solvent was evaporated to give methyl (S)-{2,3,9-trimethyl-4-(4-piperazin-1-ylphenyl)-6H-thieno[3,2-f][1,2,4]triazolo[4,3-a][1,4]diazepin-6-yl}acetate (394 mg). The obtained compound (232 mg) was dissolved in methylene chloride (3 mL). Triethylamine (0.5 mL) and isonicotinoylchloride hydrochloride (214 mg) were successively added, and the mixture was stirred at room temperature for 24 hr. After completion of the reaction, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (115 mg).

$^1$H-NMR (400 MHz, DMSO-d$_6$) δ: 1.69 (3H, s), 2.42 (3H, s), 2.59 (3H, s), 3.2-3.5 (8H, m), 3.66 (3H, s), 3.7-3.8 (2H, m), 4.42 (1H, t, J=7.2 Hz), 6.94 (2H, d, J=8.8 Hz), 7.29 (2H, d, J=8.8 Hz), 7.43 (2H, d, J=4.8 Hz), 8.68 (2H, d, J=4.8 Hz)

MS (ESI) m/z: 570 (M+H)$^+$.

Example 219

Methyl (S)-{2,3,9-trimethyl-4-(4-styrylphenyl)-6H-thieno[3,2-f][1,2,4]triazolo[4,3-a][1,4]diazepin-6-yl}acetate The title compound (280 mg) was obtained from the compound (415 mg) described in Example 1 by a treatment in the same manner as in Example 2 and using trans-2-phenylvinylboronic acid (222 mg) instead of 4-methylthiophenylboronic acid.

$^1$H-NMR (270 MHz, DMSO-d$_6$) δ: 1.67 (3H, s), 2.43 (3H, s), 2.62 (3H, s), 3.3-3.6 (2H, m), 3.68 (3H, s), 4.50 (1H, t, J=7.3 Hz), 7.20-7.50 (7H, m), 7.5-7.8 (4H, m)

MS (ESI) m/z: 483 (M+H)$^+$.

Example 220

Methyl (S)-(4-{4-[2-(4-fluorophenyl)vinyl]phenyl}-2,3,9-trimethyl-6H-thieno[3,2-f][1,2,4]triazolo[4,3-a][1,4]diazepin-6-yl)acetate The title compound (278 mg) was obtained from the compound (415 mg) described in Example 1 by a treatment in the same manner as in Example 2 and using trans-2-(4-fluorophenyl)vinylboronic acid (249 mg) instead of 4-methylthiophenylboronic acid.

$^1$H-NMR (400 MHz, DMSO-d$_6$) δ: 1.66 (3H, s), 2.43 (3H, s), 2.62 (3H, s), 3.3-3.6 (2H, m), 3.68 (3H, s), 4.50 (1H, d, J=7.2 Hz), 7.2-7.4 (4H, m), 7.42 (2H, d, J=8.4 Hz), 7.6-7.7 (4H, m)

MS (ESI) m/z: 501 (M+H)$^+$.

Example 221

Methyl (S)-(4-{4-[2-(4-methoxyphenyl)vinyl]phenyl}-2,3,9-trimethyl-6H-thieno[3,2-f][1,2,4]triazolo[4,3-a][1,4]diazepin-6-yl)acetate To a mixture of the compound (415 mg) described in Example 1, tris(dibenzylideneacetone)dipalladium (0) chloroform adduct (52 mg) and tri-tert-butylphosphoniumtetrafluoroborate (58 mg) were successively added dioxane (1 mL), dicyclohexylmethylamine (320 μL) and 4-methoxystyrene (400 μL), and the mixture was heated under reflux for 16 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (512 mg).

$^1$H-NMR (400 MHz, DMSO-d$_6$) δ: 1.67 (3H, s), 2.43 (3H, s), 2.62 (3H, s), 3.43 (1H, dd, J=16.8, 7.2 Hz), 3.51 (1H, dd, J=16.8, 7.2 Hz), 3.68 (3H, s), 3.78 (3H, s), 4.49 (1H, t, J=7.2 Hz), 6.96 (2H, d, J=8.4 Hz), 7.13 (1H, d, J=8.4 Hz), 7.28 (1H, d, J=8.4 Hz), 7.40 (2H, d, J=8.4 Hz), 7.56 (2H, d, J=8.4 Hz), 7.60 (2H, d, J=8.4 Hz)

MS (ESI) m/z: 513 (M+H)$^+$.

Example 222

Methyl (S)-(2,3,9-trimethyl-4-{4-[2-(4-methylthiazole-5-yl)vinyl]phenyl}-6H-thieno[3,2-f][1,2,4]triazolo[4,3-a][1,4]diazepin-6-yl)acetate To a mixture of the compound (415 mg) described in Example 1, tris(dibenzylideneacetone)dipalladium (0) chloroform adduct (26 mg) and tri-tert-butylphosphoniumtetrafluoroborate (29 mg) were successively added dioxane (1 mL), dicyclohexylmethylamine (320 μL) and 4-methyl-5-vinylthiazole (340 μL), and the mixture was heated under reflux for 16 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (289 mg).

$^1$H-NMR (400 MHz, DMSO-d$_6$) δ: 1.65 (3H, s), 2.43 (3H, s), 2.50 (3H, s), 2.62 (3H, s), 3.43 (1H, dd, J=16.4, 6.8 Hz), 3.50 (1H, dd, J=16.4, 6.8 Hz), 3.67 (3H, s), 4.50 (1H, t, J=6.8 Hz), 6.90 (1H, d, J=16.0 Hz), 7.40 (2H, d, J=8.0 Hz), 7.52 (1H, d, J=16.0 Hz), 7.69 (2H, d, J=8.0 Hz), 8.93 (1H, s)

MS (ESI) m/z: 504 (M+H)$^+$.

Example 223

Methyl (S)-(4-{4-[2-(3-hydroxymethylphenyl)vinyl]phenyl}-2,3,9-trimethyl-6H-thieno[3,2-f][1,2,4]triazolo[4,3-a][1,4]diazepin-6-yl)acetate A compound obtained by a treatment in the same manner as in Example 222 and using 3-vinylbenzaldehyde instead of 4-methyl-5-vinylthiazole was dissolved in methanol (10 mL). Sodium borohydride (38 mg) was added, and the mixture was stirred for 1 hr under water-cooling. After completion of the reaction, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (120 mg).

$^1$H-NMR (400 MHz, DMSO-d$_6$) δ: 1.67 (3H, s), 2.43 (3H, s), 2.62 (3H, s), 3.43 (1H, dd, J=16.4, 6.8 Hz), 3.50 (1H, dd, J=16.4, 6.8 Hz), 3.68 (3H, s), 4.48-4.53 (3H, m), 5.23 (1H, brs), 7.24 (1H, d, J=8.4 Hz), 7.29-7.37 (3H, m), 7.41 (2H, d, J=8.4 Hz), 7.49 (1H, d, J=8.4 Hz), 7.58 (1H, s), 7.65 (2H, d, J=8.4 Hz)

MS (ESI) m/z: 513 (M+H)$^+$.

Example 224

Methyl (S)-{2,3,9-trimethyl-4-[4-(2-phenylcarbamoylvinyl)phenyl]-6H-thieno[3,2-f][1,2,4]triazolo[4,3-a][1,4]diazepin-6-yl}acetate The title compound (29 mg) was obtained from the compound (415 mg) described in Example 1 by a treatment in the same manner as in Example 222 and using N-phenylacrylamide (442 mg) instead of 4-methyl-5-vinylthiazole.

$^1$H-NMR (400 MHz, DMSO-d$_6$) δ: 1.66 (3H, s), 2.43 (3H, s), 2.62 (3H, s), 3.43 (1H, dd, J=16.4, 6.8 Hz), 3.50 (1H, dd, J=16.4, 6.8 Hz), 3.68 (3H, s), 4.52 (1H, d, J=6.8 Hz), 6.89 (1H, d, J=15.6 Hz), 7.07 (1H, t, J=8.4 Hz), 7.34 (2H, t, J=8.4 Hz), 7.48 (2H, d, J=8.4 Hz), 7.60 (1H, d, J=15.6 Hz), 7.68 (2H, d, J=8.4 Hz), 7.70 (2H, d, J=8.4 Hz)

MS (ESI) m/z: 526 (M+H)$^+$.

Example 225

Methyl (S)-(4-{4-[2-(4-hydroxyphenyl)vinyl]phenyl}-2,3,9-trimethyl-6H-thieno[3,2-f][1,2,4]triazolo[4,3-a][1,4]diazepin-6-yl)acetate A compound (1 g) obtained by a treatment in the same manner as in Example 222 and using 4-acetoxystyrene instead of 4-methyl-5-vinylthiazole was dissolved in methanol (6 mL), 28% sodium methoxide-methanol solution (390 μL) was added under ice-cooling, and the mixture was stirred at 0° C. for 1 hr. After completion of the reaction, the mixture was acidified with hydrochloric acid, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (250 mg).

$^1$H-NMR (400 MHz, DMSO-d$_6$) δ: 1.67 (3H, s), 2.43 (3H, s), 2.61 (3H, s), 3.42 (1H, dd, J=16.4, 6.8 Hz), 3.49 (1H, dd, J=16.4, 6.8 Hz), 3.68 (3H, s), 4.49 (1H, t, J=6.8 Hz), 6.77 (2H, d, J=8.4 Hz), 7.04 (1H, d, J=16.8 Hz), 7.22 (1H, d, J=16.8 Hz), 7.39 (2H, d, J=8.4 Hz), 7.44 (2H, d, J=8.4 Hz), 7.57 (2H, d, J=8.4 Hz)

MS (ESI) m/z: 499 (M+H)$^+$.

Example 226

Methyl (S)-(4-{4-[2-(3-cyanophenyl)vinyl]phenyl}-2,3,9-trimethyl-6H-thieno[3,2-f][1,2,4]triazolo[4,3-a][1,4]diazepin-6-yl)acetate To a mixture of the compound (1.5 g) described in Example 223 and dichloro(tri-o-tolyl)bismuth (1.78 g) were added toluene (40 mL) and 1,8-diazabicyclo[5.4.0]-7-undecene (DBU, 480 μL), and the mixture was stirred at room temperature for 1 hr. After completion of the reaction, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1). The obtained compound was dissolved in methylene chloride (20 mL). Triethylamine (410 μL) and hydroxylamine hydrochloride (204 mg) were successively added, and the mixture was stirred at room temperature for 24 hr. To the reaction mixture were successively added triethylamine (820 μL), 2-chloro-1,3-dimethyl-2-imidazolium tetrafluoroborate (816 mg), and the mixture was stirred at room temperature for 24 hr. After completion of the reaction, water was added, and the mixture was extracted with chloroform. The organic layer was washed with aqueous hydrochloric acid and saturated brine, dried over anhydrous sodium sulfate, and the solvent was evaporated. The residue was purified by column chromatography (chloroform:methanol=100:1) to give the title compound (924 mg).

$^1$H-NMR (400 MHz, DMSO-d$_6$) δ: 1.66 (3H, s), 2.43 (3H, s), 2.62 (3H, s), 3.3-3.6 (2H, m), 3.68 (3H, s), 4.51 (1H, t, J=7.2 Hz), 7.37 (1H, d, J=16.8 Hz), 7.4-7.5 (3H, m), 7.60 (1H, t, J=7.6 Hz), 7.66 (2H, d, J=8.4 Hz), 7.74 (1H, d, J=7.6 Hz), 7.95 (1H, d, J=7.6 Hz), 8.13 (1H, s)

MS (ESI) m/z: 508 (M+H)$^+$.

Example 227

Methyl (S)-(4-{4-[2-(3-cyanophenylcarbamoyl)vinyl]phenyl}-2,3,9-trimethyl-6H-thieno[3,2-f][1,2,4]triazolo[4,3-a][1,4]diazepin-6-yl)acetate A compound (25 g) obtained by a treatment in the same manner as in Example 222 and using acrylic acid tert-butyl ester instead of 4-methyl-5-vinylthiazole was dissolved in methylene chloride (25 mL). Trifluoroacetic acid (25 mL) was added, and the mixture was stirred at room temperature for 24 hr. After completion of the reaction, water was added, and the mixture was extracted with chloroform. The organic layer was washed with saturated brine, dried over anhydrous sodium sulfate, and the solvent was evaporated. The residue was purified by column chromatography (chloroform:methanol=10:1) to give a compound (7.8 g). The obtained compound (3.6 g) was dissolved in methylene chloride (30 mL). 3-Cyanoaniline (1.9 g) and 1-ethyl-3-(3-dimethylaminopropyl)carbodiimide hydrochloride (WSC.HCl, 4.5 g) were successively added, and the mixture was stirred at room temperature for 24 hr. After completion of the reaction, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (988 mg).

$^1$H-NMR (400 MHz, DMSO-d$_6$) δ: 1.65 (3H, s), 2.43 (3H, s), 2.62 (3H, s), 3.43 (1H, dd, J=16.8, 7.2 Hz), 3.50 (1H, dd, J=16.8 7.2 Hz), 3.68 (3H, s), 4.52 (1H, t, J=7.2 Hz), 6.87 (1H, d, J=16.0 Hz), 7.49 (2H, d, J=8.0 Hz), 7.53-7.71 (5H, m), 7.86-7.89 (1H, m), 8.21 (1H, s), 10.6 (1H, s)

MS (ESI) m/z: 551 (M+H)$^+$.

Example 228

Ethyl (S)-(2,3,9-trimethyl-4-{4-[2-(4-methylthiazole-5-yl)vinyl]phenyl}-6H-thieno[3,2-f][1,2,4]triazolo[4,3-a][1,4]diazepin-6-yl)acetate The title compound (1.2 g) was obtained by an operation in the same manner as in Example 222 and using the compound (1.3 g) described in Example 62 instead of the compound described in Example 1.

¹H-NMR (400 MHz, DMSO-d₆) δ: 1.21 (3H, t, J=7.2 Hz), 1.65 (3H, s), 2.43 (3H, s), 2.67 (3H, s), 3.3-3.5 (5H, m), 4.0-4.3 (2H, m), 4.49 (1H, t, J=6.8 Hz), 6.90 (1H, d, J=16.0 Hz), 7.40 (2H, d, J=8.0 Hz), 7.52 (1H, d, J=16.0 Hz), 7.68 (2H, d, J=8.0 Hz), 8.92 (1H, s)

MS (ESI) m/z: 518 (M+H)⁺.

Example 229

Methyl (S)-{4-[4-(3-oxo-3-phenylpropyl)phenyl]-2, 3,9-trimethyl-6H-thieno[3,2-f][1,2,4]triazolo[4,3-a] [1,4]diazepin-6-yl}acetate The title compound (121 mg) was obtained from the compound (415 mg) described in Example 1 by a treatment in the same manner as in Example 222 and using vinylbenzyl alcohol (390 μL) instead of 4-methyl-5-vinylthiazole.

¹H-NMR (400 MHz, DMSO-d₆) δ: 1.61 (3H, s), 2.41 (3H, s), 2.60 (3H, s), 2.98 (2H, d, J=7.6 Hz), 3.3-3.5 (4H, m), 3.66 (3H, s), 4.47 (1H, t, J=7.6 Hz), 7.32 (4H, s), 7.51 (2H, t, J=8.0 Hz), 7.62 (1H, t, J=7.6 Hz), 7.95 (2H, d, J=8.0 Hz)

MS (ESI) m/z: 513 (M+H)⁺.

Example 230

Methyl (S)-(4-{4-[2-(4-methoxyphenyl)-2-oxoethyl]-phenyl}-2,3,9-trimethyl-6H-thieno[3,2-f][1,2,4] triazolo[4,3-a][1,4]diazepin-6-yl)acetate A mixture of the compound (415 mg) described in Example 1, palladium acetate (11 mg), 2-(dicyclohexylphosphino)-2-(N,N-dimethylamino)biphenyl (39 mg), tripotassium phosphate (531 mg), 4-methoxyphenol (25 mg) and 4-methoxyacetophenone (330 mg) was heated under reflux for 8 hr in toluene (1 mL). After cooling, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) to give the title compound (39 mg).

¹H-NMR (400 MHz, DMSO-d₆) δ: 1.62 (3H, s), 2.41 (3H, s), 2.60 (3H, s), 3.40 (1H, dd, J=16.4, 6.8 Hz), 3.48 (1H, dd, J=16.4, 6.8 Hz), 3.66 (3H, s), 3.83 (3H, s), 4.38 (2H, s), 4.48 (1H, t, J=6.8 Hz), 7.03 (2H, d, J=8.8 Hz), 7.29 (2H, d, J=8.4 Hz), 7.35 (1H, d, J=8.0 Hz), 7.99 (2H, d, J=8.8 Hz)

MS (ESI) m/z: 529 (M+H)⁺.

Example 231

Methyl (S)-{4-(4-chlorophenyl)-2-hydroxymethyl-3, 9-dimethyl-6H-thieno[3,2-f][1,2,4]triazolo[4,3-a][1, 4]diazepin-6-yl}acetate To a mixture of acetic acid (24 mL) and acetic anhydride (12 mL) was added dropwise (10-25° C.) concentrated sulfuric acid (3.8 mL) under ice-cooling. The compound (5 g) described in Example 1 was added, manganese acetate (III). dihydrate (6.4 g) was further added (15-25° C.), and the mixture was stirred at room temperature for 8 hr. Furthermore, manganese acetate (III).dihydrate (640 mg) was added, and the mixture was stirred at room temperature for 40 hr. The reaction mixture was ice-cooled, chloroform (40 mL) was added, and water (60 mL) was added dropwise (10-30° C.). After partitioning, the mixture was further extracted with chloroform (40 mL). The organic layer was washed with water (40 mL), saturated aqueous sodium hydrogencarbonate (40 mL) and saturated brine (40 mL). The solvent was evaporated under reduced pressure (azeotroped twice with methanol) to give a yellow oil.

To a solution of the obtained yellow oil in methanol (40 mL) was added potassium carbonate (4 g), and the mixture was stirred at room temperature for 1 hr. Sodium borohydride (98 mg) was added thereto, and the mixture was stirred for 30 min. After disappearance of the starting material, the mixture was partitioned by adding water (40 mL) and chloroform (40 mL), and further extracted with chloroform (40 mL). The organic layer was washed with water (40 mL) and saturated brine (40 mL), dried over anhydrous sodium sulfate, and the solvent was evaporated under reduced pressure (azeotroped once with ethyl). To the residue were added ethyl acetate (10 mL) and methanol (1 mL), and the mixture was dissolved with heating under reflux. Then, the mixture was stirred with water-cooling to allow precipitation of crystals at an inside temperature of 33° C. The mixture was stirred in situ for 1 hr, and the precipitated crystals were collected by filtration to give the title compound (2 g).

¹H-NMR (400 MHz, DMSO-d₆) δ: 1.64 (3H, s), 2.62 (3H, s), 3.41 (1H, dd, J=16.4, 6.8 Hz), 3.49 (1H, dd, J=16.4, 6.8 Hz), 3.67 (3H, s), 4.49 (1H, t, J=7.2 Hz), 4.6-4.8 (2H, m), 5.85 (1H, s), 7.43 (2H, d, J=8.5 Hz), 7.49 (2H, d, J=8.5 Hz)

MS (ESI) m/z: 431 (M+H)⁺.

Example 232 methyl (S)-{4-[4-(phenylamino)phenyl]-2-hydroxymethyl-3,9-dimethyl-6H-thieno[3,2-f][1,2,4] triazolo[4,3-a][1,4]diazepin-6-yl}acetate To a mixture of the compound (1.1 g) described in Starting Material Synthetic Example 5, palladium acetate (23 mg), 2-(dicyclohexylphosphino)biphenyl (71 mg) and tripotassium phosphate (600 mg) were added dimethoxyethane (4 mL) and aniline (260 μL), and the mixture was heated under reflux for 8 hr. After completion of the reaction, the reaction mixture was poured into ice water, and the mixture was extracted with ethyl acetate. The organic layer was washed with water and saturated brine, dried over anhydrous sodium sulfate, and the solvent was evaporated. The residue was purified by column chromatography (hexane:ethyl acetate=2: 3) to give methyl (S)-{4-[4-(phenylamino)phenyl]-2-(tert-butyldimethylsilyloxymethyl)-3,9-dimethyl-6H-thieno[3,2-f][1,2,4]triazolo[4,3-a][1,4]diazepin-6-yl}acetate (1.1 g). The obtained compound (1.1 g) was dissolved in tetrahydrofuran (20 mL). A solution (2.2 mL) of 1 M tetra-n-ammonium fluoride in tetrahydrofuran was added, and the mixture was stirred at room temperature for 1 hr. After completion of the reaction, the reaction mixture was poured into ice water, and the mixture was extracted with ethyl acetate. The organic layer was washed with water and saturated brine, dried over anhydrous sodium sulfate, and the solvent was evaporated. The residue was purified by column chromatography (chloroform:methanol=50:1) to give the title compound (680 mg).

¹H-NMR (300 MHz, CDCl₃) δ: 1.84 (3H, s), 2.68 (3H, s), 3.64 (2H, m), 3.77 (3H, m), 4.59 (1H, dd, J=6.3, 7.2 Hz), 4.85 (2H, d, J=3.3 Hz), 5.97 (1H, s), 6.99 (3H, m), 7.11 (2H, d, J=8.1 Hz), 7.28 (2H, d, J=8.7 Hz), 7.34 (2H, d, J=8.7 Hz)

MS (ESI) m/z: 488 (M+H)⁺.

Example 233

Methyl (S)-{4-[4-(4-fluorophenylamino)phenyl]-2-hydroxymethyl-3,9-dimethyl-6H-thieno[3,2-f][1,2,4] triazolo[4,3-a][1,4]diazepin-6-yl}acetate The title compound (0.98 g) was obtained from the compound (1.1 g) described in Starting Material Synthetic Example 5 by a treatment in the same manner as in Example 232 and using 4-fluoroaniline (0.27 mL) instead of aniline.

$^1$H-NMR (300 MHz, CDCl$_3$) δ: 1.83 (3H, s), 2.68 (3H, s), 3.63 (2H, m), 3.76 (3H, m), 4.58 (1H, dd, J=6.6, 7.5 Hz), 4.85 (2H, brs), 5.87 (1H, s), 6.85 (2H, d, J=8.7 Hz), 7.07 (4H, m), 7.32 (2H, d, J=8.7 Hz)

MS (ESI) m/z: 506 (M+H)$^+$.

Example 234

Methyl (S)-{2-hydroxymethyl-4-(4'-methoxybiphenyl-4-yl)-3,9-dimethyl-6H-thieno[3,2-f][1,2,4]triazolo[4,3-a][1,4]diazepin-6-yl}acetate To a mixture of the compound (8.4 g) described in Example 231, palladium acetate (175 mg), 2-dicyclohexylphosphino-2,6-dimethoxybiphenyl (320 mg), 4-methoxyphenylboronic acid (3.6 g) and tripotassium phosphate (10 g) were added tetrahydrofuran (40 mL) and water (1.2 mL), and the mixture was heated under reflux for 20 min. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (7.9 g)

$^1$H-NMR (400 MHz, DMSO-d$_6$) δ: 1.70 (3H, s), 2.63 (3H, s), 3.44 (1H, dd, J=16.4, 7.2 Hz), 3.50 (1H, dd, J=16.4 7.2 Hz), 3.68 (3H, s), 3.80 (3H, s), 4.51 (1H, t, J=7.2 Hz), 4.70 (2H, s), 5.85 (1H, s), 7.03 (2H, d, J=8.7 Hz), 7.47 (2H, d, J=8.4 Hz), 7.65 (2H, d, J=8.7 Hz), 7.68 (2H, d, J=8.4 Hz)

MS (ESI) m/z: 503 (M+H)$^+$.

Example 235

Methyl (S)-{4-(3'-cyanobiphenyl-4-yl)-2-hydroxymethyl-3,9-dimethyl-6H-thieno[3,2-f][1,2,4]triazolo[4,3-a][1,4]diazepin-6-yl}acetate To a mixture of the compound (273 mg) described in Starting Material Synthetic Example 5, palladium acetate (6 mg), 2-(di-tert-butylphosphino)biphenyl (15 mg), potassium fluoride (87 mg) and 3-cyanophenylboronic acid (110 mg) was added tetrahydrofuran (1.5 mL), and the mixture was heated under reflux for 8 hr. After cooling, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1). The obtained compound was dissolved in tetrahydrofuran (5 mL). A solution (1 M, 0.6 mL) of tetra-n-ammonium fluoride in tetrahydrofuran was added, and the mixture was stirred at room temperature for 1 hr. After completion of the reaction, the reaction mixture was poured into ice water, and the mixture was extracted with ethyl acetate. The organic layer was washed with water and saturated brine, dried over anhydrous sodium sulfate, and the solvent was evaporated. The residue was purified by column chromatography (chloroform:methanol=50:1) to give the title compound (180 mg).

$^1$H-NMR (270 MHz, DMSO-d$_6$) δ: 1.68 (3H, s), 2.64 (3H, s), 3.48 (2H, t, J=5.9 Hz), 3.69 (3H, s), 4.53 (1H, t, J=7.6 Hz), 4.70 (2H, d, J=5.1 Hz), 5.86 (1H, d, J=5.4 Hz), 7.53 (2H, d, J=8.4 Hz), 7.69 (1H, t, J=7.8 Hz), 7.8-7.9 (3H, m), 8.07 (1H, d, J=8.1 Hz), 8.21 (1H, s)

MS (ESI) m/z: 498 (M+H)$^+$.

Example 236

Methyl (S)-{2-hydroxymethyl-4-(3'-methoxybiphenyl-4-yl)-3,9-dimethyl-6H-thieno[3,2-f][1,2,4]triazolo[4,3-a][1,4]diazepin-6-yl}acetate The title compound (544 mg) was obtained from the compound (1 g) described in Starting Material Synthetic Example 5 by a treatment in the same manner as in Example 235 and using 3-methoxyphenylboronic acid (420 mg) instead of 3-cyanophenylboronic acid.

$^1$H-NMR (400 MHz, CDCl$_3$) δ: 1.79 (3H, s), 2.71 (3H, s), 2.99 (1H, brs), 1.57-3.70 (2H, m), 3.78 (3H, s), 3.86 (3H, s), 4.65 (1H, t, J=6.8 Hz), 4.87 (2H, brs), 6.91 (1H, d J=8.0 Hz), 7.11 (1H, brs), 7.16 (1H, d, J=8.0 Hz), 7.36 (1H, dd, J=8.0, 8.0 Hz), 7.52 (2H, d, J=8.0 Hz), 7.56 (2H, d, J=8.0 Hz)

MS (ESI) m/z: 503 (M+H)$^+$.

Example 237

Methyl (S)-{4-[4-(3,4-dihydro-1H-isoquinolin-2-yl)phenyl]-2-hydroxymethyl-3,9-dimethyl-6H-thieno[3,2-f][1,2,4]triazolo[4,3-a][1,4]diazepin-6-yl}acetate The title compound (185 mg) was obtained from the compound (1 g) described in Starting Material Synthetic Example 5 by a treatment in the same manner as in Example 232 and using 1,2,3,4-tetrahydroisoquinoline (260 mg) instead of aniline.

$^1$H-NMR (400 MHz, CDCl$_3$) δ 1.81 (3H, s), 2.67 (3H, s), 2.93-3.01 (2H, m), 3.55-3.69 (4H, m), 3.76 (3H, s), 4.45 (2H, s), 4.57 (1H, t, J=6.4 Hz), 4.86 (2H, s), 6.82 (2H, d, J=8.8 Hz), 7.10-7.25 (4H, m), 7.36 (2H, d, J=8.8 Hz)

MS (ESI) m/z: 528 (M+H)$^+$.

Example 238

Methyl (S)-{4-(3'-acetylbiphenyl-4-yl)-2-hydroxymethyl-3,9-dimethyl-6H-thieno[3,2-f][1,2,4]triazolo[4,3-a][1,4]diazepin-6-yl}acetate The title compound (670 mg) was obtained from the compound (1.5 g) described in Starting Material Synthetic Example 5 by a treatment in the same manner as in Example 235 and using 3-acetoxyphenylboronic acid (496 mg) instead of 3-cyanophenylboronic acid.

$^1$H-NMR (400 MHz, CDCl$_3$) δ: 1.79 (3H, s), 2.55 (1H, brs), 2.66 (3H, s), 2.72 (3H, s), 3.66 (2H, d, J=7.2 Hz), 3.79 (3H, s), 4.66 (1H, t, J=7.2 Hz), 4.89 (2H, s), 7.51-7.56 (3H, m), 7.61 (2H, d, J=8.8 Hz), 7.78 (1H, d, J=8.0 Hz), 7.95 (1H, d, J=7.6 Hz), 8.17 (1H, s)

MS (ESI) m/z: 515 (M+H)$^+$.

Example 239

Methyl (S)-[4-(4-benzylaminophenyl)-2-hydroxymethyl-3,9-dimethyl-6H-thieno[3,2-f][1,2,4]triazolo[4,3-a][1,4]diazepin-6-yl]acetate The title compound (121 mg) was obtained from the compound (430 mg) described in Starting Material Synthetic Example 5 by a treatment in the same manner as in Example 232 and using benzylamine (102 mg) instead of aniline.

$^1$H-NMR (400 MHz, CDCl$_3$) δ 1.82 (3H, s), 2.66 (3H, s), 2.87 (1H, brs), 3.53-3.66 (2H, m), 3.74 (3H, s), 4.33-4.37 (3H, m), 4.55 (1H, t, J=6.4 Hz), 4.83 (2H, d, J=4.4 Hz), 6.53 (2H, d, J=8.4 Hz), 7.21-7.38 (7H, m)

MS (ESI) m/z: 502 (M+H)$^+$.

Example 240

Methyl (S)-{2-hydroxymethyl-3,9-dimethyl-4-[4-(2,4,6-trifluorophenylamino)phenyl]-6H-thieno[3,2-f][1,2,4]triazolo[4,3-a][1,4]diazepin-6-yl}acetate The title compound (231 mg) was obtained from the compound (1.1 g) described in Starting Material Synthetic Example 5 by a treatment in the same manner as in Example 232 and using 2,4,6-trifluoroaniline instead of aniline.

$^1$H-NMR (400 MHz, DMSO-$d_6$) δ: 1.73 (3H, s), 2.60 (3H, s), 3.41 (2H, m), 3.65 (3H, s), 4.41 (1H, t, J=7.4 Hz), 4.68 (2H, m), 5.80 (1H, t, J=5.4 Hz), 6.62 (2H, d, J=8.4 Hz), 7.23-7.32 (4H, m), 8.14 (1H, s)

MS (ESI) m/z: 542 (M+H)$^+$.

Example 241

Methyl (S)-(2-hydroxymethyl-3,9-dimethyl-4-{4-[methyl-(2,4,6-trifluorophenyl)amino]phenyl}-6H-thieno[3,2-f][1,2,4]triazolo[4,3-a][1,4]diazepin-6-yl)acetate The title compound (560 mg) was obtained from the compound (1.1 g) described in Starting Material Synthetic Example 5 by a treatment in the same manner as in Example 232 and using methyl-(2,4,6-trifluorophenyl)amine (966 mg) instead of aniline.

$^1$H-NMR (400 MHz, DMSO-$d_6$) δ: 1.71 (3H, s), 2.60 (3H, s), 3.22 (3H, s), 3.34-3.49 (2H, m), 3.65 (3H, s), 3.42 (1H, t, J=7.4 Hz), 4.67-4.69 (2H, m), 5.80 (1H, t, J=5.2 Hz), 6.61 (2H, d, J=8.8 Hz), 7.27 (2H, d, J=8.8 Hz), 7.37 (2H, t, J=8.6 Hz)

MS (ESI) m/z: 556 (M+H)$^+$.

Example 242

Methyl (S)-(4-{4-[(4-fluorophenyl)methylamino]phenyl}-2-hydroxymethyl-3,9-dimethyl-6H-thieno[3,2-f][1,2,4]triazolo[4,3-a][1,4]diazepin-6-yl)acetate The title compound (139 mg) was obtained from the compound (545 mg) described in Starting Material Synthetic Example 5 by a treatment in the same manner as in Example 232 and using 4-fluoro-N-methylaniline (158 μL) instead of aniline.

$^1$H-NMR (400 MHz, DMSO-$d_6$) δ: 1.73 (3H, s), 2.60 (3H, s), 3.26 (3H, s), 3.34-3.48 (2H, m), 3.65 (3H, s), 4.42 (1H, t, J=7.2 Hz), 4.69 (2H, m), 5.80 (1H, t, J=4.8 Hz), 6.74 (2H, d, J=8.4 Hz), 7.21-7.26 (6H, m)

MS (ESI) m/z: 520 (M+H)$^+$.

Example 243

Methyl (S)-(4-{4-[(2,4-difluorophenyl)methylamino]phenyl}-2-hydroxymethyl-3,9-dimethyl-6H-thieno[3,2-f][1,2,4]triazolo[4,3-a][1,4]diazepin-6-yl)acetate The title compound (154 mg) was obtained from the compound (545 mg) described in Starting Material Synthetic Example 5 by a treatment in the same manner as in Example 232 and using methyl-(2,4-difluorophenyl)amine (135 μL) instead of aniline.

$^1$H-NMR (400 MHz, DMSO-$d_6$) δ: 1.72 (3H, s), 2.59 (3H, s), 3.23 (3H, s), 3.33-3.48 (2H, m), 3.65 (3H, s), 4.41 (1H, t, J=7.2 Hz), 4.68 (2H, m), 5.80 (1H, m), 6.60 (2H, d, J=8.8 Hz), 7.17 (1H, t, J=8.0 Hz), 7.25 (2H, d, J=8.0 Hz), 7.37-7.46 (2H, m)

MS (ESI) m/z: 538 (M+H)$^+$.

Example 244

Methyl (S)-{4-[4-(4-fluorobenzylamino)phenyl]-2-hydroxymethyl-3,9-dimethyl-6H-thieno[3,2-f][1,2,4]triazolo[4,3-a][1,4]diazepin-6-yl}acetate The title compound (165 mg) was obtained from the compound (500 mg) described in Starting Material Synthetic Example 5 by a treatment in the same manner as in Example 232 and using 4-fluorobenzylamine (153 mg) instead of aniline.

$^1$H-NMR (400 MHz, CDCl$_3$) δ 1.82 (3H, s), 2.53-2.73 (1H, m), 2.66 (3H, s), 3.52-3.69 (2H, m), 3.75 (3H, s), 4.26-4.38 (3H, m), 4.55 (1H, t, J=6.4 Hz), 4.77-4.89 (2H, m), 6.52 (2H, d, J=8.4 Hz), 6.98-7.03 (2H, m), 7.26-7.30 (4H, m)

MS (ESI) m/z: 520 (M+H)$^+$.

Example 245

Methyl (S)-(4-{4-[2-(2-fluorophenyl)ethylamino]phenyl}-2-hydroxymethyl-3,9-dimethyl-6H-thieno[3,2-f][1,2,4]triazolo[4,3-a][1,4]diazepin-6-yl)acetate The title compound (84 mg) was obtained from the compound (500 mg) described in Starting Material Synthetic Example 5 by a treatment in the same manner as in Example 232 and using 2-fluorophenethylamine (153 mg) instead of aniline.

$^1$H-NMR (400 MHz, CDCl$_3$) δ 1.81 (3H, s), 2.66 (3H, s), 2.85-2.97 (3H, m), 3.39-3.43 (2H, dd, J=6.8, 6.8 Hz), 3.55-3.68 (2H, m), 3.75 (3H, s), 4.07 (1H, m), 4.55 (1H, t, J=6.4 Hz), 4.83 (2H, d, J=4.8 Hz), 6.51 (2H, d, J=8.8 Hz), 6.98-7.34 (6H, m)

MS (ESI) m/z: 534 (M+H)$^+$.

Example 246

Methyl (S)-(4-{4-[2-(3-fluorophenyl)ethylamino]phenyl}-2-hydroxymethyl-3,9-dimethyl-6H-thieno[3,2-f][1,2,4]triazolo[4,3-a][1,4]diazepin-6-yl)acetate The title compound (18 mg) was obtained from the compound (500 mg) described in Starting Material Synthetic Example 5 by a treatment in the same manner as in Example 232 and using 3-fluorophenethylamine (153 mg) instead of aniline.

$^1$H-NMR (400 MHz, CDCl$_3$) δ 1.81 (3H, s), 2.66 (3H, s), 2.84-3.04 (3H, m), 3.35-3.46 (2H, m), 3.52-3.68 (2H, m), 3.75 (3H, s), 3.95-4.03 (1H, m), 4.55 (1H, t, J=6.4 Hz), 4.83 (2H, d, J=4.4 Hz), 6.50 (2H, d, J=8.8 Hz), 6.85-6.99 (3H, m), 7.23-7.34 (3H, m)

MS (ESI) m/z: 534 (M+H)$^+$.

Example 247

Methyl (S)-(2-hydroxymethyl-4-{4-[(3-methoxyphenyl)methylamino]phenyl}-3,9-dimethyl-6H-thieno[3,2-f][1,2,4]triazolo[4,3-a][1,4]diazepin-6-yl)acetate The title compound (76 mg) was obtained from the compound (1.3 g) described in Starting Material Synthetic Example 5 by a treatment in the same manner as in Example 232 and using 3-methoxy-N-methylaniline (0.53 g) instead of aniline.

$^1$H-NMR (300 MHz, DMSO-d$_6$) δ: 1.74 (3H, s), 2.60 (3H, s), 3.28 (3H, s), 3.34-3.49 (2H, m), 3.65 (3H, s), 3.72 (3H, s), 4.43 (1H, t, J=7.2 Hz), 4.69 (2H, t, 3.6 Hz), 5.81 (1H, t, J=5.4 Hz), 6.68-6.69 (3H, m), 6.86-6.88 (2H, m), 7.23-7.28 (3H, m)
MS (ESI) m/z: 532 (M+H)$^+$.

Example 248

Methyl (S)-{4-(3'-methoxybiphenyl-4-yl)-2-methoxymethyl-3,9-dimethyl-6H-thieno[3,2-f][1,2,4]triazolo[4,3-a][1,4]diazepin-6-yl}acetate To a solution (35 mL) of the compound (3.7 g) described in Example 236 in chloroform were added methylsulfonyl chloride (0.85 mL) and triethylamine (2.05 mL), and the mixture was stirred at room temperature overnight. Water was added to the reaction mixture, and the mixture was extracted with chloroform. The organic layer was washed twice with water. After drying over anhydrous sodium sulfate, the solvent was evaporated under reduced pressure to give an oil. To a solution (35 mL) of the oil in methanol was added sodium methoxide (28% methanol solution, 3 mL), and the mixture was heated under reflux for 6 hr. Water was added to the reaction mixture, and the mixture was extracted with ethyl acetate. The organic layer was washed twice with water. After drying over anhydrous sodium sulfate, the solvent was evaporated under reduced pressure, and the obtained residue was purified by silica gel column chromatography (chloroform:methanol=100:1) to give the title compound (1.5 g).

$^1$H-NMR (300 MHz, CDCl$_3$) δ 1.63 (s, 3H), 2.71 (s, 3H), 3.51 (s, 3H), 3.60-3.74 (m, 2H), 3.79 (s, 3H), 3.86 (s, 3H), 4.57-4.68 (m, 3H), 6.92 (d, 1H, J=6.0 Hz), 7.11 (s, 1H), 7.17 (d, 1H, J=6.0 Hz), 7.36 (t, 1H, J=6.0 Hz), 7.51-7.61 (m, 4H)
MS (ESI) m/z: 517 (M+H)$^+$.

Example 249

Methyl (S)-{4-(3'-cyanobiphenyl-4-yl)-2-methoxymethyl-3,9-dimethyl-6H-thieno[3,2-f][1,2,4]triazolo[4,3-a][1,4]diazepin-6-yl}acetate To a mixture of the compound (630 mg) described in Starting Material Synthetic Example 5, palladium acetate (12 mg), 2-(di-tert-butylphosphino)biphenyl (30 mg), potassium fluoride (200 mg) and 3-cyanophenylboronic acid (253 mg) was added tetrahydrofuran (3 ml), and the mixture was heated under reflux for 8 hr. After cooling, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1). The obtained compound was dissolved in tetrahydrofuran (12 mL). A solution (1 M, 1.2 mL) of tetra-n-ammonium fluoride in tetrahydrofuran was added, and the mixture was stirred at room temperature for 1 hr. After completion of the reaction, the reaction mixture was poured into ice water, and the mixture was extracted with ethyl acetate. The organic layer was washed with water and saturated brine, dried over anhydrous sodium sulfate, and the solvent was evaporated. The residue was dissolved in chloroform (8 mL). Methylsulfonyl chloride (0.2 mL) and triethylamine (0.5 mL) were successively added, and the mixture was stirred at room temperature overnight. Water was added to the reaction mixture, and the mixture was extracted with chloroform. The organic layer was washed twice with water. After drying over anhydrous sodium sulfate, the solvent was evaporated under reduced pressure. The residue was dissolved in methanol (8 mL). Sodium methoxide (28% methanol solution, 1 mL) was added, and the mixture was heated under reflux for 6 hr. Water was added to the reaction mixture, and the mixture was extracted with ethyl acetate. The organic layer was washed twice with water. After drying over anhydrous sodium sulfate, the solvent was evaporated under reduced pressure, and the obtained residue was purified by silica gel column chromatography (chloroform:methanol=100:1) to give the title compound (52 mg).

$^1$H-NMR (300 MHz, CDCl$_3$) δ 1.80 (s, 3H), 2.73 (s, 3H), 3.52 (s, 3H), 3.59-3.75 (m, 2H), 3.79 (s, 3H), 4.61 (dd, 2H, J=12.3, 9.6 Hz), 4.68 (t, 1H, J=5.4 Hz), 7.54-7.62 (m, 5H), 7.66 (d, 1H, J=5.7 Hz), 7.82 (d, 1H, J=5.7 Hz), 7.88 (s, 1H)
MS (ESI) m/z: 512 (M+H)$^+$.

Example 250

Methyl (S)-{4-(3'-acetylbiphenyl-4-yl)-2-methoxymethyl-3,9-dimethyl-6H-thieno[3,2-f][1,2,4]triazolo[4,3-a][1,4]diazepin-6-yl}acetate The title compound (6 mg) was obtained from the compound (1.5 g) described in Starting Material Synthetic Example 5 by a treatment in the same manner as in Example 249 and using 3-acetylphenylboronic acid (496 mg) instead of 3-cyanophenylboronic acid.

$^1$H-NMR (300 MHz, CDCl$_3$) δ 1.81 (s, 3H), 2.66 (s, 3H), 2.72 (s, 3H), 3.51 (s, 3H), 3.58-3.74 (m, 2H), 3.80 (s, 3H), 4.60 (dd, 2H, J=12.0, 9.6 Hz), 4.67 (t, 1H, J=5.4 Hz), 7.54-7.63 (m, 5H), 7.79 (d, 1H, J=5.7 Hz), 7.95 (d, 1H, J=5.7 Hz), 8.18 (s, 1H)
MS (ESI) m/z: 529 (M+H)$^+$.

Example 251

Ethyl (S)-{4-(3'-cyanobiphenyl-4-yl)-2-ethoxymethyl-3,9-dimethyl-6H-thieno[3,2-f][1,2,4]triazolo[4,3-a][1,4]diazepin-6-yl}acetate To a solution (27 mL) of the compound (1.3 g) described in Example 235 in chloroform were successively added triethylamine (0.45 mL) and methylsulfonyl chloride (0.25 mL) under ice-cooling, and the mixture was stirred at room temperature overnight. Water was added to the reaction mixture, and the mixture was extracted with chloroform. The organic layer was washed with saturated brine, dried over anhydrous sodium sulfate, and the solvent was evaporated under reduced pressure to give a compound (2.4 g). The obtained compound (1 g) was dissolved in ethanol (40 mL). Sodium ethoxide (145 mg) was added, and the mixture was heated under reflux for 30 min. After cooling, water was added to the reaction mixture, and the mixture was extracted with ethyl acetate. The organic layer was washed with saturated brine, dried over anhydrous sodium sulfate, and the solvent was evaporated under reduced pressure. The obtained residue was purified by silica gel column chromatography (chloroform:methanol=100:1) to give the title compound (350 mg).

$^1$H-NMR (400 MHz, DMSO-d$_6$) δ: 1.22 (6H, m), 1.72 (3H, s), 2.65 (3H, s), 3.45 (2H, d, J=6.4 Hz), 3.61 (2H, m), 4.16 (2H, m), 4.55 (1H, t, J=6.4 Hz), 4.69 (2H, s), 7.54 (2H, d, J=7.2 Hz), 7.69 (1H, t, J=7.4 Hz), 7.83 (3H, m), 8.07 (1H, d, J=7.2 Hz)
MS (ESI) m/z: 540 (M+H)$^+$.

Example 252

Methyl (S)-{4-(3'-cyanobiphenyl-4-yl)-2-ethoxymethyl-3,9-dimethyl-6H-thieno[3,2-f][1,2,4]triazolo[4,3-a][1,4]diazepin-6-yl}acetate The compound (350 mg) described in Example 251 was dissolved in 40% hydrochloric acid-methanol solution (0.6 mL), and the mixture was stirred at 75° C. for 6 hr. After cooling, water was added to the reaction mixture, and the mixture was extracted with ethyl acetate. The organic layer was washed with saturated aqueous sodium hydrogencarbonate and saturated brine. After drying over anhydrous sodium sulfate, the solvent was evaporated under reduced pressure, and the obtained residue was purified by silica gel column chromatography (chloroform:methanol=100:1) to give the title compound (155 mg).

$^1$H-NMR (400 MHz, DMSO-$d_6$) δ: 1.24 (3H, t, J=7.3 Hz), 1.72 (3H, s), 2.64 (3H, s), 3.40 (3H, s), 3.45 (2H, d, J=6.8 Hz), 4.16 (2H, m), 4.54 (1H, t, J=6.8 Hz), 4.65 (2H, s), 7.53 (2H, d, J=7.6 Hz), 7.69 (1H, t, J=7.6 Hz), 7.84 (3H, m), 8.07 (1H, d, J=7.2 Hz), 8.21 (1H, s)

MS (ESI) m/z: 526 (M+H)$^+$.

Example 253

4-(3'-cyanobiphenyl-4-yl)-2,3,9-trimethyl-6H-thieno[3,2-f][1,2,4]triazolo[4,3-a][1,4]diazepin To a mixture of starting material A (343 mg), palladium acetate (11 mg), 2-(di-tert-butylphosphino)biphenyl (30 mg), potassium fluoride (174 mg) and 3-cyanophenylboronic acid (220 mg) was added tetrahydrofuran (3 mL), and the mixture was heated under reflux for 8 hr. After cooling, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) to give the title compound (400 mg).

$^1$H-NMR (300 MHz, CDCl$_3$) δ: 1.74 (3H, s), 2.44 (3H, s), 2.72 (3H, s), 4.16 (1H, d, J=12.8 Hz), 5.55 (1H, d, J=12.8 Hz), 7.5-7.8 (6H, m), 7.8-7.9 (2H, m)

MS (ESI) m/z: 410 (M+H)$^+$.

Example 254

4-(3'-acetylbiphenyl-4-yl)-2,3,9-trimethyl-6H-thieno[3,2-f][1,2,4]triazolo[4,3-a][1,4]diazepin The title compound (310 mg) was obtained from the starting material A (342 mg) by a treatment in the same manner as in Example 253 and using 3-acetylphenylboronic acid (492 mg) instead of 3-cyanophenylboronic acid.

$^1$H-NMR (300 MHz, CDCl$_3$) δ: 1.75 (3H, s), 2.45 (3H, s), 2.67 (3H, s), 2.73 (3H, s), 4.16 (1H, d, J=12.6 Hz), 5.55 (1H, d, J=12.6 Hz), 7.4-7.7 (4H, m), 7.80 (1H, d, J=7.5 Hz), 7.9-8.1 (2H, m), 8.1-8.2 (1H, m)

MS (ESI) m/z: 426 (M+H)$^+$.

Example 255

1-[4'-(2,3,9-trimethyl-6H-thieno[3,2-f][1,2,4]triazolo[4,3-a][1,4]diazepin-4-yl)biphenyl-3-yl]ethanol The compound (416 mg) described in Example 254 was dissolved in methanol (5 mL). Sodium borohydride (37 mg) was added under ice-cooling, and the mixture was stirred at room temperature for 5 hr. After completion of the reaction, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) to give the title compound (103 mg).

$^1$H-NMR (300 MHz, CDCl$_3$) δ: 1.54 (3H, d, J=6.4 Hz), 1.73 (3H, s), 2.15 (1H, dd, J=6.8, 3.5 Hz), 2.43 (3H, s), 2.70 (3H, s), 4.14 (1H, d, J=12.6 Hz), 4.8-5.2 (1H, m), 5.55 (1H, d, J=12.6 Hz), 7.3-7.7 (8H, m)

MS (ESI) m/z: 429 (M+H)$^+$.

Example 256

4-(3'-cyano-4'-hydroxybiphenyl-4-yl)-2,3,9-trimethyl-6H-thieno[3,2-f][1,2,4]triazolo[4,3-a][1,4]diazepin To a mixture of the compound (841 mg) described in Starting Material Synthetic Example 7, dichlorobis(triphenylphosphine)palladium (II) (70 mg), sodium carbonate (1.3 g) and 5-bromo-2-hydroxybenzonitrile (792 mg) were added tetrahydrofuran (6 mL) and water (6 mL), and the mixture was stirred at 100° C. for 4 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) and recrystallized from hexane-ethyl acetate to give the title compound (340 mg).

$^1$H-NMR (400 MHz, DMSO-$d_6$) δ: 1.65 (3H, s), 2.41 (3H, s), 2.61 (3H, s), 4.16 (1H, d, 12.4 Hz), 5.27 (1H, d, 12.4 Hz), 7.11 (1H, d, 8.8 Hz), 7.51 (2H, d, 8.0 Hz), 7.72 (2H, d, 8.0 Hz), 7.87 (1H, dd, 8.8, 2.4 Hz), 7.98 (1H, d, 2.4 Hz), 11.3 (1H, brs)

MS (ESI) m/z: 426 (M+H)$^+$.

Example 257

2,3,9-trimethyl-4-(4-pyridin-4-ylphenyl)-6H-thieno[3,2-f][1,2,4]triazolo[4,3-a][1,4]diazepine To a mixture of starting material A (515 mg), palladium acetate (3.4 mg), 2-(di-tert-butylphosphino)biphenyl (9 mg), cesium fluoride (684 mg) and 4-pyridineboronic acid (277 mg) was added tetrahydrofuran (1.5 mL), and the mixture was heated under reflux for 16 hr. After cooling, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) to give the title compound (113 mg).

$^1$H-NMR (270 MHz, DMSO-$d_6$) δ: 1.65 (3H, s), 2.41 (3H, s), 2.62 (3H, s), 4.18 (1H, d, 12.4 Hz), 5.29 (1H, d, 12.4 Hz), 7.60 (2H, d, 8.4 Hz), 7.75 (2H, d, 6.2 Hz), 7.89 (2H, d, 8.4 Hz), 8.66 (2H, d, 6.2 Hz),

MS (ESI) m/z: 386 (M+H)$^+$.

Example 258

4-[4-(5-acetylthiophen-2-yl)phenyl]-2,3,9-trimethyl-6H-thieno[3,2-f][1,2,4]triazolo[4,3-a][1,4]diazepine The title compound (367 mg) was obtained from starting material A (342 mg) by a treatment in the same manner as in Example 253 and using 5-acetyl-2-thiopheneboronic acid (510 mg) instead of 3-cyanophenylboronic acid.
$^1$H-NMR (300 MHz, CDCl$_3$) δ: 1.72 (3H, s), 2.43 (3H, s), 2.58 (3H, s), 2.70 (3H, s), 4.14 (1H, d, J=12.6 Hz), 5.53 (1H, d, J=12.6 Hz), 7.38 (1H, d, J=4.0 Hz), 7.56 (2H, d, J=8.4 Hz), 7.6-7.7 (3H, m)
MS (ESI) m/z: 433 (M+H)$^+$.

Example 259

4-[4-(5-hydroxymethylthiophen-2-yl)phenyl]-2,3,9-trimethyl-6H-thieno[3,2-f][1,2,4]triazolo[4,3-a][1,4]diazepine To a mixture of starting material A (684 mg), palladium acetate (22 mg), 2-(di-tert-butylphosphino)biphenyl (60 mg), potassium fluoride (698 mg) and 5-formyl-2-thiopheneboronic acid (936 mg) was added tetrahydrofuran (6 mL), and the mixture was heated under reflux for 8 hr. After cooling, water was added, and the mixture was extracted with ethyl acetate. The organic layer was washed with saturated brine, dried over anhydrous sodium sulfate, and the solvent was evaporated. The residue was dissolved in methanol (10 mL). Sodium borohydride (76 mg) was added, and the mixture was stirred at room temperature for 2 hr. After completion of the reaction, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (351 mg).
$^1$H-NMR (300 MHz, CDCl$_3$) δ: 1.72 (3H, s), 2.42 (3H, s), 2.69 (3H, s), 2.73 (3H, s), 4.12 (1H, d, J=12.6 Hz), 4.83 (2H, s), 5.51 (1H, d, J=12.6 Hz), 6.96 (1H, d, J=3.9 Hz), 7.21 (1H, d, J=3.9 Hz), 7.48 (2H, d, J=8.1 Hz), 7.57 (2H, d, J=8.1 Hz)
MS (ESI) m/z: 421 (M+H)$^+$.

Example 260

1-{5-[4-(2,3,9-trimethyl-6H-thieno[3,2-f][1,2,4]triazolo[4,3-a][1,4]diazepin-4-yl)phenyl]thiophen-2-yl}ethanol The title compound (152 mg) was obtained by an operation in the same manner as in Example 255 and using the compound (265 mg) described in Example 258 instead of the compound described in Example 254.
$^1$H-NMR (300 MHz, CDCl$_3$) δ: 1.62 (3H, d, J=6.6 Hz), 1.72 (3H, s), 2.42 (3H, s), 2.51 (1H, m), 2.69 (3H, s), 4.12 (1H, d, J=12.6 Hz), 5.0-5.2 (1H, m), 5.51 (1H, d, J=12.6 Hz), 6.92 (1H, d, J=3.6 Hz), 7.20 (1H, d, J=3.6 Hz), 7.4-7.5 (2H, m), 7.56 (2H, d, J=8.4 Hz)
MS (ESI) m/z: 435 (M+H)$^+$.

Example 261

2,3,9-trimethyl-4-[4-(thiazole-2-yl)phenyl]-6H-thieno[3,2-f][1,2,4]triazolo[4,3-a][1,4]diazepine The title compound (232 mg) was obtained from starting material A (402 mg) by a treatment in the same manner as in Example 256 and using 2-bromothiazole (450 μL) instead of 5-bromo-2-hydroxybenzonitrile.
$^1$H-NMR (400 MHz, DMSO-d$_6$) δ: 1.65 (3H, s), 2.41 (3H, s), 2.62 (3H, s), 4.18 (1H, d, J=12.6 Hz), 5.29 (1H, d, J=12.6 Hz), 7.59 (2H, d, J=8.2 Hz), 7.84 (1H, d, J=3.2 Hz), 7.96 (1H, d, J=3.2 Hz), 8.00 (2H, d, J=8.2 Hz)
MS (ESI) m/z: 392 (M+H)$^+$.

Example 262

4-[4-(4-cyanopyridin-2-yl)phenyl]-2,3,9-trimethyl-6H-thieno[3,2-f][1,2,4]triazolo[4,3-a][1,4]diazepine The title compound (559 mg) was obtained from the compound (841 mg) described in Starting Material Synthetic Example 7 by a treatment in the same manner as in Example 256 and using 2-chloroisonicotinonitrile (1.1 g) instead of 5-bromo-2-hydroxybenzonitrile.
$^1$H-NMR (400 MHz, DMSO-d$_6$) δ: 1.64 (3H, s), 2.41 (3H, s), 2.62 (3H, s), 4.19 (1H, d, J=12.4 Hz), 5.29 (1H, d, J=12.4 Hz), 7.60 (2H, d, J=8.0 Hz), 7.84 (1H, d, J=4.4 Hz), 8.22 (2H, d, J=8.0 Hz), 8.53 (1H, s), 8.92 (1H, d, J=4.4 Hz)
MS (ESI) m/z: 411 (M+H)$^+$.

Example 263

4-[4-(5-cyanopyridin-3-yl)phenyl]-2,3,9-trimethyl-6H-thieno[3,2-f][1,2,4]triazolo[4,3-a][1,4]diazepine The title compound (2.6 g) was obtained from the compound (5 g) described in Starting Material Synthetic Example 7 by a treatment in the same manner as in Example 256 and using 5-bromonicotinonitrile (4.1 g) instead of 5-bromo-2-hydroxybenzonitrile.
$^1$H-NMR (400 MHz, DMSO-d$_6$) δ: 1.65 (3H, s), 2.46 (3H, s), 2.62 (3H, s), 4.19 (1H, d, J=12.8 Hz), 5.29 (1H, d, J=12.8 Hz), 7.60 (2H, d, J=8.4 Hz), 7.90 (2H, d, J=8.4 Hz), 8.71 (1H, t, J=1.6 Hz), 9.03 (1H, d, J=1.6 Hz), 9.24 (1H, d, J=1.6 Hz)
MS (ESI) m/z: 410 (M+H)$^+$.

Example 264

4-[4-(6-aminopyridin-2-yl)phenyl]-2,3,9-trimethyl-6H-thieno[3,2-f][1,2,4]triazolo[4,3-a][1,4]diazepine The title compound (389 mg) was obtained from the compound (841 mg) described in Starting Material Synthetic Example 7 by a treatment in the same manner as in Example 256 and using 2-amino-6-bromopyridine (1.4 g) instead of 5-bromo-2-hydroxybenzonitrile.
$^1$H-NMR (400 MHz, DMSO-d$_6$) δ: 1.65 (3H, s), 2.41 (3H, s), 2.61 (3H, s), 4.16 (1H, d, J=12.8 Hz), 5.28 (1H, d, J=12.8 Hz), 5.98 (2H, s), 6.44 (1H, d, J=8.0 Hz), 7.09 (1H, d, J=8.0 Hz), 7.47 (1H, t, J=8.0 Hz), 7.51 (2H, d, J=8.0 Hz), 8.00 (2H, d, J=8.0 Hz)
MS (ESI) m/z: 401 (M+H)$^+$.

Example 265

2,3,9-trimethyl-4-(4-pyrimidin-5-ylphenyl)-6H-thieno[3,2-f][1,2,4]triazolo[4,3-a][1,4]diazepine The title compound (499 mg) was obtained from the compound (841 mg) described in Starting Material Synthetic Example 7 by a treatment in the same manner as in Example 256 and using 5-bromopyrimidine (1.3 g) instead of 5-bromo-2-hydroxybenzonitrile.
$^1$H-NMR (400 MHz, DMSO-d$_6$) δ: 1.66 (3H, s), 2.42 (3H, s), 2.62 (3H, s), 4.19 (1H, d, J=12.4 Hz), 5.29 (1H, d, J=12.4 Hz), 7.61 (2H, d, J=8.4 Hz), 7.89 (2H, d, J=8.4 Hz), 9.19 (2H, s), 9.20 (1H, s)
MS (ESI) m/z: 387 (M+H)$^+$.

Example 266

2,3,9-trimethyl-4-(4-pyridin-3-ylphenyl)-6H-thieno[3,2-f][1,2,4]triazolo[4,3-a][1,4]diazepine The title compound (359 mg) was obtained from the compound (841 mg) described in Starting Material Synthetic Example 7 by a treatment in the same manner as in Example 256 and using 3-bromopyridine (1.3 g) instead of 5-bromo-2-hydroxybenzonitrile.

$^1$H-NMR (400 MHz, DMSO-$d_6$) δ: 1.67 (3H, s), 2.42 (3H, s), 2.62 (3H, s), 4.18 (1H, d, J=12.4 Hz), 5.29 (1H, d, J=12.4 Hz), 7.50 (1H, dd, J=8.0, 4.8 Hz), 7.58 (2H, d, J=8.0 Hz), 7.80 (2H, d, J=8.0 Hz), 8.12 (1H, dt, J=8.0, 4.8 Hz), 8.59 (1H, dd, J=4.8, 2.4 Hz), 8.94 (1H, d, J=2.4 Hz)

MS (ESI) m/z: 386 (M+H)$^+$.

Example 267

4-[4-(6-cyanopyridin-2-yl)phenyl]-2,3,9-trimethyl-6H-thieno[3,2-f][1,2,4]triazolo[4,3-a][1,4]diazepine To a mixture of the compound (1.7 g) described in Starting Material Synthetic Example 7, dichlorobis(triphenylphosphine)palladium (II) (140 mg), sodium hydrogencarbonate (2.5 g) and 2-bromo-6-formylpyridine (1.5 g) were added tetrahydrofuran (6 mL) and water (6 mL), and the mixture was stirred at 100° C. for 3 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give an intermediate (1.1 g). The obtained compound (1.1 g) was dissolved in methylene chloride (10 mL). Triethylamine (740 μL) and hydroxylamine hydrochloride (370 mg) were successively added, and the mixture was stirred at room temperature for 24 hr. After completion of the reaction, water was added, and the mixture was extracted with methylene chloride. To the extract were successively added 2-chloro-1,3-dimethyl-2-imidazolium tetrafluoroborate (889 mg) and triethylamine (890 μL), and the mixture was stirred at room temperature for 24 hr. After completion of the reaction, water was added, and the mixture was extracted with ethyl acetate. The organic layer was successively washed with 1 M hydrochloric acid, saturated aqueous sodium hydrogencarbonate and saturated brine, dried over anhydrous sodium sulfate, and the solvent was evaporated. The residue was purified by column chromatography (chloroform:methanol=100:1) and recrystallized from hexane-ethyl acetate to give the title compound (459 mg).

$^1$H-NMR (400 MHz, DMSO-$d_6$) δ: 1.65 (3H, s), 2.41 (3H, s), 2.62 (3H, s), 4.19 (1H, d, J=12.8 Hz), 5.30 (1H, d, J=12.8 Hz), 7.62 (2H, d, J=8.4 Hz), 8.20 (2H, d, J=8.4 Hz), 8.64 (1H, d, J=2.4 Hz), 8.74 (1H, s), 9.30 (1H, s)

MS (ESI) m/z: 411 (M+H)$^+$.

Example 268

2,3,9-trimethyl-4-[4-(1-methyl-1H-pyrazol-4-yl)phenyl]-6H-thieno[3,2-f][1,2,4]triazolo[4,3-a][1,4]diazepine The title compound (110 mg) was obtained from the compound (420 mg) described in Starting Material Synthetic Example 7 by a treatment in the same manner as in Example 256 and using 1-methyl-4-iodo-1H-pyrazole (416 mg) instead of 5-bromo-2-hydroxybenzonitrile.

$^1$H-NMR (400 MHz, DMSO-$d_6$) δ: 1.66 (3H, s), 2.41 (3H, s), 2.61 (3H, s), 3.86 (3H, s), 4.13 (1H, d, J=12.6 Hz), 5.24 (1H, d, J=12.6 Hz), 7.43 (2H, d, J=8.0 Hz), 7.60 (2H, d, J=8.4 Hz), 7.90 (1H, s), 8.19 (1H, s)

MS (ESI) m/z: 389 (M+H)$^+$.

Example 269

4-[4-(5-bromo-thiazole-2-yl)phenyl]-2,3,9-trimethyl-6H-thieno[3,2-f][1,2,4]triazolo[4,3-a][1,4]diazepine The title compound (47 mg) was obtained from the compound (420 mg) described in Starting Material Synthetic Example 7 by a treatment in the same manner as in Example 256 and using 2,5-dibromothiazole (122 mg) instead of 5-bromo-2-hydroxybenzonitrile.

$^1$H-NMR (400 MHz, DMSO-$d_6$) δ: 1.64 (3H, s), 2.41 (3H, s), 2.61 (3H, s), 4.18 (1H, d, J=12.6 Hz), 5.29 (1H, d, J=12.6 Hz), 7.59 (2H, d, J=8.2 Hz), 7.95 (2H, d, J=8.2 Hz), 8.05 (1H, s)

MS (ESI) m/z: 470 (M+H)$^+$.

Example 270

2,3,9-trimethyl-4-[4-(pyrimidin-2-yl)phenyl]-6H-thieno[3,2-f][1,2,4]triazolo[4,3-a][1,4]diazepine The title compound (152 mg) was obtained from the compound (420 mg) described in Starting Material Synthetic Example 7 by a treatment in the same manner as in Example 256 and using 2-chloropyrimidine (688 mg) instead of 5-bromo-2-hydroxybenzonitrile.

$^1$H-NMR (400 MHz, DMSO-$d_6$) δ: 1.64 (3H, s), 2.41 (3H, s), 2.62 (3H, s), 4.19 (1H, d, J=12.6 Hz), 5.30 (1H, d, J=12.6 Hz), 7.48 (1H, t, J=4.8 Hz), 7.62 (2H, d, J=8.0 Hz), 8.43 (2H, d, J=8.0 Hz), 8.93 (2H, d, J=4.8 Hz)

MS (ESI) m/z: 387 (M+H)$^+$.

Example 271

4-[4-(6-chloro-pyrimidin-4-yl)phenyl]-2,3,9-trimethyl-6H-thieno[3,2-f][1,2,4]triazolo[4,3-a][1,4]diazepine The title compound (974 mg) was obtained from the compound (1.7 g) described in Starting Material Synthetic Example 7 by a treatment in the same manner as in Example 256 and using 4,6-dichloropyrimidine (1.2 g) instead of 5-bromo-2-hydroxybenzonitrile.

$^1$H-NMR (400 MHz, DMSO-$d_6$) δ: 1.62 (3H, s), 2.41 (3H, s), 2.63 is (3H, s), 4.21 (1H, d, J=12.4 Hz), 5.31 (1H, d, J=12.4 Hz), 7.64 (2H, d, J=8.0 Hz), 8.31 (2H, d, J=8.0 Hz), 8.37 (1H, s), 9.12 (1H, s)

MS (ESI) m/z: 420 (M+H)$^+$.

Example 272

4-{4-[(4-fluorophenyl)methylamino]phenyl}-2,3,9-trimethyl-6H-thieno[3,2-f][1,2,4]triazolo[4,3-a][1,4]diazepine To a mixture of starting material A (1.4 g), palladium acetate (44 mg), 2-(dicyclohexylphosphino)biphenyl (144 mg) and tripotassium phosphate (1.2 g) were added dimethoxyethane (8 mL) and 4-fluoro-N-methylaniline (0.8 mL), and the mixture was heated under reflux for 8 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (1.3 g).

$^1$H-NMR (400 MHz, DMSO-$d_6$) δ: 1.70 (3H, s), 2.40 (3H, s), 2.61 (3H, s), 3.26 (3H, s), 4.05 (1H, d, J=12.8 Hz), 5.15 (1H, d, J=12.8 Hz), 6.74 (2H, d, J=8.0 Hz), 7.23 (4H, d, J=7.2 Hz), 7.29 (2H, d, J=8.0 Hz)

MS (ESI) m/z: 432 (M+H)$^+$.

Example 273

4-[4-(phenylamino)phenyl]-2,3,9-trimethyl-6H-thieno[3,2-f][1,2,4]triazolo[4,3-a][1,4]diazepine The title compound (298 mg) was obtained from starting material A (500 mg) by a treatment in the same manner as in Example 272 and using aniline (177 mg) instead of 4-fluoro-N-methylaniline.

$^1$H-NMR (300 MHz, CDCl$_3$) δ: 1.78 (3H, s), 2.42 (3H, s), 2.67 (3H, s), 4.07 (1H, d, J=12.6 Hz), 5.43 (1H, d, J=12.6 Hz), 5.98 (1H, s), 6.99 (2H, d, J=8.2 Hz), 7.13 (2H, d, J=8.2 Hz), 7.2-7.5 (5H, m)

MS (ESI) m/z: 400 (M+H)$^+$.

Example 274

4-[4-(4-fluorophenylamino)phenyl]-2,3,9-trimethyl-6H-thieno[3,2-f][1,2,4]triazolo[4,3-a][1,4]diazepine The title compound (306 mg) was obtained from starting material A (500 mg) by a treatment in the same manner as in Example 272 and using 4-fluoroaniline (211 mg) instead of 4-fluoro-N-methylaniline.

$^1$H-NMR (300 MHz, CDCl$_3$) δ: 1.77 (3H, s), 2.41 (3H, s), 2.67 (3H, s), 4.07 (1H, d, J=12.6 Hz), 5.43 (1H, d, J=12.6 Hz), 5.86 (1H, s), 6.88 (2H, d, J=8.8 Hz), 7.0-7.2 (4H, m), 7.38 (2H, d, J=8.8 Hz)

MS (ESI) m/z: 418 (M+H)$^+$.

Example 275

4-[4-(2-methoxyphenylamino)phenyl]-2,3,9-trimethyl-6H-thieno[3,2-f][1,2,4]triazolo[4,3-a][1,4]diazepine The title compound (1.2 g) was obtained from starting material A (1 g) by a treatment in the same manner as in Example 272 and using 2-anisidine (467 mg) instead of 4-fluoro-N-methylaniline.

$^1$H-NMR (300 MHz, CDCl$_3$) δ: 1.77 (3H, s), 2.42 (3H, s), 2.68 (3H, s), 3.89 (3H, s), 4.08 (1H, d, J=12.6 Hz), 5.44 (1H, d, J=12.6 Hz), 6.30 (1H, s), 6.9-7.0 (3H, m), 7.08 (2H, d, J=9.0 Hz), 7.3-7.5 (3H, m)

MS (ESI) m/z: 430 (M+H)$^+$.

Example 276

4-{4-[(5-cyanopyridin-2-yl)amino]phenyl}-2,3,9-trimethyl-6H-thieno[3,2-f][1,2,4]triazolo[4,3-a][1,4]diazepine To a mixture of the compound (500 mg) described in Starting Material Synthetic Example 9, palladium acetate (9 mg), 2-(dicyclohexylphosphino)biphenyl (54 mg), tripotassium phosphate (460 mg) and 6-chloronicotinonitrile (214 mg) was added dimethoxyethane (5 mL), and the mixture was stirred at 80° C. for 7 hr and at 105° C. for 2 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (97 mg).

$^1$H-NMR (300 MHz, DMSO-$d_6$) δ: 1.68 (3H, s), 2.41 (3H, s), 2.60 (3H, s), 4.11 (1H, d, J=12.9 Hz), 5.21 (1H, d, J=12.6 Hz), 6.94 (1H, d, J=8.7 Hz), 7.44 (2H, d, J=8.7 Hz), 7.76 (2H, d, J=8.7 Hz), 7.95 (1H, dd, J=9.0, 2.4 Hz), 8.62 (1H, d, J=2.4 Hz), 10.0 (1H, s)

MS (ESI) m/z: 426 (M+H)$^+$.

Example 277

4-[4-(3-methoxyphenylamino)phenyl]-2,3,9-trimethyl-6H-thieno[3,2-f][1,2,4]triazolo[4,3-a][1,4]diazepine The title compound (1.2 g) was obtained from starting material A (1 g) by a treatment in the same manner as in Example 272 and using 3-anisidine (467 mg) instead of 4-fluoro-N-methylaniline.

$^1$H-NMR (300 MHz, CDCl$_3$) δ: 1.77 (3H, s), 2.42 (3H, s), 2.68 (3H, s), 3.78 (3H, s), 4.08 (1H, d, J=12.6 Hz), 5.44 (1H, d, J=12.6 Hz), 6.5-6.6 (1H, m), 6.7-6.8 (2H, m), 7.02 (2H, d, J=8.8 Hz), 7.19 (1H, d, J=7.4 Hz), 7.40 (2H, d, J=8.8 Hz),

MS (ESI) m/z: 430 (M+H)$^+$.

Example 278

4-[4-(3-fluorophenylamino)phenyl]-2,3,9-trimethyl-6H-thieno[3,2-f][1,2,4]triazolo[4,3-a][1,4]diazepine The title compound (393 mg) was obtained from starting material A (500 mg) by a treatment in the same manner as in Example 272 and using 3-fluoroaniline (211 mg) instead of 4-fluoro-N-methylaniline.

$^1$H-NMR (300 MHz, CDCl$_3$) δ: 1.77 (3H, s), 2.42 (3H, s), 2.68 (3H, s), 4.09 (1H, d, J=12.6 Hz), 5.45 (1H, d, J=12.6 Hz), 6.06 (1H, s), 6.6-6.7 (1H, m), 6.8-6.9 (2H, m), 7.04 (2H, d, J=8.7 Hz), 7.1-7.3 (1H, m), 7.43 (2H, d, J=8.7 Hz),

MS (ESI) m/z: 418 (M+H)$^+$.

Example 279

4-[4-(2-fluorophenylamino)phenyl]-2,3,9-trimethyl-6H-thieno[3,2-f][1,2,4]triazolo[4,3-a][1,4]diazepine The title compound (482 mg) was obtained from starting material A (500 mg) by a treatment in the same manner as in Example 272 and using 2-fluoroaniline (211 mg) instead of 4-fluoro-N-methylaniline.

$^1$H-NMR (300 MHz, CDCl$_3$) δ: 1.77 (3H, s), 2.42 (3H, s), 2.68 (3H, s), 4.08 (1H, d, J=12.6 Hz), 5.44 (1H, d, J=12.6 Hz), 6.01 (1H, s), 6.9-7.0 (1H, m), 7.0-7.2 (4H, m), 7.3-7.5 (3H, m)

MS (ESI) m/z: 418 (M+H)$^+$.

Example 280

4-[4-(2,4-difluorophenylamino)phenyl]-2,3,9-trimethyl-6H-thieno[3,2-f][1,2,4]triazolo[4,3-a][1,4]diazepine The title compound (332 mg) was obtained from starting material A (500 mg) by a treatment in the same manner as in Example 272 and using 2,4-difluoroaniline (245 mg) instead of 4-fluoro-N-methylaniline.
$^1$H-NMR (300 MHz, CDCl$_3$) δ: 1.76 (3H, s), 2.42 (3H, s), 2.67 (3H, s), 4.08 (1H, d, J=12.6 Hz), 5.44 (1H, d, J=12.6 Hz), 5.81 (1H, s), 6.8-7.0 (4H, m), 7.2-7.3 (1H, m), 7.3-7.5 (2H, m)
MS (ESI) m/z: 436 (M+H)$^+$.

Example 281

4-{4-[(benzo[1,3]dioxol-5-yl)amino]phenyl}-2,3,9-trimethyl-6H-thieno[3,2-f][1,2,4]triazolo[4,3-a][1,4]diazepine The title compound (257 mg) was obtained from starting material A (500 mg) by a treatment in the same manner as in Example 272 and using 3,4-(methylenedioxy)aniline (260 mg) instead of 4-fluoro-N-methylaniline.
$^1$H-NMR (300 MHz, CDCl$_3$) δ: 1.70 (3H, s), 2.41 (3H, s), 2.67 (3H, s), 4.06 (1H, d, J=12.6 Hz), 5.42 (1H, d, J=12.6 Hz), 5.78 (1H, s), 5.96 (2H, s), 6.59 (1H, d, J=8.3, 2.0 Hz), 6.7-6.8 (2H, m), 6.84 (2H, d, J=8.7 Hz), 7.35 (2H, d, J=8.7 Hz)
MS (ESI) m/z: 444 (M+H)$^+$.

Example 282

4-[4-(3-cyanophenylamino)phenyl]-2,3,9-trimethyl-6H-thieno[3,2-f][1,2,4]triazolo[4,3-a][1,4]diazepine The title compound (301 mg) was obtained from starting material A (500 mg) by a treatment in the same manner as in Example 272 and using 3-aminobenzonitrile (224 mg) instead of 4-fluoro-N-methylaniline.
$^1$H-NMR (300 MHz, CDCl$_3$) δ: 1.78 (3H, s), 2.43 (3H, s), 2.68 (3H, s), 4.09 (1H, d, J=12.6 Hz), 5.46 (1H, d, J=12.6 Hz), 6.16 (1H, s), 7.04 (2H, d, J=8.4 Hz), 7.2-7.3 (2H, m), 7.3-7.4 (2H, m), 7.45 (2H, d, J=8.4 Hz)
MS (ESI) m/z: 425 (M+H)$^+$.

Example 283

4-[4-(2-cyanophenylamino)phenyl]-2,3,9-trimethyl-6H-thieno[3,2-f][1,2,4]triazolo[4,3-a][1,4]diazepine The title compound (31 mg) was obtained from starting material A (500 mg) by a treatment in the same manner as in Example 272 and using 2-aminobenzonitrile (224 mg) instead of 4-fluoro-N-methylaniline.
$^1$H-NMR (300 MHz, CDCl$_3$) δ: 1.76 (3H, s), 2.43 (3H, s), 2.69 (3H, s), 4.11 (1H, d, J=12.6 Hz), 5.48 (1H, d, J=12.6 Hz), 6.43 (1H, s), 6.94 (1H, t, J=7.8 Hz), 7.15 (2H, d, J=9.0 Hz), 7.2-7.6 (5H, m)
MS (ESI) m/z: 425 (M+H)$^+$.

Example 284

4-[4-(2,4,6-trifluorophenylamino)phenyl]-2,3,9-trimethyl-6H-thieno[3,2-f][1,2,4]triazolo[4,3-a][1,4]diazepine The title compound (194 mg) was obtained from starting material A (500 mg) by a treatment in the same manner as in Example 272 and using 2,4,6-trifluoroaniline (279 mg) instead of 4-fluoro-N-methylaniline.
$^1$H-NMR (300 MHz, CDCl$_3$) δ: 1.75 (3H, s), 2.41 (3H, s), 2.66 (3H, s), 4.07 (1H, d, J=12.6 Hz), 5.43 (1H, d, J=12.6 Hz), 5.48 (1H, s), 6.66 (2H, d, J=8.4 Hz), 6.7-6.8 (2H, m), 7.38 (2H, d, J=8.4 Hz)
MS (ESI) m/z: 454 (M+H)$^+$.

Example 285

2,3,9-trimethyl-4-{4-[methyl-(2,4,6-trifluorophenyl)amino]phenyl}-6H-thieno[3,2-f][1,2,4]triazolo[4,3-a][1,4]diazepine To a mixture of the compound (500 mg) described in Example 284, pulverized sodium hydroxide (176 mg), potassium carbonate (152 mg) and tetra-n-butylammonium bromide (7.4 mg) was added toluene, and the mixture was stirred at 35° C. for 1 hr. Methyl iodide (95 μL) was added thereto, and the mixture was stirred at 80° C. for 6 hr. After cooling, water was added, and the mixture was extracted with ethyl acetate. The organic layer was washed with saturated brine, dried over anhydrous sodium sulfate, and the solvent was evaporated. The residue was recrystallized from hexane-ethyl acetate to give the title compound (310 mg).
$^1$H-NMR (400 MHz, DMSO-d$_6$) δ: 1.68 (3H, s), 2.40 (3H, s), 2.58 (3H, s), 4.05 (1H, d, J=12.8 Hz), 5.41 (1H, d, J=12.6 Hz), 6.61 (2H, d, J=8.6 Hz), 7.32 (2H, d, J=8.6 Hz), 7.37 (2H, t, J=8.6 Hz)
MS (ESI) m/z: 468 (M+H)$^+$.

Example 286

2,3,9-trimethyl-4-{4-[methyl-(3-cyanophenyl)amino]phenyl}-6H-thieno[3,2-f][1,2,4]triazolo[4,3-a][1,4]diazepine To a mixture of the compound (300 mg) described in Starting Material Synthetic Example 10, palladium acetate (10 mg), 2-(dicyclohexylphosphino)biphenyl (31 mg), tripotassium phosphate (378 mg) and 3-bromobenzonitrile (226 mg) was added dimethoxyethane (2 mL), and the mixture was heated under reflux for 24 hr. After cooling, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) to give the title compound (134 mg).
$^1$H-NMR (400 MHz, DMSO-d$_6$) δ: 1.71 (3H, s), 2.43 (3H, s), 2.62 (3H, s), 3.37 (3H, s), 4.35 (1H, d, J=13.0 Hz), 5.20 (1H, d, J=13.0 Hz), 7.04 (2H, d, J=8.4 Hz), 7.45 (3H, m), 7.55 (2H, br.s), 7.62 (1H, br.s)
MS (ESI) m/z: 439 (M+H)$^+$.

Example 287

2,3,9-trimethyl-4-{4-[methyl-(4-cyanophenyl)amino]phenyl}-6H-thieno[3,2-f][1,2,4]triazolo[4,3-a][1,4]diazepine The title compound (191 mg) was obtained from the compound (300 mg) described in Starting Material Synthetic Example 10 by a treatment in the same manner as in Example 286 and using 4-bromobenzonitrile instead of 3-bromobenzonitrile.
$^1$H-NMR (400 MHz, DMSO-d$_6$) δ: 1.71 (3H, s), 2.43 (3H, s), 2.62 (3H, s), 3.38 (3H, s), 4.28 (1H, d, J=13.0 Hz), 5.24

(1H, d, J=13.0 Hz), 7.06 (2H, d, J=7.2 Hz), 7.24 (2H, d, J=7.6 Hz), 7.51 (2H, d, J=7.2 Hz), 7.66 (2H, d, J=7.6 Hz)
MS (ESI) m/z: 439 (M+H)+.

Example 288

2,3,9-trimethyl-4-{4-[(methylpyridin-3-ylmethyl)amino]phenyl}-6H-thieno[3,2-f][1,2,4]triazolo[4,3-a][1,4]diazepine The title compound (237 mg) was obtained from starting material A (343 mg) by a treatment in the same manner as in Example 272 and using N-methyl-N-(3-pyridylmethyl)amine (244 mg) instead of 4-fluoro-N-methylaniline.
1H-NMR (400 MHz, DMSO-d6) δ: 1.69 (3H, s), 2.40 (3H, s), 2.61 (3H, s), 3.06 (3H, s), 4.02 (1H, t, J=12.8 Hz), 4.67 (2H, s), 5.12 (1H, d, J=12.8 Hz), 6.74 (2H, d, J=8.8 Hz), 7.30 (3H, m), 7.55 (1H, d, J=7.6 Hz), 8.43 (2H, s)
MS (ESI) m/z: 429 (M+H)+.

Example 289

4-{4-[(5-trifluoromethylpyridin-2-yl)amino]phenyl}-2,3,9-trimethyl-6H-thieno[3,2-f][1,2,4]triazolo[4,3-a][1,4]diazepine To a mixture of the compound (500 mg) described in Starting Material Synthetic Example 9, palladium acetate (9 mg), 2-(dicyclohexylphosphino)biphenyl (54 mg), tripotassium phosphate (460 mg) and 2-chloro-5-(trifluoromethyl)pyridine (365 mg) was added dimethoxyethane (3 mL), and the mixture was heated under reflux for 8 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (76 mg).
1H-NMR (300 MHz, CDCl3) δ: 1.76 (3H, s), 2.43 (3H, s), 2.68 (3H, s), 4.11 (1H, d, J=12.6 Hz), 5.48 (1H, d, J=12.6 Hz), 6.89 (1H, d, J=9.0 Hz), 7.23 (1H, s), 7.4-7.6 (4H, m), 7.69 (1H, d, J=9.0, 2.4 Hz), 8.48 (1H, s)
MS (ESI) m/z: 469 (M+H)+.

Example 290

4-{4-[(5-fluoropyridin-2-yl)amino]phenyl}-2,3,9-trimethyl-6H-thieno[3,2-f][1,2,4]triazolo[4,3-a][1,4]diazepine The title compound (419 mg) was obtained from starting material A (500 mg) by a treatment in the same manner as in Example 272 and using 2-amino-5-fluoropyridine (213 mg) instead of 4-fluoro-N-methylaniline.
1H-NMR (300 MHz, CDCl3) δ: 1.76 (3H, s), 2.42 (3H, s), 2.68 (3H, s), 4.09 (1H, d, J=12.6 Hz), 5.46 (1H, d, J=12.6 Hz), 6.89 (1H, dd, J=9.0, 3.3 Hz), 6.95 (1H, s), 7.2-7.3 (1H, m), 7.38 (2H, d, J=9.0 Hz), 7.45 (2H, d, J=9.0 Hz), 8.09 (1H, dd, J=3.0 Hz)
MS (ESI) m/z: 419 (M+H)+.

Example 291

4-{4-[(6-methoxypyridin-2-yl)amino]phenyl}-2,3,9-trimethyl-6H-thieno[3,2-f][1,2,4]triazolo[4,3-a][1,4]diazepine The title compound (319 mg) was obtained from the compound (500 mg) described in Starting Material Synthetic Example 9 by a treatment in the same manner as in Example 289 and using 2-chloro-6-methoxypyridine (289 mg) instead of 2-chloro-5-(trifluoromethyl)pyridine.
1H-NMR (300 MHz, CDCl3) δ: 1.76 (3H, s), 2.42 (3H, s), 2.68 (3H, s), 3.91 (3H, s), 4.09 (1H, d, J=12.6 Hz), 5.46 (1H, d, J=12.6 Hz), 6.25 (1H, d, J=7.9 Hz), 6.40 (1H, d, J=7.9 Hz), 6.58 (1H, s), 7.4-7.5 (5H, m)
MS (ESI) m/z: 431 (M+H)+.

Example 292

4-{4-[(5-chloro-pyridin-2-yl)amino]phenyl}-2,3,9-trimethyl-6H-thieno[3,2-f][1,2,4]triazolo[4,3-a][1,4]diazepine To a mixture of the compound (500 mg) described in Starting Material Synthetic Example 9, palladium acetate (17 mg), 2-(dicyclohexylphosphino)biphenyl (54 mg), tripotassium phosphate (460 mg), potassium carbonate (641 mg) and 2,5-dichloropyridine (390 mg) was added dimethoxyethane (3.1 mL), and the mixture was heated under reflux for 16 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (480 mg).
1H-NMR (400 MHz, DMSO-d6) δ: 1.69 (3H, s), 2.41 (3H, s), 2.60 (3H, s), 4.19 (1H, d, J=12.4 Hz), 5.19 (1H, d, J=12.4 Hz), 6.91 (1H, d, J=9.2 Hz), 7.38 (2H, d, J=8.4 Hz), 7.6-7.8 (3H, m), 8.19 (1H, d, J=2.4 Hz), 9.51 (1H, s)
MS (ESI) m/z: 419 (M+H)+.

Example 293

4-{4-[(2-fluoropyridin-5-yl)amino]phenyl}-2,3,9-trimethyl-6H-thieno[3,2-f][1,2,4]triazolo[4,3-a][1,4]diazepine The title compound (35 mg) was obtained from the compound (350 mg) described in Starting Material Synthetic Example 9 by a treatment in the same manner as in Example 289 and using 5-bromo-2-fluoropyridine (170 μL) instead of 2-chloro-5-(trifluoromethyl)pyridine.
1H-NMR (300 MHz, DMSO-d6) δ: 1.69 (3H, s), 2.39 (3H, s), 2.56 (3H, s), 3.05 (1H, d, J=12.6, Hz), 5.14 (1H, d, J=12.6 Hz), 6.98 (2H, d, J=8.7 Hz), 7.08 (1H, dd, J=9.0, 3.3 Hz), 7.33 (2H, d, J=8.7 Hz), 7.71 (1H, ddd, J=9.0, 6.3, 3.3 Hz), 7.98 (1H, s), 8.65 (1H, s)
MS (ESI) m/z: 419 (M+H)+.

Example 294

2,3,9-trimethyl-4-[4-(pyridin-3-ylamino)phenyl]6H-thieno[3,2-f][1,2,4]triazolo[4,3-a][1,4]diazepine The title compound (370 mg) was obtained from the compound (500 mg) described in Starting Material Synthetic Example 9 by a treatment in the same manner as in Example 272 and using 3-aminopyridine (205 mg) instead of 4-fluoro-N-methylaniline.
1H-NMR (300 MHz, DMSO-d6) δ: 1.70 (3H, s), 2.38 (3H, s), 2.56 (3H, s), 4.05 (1H, d, J=12.6 Hz), 5.15 (1H, d, J=12.6 Hz), 7.04 (2H, d, J=8.4 Hz), 7.25 (1H, dd, J=8.1, 4.5 Hz), 7.34 (2H, d, J=8.4 Hz), 7.51 (1H, d, J=8.1 Hz), 8.08 (1H, d, J=4.5 Hz), 8.37 (1H, s), 8.68 (1H, s)
MS (ESI) m/z: 401 (M+H)+.

Example 295

2,3,9-trimethyl-4-{4-[(pyridin-4-ylmethyl)amino]phenyl}-6H-thieno[3,2-f][1,2,4]triazolo[4,3-a][1,4]diazepine The title compound (131 mg) was obtained from starting material A (300 mg) by a treatment in the same manner as in Example 272 and using 4-picolylamine (130 μL) instead of 4-fluoro-N-methylaniline.

$^1$H-NMR (400 MHz, DMSO-d$_6$) δ: 1.69 (3H, s), 2.39 (3H, s), 2.56 (3H, s), 4.00 (1H, d, J=12.8 Hz), 4.35 (2H, d, J=6.4 Hz), 5.09 (1H, d, J=12.8 Hz), 6.53 (2H, d, J=8.0 Hz), 6.88 (1H, m), 7.19 (2H, d, J=7.6 Hz), 7.32 (2H, m), 8.50 (2H, m)
MS (ESI) m/z: 415 (M+H)$^+$.

Example 296

2,3,9-trimethyl-4-[4-(2-pyridin-4-yl-ethylamino)phenyl]-6H-thieno[3,2-f][1,2,4]triazolo[4,3-a][1,4]diazepine The title compound (159 mg) was obtained from starting material A (500 mg) by a treatment in the same manner as in Example 272 and using 4-(2-aminoethyl)pyridine (0.2 ml) instead of 4-fluoro-N-methylaniline.

$^1$H-NMR (300 MHz, CDCl$_3$) δ 1.76 (s, 3H), 2.41 (s, 3H), 2.66 (s, 3H), 2.91 (t, 2H, J=5.1 Hz), 3.47 (dt, 2H, J=5.1, 4.5 Hz), 3.98 (t, 1H, J=4.5 Hz), 4.05 (d, 1H, J=9.6 Hz), 5.40 (d, 1H, J=9.6 Hz), 6.54 (d, 2H, J=6.6 Hz), 7.12 (d, 2H, J=4.5 Hz), 7.34 (d, 2H, J=6.6 Hz), 8.52 (d, 2H, J=4.5 Hz)
MS (ESI) m/z: 429 (M+H)$^+$.

Example 297

4-[4-(4-fluorophenylamino)phenyl]-2-hydroxymethyl-3,9-dimethyl-6H-thieno[3,2-f][1,2,4]triazolo[4,3-a][1,4]diazepine To a mixture of the compound (496 mg) described in Starting Material Synthetic Example 6, palladium acetate (12 mg), 2-(dicyclohexylphosphino)biphenyl (37 mg) and tripotassium phosphate (456 mg) were successively added dimethoxyethane (2 mL) and 4-fluoroaniline (139 μL), and the mixture was heated under reflux for 8 hr. After cooling, water was added, and the mixture was extracted with ethyl acetate. The organic layer was washed with water and saturated brine, dried over anhydrous sodium sulfate, and the solvent was evaporated. The residue was purified by column chromatography (chloroform:methanol=100:1) to give 4-[4-(4-fluorophenylamino)phenyl]-2-(tert-butyldimethylsilyloxymethyl)-3,9-dimethyl-trimethyl-6H-thieno[3,2-f][1,2,4]triazolo[4,3-a][1,4]diazepine (460 mg). The obtained compound (370 mg) was dissolved in tetrahydrofuran (6 mL). A solution (1 mL) of 1 M tetra-n-ammonium fluoride in tetrahydrofuran was added, and the mixture was stirred at room temperature for 5 hr. After completion of the reaction, the reaction mixture was poured into ice water, and the mixture was extracted with ethyl acetate. The organic layer was washed with water and saturated brine, dried over anhydrous sodium sulfate, and the solvent was evaporated. The residue was purified by column chromatography (chloroform:methanol=20:1) to give the title compound (200 mg).

$^1$H-NMR (300 MHz, CDCl$_3$) δ: 1.84 (3H, s), 2.51 (1H, brs), 2.69 (3H, s), 4.07 (1H, d, J=12.6 Hz), 4.87 (2H, brs), 5.43 (1H, d, J=12.6 Hz), 5.83 (1H, s), 6.87 (2H, d, J=8.7 Hz), 7.05 (4H, m), 7.36 (2H, d, J=8.7 Hz)
MS (ESI) m/z: 434 (M+H)$^+$.

Example 298

4-[4-(2,4-difluorophenylamino)phenyl]-2-hydroxymethyl-3,9-dimethyl-6H-thieno[3,2-f][1,2,4]triazolo[4,3-a][1,4]diazepine The title compound (207 mg) was obtained from the compound (496 mg) described in Starting Material Synthetic Example 6 by a treatment in the same manner as in Example 297 and using 2,4-difluoroaniline (149 μL) instead of 4-fluoroaniline.

$^1$H-NMR (300 MHz, CDCl$_3$) δ: 1.83 (3H, s), 2.56 (1H, brs), 2.69 (3H, s), 4.07 (1H, d, J=12.6 Hz), 4.87 (2H, brs), 5.44 (1H, d, J=12.6 Hz), 5.76 (1H, s), 6.88 (4H, m), 7.30 (1H, m), 7.39 (2H, d, J=8.4 Hz)
MS (ESI) m/z: 452 (M+H)$^+$.

Example 299

2-hydroxymethyl-4-[4-(3-methoxyphenylamino)phenyl]-3,9-dimethyl-6H-thieno[3,2-f][1,2,4]triazolo[4,3-a][1,4]diazepine The title compound (190 mg) was obtained from the compound (496 mg) described in Starting Material Synthetic Example 6 by a treatment in the same manner as in Example 297 and using 3-methoxyaniline (165 μL) instead of 4-fluoroaniline.

$^1$H-NMR (300 MHz, CDCl$_3$) δ: 1.84 (3H, s), 2.70 (3H, s), 3.11 (1H, brs), 3.79 (3H, s), 4.07 (1H, d, J=12.7 Hz), 4.89 (2H, brs), 5.43 (1H, d, J=12.7 Hz), 6.01 81H, s), 6.57 (1H, m), 6.72 (2H, m), 7.01 (2H, d, J=8.9 Hz), 7.21 (1H, t, J=7.9 Hz), 7.39 (2H, d, J=8.9 Hz)
MS (ESI) m/z: 446 (M+H)$^+$.

Example 300

2-hydroxyethyl (S)-{4-(3'-cyanobiphenyl-4-yl)-2,3,9-trimethyl-6H-thieno[3,2-f][1,2,4]triazolo[4,3-a][1,4]diazepin-6-yl}acetate The compound (2.9 g) described in Example 8 was dissolved in methanol (14 mL). 4 M aqueous sodium hydroxide solution (3.5 mL) was added, and the mixture was stirred at room temperature for 3 hr. After completion of the reaction, 1 M aqueous hydrochloric acid (16 mL) was added, and the mixture was extracted with chloroform. The organic layer was washed with saturated brine and dried over anhydrous sodium sulfate. Recrystallization from hexane-ethyl acetate gave (S)-4-(3'-cyanobiphenyl-4-yl)-2,3,9-trimethyl-6H-thieno[3,2-f][1,2,4]triazolo[4,3-a][1,4]diazepin-6-acetic acid (2.8 g). The obtained compound (234 mg) and 2-chloro-1,3-dimethyl-2-imidazolium tetrafluoroborate (140 mg) were dissolved in methylene chloride (2 mL). Pyridine (80 μL) and ethylene glycol (140 μL) were added, and the mixture was stirred at room temperature for 24 hr. After completion of the reaction, water was added, and the mixture was extracted with chloroform. The organic layer was washed with saturated brine, dried over anhydrous sodium sulfate, and the solvent was evaporated. The residue was purified by column chromatography (chloroform:methanol=100:1) and recrystallized from hexane-ethyl acetate to give the title compound (123 mg).

¹H-NMR (400 MHz, DMSO-d₆) δ: 1.67 (3H, s), 2.44 (3H, s), 2.63 (3H, s), 3.4-3.6 (2H, m), 3.6-3.7 (2H, m), 4.1-4.2 (2H, m), 4.54 (1H, t, J=8.0 Hz), 4.87 (1H, t, J=5.2 Hz), 7.53 (2H, d, J=8.4 Hz), 7.69 (1H, t, J=8.0 Hz), 7.8-7.9 (3H, m), 8.07 (1H, d, J=8.0 Hz), 8.32 (1H, s)

MS (ESI) m/z: 512 (M+H)⁺.

Example 301

2-methoxyethyl (S)-{4-(3'-cyanobiphenyl-4-yl)-2,3,9-trimethyl-6H-thieno[3,2-f][1,2,4]triazolo[4,3-a][1,4]diazepin-6-yl}acetate The title compound (278 mg) was obtained from the intermediate of (S)-4-(3'-cyanobiphenyl-4-yl)-2,3,9-trimethyl-6H-thieno[3,2-f][1,2,4]triazolo[4,3-a][1,4]diazepin-6-acetic acid (468 mg) by a treatment in the same manner as in Example 300 and using methoxyethanol (80 µL) instead of ethylene glycol.

¹H-NMR (400 MHz, DMSO-d₆) δ: 1.67 (3H, s), 2.44 (3H, s), 2.63 (3H, s), 3.27 (3H, s), 3.4-3.5 (2H, m), 3.5-3.6 (2H, m), 4.23 (2H, dd, J=8.0, 4.4 Hz), 4.52 (1H, t, J=7.6 Hz), 7.53 (2H, d, J=8.4 Hz), 7.69 (1H, t, J=7.6 Hz), 7.3-7.4 (3H, m), 8.07 (1H, d, J=8.4 Hz), 8.22 (1H, s)

MS (ESI) m/z: 526 (M+H)⁺.

Example 302

2-morpholin-4-ylethyl (S)-{4-(3'-cyanobiphenyl-4-yl)-2,3,9-trimethyl-6H-thieno[3,2-f][1,2,4]triazolo[4,3-a][1,4]diazepin-6-yl}acetate The title compound (103 mg) was obtained from the intermediate of (S)-4-(3'-cyanobiphenyl-4-yl)-2,3,9-trimethyl-6H-thieno[3,2-f][1,2,4]triazolo[4,3-a][1,4]diazepin-6-acetic acid (234 mg) by a treatment in the same manner as in Example 300 and using N-(2-hydroxyethyl)morpholine (120 µL) instead of ethylene glycol.

¹H-NMR (400 MHz, DMSO-d₆) δ: 1.68 (3H, s), 2.3-2.4 (4H, m), 2.43 (3H, s), 2.56 (2H, t, J=5.6 Hz), 2.62 (3H, s), 3.4-3.6 (6H, m), 4.21 (2H, t, J=5.6 Hz), 4.53 (1H, t, J=7.6 Hz), 7.54 (2H, d, J=8.4 Hz), 7.69 (1H, t, J=8.0 Hz), 7.8-7.9 (3H, m), 8.07 (1H, d, J=8.0 Hz), 8.21 (1H, s)

MS (ESI) m/z: 581 (M+H)⁺.

Example 303

2-(N,N-dimethylamino)ethyl (S)-{4-(3'-cyanobiphenyl-4-yl)-2,3,9-trimethyl-6H-thieno[3,2-f][1,2,4]triazolo[4,3-a][1,4]diazepin-6-yl}acetate The title compound (96 mg) was obtained from the intermediate of (S)-4-(3'-cyanobiphenyl-4-yl)-2,3,9-trimethyl-6H-thieno[3,2-f][1,2,4]triazolo[4,3-a][1,4]diazepin-6-acetic acid (234 mg) by a treatment in the same manner as in Example 300 and using N,N-dimethylaminoethanol (100 µL) instead of ethylene glycol.

¹H-NMR (400 MHz, DMSO-d₆) δ: 1.67 (3H, s), 2.16 (6H, s), 2.43 (3H, s), 2.5-2.6 (2H, m), 2.62 (3H, s), 3.4-3.5 (2H, m), 4.1-4.3 (2H, m), 4.52 (1H, t, J=6.4 Hz), 7.54 (2H, d, J=8.4 Hz), 7.69 (1H, t, J=8.0 Hz), 7.8-7.9 (3H, m), 8.07 (1H, d, J=8.0 Hz), 8.21 (1H, s)

MS (ESI) m/z: 539 (M+H)⁺.

Example 304

2-methoxyethyl (S)-{4-[4-(2-ethyl-2H-pyrazol-3-ylamino)phenyl]-2,3,9-trimethyl-6H-thieno[3,2-f][1,2,4]triazolo[4,3-a][1,4]diazepin-6-yl}acetate Thionyl chloride (230 µL) and the intermediate synthesized in Example 151, (S)-4-[4-(2-ethyl-2H-pyrazol-3-ylamino)phenyl]-2,3,9-trimethyl-6H-thieno[3,2-f][1,2,4]triazolo[4,3-a][1,4]diazepin-6-acetic acid (500 mg), were successively added to methoxy ethanol (10 mL) at 0° C., and the mixture was stirred at room temperature for 1 day. After completion of the reaction, the mixture was partitioned by adding water and ethyl acetate. The organic layer was washed with aqueous sodium hydrogencarbonate, and the solvent was evaporated. The residue was purified by column chromatography (chloroform:methanol=100:1) to give the title compound (410 mg).

¹H-NMR (300 MHz, DMSO-d₆) δ: 1.22 (3H, t, J=7.2 Hz), 1.69 (3H, s), 2.39 (3H, s), 2.56 (3H, s), 3.22 (3H, S), 3.4 (2H, m), 3.50 (2H, t, J=4.8 Hz), 3.93 (2H, q, J=7.2 Hz), 4.1-4.2 (2H, m), 4.39 (1H, t, J=7.8 Hz), 6.01 (1H, d, J=1.8 Hz), 6.75 (2H, d, J=8.1 Hz), 7.24 (2H, d, J=8.1 Hz), 7.38 (1H, d, J=1.8 Hz), 8.26 (1H, s)

MS (ESI) m/z: 534 (M+H)⁺.

Example 305

2-hydroxyethyl (S)-{4-[4-(2-ethyl-2H-pyrazol-3-ylamino)phenyl]-2,3,9-trimethyl-6H-thieno[3,2-f][1,2,4]triazolo[4,3-a][1,4]diazepin-6-yl}acetate The title compound (190 mg) was obtained by a treatment in the same manner as in Example 300 and using the intermediate of (S)-4-[4-(2-ethyl-2H-pyrazol-3-ylamino)phenyl]-2,3,9-trimethyl-6H-thieno[3,2-f][1,2,4]triazolo[4,3-a][1,4]diazepin-6-acetic acid (500 mg) synthesized in Example 151 instead of the intermediate of (S)-4-(3'-cyanobiphenyl-4-yl)-2,3,9-trimethyl-6H-thieno[3,2-f][1,2,4]triazolo[4,3-a][1,4]diazepin-6-acetic acid synthesized in Example 300.

¹H-NMR (300 MHz, DMSO-d₆) δ: 1.22 (3H, t, J=7.2 Hz), 1.69 (3H, s), 2.40 (3H, s), 2.56 (3H, s), 3.34 (1H, dd, J=16.5 Hz, 8.1 Hz), 3.42 (1H, dd, J=16.5 Hz, 6.6 Hz), 3.56 (2H, td, J=5.4 Hz), 3.93 (2H, q, J=7.2 Hz), 4.06 (2H, t, J=5.4 Hz), 4.40 (1H, t, J=7.5 Hz), 4.81 (1H, t, J=5.4 Hz), 6.01 (1H, d, J=1.8 Hz), 6.75 (2H, d, J=8.7 Hz), 7.25 (2H, d, J=8.7 Hz), 7.38 (1H, d, J=1.8 Hz), 8.24 (1H, s)

MS (ESI) m/z: 520 (M+H)⁺.

Example 306

2-hydroxyethyl (S)-{4-(4-benzylaminophenyl)-2,3,9-trimethyl-6H-thieno[3,2-f][1,2,4]triazolo[4,3-a][1,4]diazepin-6-yl}acetate An intermediate, (S)-4-(4-benzylaminophenyl)-2,3,9-trimethyl-6H-thieno[3,2-f][1,2,4]triazolo[4,3-a][1,4]diazepin-6-acetic acid (7 g), was obtained by a treatment in the same manner as in Example 300 and using the compound (7 g) described in Example 167 instead of the compound described in Example 8, and 688 mg thereof was treated in the same manner as in Example 300 to give the title compound (170 g).

¹H-NMR (400 MHz, DMSO-d₆) δ: 1.71 (3H, s), 2.41 (3H, s), 2.56 (3H, s), 3.3-3.5 (2H, m), 3.5-3.7 (2H, m), 4.07 (2H, t,

J=6.0 Hz), 4.29 (2H, d, J=6.0 Hz), 4.38 (1H, t-like), 4.79 (1H, brs), 6.56 (2H, d, J=8.4 Hz), 6.77 (1H, t-like), 7.1-7.4 (7H, m)
MS (ESI) m/z: 516 (M+H)$^+$.

Example 307

2-hydroxyethyl (S)-{2,3,9-trimethyl-4-[4-(1,3,5-trimethyl-1H-pyrazol-4-ylamino)phenyl]-6H-thieno[3,2-f][1,2,4]triazolo[4,3-a][1,4]diazepin-6-yl}acetate An intermediate, (S)-{2,3,9-trimethyl-4-[4-(1,3,5-trimethyl-1H-pyrazol-4-ylamino)phenyl]-6H-thieno[3,2-f][1,2,4]triazolo[4,3-a][1,4]diazepin-6-acetic acid (5.3 g), was obtained by a treatment in the same manner as in Example 300 and using the compound (8 g) described in Example 148 instead of the compound described in Example 8, and treated in the same manner as in Example 300 to give the title compound (3.1 g).
$^1$H-NMR (300 MHz, DMSO-d$_6$) δ: 1.71 (3H, s), 1.87 (3H, s), 1.98 (3H, s), 2.39 (3H, s), 2.55 (3H, s), 3.33 (1H, dd, J=16.5 Hz, 8.1 Hz), 3.41 (1H, dd, J=16.5 Hz, 6.6 Hz), 3.55 (2H, m), 3.62 (3H, s), 4.06 (2H, t, J=4.8 Hz), 4.37 (1H, t, J=7.2 Hz), 4.79 (1H, brs), 6.41 (2H, d, J=8.4 Hz), 7.14 (2H, d, J=8.4 Hz), 7.42 (1H, s)
MS (ESI) m/z: 534 (M+H)$^+$.

Example 308

Methyl (S)-{4-[4-(4-trifluoromethylbenzamido)phenyl]-2,3,9-trimethyl-6H-thieno[3,2-f][1,2,4]triazolo[4,3-a][1,4]diazepin-6-yl}acetate The compound (200 mg) described in Starting Material Synthetic Example 4 was dissolved in methylene chloride (2.5 mL). Pyridine (120 μL) and 4-trifluoromethylbenzoylchloride (100 μL) were successively added, and the mixture was stirred at room temperature for 20 hr. After completion of the reaction, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (240 mg).
$^1$H-NMR (300 MHz, DMSO-d$_6$) δ: 1.65 (3H, s), 2.40 (3H, s), 2.59 (3H, s), 3.4 (2H, m), 3.65 (3H, s), 4.46 (1H, t, J=7.2 Hz), 7.41 (2H, d, J=7.8 Hz), 7.83 (2H, d, J=7.8 Hz), 7.89 (2H, d, J=7.8 Hz), 8.13 (2H, d, J=7.8 Hz), 10.62 (1H, s);
MS (ESI) m/z: 568 (M+H)$^+$.

Example 309

Methyl (S)-{4-[4-(3-cyanobenzoylamino)phenyl]-2,3,9-trimethyl-6H-thieno[3,2-f][1,2,4]triazolo[4,3-a][1,4]diazepin-6-yl}acetate The title compound (174 mg) was obtained from the compound (200 mg) described in Starting Material Synthetic Example 4 by a treatment in the same manner as in Example 308 and using 3-cyanobenzoylchloride (109 mg) instead of 4-trifluoromethylbenzoylchloride.
$^1$H-NMR (300 MHz, DMSO-d$_6$) δ: 1.65 (3H, s), 2.41 (3H, s), 2.60 (3H, s), 3.3-3.5 (2H, m), 3.65 (3H, s), 4.48 (1H, t, J=7.2 Hz), 7.18 (2H, d, J=8.4 Hz), 7.73 (1H, dd, J=7.8 Hz, 7.8 Hz), 7.82 (2H, d, J=8.4 Hz), 8.05 (1H, d, J=7.8 Hz), 8.33 (1H, d, J=7.8 Hz), 8.39 (1H, s), 10.62 (1H, s)
MS (ESI) m/z: 525 (M+H)$^+$.

Example 310

Methyl (S)-{4-[4-(2-acetoxybenzoylamino)phenyl]-2,3,9-trimethyl-6H-thieno[3,2-f][1,2,4]triazolo[4,3-a][1,4]diazepin-6-yl}acetate The title compound (142 mg) was obtained from the compound (200 mg) described in Starting Material Synthetic Example 4 by a treatment in the same manner as in Example 308 and using O-acetylsalicyloyl chloride (130 mg) instead of 4-trifluoromethylbenzoylchloride.
$^1$H-NMR (300 MHz, DMSO-d$_6$) δ: 1.66 (3H, s), 2.15 (3H, s), 2.41 (3H, s), 2.58 (3H, s), 3.38 (1H, dd, J=16.8 Hz, 8.1 Hz), 3.47 (1H, dd, J=16.8 Hz, 6.9 Hz), 3.65 (3H, s), 4.45 (1H, t, J=7.2 Hz), 7.23 (1H, d, J=8.1 Hz), 7.37 (1H, m), 7.38 (2H, d, J=8.7 Hz), 7.56 (1H, ddd, J=8.1 Hz, 8.1 Hz, 1.5 Hz), 7.68 (1H, dd, J=6.6 Hz, 1.5 Hz), 7.73 (2H, d, J=8.7 Hz), 10.54 (1H, s);
MS (ESI) m/z: 558 (M+H)$^+$.

Example 311

Methyl (S)-{2,3,9-trimethyl-4-[4-(3-phenylpropionylamino)phenyl]-6H-thieno[3,2-f][1,2,4]triazolo[4,3-a][1,4]diazepin-6-yl}acetate 3-Phenylpropionic acid (69 mg) was dissolved in methylene chloride (2.5 mL), triethylamine (390 μL), the compound (200 mg) described in Starting Material Synthetic Example 4 and 2-chloro-1-methylpyridinium iodide (470 mg) were successively added, and the mixture was heated under reflux for 2 hr. After completion of the reaction, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) to give the title compound (135 mg).
$^1$H-NMR (300 MHz, DMSO-d$_6$) δ: 1.63 (3H, s), 2.40 (3H, s), 2.58 (3H, s), 2.61 (2H, t, J=7.8 Hz), 2.88 (2H, t, J=7.8 Hz), 3.3-3.5 (2H, m), 3.64 (3H, s), 4.44 (1H, t, J=7.2 Hz), 7.1-7.3 (5H, m), 7.38 (2H, d, J=8.4 Hz), 7.60 (2H, d, J=8.4 Hz), 10.12 (1H, s);
MS (ESI) m/z: 528 (M+H)$^+$.

Example 312

Methyl (S)-(4-{4-[3-(4-methoxyphenyl)propionylamino]phenyl}-2,3,9-trimethyl-6H-thieno[3,2-f][1,2,4]triazolo[4,3-a][1,4]diazepin-6-yl)acetate The compound (200 mg) described in Starting Material Synthetic Example 4 and 3-(4-methoxyphenyl)propionic acid (120 mg) were dissolved in methylene chloride (2.5 mL). 1-Ethyl-3-(3-dimethylaminopropyl)carbodiimide hydrochloride (WSC.HCl) (120 mg) was added, and the mixture was stirred at room temperature for 7 hr. After completion of the reaction, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (230 mg).
$^1$H-NMR (300 MHz, DMSO-d$_6$) δ: 1.63 (3H, s), 2.40 (3H, s), 2.58 (3H, s), 2.58 (2H, t, J=7.5 Hz), 2.81 (2H, t, J=7.5 Hz), 3.37 (1H, dd, J=16.5 Hz, 7.5 Hz), 3.46 (1H, dd, J=16.5 Hz, 6.9 Hz), 3.64 (3H, s), 3.68 (3H, s), 4.43 (1H, t, J=7.2 Hz), 6.81

(2H, d, J=8.7 Hz), 7.13 (2H, d, J=8.7 Hz), 7.35 (2H, d, J=8.7 Hz), 7.60 (2H, d, J=8.7 Hz), 10.08 (1H, s);
MS (ESI) m/z: 558 (M+H)$^+$.

Example 313

Methyl (S)-(4-{4-[2-(4-methoxyphenyl)acetylamino]phenyl}-2,3,9-trimethyl-6H-thieno[3,2-f][1,2,4]triazolo[4,3-a][1,4]diazepin-6-yl)acetate The title compound (250 mg) was obtained from the compound (200 mg) described in Starting Material Synthetic Example 4 by a treatment in the same manner as in Example 312 and using 4-methoxyphenylacetic acid (110 mg) instead of 3-(4-methoxyphenyl)propionic acid.
$^1$H-NMR (300 MHz, DMSO-d$_6$) δ: 1.62 (3H, s), 2.39 (3H, s), 2.57 (3H, s), 3.37 (1H, dd, J=16.5 Hz, 7.5 Hz), 3.46 (1H, dd, J=16.5 Hz, 6.9 Hz), 3.54 (2H, s), 3.64 (3H, s), 3.70 (3H, s), 4.43 (1H, t, J=7.2 Hz), 6.86 (2H, d, J=8.7 Hz), 7.22 (2H, d, J=8.7 Hz), 7.33 (2H, d, J=8.7 Hz), 7.61 (2H, d, J=8.7 Hz), 10.27 (1H, s);
MS (ESI) m/z: 544 (M+H)$^+$.

Example 314

Methyl (S)-(4-{4-[3-(4-fluorophenyl)propionylamino]phenyl}-2,3,9-trimethyl-6H-thieno[3,2-f][1,2,4]triazolo[4,3-a][1,4]diazepin-6-yl)acetate The title compound (260 mg) was obtained from the compound (200 mg) described in Starting Material Synthetic Example 4 by a treatment in the same manner as in Example 312 and using 3-(4-fluorophenyl)propionic acid (110 mg) instead of 3-(4-methoxyphenyl)propionic acid.
$^1$H-NMR (300 MHz, DMSO-d$_6$) δ: 1.62 (3H, s), 2.40 (3H, s), 2.58 (3H, s), 2.60 (2H, t, J=7.8 Hz), 2.87 (2H, t, J=7.8 Hz), 3.37 (1H, dd, J=16.8 Hz, 7.5 Hz), 3.46 (1H, dd, J=16.8 Hz, 6.9 Hz), 3.64 (3H, s), 4.43 (1H, t, J=7.2 Hz), 7.08 (2H, dd, J=8.7 Hz, 8.7 Hz), 7.25 (2H, dd, J=8.7 Hz, 5.7 Hz), 7.33 (2H, d, J=8.7 Hz), 7.60 (2H, d, J=8.7 Hz), 10.11 (1H, s);
MS (ESI) m/z: 546 (M+H)$^+$.

Example 315

Methyl (S)-(4-{4-[2-(4-fluorophenyl)acetylamino]phenyl}-2,3,9-trimethyl-6H-thieno[3,2-f][1,2,4]triazolo[4,3-a][1,4]diazepin-6-yl)acetate The title compound (219 mg) was obtained from the compound (200 mg) described in Starting Material Synthetic Example 4 by a treatment in the same manner as in Example 312 and using 4-fluorophenylacetic acid (100 mg) instead of 3-(4-methoxyphenyl)propionic acid.
$^1$H-NMR (300 MHz, DMSO-d$_6$) δ: 1.61 (3H, s), 2.39 (3H, s), 2.57 (3H, s), 3.36 (1H, dd, J=16.8 Hz, 7.8 Hz), 3.46 (1H, dd, J=16.8 Hz, 6.9 Hz), 3.63 (2H, s), 3.64 (3H, s), 4.43 (1H, t, J=7.5 Hz), 7.12 (2H, dd, J=8.7 Hz, 8.7 Hz), 7.3 (2H, m), 7.33 (2H, d, J=8.7 Hz), 7.61 (2H, d, J=8.7 Hz), 10.36 (1H, s);
MS (ESI) m/z: 532 (M+H)$^+$.

Example 316

Methyl (S)-{4-(4-phenylacetylaminophenyl)-2,3,9-trimethyl-6H-thieno[3,2-f][1,2,4]triazolo[4,3-a][1,4]diazepin-6-yl}acetate The title compound (160 mg) was obtained from the compound (200 mg) described in Starting Material Synthetic Example 4 by a treatment in the same manner as in Example 308 and using phenylacetyl chloride (85 μL) instead of 4-trifluoromethylbenzoylchloride.
$^1$H-NMR (300 MHz, DMSO-d$_6$) δ: 1.62 (3H, s), 2.39 (3H, s), 2.57 (3H, s), 3.37 (1H, dd, J=16.5 Hz, 7.8 Hz), 3.46 (1H, dd, J=16.5 Hz, 6.9 Hz), 3.63 (2H, s), 3.64 (3H, s), 4.43 (1H, t, J=7.2 Hz), 7.2-7.3 (5H, m), 7.33 (2H, d, J=8.7 Hz), 7.62 (2H, d, J=8.7 Hz), 10.33 (1H, s);
MS (ESI) m/z: 514 (M+H)$^+$.

Example 317

Methyl (S)-{4-[4-(4-methoxybenzoylamino)phenyl]-2,3,9-trimethyl-6H-thieno[3,2-f][1,2,4]triazolo[4,3-a][1,4]diazepin-6-yl}acetate The title compound (135 mg) was obtained from the compound (200 mg) described in Starting Material Synthetic Example 4 by a treatment in the same manner as in Example 312 and using 4-methoxybenzoic acid (100 mg) instead of 3-(4-methoxyphenyl)propionic acid.
$^1$H-NMR (300 MHz, DMSO-d$_6$) δ: 1.65 (3H, s), 2.40 (3H, s), 2.59 (3H, s), 3.32-3.49 (2H, m), 3.65 (3H, s), 3.81 (3H, s), 4.45 (1H, t, J=6.9 Hz), 7.04 (2H, d, J=8.1 Hz), 7.38 (2H, d, J=8.1 Hz), 7.81 (2H, d, J=8.1 Hz), 7.94 (2H, d, J=8.1 Hz), 10.27 (1H, s);
MS (ESI) m/z: 530 (M+H)$^+$.

Example 318

Methyl (S)-{4-[4-(4-fluorobenzoylamino)phenyl]-2,3,9-trimethyl-6H-thieno[3,2-f][1,2,4]triazolo[4,3-a][1,4]diazepin-6-yl}acetate The title compound (350 mg) was obtained from the compound (200 mg) described in Starting Material Synthetic Example 4 by a treatment in the same manner as in Example 312 and using 4-fluorobenzoic acid (92 mg) instead of 3-(4-methoxyphenyl)propionic acid.
$^1$H-NMR (300 MHz, DMSO-d$_6$) δ: 1.65 (3H, s), 2.41 (3H, s), 2.59 (3H, s), 3.39 (1H, dd, J=16.8 Hz, 7.8 Hz), 3.47 (1H, dd, J=16.8 Hz, 6.9 Hz), 3.65 (3H, s), 4.45 (1H, t, J=7.5 Hz), 7.34 (2H, d, J=9.0 Hz), 7.38 (2H, dd, J=8.4 Hz, 8.4 Hz), 7.81 (2H, d, J=9.0 Hz), 8.02 (2H, d, J=8.4 Hz, 5.4 Hz), 10.44 (1H, s);
MS (ESI) m/z: 530 (M+H)$^+$.

Example 319

Methyl (S)-{2,3,9-trimethyl-4-[4-(3-phenylacryloylamino)phenyl]-6H-thieno[3,2-f][1,2,4]triazolo[4,3-a][1,4]diazepin-6-yl}acetate The title compound (450 mg) was obtained from the compound (700 mg) described in Starting Material Synthetic Example 4 by a treatment in the same manner as in Example 312 and using trans-cinnamic acid (400 mg) instead of 3-(4-methoxyphenyl)propionic acid.
$^1$H-NMR (300 MHz, DMSO-d$_6$) δ: 1.65 (3H, s), 2.40 (3H, s), 2.58 (3H, s), 3.38 (2H, dd, J=16.8 Hz, 8.4 Hz), 3.47 (2H, t, J=16.8 Hz, 6.9 Hz), 3.65 (3H, s), 4.45 (1H, t, J=7.2 Hz), 6.82 (1H, d, J=15.6 Hz), 7.38 (2H, d, J=8.4 Hz), 7.4-7.6 (5H, m), 7.58 (1H, d, J=15.6 Hz), 7.73 (2H, d, J=8.4 Hz), 10.42 (1H, s);
MS (ESI) m/z: 526 (M+H)$^+$.

Example 320

Methyl (S)-(4-{4-[methyl-(3-phenylacryloyl)amino]phenyl}-2,3,9-trimethyl-6H-thieno[3,2-f][1,2,4]triazolo[4,3-a][1,4]diazepin-6-yl)acetate The compound (1 g) described in Starting Material Synthetic Example 8 and trans-cinnamic acid (540 mg) were dissolved in methylene chloride (12 mL). 1-Ethyl-3-(3-dimethylaminopropyl)carbodiimide hydrochloride (WSC.HCl, 700 mg) was added, and the mixture was stirred at room temperature for 6 hr. After completion of the reaction, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (650 mg).

$^1$H-NMR (300 MHz, DMSO-$d_6$) δ: 1.66 (3H, s), 2.40 (3H, s), 2.59 (3H, s), 3.25 (3H, s), 3.41 (1H, dd, J=16.5 Hz, 7.8 Hz), 3.49 (1H, dd, J=16.5 Hz, 6.9 Hz), 3.65 (3H, s), 4.50 (1H, t, J=7.2 Hz), 6.38 (2H, d, J=15.3 Hz), 7.3-7.5 (10H, m);

MS (ESI) m/z: 540 (M+H)$^+$.

Example 321

Methyl (S)-(4-{4-[(5-bromopyridine-3-carbonyl)amino]phenyl}-2,3,9-trimethyl-6H-thieno[3,2-f][1,2,4]triazolo[4,3-a][1,4]diazepin-6-yl)acetate The title compound (420 mg) was obtained from the compound (400 mg) described in Starting Material Synthetic Example 4 by a treatment in the same manner as in Example 312 and using 5-bromonicotinic acid (265 mg) instead of 3-(4-methoxyphenyl)propionic acid.

$^1$H-NMR (300 MHz, DMSO-$d_6$) δ: 1.65 (3H, s), 2.41 (3H, s), 2.59 (3H, s), 3.40 (1H, m), 3.48 (1H, dd, J=16.5 Hz, 6.9 Hz), 3.65 (3H, s), 4.46 (1H, t, J=6.9 Hz), 7.42 (2H, d, J=8.4 Hz), 7.80 (2H, d, J=8.4 Hz), 8.52 (1H, d, J=1.5 Hz), 8.88 (1H, d, J=1.5 Hz), 9.04 (1H, s), 10.65 (1H, s)

MS (ESI) m/z: 579 (M+H)$^+$, 581 (M+2+H)$^+$.

Example 322

Methyl (S)-{2,3,9-trimethyl-4-[4-(3-pyridin-3-yl-acryloylamino)phenyl]-6H-thieno[3,2-f][1,2,4]triazolo[4,3-a][1,4]diazepin-6-yl}acetate The title compound (197 mg) was obtained from the compound (500 mg) described in Starting Material Synthetic Example 4 by a treatment in the same manner as in Example 312 and using 3-(3-pyridyl)acrylic acid (245 mg) instead of 3-(4-methoxyphenyl)propionic acid.

$^1$H-NMR (300 MHz, DMSO-$d_6$) δ: 1.66 (3H, s), 2.41 (3H, s), 2.58 (3H, s), 3.38 (1H, dd, J=16.5 Hz, 7.8 Hz), 3.47 (1H, dd, J=16.5 Hz, 6.9 Hz), 3.65 (3H, s), 4.45 (1H, t, J=7.2 Hz), 6.91 (1H, d, J=15.6 Hz), 7.38 (2H, d, J=8.7 Hz), 7.46 (1H, dd, J=8.1 Hz, 4.5 Hz), 7.62 (1H, d, J=15.6 Hz), 7.73 (2H, d, J=8.7 Hz), 8.01 (1H, d, J=8.1 Hz), 8.56 (1H, dd, J=4.5 Hz, 1.5 Hz), 8.79 (1H, d, J=1.5 Hz), 10.46 (1H, s)

MS (ESI) m/z: 527 (M+H)$^+$.

Example 323

Methyl (S)-{4-[4-(3-methyl-3-phenylureido)phenyl]-2,3,9-trimethyl-6H-thieno[3,2-f][1,2,4]triazolo[4,3-a][1,4]diazepin-6-yl}acetate The title compound (310 mg) was obtained from the compound (350 mg) described in Starting Material Synthetic Example 4 by a treatment in the same manner as in Example 308 and using N-methyl-N-phenylcarbamoyl chloride (195 mg) instead of 4-trifluoromethylbenzoylchloride.

$^1$H-NMR (300 MHz, DMSO-$d_6$) δ: 1.64 (3H, s), 2.40 (3H, s), 2.58 (3H, s), 3.25 (3H, s), 3.36 (1H, dd, J=16.8 Hz, 7.5 Hz), 3.46 (1H, dd, J=16.8 Hz, 7.5 Hz), 3.64 (3H, s), 4.42 (1H, t, J=7.5 Hz), 7.2-7.4 (7H, m), 7.48 (2H, d, J=8.7 Hz), 8.37 (1H, s)

MS (ESI) m/z: 529 (M+H)$^+$.

Example 324

Methyl (S)-{4-[4-(3-benzylureido)phenyl]-2,3,9-trimethyl-6H-thieno[3,2-f][1,2,4]triazolo[4,3-a][1,4]diazepin-6-yl}acetate The compound (200 mg) described in Starting Material Synthetic Example 4 was dissolved in dimethylformamide (4.2 mL). Pyridine (204 μL) and ethyl chloroformate (240 μL) were successively added under ice-cooling, and the mixture was stirred at 70° C. for 1 hr. After cooling, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) to give a compound (420 mg). The obtained compound (420 mg) was dissolved in dioxane (3 mL). 1,8-Diazabicyclo[5.4.0]-7-undecene (DBU, 150 μL) and benzylamine (110 μL) were successively added, and the mixture was stirred at 100° C. for 11 hr. After cooling, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) to give the title compound (230 mg).

$^1$H-NMR (300 MHz, DMSO-$d_6$) δ: 1.65 (3H, s), 2.40 (3H, s), 2.57 (3H, s), 3.36 (1H, dd, J=16.5 Hz, 7.5 Hz), 3.45 (1H, dd, J=16.5 Hz, 6.9 Hz), 4.27 (2H, d, J=5.7 Hz), 4.42 (1H, t, J=7.2 Hz), 6.67 (1H, t, J=5.7 Hz), 7.2-7.3 (7H, m), 7.42 (2H, d, J=8.7 Hz), 8.84 (1H, s)

MS (ESI) m/z: 529 (M+H)$^+$.

Example 325

Methyl (S)-{4-[4-(4-trifluoromethylbenzenesulfonylamino)phenyl]-2,3,9-trimethyl-6H-thieno[3,2-f][1,2,4]triazolo[4,3-a][1,4]diazepin-6-yl}acetate The title compound (156 mg) was obtained from the compound (200 mg) described in Starting Material Synthetic Example 4 by a treatment in the same manner as in Example 308 and using 4-(trifluoromethyl)benzenesulfonyl chloride (160 mg) instead of 4-trifluoromethylbenzoylchloride.

$^1$H-NMR (300 MHz, DMSO-$d_6$) δ: 1.47 (3H, s), 2.36 (3H, s), 2.54 (3H, s), 3.3-3.5 (2H, m), 3.63 (3H, s), 4.40 (1H, t, J=7.2 Hz), 7.10 (2H, d, J=8.7 Hz), 7.25 (2H, d, J=8.7 Hz), 7.91 (4H, s)

MS (ESI) m/z: 504 (M+H)$^+$.

Example 326

Methyl (S)-{4-[4-(2,3-dichlorothiophene-5-sulfonylamino)phenyl]-2,3,9-trimethyl-6H-thieno[3,2-f][1,2,4]triazolo[4,3-a][1,4]diazepin-6-yl}acetate The title compound (253 mg) was obtained from the compound (340 mg) described in Starting Material Synthetic Example 4 by a treatment in the same manner as in Example 308 and using 2,3-dichlorothiophene-5-sulfonylchloride (281 mg) instead of 4-trifluoromethylbenzoylchloride.
$^1$H-NMR (300 MHz, DMSO-$d_6$) δ: 1.54 (3H, s), 2.38 (3H, s), 2.56 (3H, s), 3.35 (2H, m), 3.64 (3H, s), 4.43 (1H, t, J=7.2 Hz), 7.17 (2H, d, J=8.4 Hz), 7.34 (2H, d, J=8.4 Hz), 7.65 (1H, s), 10.94 (1H, s)
MS (ESI) m/z: 610 (M+H)$^+$.

Example 327

Methyl (S)-{4-[4-(4-chlorobenzenesulfonylamino)phenyl]-2,3,9-trimethyl-6H-thieno[3,2-f][1,2,4]triazolo[4,3-a][1,4]diazepin-6-yl}acetate The title compound (28 mg) was obtained from the compound (50 mg) described in Starting Material Synthetic Example 4 by a treatment in the same manner as in Example 308 and using 4-chlorobenzenesulfonylchloride (32 mg) instead of 4-trifluoromethylbenzoylchloride.
$^1$H-NMR (300 MHz, DMSO-$d_6$) δ: 1.50 (3H, s), 2.37 (3H, s), 2.55 (3H, s), 3.3-3.5 (2H, m), 3.63 (3H, s), 4.40 (1H, t, J=7.2 Hz), 7.08 (2H, d, J=8.4 Hz), 7.25 (2H, d, J=8.4 Hz), 7.57 (2H, d, J=8.4 Hz), 7.70 (2H, d, J=8.4 Hz), 10.59 (1H, s);
MS (ESI) m/z: 517 (M+H)$^+$.

Example 328

Methyl (S)-{4-[4-(4-fluorobenzenesulfonylamino)phenyl]-2,3,9-trimethyl-6H-thieno[3,2-f][1,2,4]triazolo[4,3-a][1,4]diazepin-6-yl}acetate The title compound (22 mg) was obtained from the compound (50 mg) described in Starting Material Synthetic Example 4 by a treatment in the same manner as in Example 308 and using 4-fluorobenzenesulfonylchloride (32 mg) instead of 4-trifluoromethylbenzoylchloride.
$^1$H-NMR (300 MHz, DMSO-$d_6$) δ: 1.51 (3H, s), 2.37 (3H, s), 2.55 (3H, s), 3.3-3.5 (2H, m), 3.63 (3H, s), 4.40 (1H, t, J=7.2 Hz), 7.09 (2H, d, J=8.7 Hz), 7.25 (2H, d, J=8.7 Hz), 7.34 (2H, dd, J=8.7 Hz, 8.7 Hz), 7.7-7.9 (2H, m), 10.54 (1H, s);
MS (ESI) m/z: 554 (M+H)$^+$.

Example 329

Methyl (S)-{4-[4-(4-methoxybenzenesulfonylamino)phenyl]-2,3,9-trimethyl-6H-thieno[3,2-f][1,2,4]triazolo[4,3-a][1,4]diazepin-6-yl}acetate The title compound (160 mg) was obtained from the compound (200 mg) described in Starting Material Synthetic Example 4 by a treatment in the same manner as in Example 308 and using 4-methoxybenzenesulfonylchloride (135 mg) instead of 4-trifluoromethylbenzoylchloride.
$^1$H-NMR (300 MHz, DMSO-$d_6$) δ: 1.51 (3H, s), 2.37 (3H, s), 2.54 (3H, s), 3.3 (2H, m), 3.62 (3H, s), 3.74 (3H, s), 4.40 (1H, t, J=7.2 Hz), 6.99 (2H, d, J=8.7 Hz), 7.08 (2H, d, J=8.7 Hz), 7.23 (2H, d, J=8.7 Hz), 7.64 (2H, d, J=8.7 Hz), 10.38 (1H, s);
MS (ESI) m/z: 566 (M+H)$^+$.

Example 330

Methyl (S)-{4-[4-(2-thiophenesulfonylamino)phenyl]-2,3,9-trimethyl-6H-thieno[3,2-f][1,2,4]triazolo[4,3-a][1,4]diazepin-6-yl}acetate The title compound (140 mg) was obtained from the compound (200 mg) described in Starting Material Synthetic Example 4 by a treatment in the same manner as in Example 308 and using thiophene-2-sulfonylchloride (119 mg) instead of 4-trifluoromethylbenzoylchloride.
$^1$H-NMR (300 MHz, DMSO-$d_6$) δ: 1.54 (3H, s), 2.38 (3H, s), 2.56 (3H, s), 3.2-3.5 (2H, m), 3.63 (3H, s), 4.41 (1H, t, J=7.2 Hz), 7.06 (1H, dd, J=4.2 Hz, 4.2 Hz), 7.14 (2H, d, J=8.4 Hz), 7.28 (2H, d, J=8.4 Hz), 7.52 (1H, d, J=4.2 Hz), 7.85 (1H, d, J=4.2 Hz), 10.65 (1H, s);
MS (ESI) m/z: 542 (M+H)$^+$.

Example 331

Methyl (S)-{4-[4-(2-chlorothiophene-5-sulfonylamino)phenyl]-2,3,9-trimethyl-6H-thieno[3,2-f][1,2,4]triazolo[4,3-a][1,4]diazepin-6-yl}acetate The title compound (80 mg) was obtained from the compound (200 mg) described in Starting Material Synthetic Example 4 by a treatment in the same manner as in Example 308 and using 5-chlorothiophene-2-sulfonylchloride (141 mg) instead of 4-trifluoromethylbenzoylchloride.
$^1$H-NMR (300 MHz, DMSO-$d_6$) δ: 1.55 (3H, s), 2.38 (3H, s), 2.56 (3H, s), 3.40 (2H, m), 3.64 (3H, s), 4.43 (1H, t, J=7.2 Hz), 7.30 (6H, m), 10.78 (1H, s)
MS (ESI) m/z: 577 (M+H)$^+$.

Example 332

Ethyl (S)-{4-[4-(benzylethylamino)phenyl]-2,3,9-trimethyl-6H-thieno[3,2-f][1,2,4]triazolo[4,3-a][1,4]diazepin-6-yl}acetate The title compound (4.4 g) was obtained from the compound (4.3 g) described in Example 62 by a treatment in the same manner as in Example 139 and using N-ethylbenzylamine (2.1 mL) instead of 4-fluoroaniline.
$^1$H-NMR (400 MHz, DMSO-$d_6$) δ: 1.12 (3H, t, J=7.0 Hz), 1.19-1.22 (3H, m), 1.73 (3H, s), 2.41 (3H, s), 2.57 (3H, s), 3.33-3.36 (2H, m), 3.43-3.52 (2H, m), 4.08-4.16 (2H, m), 4.38 (1H, t, J=7.2 Hz), 4.57 (2H, s), 6.65 (2H, d, J=8.8 Hz), 7.17-7.22 (5H, m), 7.27-7.31 (2H, m)
MS (ESI) m/z: 528 (M+H)$^+$.

Example 333

Methyl (S)-{4-(2'-methoxybiphenyl-4-yl)-2,3,9-trimethyl-6H-thieno[3,2-f][1,2,4]triazolo[4,3-a][1,4]diazepin-6-yl}acetate The title compound (448 mg) was obtained from the compound (415 mg) described in Example 1 by a treatment in the same manner as in Example 2 and using 2-methoxyphenylboronic acid (228 mg) instead of 4-methylthiophenylboronic acid.

¹H-NMR (270 MHz, DMSO-d₆) δ: 1.72 (3H, s), 2.44 (3H, s), 2.62 (3H, s), 3.3-3.6 (2H, m), 3.68 (3H, s), 3.75 (3H, s), 4.51 (1H, t, J=7.8 Hz), 7.04 (1H, t, J=6.5 Hz), 7.05 (1H, d, J=7.6 Hz), 7.2-7.6 (6H, m)
MS (ESI) m/z: 487 (M+H)⁺.

Example 334

Methyl (S)-{4-(4'-acetylamino-3'-cyanobiphenyl-4-yl)-2,3,9-trimethyl-6H-thieno[3,2-f][1,2,4]triazolo[4,3-a][1,4]diazepin-6-yl}acetate The title compound (422 mg) was obtained the intermediate of methyl (S)-{4-(4'-amino-3'-cyanobiphenyl-4-yl)-2,3,9-trimethyl-6H-thieno[3,2-f][1,2,4]triazolo[4,3-a][1,4]diazepin-6-yl}acetate (2 g) by a treatment in the same manner as in Example 59 and using acetic anhydride (1.1 mL) instead of isonicotinoylchloride hydrochloride.
¹H-NMR (400 MHz, DMSO-d₆) δ: 1.67 (3H, s), 2.13 (3H, s), 2.43 (3H, s), 2.62 (3H, s), 3.44 (1H, dd, J=16.4, 7.2 Hz), 3.50 (1H, dd, J=16.4 7.2 Hz), 3.68 (3H, s), 4.52 (1H, t, J=7.2 Hz), 7.51 (2H, d, J=8.4 Hz), 7.73 (1H, d, J=8.8 Hz), 7.80 (2H, d, J=8.4 Hz), 8.02 (1H, dd, J=8.8, 2.4 Hz), 8.15 (1H, d, J=2.4 Hz), 10.2 (1H, s),
MS (ESI) m/z: 539 (M+H)⁺.

Example 335

4-(4-benzylaminophenyl)-2,3,9-trimethyl-6H-thieno[3,2-f][1,2,4]triazolo[4,3-a][1,4]diazepine The title compound (8.3 g) was obtained from starting material A (17.1 g) by a treatment in the same manner as in Example 272 and using benzylamine (8.2 mL) instead of 4-fluoro-N-methylaniline.
1H-NMR (400 MHz, DMSO-d₆) δ: 1.70 (3H, s), 2.39 (3H, s), 2.56 (3H, s), 4.00 (1H, d, J=12.8 Hz), 4.29 (2H, d, J=6.0 Hz), 5.09 (1H, d, J=12.8 Hz), 6.56 (2H, d, J=8.8 Hz), 6.75 (1H, d, J=6.0 Hz), 7.3-7.4 (7H, m)
MS (ESI) m/z: 414 (M+H)+.

Example 336

4-[4-(4-fluorobenzylamino)phenyl]-2,3,9-trimethyl-6H-thieno[3,2-f][1,2,4]triazolo[4,3-a][1,4]diazepine The title compound (87 mg) was obtained from starting material A (500 mg) by a treatment in the same manner as in Example 272 and using 4-fluorobenzylamine (0.2 mL) instead of 4-fluoro-N-methylaniline.
1H-NMR (300 MHz, CDCl₃) δ 1.76 (s, 3H), 2.40 (s, 3H), 2.65 (s, 3H), 4.04 (d, 1H, J=9.6 Hz), 4.28-4.35 (m, 3H), 5.39 (d, 1H, J=9.6 Hz), 6.55 (d, 2H, J=6.9 Hz), 6.99-7.03 (m, 2H), 7.26-7.35 (m, 4H)
MS (ESI) m/z: 432 (M+H)+.

Example 337

4-[4-(3,4-difluorobenzylamino)phenyl]-2,3,9-trimethyl-6H-thieno[3,2-f][1,2,4]triazolo[4,3-a][1,4]diazepine The title compound (107 mg) was obtained from starting material A (500 mg) by a treatment in the same manner as in Example 272 and using 3,4-difluorobenzylamine (0.2 mL) instead of 4-fluoro-N-methylaniline.

1H-NMR (300 MHz, CDCl₃) δ 1.75 (s, 3H), 2.40 (s, 3H), 2.65 (s, 3H), 4.04 (d, 1H, J=9.6 Hz), 4.33 (d, 2H, J=4.2 Hz), 4.43 (t, 1H, J=4.2 Hz), 5.39 (d, 1H, J=9.6 Hz), 6.53 (d, 2H, J=6.6 Hz), 7.05-7.17 (m, 3H), 7.32 (d, 2H, J=6.6 Hz)
MS (ESI) m/z: 450 (M+H)+.

Example 338

4-[4-(3,5-difluorobenzylamino)phenyl]-2,3,9-trimethyl-6H-thieno[3,2-f][1,2,4]triazolo[4,3-a][1,4]diazepine The title compound (82 mg) was obtained from starting material A (500 mg) by a treatment in the same manner as in Example 272 and using 3,5-difluorobenzylamine (0.2 mL) instead of 4-fluoro-N-methylaniline.
1H-NMR (300 MHz, CDCl₃) δ 1.75 (s, 3H), 2.40 (s, 3H), 2.65 (s, 3H), 4.04 (d, 1H, J=9.6 Hz), 4.35-4.37 (m, 2H), 4.43-4.46 (m, 1H), 5.40 (d, 1H, J=9.6 Hz), 6.52 (d, 2H, J=6.6 Hz), 6.65-6.72 (m, 1H), 6.82-6.89 (m, 2H), 7.33 (d, 2H, J=6.6 Hz)
MS (ESI) m/z: 450 (M+H)+.

Example 339

4-[4-(2,5-difluorobenzylamino)phenyl]-2,3,9-trimethyl-6H-thieno[3,2-f][1,2,4]triazolo[4,3-a][1,4]diazepine The title compound (113 mg) was obtained from starting material A (500 mg) by a treatment in the same manner as in Example 272 and using 2,5-difluorobenzylamine (0.2 mL) instead of 4-fluoro-N-methylaniline.
1H-NMR (300 MHz, CDCl₃) δ 1.75 (s, 3H), 2.40 (s, 3H), 2.65 (s, 3H), 4.04 (d, 1H, J=9.6 Hz), 4.41 (m, 3H), 5.40 (d, 1H, J=9.6 Hz), 6.55 (d, 2H, J=6.3 Hz), 6.88-7.04 (m, 3H), 7.33 (d, 2H, J=6.3 Hz)
MS (ESI) m/z: 450 (M+H)+.

Example 340

4-{4-[(tetrahydrofuran-3-ylmethyl)amino]phenyl}-2,3,9-trimethyl-6H-thieno[3,2-f][1,2,4]triazolo[4,3-a][1,4]diazepine To a mixture of starting material A (500 mg), palladium acetate (33 mg), 2-(dicyclohexylphosphino)biphenyl (102 mg), (tetrahydrofuran-3-yl)methylamine hydrochloride (301 mg) and tripotassium phosphate (743 mg) were successively added dimethoxyethane (3 mL) and triethylamine (222 mg), and the mixture was heated under reflux for 8 hr. After cooling, water was added, and the mixture was extracted with chloroform. The organic layer was washed with saturated brine, dried over anhydrous sodium sulfate, and the solvent was evaporated. The residue was purified by column chromatography (chloroform:methanol=100:1) to give the title compound (130 mg).
1H-NMR (400 MHz, DMSO-d₆) δ: 1.5-1.6 (1H, m), 1.71 (3H, s), 1.9-2.1 (1H, m), 2.40 (3H, s), 2.4-2.5 (1H, m), 2.60 (3H, s), 3.01 (2H, t, J=6.4 Hz), 3.4-3.5 (1H, m), 3.6-3.7 (1H, m), 3.7-3.8 (2H, m), 4.01 (1H, d, J=12.4 Hz), 5.10 (1H, d, J=12.4 Hz), 6.24 (1H, t, J=5.6 Hz), 6.55 (2H, d, J=8.0 Hz), 7.20 (2H, d, J=8.0 Hz)
MS (ESI) m/z: 408 (M+H)+.

Example 341

4-{4-[(tetrahydropyran-4-ylmethyl)amino]phenyl}-2,3,9-trimethyl-6H-thieno[3,2-f][1,2,4]triazolo[4,3-a][1,4]diazepine The title compound (317 mg) was obtained from starting material A (500 mg) by a treatment in the same manner as in Example 340 and using (tetrahydropyran-4-yl)methylamine (252 mg) instead of (tetrahydrofuran-3-yl)methylamine hydrochloride.

1H-NMR (400 MHz, DMSO-$d_6$) δ: 1.1-1.3 (2H, m), 1.6-1.7 (2H, m), 1.72 (3H, s), 1.8-1.9 (1H, m), 2.40 (3H, s), 2.57 (3H, s), 2.93 (2H, t, J=6.0 Hz), 3.2-3.3 (2H, m), 3.8-3.9 (2H, m), 4.0-4.1 (1H, m), 5.10 (1H, d, J=12.8 Hz), 6.20 (1H, t, J=5.6 Hz), 6.54 (2H, d, J=8.0 Hz), 7.20 (2H, d, J=8.0 Hz)

MS (ESI) m/z: 422 (M+H)+.

Example 342

Methyl (S)-[4-{(3-cyanopyridin-5-yl)-phenyl}-3,9-dimethyl-6H-thieno[3,2-f][1,2,4]triazolo[4,3-a][1,4]diazepin-6-yl]acetate The compound (37.36 g) described in Example 1 and concentrated sulfuric acid (48.3 mL) were dissolved in acetic acid (32 mL). Acetic anhydride (189 mL) and manganese acetate (III) dihydrate (50.00 g) were successively added, and the mixture was stirred at room temperature for 1 hr. After completion of the reaction, water was added, and the mixture was extracted with ethyl acetate, and washed with 3N aqueous sodium hydroxide solution until the aqueous layer became pH 8. The organic layer was washed with saturated brine, dried over anhydrous sodium sulfate, and the solvent was evaporated to give a brown oil (about 70 g). The obtained brown oil (about 70 g) was dissolved in methanol (300 mL). Sodium methoxide (81 g) was added, and the mixture was stirred at room temperature for 2 hr. After completion of the reaction, methanol was evaporated under reduced pressure. 1N hydrochloric acid (500 mL) was added, and the mixture was extracted with ethyl acetate. The organic layer was washed with saturated brine, dried over anhydrous sodium sulfate, and the solvent was evaporated. The residue was purified by column chromatography (chloroform:methanol=97:3) to give methyl (S)-{4-(4-chlorophenyl)-2-hydroxymethyl-3,9-dimethyl-6H-thieno[3,2-f][1,2,4]triazolo[4,3-a][1,4]diazepin-6-yl}acetate (19.85 g) and methyl (S)-{4-(4-chlorophenyl)-2-formyl-3,9-dimethyl-6H-thieno[3,2-f][1,2,4]triazolo[4,3-a][1,4]diazepin-6-yl}acetate (4.82 g). The obtained methyl (S)-{4-(4-chlorophenyl)-2-formyl-3,9-dimethyl-6H-thieno[3,2-f][1,2,4]triazolo[4,3-a][1,4]diazepin-6-yl}acetate (2.8 g) was dissolved in acetonitrile (20 mL), and aqueous sodium dihydrogen phosphate solution (640 mg/8 ml) was added. To the reaction mixture were successively added 35% hydrogen peroxide solution (3.2 mL) and aqueous sodium chlorite solution (1 g/2.8 ml) at 10° C., and the mixture was stirred for 1 hr on a water bath. After completion of the reaction, water was added, and the mixture was worked up with sodium sulfite. The aqueous layer was acidified and extracted with ethyl acetate. The organic layer was washed with saturated brine, dried over anhydrous sodium sulfate, and the solvent was evaporated to give (S)-4-(4-chlorophenyl)-6-methoxycarbonylmethyl-3,9-dimethyl-6H-thieno[3,2-f][1,2,4]triazolo[4,3-a][1,4]diazepin-2-carboxylic acid (3 g). The obtained (S)-4-(4-chlorophenyl)-6-methoxycarbonylmethyl-3,9-dimethyl-6H-thieno[3,2-f][1,2,4]triazolo[4,3-a][1,4]diazepin-2-carboxylic acid (3.6 g) and copper (357 mg) were reacted at 150° C. for 15 min in quinoline (14 mL). After completion of the reaction, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) and recrystallized from hexane-ethyl acetate to give methyl (S)-{4-(4-chlorophenyl)-3,9-dimethyl-6H-thieno[3,2-f][1,2,4]triazolo[4,3-a][1,4]diazepin-6-yl}acetate (821 mg). A mixture of the obtained methyl (S)-{4-(4-chlorophenyl)-3,9-dimethyl-6H-thieno[3,2-f][1,2,4]triazolo[4,3-a][1,4]diazepin-6-yl}acetate (800 mg), dichlorobis(tricyclohexylphosphine)palladium (148 mg), bisneopentylglycolatodiboron (542 mg) and potassium acetate (294 mg) was stirred at 100° C. for 5 hr in dioxane (7 mL). After cooling, the mixture was partitioned by adding water and ethyl acetate. The organic layer was washed with saturated brine, and the solvent was evaporated. The residue was purified by column chromatography (chloroform:methanol=100:1) to give a boronic acid derivative (180 mg). To a mixture of the obtained boronic acid derivative (164 mg), dichlorobis(triphenylphosphine)palladium (II) (15 mg) and 5-bromonicotinonitrile (137 mg) were added 2 M aqueous sodium carbonate solution (1 mL) and tetrahydrofuran (1.6 mL), and the mixture was stirred at 100° C. for 4 hr. After cooling, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) and recrystallized from hexane-ethyl acetate to give the title compound (105 mg).

1H-NMR (400 MHz, DMSO-$d_6$) δ: 1.78 (3H, s), 2.65 (3H, s), 3.42-3.55 (2H, m), 3.69 (3H, s), 4.54 (1H, t, J=7.0 Hz), 7.45 (1H, s), 7.55 (2H, d, J=8.0 Hz), 7.91 (2H, d, J=8.0 Hz), 8.71 (1H, s), 9.03 (1H, s), 9.24 (1H, s);

MS (ESI) m/z: 469 (M+H)+.

Example 343

Methyl (S)-{4-(3'-cyanobiphenyl-4-yl)-3,9-dimethyl-6H-thieno[3,2-f][1,2,4]triazolo[4,3-a][1,4]diazepin-6-yl}acetate To a mixture of methyl (S)-{4-(4-chlorophenyl)-2-formyl-3,9-dimethyl-6H-thieno[3,2-f][1,2,4]triazolo[4,3-a][1,4]diazepin-6-yl}acetate (429 mg) synthesized in Example 342 as an intermediate, palladium acetate (11 mg), 2-(di-tert-butylphosphino)biphenyl (30 mg), potassium fluoride (349 mg) and 3-cyanophenylboronic acid (441 mg) was added tetrahydrofuran (4 mL), and the mixture was heated under reflux for 6 hr. After cooling, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) to give methyl (S)-{4-(3'-cyanobiphenyl-4-yl)-2-formyl-3,9-dimethyl-6H-thieno[3,2-f][1,2,4]triazolo[4,3-a][1,4]diazepin-6-yl}acetate (588 mg). The obtained methyl (S)-{4-(3'-cyanobiphenyl-4-yl)-2-formyl-3,9-dimethyl-6H-thieno[3,2-f][1,2,4]triazolo[4,3-a][1,4]diazepin-6-yl}acetate (564 mg) was dissolved in acetonitrile (4 mL), and aqueous sodium dihydrogen phosphate solution (128 mg/1.6 mL) was added. To the reaction mixture were successively added 35% hydrogen peroxide solution (0.5 mL) and aqueous sodium chlorite solution (174 mg/0.6 mL) at 0° C., and the mixture was stirred for 1 hr on a water bath. After completion of the reaction, water was added, and the mixture was worked up with sodium sulfite. The aqueous layer was acidified and extracted with ethyl acetate. The organic layer was washed with saturated brine, dried over anhydrous sodium sulfate, and the solvent was evaporated to give (S)-4-(3'-cyanobiphenyl-4-yl)-6-methoxycarbonylmethyl-3,9-dimethyl-6H-thieno[3,2-f][1,2,4]triazolo[4,3-a][1,4]diazepin-2-carboxylic acid (500 mg). The obtained (S)-4-(3'-cyanobiphenyl-4-yl)-6-methoxycarbonylmethyl-3,9-dimethyl-6H-thieno[3,2-f][1,2,4]triazolo[4,3-a][1,4]diazepin-2-carboxylic acid (487 mg) and copper (50 mg) were reacted at 150° C. for 30 min in quinoline. After completion of the reaction, water was added, and the mixture was extracted with ethyl acetate. The organic layer was washed with saturated brine, dried over anhydrous sodium sulfate, and the solvent was evaporated. The residue was purified by column chromatography (chloroform:methanol=100:1) and recrystallized from ethyl acetate to give the title compound (217 mg).

$^1$H-NMR (400 MHz, DMSO-d$_6$) δ: 1.79 (3H, s), 2.65 (3H, s), 3.46-3.51 (2H, m), 3.69 (3H, s), 4.53 (1H, t, J=7.2 Hz), 7.45 (1H, s), 7.52 (2H, d, J=8.4 Hz), 7.69 (1H, t, J=8.0 Hz), 7.82-7.87 (3H, m), 8.06-8.08 (1H, m), 8.21 (1H, s);

MS (ESI) m/z: 468 (M+H)$^+$.

Example 344 methyl (S)-{2-chloro-4-(3'-cyanobiphenyl-4-yl)-3,9-dimethyl-6H-thieno[3,2-f][1,2,4]triazolo[4,3-a][1,4]diazepin-6-yl}acetate The compound (103 mg) described in Example 343 was dissolved in acetic acid (1 mL). Sulfuryl chloride (2.2 mL) was added, and the mixture was stirred at 50° C. for 2 days. After completion of the reaction, water was added, and the mixture was extracted with ethyl acetate. The organic layer was washed with saturated brine, dried over anhydrous sodium sulfate, and the solvent was evaporated. The residue was purified by column chromatography (chloroform:methanol 100:1) to give the title compound (17 mg).

$^1$H-NMR (400 MHz, DMSO-d$_6$) δ: 1.73 (3H, s), 2.64 (3H, s), 3.46-3.50 (2H, m), 3.69 (3H, s), 4.65 (1H, t, J=7.4 Hz), 7.57 (2H, d, J=8.0 Hz), 7.69 (1H, t, J=7.8 Hz), 7.83-7.87 (3H, m), 8.07 (1H, d, J=8.0 Hz), 8.21 (1H, s);

MS (ESI) m/z: 502 (M+H)+.

Example 345

Methyl (S)-{2-bromo-4-(3'-cyanobiphenyl-4-yl)-3,9-dimethyl-6H-thieno[3,2-f][1,2,4]triazolo[4,3-a][1,4]diazepin-6-yl}acetate The compound (700 mg) described in Example 343 was dissolved in chloroform (3 mL). Acetic acid (3 mL) and N-bromosuccinic acid imide (267 mg) were successively added, and the mixture was stirred at room temperature for 1 day. After completion of the reaction, water was added, and the mixture was extracted with ethyl acetate. The organic layer was washed with saturated brine, dried over anhydrous sodium sulfate, and the solvent was evaporated. The residue was recrystallized from ethyl acetate to give the title compound (211 mg).

$^1$H-NMR (400 MHz, DMSO-d$_6$) δ: 1.72 (3H, s), 2.64 (3H, s), 3.42-3.54 (2H, m), 3.69 (3H, s), 4.63 (1H, t, J=7.2 Hz), 7.56 (2H, d, J=8.0 Hz), 7.69 (1H, t, J=7.8 Hz), 7.83-7.87 (3H, m), 8.07 (1H, d, J=8.0 Hz), 8.21 (1H, s);

MS (ESI) m/z: 546 (M+H)$^+$.

Example 346

6-{4-(3'-cyanobiphenyl-4-yl)}-8,9-dihydro-1-methyl-4H,7H-cyclopenta[4,5]thieno[3,2-f][1,2,4]triazolo[4,3-a][1,4]diazepine 4-Chlorophenylcyanomethylketone (36 g), morpholine (18 g) and cyclopentanone (17 g) were dissolved in ethanol (200 mL). The mixture was suspended in sulfur (6 g), and heated under reflux for 3 hr. After completion of the reaction, the solvent was evaporated under reduced pressure, and the residue was dissolved in chloroform (500 mL). The mixture was washed with water and dried over anhydrous magnesium sulfate. Chloroacetyl chloride (23 g) was added dropwise, and the mixture was stirred at room temperature for 2 hr. After completion of the reaction, the mixture was washed with aqueous sodium hydrogencarbonate, dried over anhydrous magnesium sulfate, and the solvent was evaporated under reduced pressure to give a residue (32 g). The residue was dissolved in tetrahydrofuran (400 mL). Sodium iodide (15 g) was suspended in the mixture, and heated under reflux for 3 hr. The reaction mixture was cooled to −50° C. in dry ice-acetone. Liquid ammonia (about 50 mL) was added, and the mixture was stirred at room temperature for 3 hr. After completion of the reaction, the solvent was evaporated under reduced pressure. The residue was dissolved in chloroform (400 mL), dried over anhydrous magnesium sulfate, and the solvent was evaporated under reduced pressure. To the residue were added isopropanol (400 mL), chloroform (40 mL) and acetic acid (7 g), and the mixture was heated under reflux. The solvent was evaporated under reduced pressure and the residue was dissolved in chloroform (500 mL). The mixture was washed with aqueous sodium hydrogencarbonate, dried over anhydrous magnesium sulfate, and the solvent was evaporated under reduced pressure to give a residue. The obtained residue (6 g) was dissolved in chloroform (650 mL). Diphosphorus pentasulfide (9 g) was added and the mixture was heated under reflux for 4 hr. After completion of the reaction, the mixture was neutralized with aqueous sodium hydrogencarbonate, dried over anhydrous magnesium sulfate, and the solvent was evaporated under reduced pressure. The residue was suspended in methanol (200 mL). 100% Hydrazine-hydrate (3 g) was added, and the mixture was stirred at room temperature for 1 hr. The solvent was half evaporated under reduced pressure, and the precipitated crystals were collected by filtration (5 g). The residue was suspended in toluene. Triethyl orthoacetate was added, and the mixture was stirred with heating. The solvent was evaporated under reduced pressure. The residue was purified by column chromatography (ethyl acetate:methanol) and recrystallized from ethyl acetate to give 6-(4-chlorophenyl)-8,9-dihydro-1-methyl-4H,7H-cyclopenta[4,5]thieno[3,2-f][1,2,4]triazolo[4,3-a][1,4]diazepine (4 g). To a mixture of the obtained 6-(4-chlorophenyl)-8,9-dihydro-1-methyl-4H,7H-cyclopenta[4,5]thieno[3,2-f][1,2,4]triazolo[4,3-a][1,4]diazepine (355 mg), palladium acetate (11 mg), 2-(di-tert-butylphosphino)biphenyl (30 mg), potassium fluoride (349 mg) and 3-cyanophenylboronic acid (441 mg) was added tetrahydrofuran (5 mL), and the mixture was heated under reflux for 9 hr. After completion of the reaction, water was added and the mixture was filtered through celite. Saturated aqueous sodium hydrogencarbonate was added and the mixture was extracted with ethyl acetate. The organic layer was washed with saturated brine, dried over anhydrous sodium sulfate, and the solvent was evaporated. The residue was purified by column chromatography (chloroform:methanol=100:1) to give the title compound (268 mg).

$^1$H-NMR (400 MHz, DMSO-d$_6$) δ: 2.12-2.14 (4H, m), 2.64 (3H, s), 2.93-2.98 (2H, m), 4.26 (1H, d, J=11.4 Hz), 5.30 (1H, d, J=11.4 Hz), 7.61 (2H, d, J=8.0 Hz), 7.69 (1H, t, J=7.8 Hz), 7.85 (3H, m), 8.10 (1H, d, J=8.0 Hz), 8.24 (1H, s);

MS (ESI) m/z: 422 (M+H)$^+$.

Example 347

Methyl (S)-{4-(3'-cyanobiphenyl-4-yl)-2,3-dimethyl-9-hydroxymethyl-6H-thieno[3,2-f][1,2,4]triazolo[4,3-a][1,4]diazepin-6-yl}acetate To a mixture of the compound (1.4 g) described in Example 8 and lead tetraacetate (4 g) was added acetic acid (13 mL), and the mixture was heated under reflux for 7 hr. After cooling, ethyl acetate and water were added, and the insoluble material was filtrated. The filtrate was partitioned. The ethyl acetate layer was washed with saturated aqueous sodium hydrogencarbonate, and the solvent was evaporated. The residue was purified by column chromatography (methylene chloride:methanol=40:1) to give a compound (1.1 g). To a mixture of the obtained compound (539 mg) and potassium carbonate (138 mg) was added methanol (7 mL), and the mixture was stirred at room temperature. The solvent was evaporated, and the residue was purified by column chromatography (methylene chloride:methanol=40:1) to give a compound (1.1 g).

$^1$H-NMR (400 MHz, CDCl$_3$) δ: 1.72 (3H, s), 2.43 (3H, s), 3.6-3.7 (2H, m), 3.79 (3H, s), 4.69 (1H, t, J=6.5 Hz), 4.86 (1H, d, J=13.9 Hz), 5.00 (1H, d, J=13.9 Hz), 7.5-7.6 (5H, m), 7.64 (1H, d, J=7.7 Hz), 7.79 (1H, d, J=7.7 Hz), 7.84 (1H, s)

MS (ESI) m/z: 498 (M+H)$^+$.

Example 348

Methyl (S)-{4-(3'-acetylbiphenyl-4-yl)-2,3-dimethyl-9-hydroxymethyl-6H-thieno[3,2-f][1,2,4]triazolo[4,3-a][1,4]diazepin-6-yl}acetate To a mixture of the compound (300 mg) described in Example 14 and lead tetraacetate (800 mg) was added acetic acid (2.4 mL) and the mixture was heated under reflux for 9 hr. After cooling, ethyl acetate and water were added. The ethyl acetate layer was washed with saturated aqueous sodium hydrogencarbonate and saturated brine, dried over sodium sulfate, and the solvent was evaporated. The obtained residue was dissolved in methanol (3 ml), potassium carbonate (85 mg) was added, and the mixture was stirred at room temperature for 30 min. Ethyl acetate and water were added. The ethyl acetate layer was washed with water and saturated brine, dried over sodium sulfate, and the solvent was evaporated. The residue was purified by silica gel chromatography to give the title compound (68 mg).

$^1$H-NMR (400 MHz, DMSO-d$_6$) δ: 1.69 (3H, s), 2.43 (3H, s), 2.66 (3H, s), 3.47 (1H, dd, J=16.8, 7.6 Hz), 3.54 (1H, dd, J=16.8, 7.0 Hz), 3.69 (3H, s), 4.56 (1H, t, J=7.3 Hz), 4.70 (1H, dd, J=13.3, 6.2 Hz), 4.83 (1H, dd, J=13.3, 5.2 Hz), 5.81 (1H, t, J=5.5 Hz), 7.52 (2H, d, J=8.3 Hz), 7.64 (1H, t, J=7.8 Hz), 7.81 (2H, d, J=8.3 Hz), 7.95-7.99 (2H, m), 8.20 (1H, s)

MS (ESI) m/z: 515 (M+H)$^+$.

Example 349

Methyl (S)-{4-(4'-methoxybiphenyl-4-yl)-2,3-dimethyl-9-hydroxymethyl-6H-thieno[3,2-f][1,2,4]triazolo[4,3-a][1,4]diazepin-6-yl}acetate The title compound (56 mg) was obtained by a treatment in the same manner as in Example 348 and using the compound (1145 mg) described in Example 5 instead of the compound described in Example 14.

$^1$H-NMR (400 MHz, CDCl$_3$) δ: 1.73 (3H, s), 2.42 (3H, s), 3.46 (1H, brs), 3.67 (2H, m), 3.79 (3H, s), 3.84 (3H, s), 4.67 (1H, t, J=8.5 Hz), 4.87 (1H, d, J=13.9 Hz), 5.01 (1H, d, J=13.9), 6.96 (2H, d, J=8.7 Hz), 7.51 (6H, m)

MS (ESI) m/z: 503 (M+H)$^+$.

The compounds obtained in the above-mentioned Examples are shown in the following.

TABLE 1

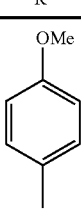

| Example | R$^3$ |
|---|---|
| 5 | OMe 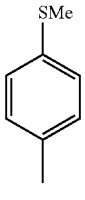 |
| 2 | SMe 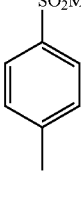 |
| 3 | SO$_2$Me 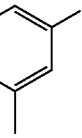 |
| 4 | OH |

TABLE 1-continued
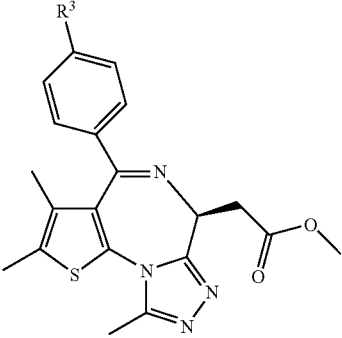
| Example | R³ |
|---|---|
| 333 | 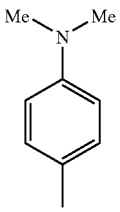 |
| 6 | 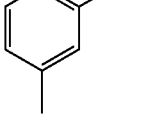 |
| 7 | 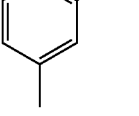 |
| 8 | 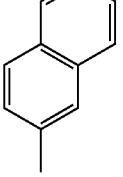 |
| 9 | 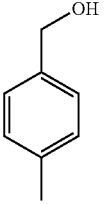 |
| 10 | 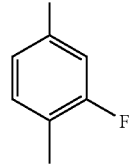 |
TABLE 1-continued
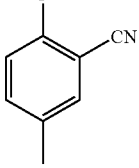
| Example | R³ |
|---|---|
| 11 | 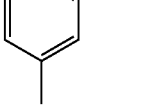 |
| 12 | 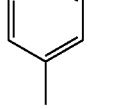 |
| 13 | 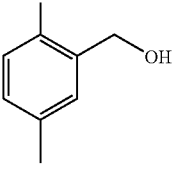 |
| 14 | 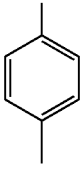 |
| 15 | 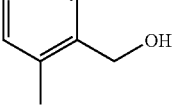 |
| 16 |  |
| 17 |  |

TABLE 1-continued
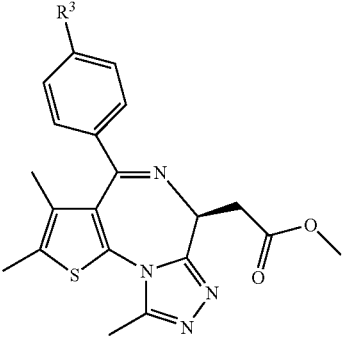
| Example | R³ |
|---|---|
| 18 | 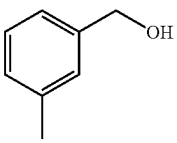 |
| 19 | 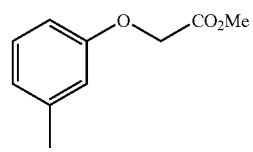 |
| 20 | 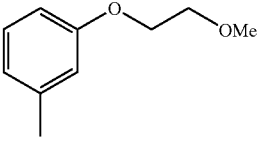 |
| 21 | 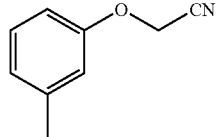 |
| 22 | 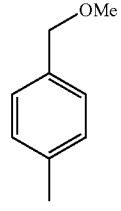 |
| 23 | 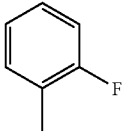 |
| 24 | 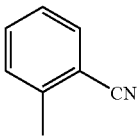 |
TABLE 1-continued
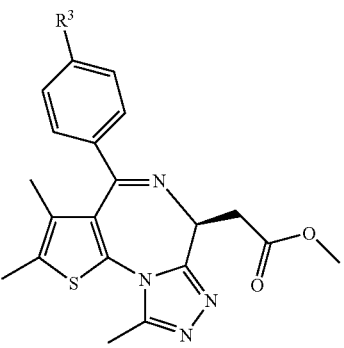
| Example | R³ |
|---|---|
| 25 | 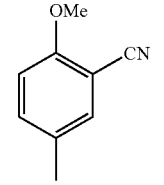 |
TABLE 2
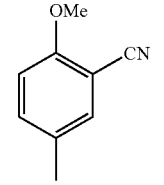
| Example | R³ |
|---|---|
| 26 | 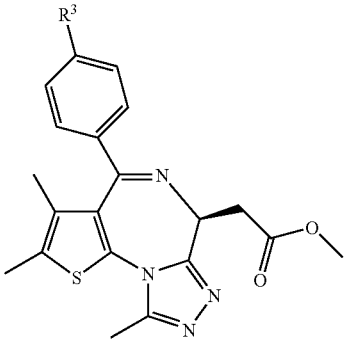 |
| 27 |  |
| 28 | 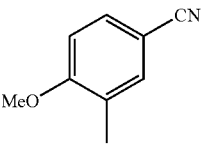 |

TABLE 2-continued
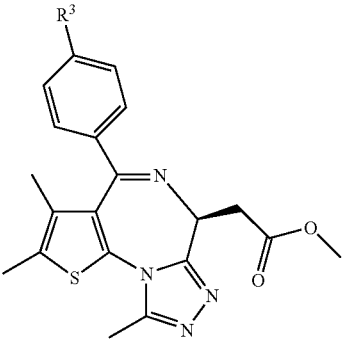
| Example | R³ |
|---|---|
| 29 | 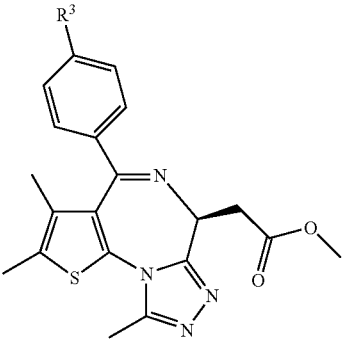 |
| 30 | 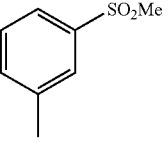 |
| 31 | 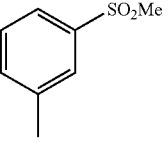 |
| 32 | 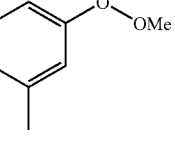 |
| 33 | 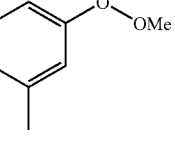 |
| 34 | 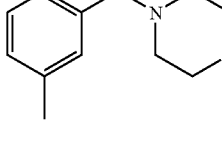 |
| 35 | 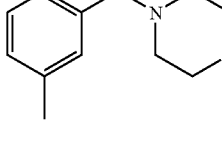 |
TABLE 2-continued
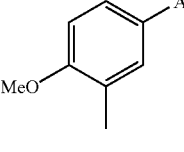
| Example | R³ |
|---|---|
| 36 | 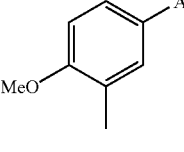 |
| 37 | 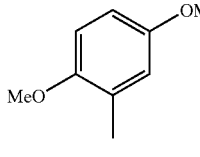 |
| 38 | 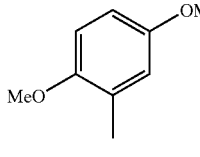 |
| 39 | 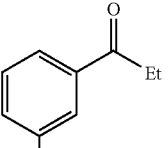 |
| 40 | 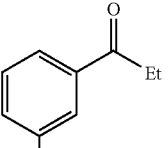 |
| 41 | 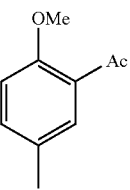 |
| 42 | 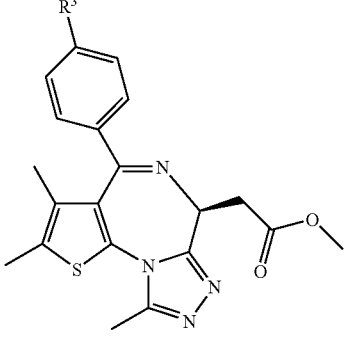 |

TABLE 2-continued

| Example | R³ |
|---|---|
| 43 | 3-(propanoylamino)phenyl |
| 44 | 3-(N,N-bis(methylsulfonyl)amino)phenyl |
| 45 | 3-((E)-3-hydroxy-3-methylbut-1-en-1-yl)phenyl |
| 46 | 3-(4-methylpiperazin-1-yl)phenyl |
| 47 | 3-(cyclopropylmethoxy)-5-methylphenyl (approx.) |
| 48 | 3-(morpholin-4-yl)phenyl |
| 49 | 3-fluorophenyl |
| 50 | 3-(allyloxy)phenyl |

TABLE 3

| Example | R³ |
|---|---|
| 51 | 3-(prop-2-yn-1-yloxy)-5-methylphenyl |
| 52 | 3-(3-hydroxypropoxy)-5-methylphenyl |

TABLE 3-continued

| Example | R³ |
|---------|-----|
| 53 | 3-(2-ethoxyethoxy)phenyl |
| 54 | 3-(2-morpholinoethoxy)phenyl |
| 55 | 3-(3-cyanopropoxy)phenyl |
| 56 | 2-hydroxy-5-methyl-3-cyanophenyl (2-hydroxy, 3-CN, with methyl) |
| 57 | 4-hydroxy-3-methyl-phenyl with CN |
| 58 | 3-(pyridin-4-ylmethoxy)phenyl |
| 59 | N-(2-cyano-4-methylphenyl)isonicotinamide |
| 60 | 3-(3-(dimethylamino)propoxy)phenyl |
| 61 | phenyl |
| 334 | 2-acetamido-5-methyl-phenyl with CN |

TABLE 4

| Example | R³ |
|---|---|
| 63 | 3-methylphenyl with Ac |
| 64 | 4-methylphenyl with OMe |
| 65 | 3-methylphenyl with CN |
| 66 | 3-methylphenyl with OMe |
| 67 | 4-methylphenyl with OH and OMe |
| 68 | 4-methylphenyl with NHSO₂Me and CN |

TABLE 4-continued

| Example | R³ |
|---|---|
| 69 | 4-methylphenyl with pyrimidin-2-yloxy and CN |
| 70 | 4-methylphenyl with pyridin-4-ylmethoxy and OMe |

TABLE 5

| Example | R³ |
|---|---|
| 71 | 5-methylthiophen-2-yl |
| 72 | 4-methylthiophen-3-yl |

TABLE 5-continued

| Example | R³ |
|---------|-----|
| 73 | 3-methylfuran-yl |
| 74 | 5-methyl-2-acetylthiophen-yl |
| 75 | (2-methylthiophen-3-yl)methanol |
| 76 | (5-methylthiophen-2-yl)methanol |
| 77 | 5-methyl-2-cyanothiophen-yl |
| 78 | 2-acetyl-3-methylthiophen-yl |
| 79 | 3-methyl-2-cyanothiophen-yl |
| 80 | 5-methyl-3-cyanopyridin-yl |

TABLE 5-continued

| Example | R³ |
|---------|-----|
| 81 | 2-methylthiazol-yl |
| 82 | 1,4-dimethyl-1H-pyrazol-yl |
| 83 | 5-bromo-2-methylthiazol-yl |
| 84 | 2-methyl-4-cyanopyridin-yl |
| 85 | 4-methyl-2-cyanopyridin-yl |
| 86 | 3-chloro-6-methylpyrazin-yl |
| 87 | 6-methyl-2-cyanopyridin-yl |

TABLE 5-continued

| Example | R³ |
|---|---|
| 88 | pyrazine-2-CN, 6-methyl |
| 89 | pyrimidine-4-CF₃, 2-methyl |
| 90 | pyrimidine-4-Cl, 6-methyl |
| 91 | pyrimidine-4-CN, 6-methyl |
| 92 | pyrimidine, 5-methyl |
| 93 | pyrimidine-2-SO₂Me, 4-methyl |
| 94 | pyrimidine-2-CN, 4-methyl |
| 95 | pyrazole-1H, 4-methyl |

TABLE 6

| Example | R³ |
|---|---|
| 96 | pyridine, 3-methyl |
| 97 | pyrimidine, 5-methyl |
| 98 | pyridine-3-CN, 6-methyl |
| 99 | pyridine-3-CONH₂, 5-methyl |
| 100 | pyridine-4-CONH₂, 2-methyl |
| 101 | pyridine-4-CN, 2-methyl |
| 102 | pyridine-2-NH₂, 6-methyl |

TABLE 6-continued
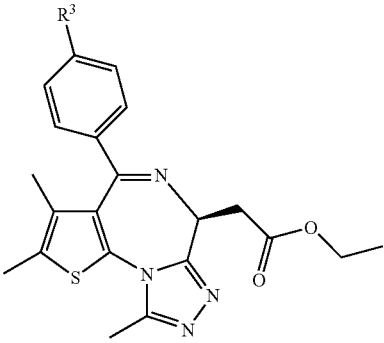
| Example | R³ |
|---|---|
| 103 | 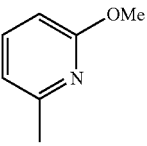 |
| 104 | 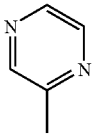 |
| 105 | 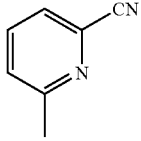 |
| 106 | 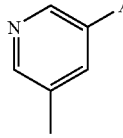 |
| 107 | 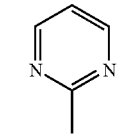 |
| 108 | 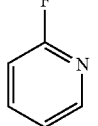 |
| 109 | 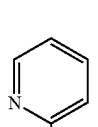 |
| 110 | 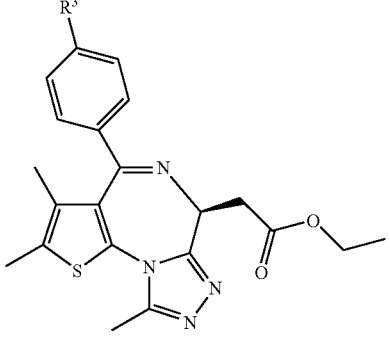 |
| 111 | 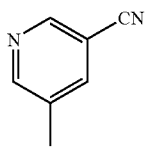 |
| 112 | 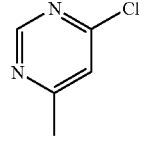 |
| 113 | 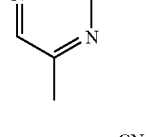 |
| 114 | 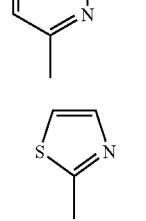 |
| 115 |  |
| 116 | 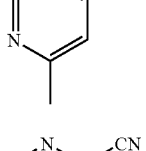 |
| 117 | 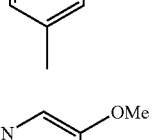 |

TABLE 6-continued
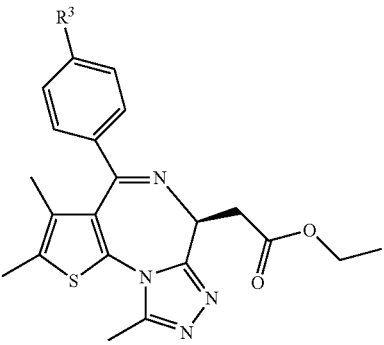
| Example | R³ |
|---|---|
| 118 | 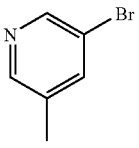 |
| 119 | 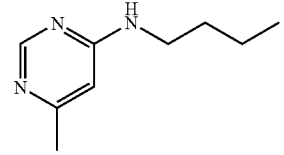 |
TABLE 7
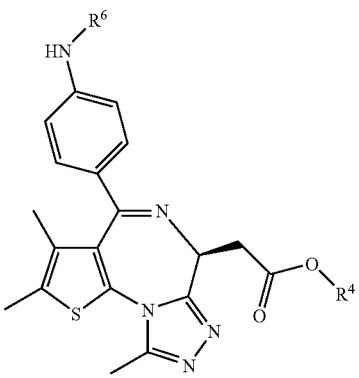
| Example | R⁶ | R⁴ |
|---|---|---|
| 120 | 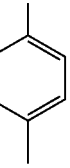 | Me |
| 121 | 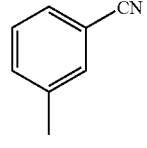 | Me |
TABLE 7-continued
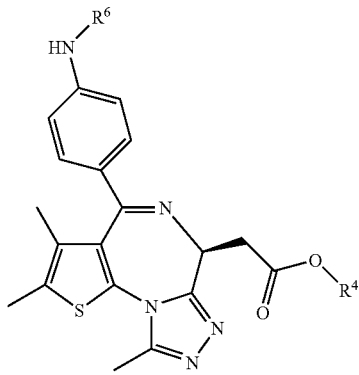
| Example | R⁶ | R⁴ |
|---|---|---|
| 122 | 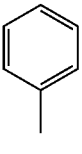 | Me |
| 123 | 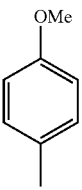 | Me |
| 124 | 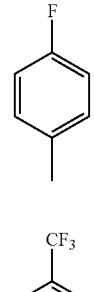 | Me |
| 125 | 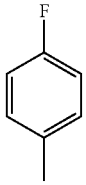 | Me |
| 126 | 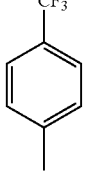 | Me |
| 127 | 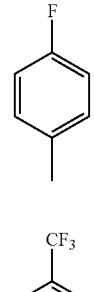 | Me |

TABLE 7-continued

| Example | R⁶ | R⁴ |
|---|---|---|
| 128 | 4-(CH₂CO₂Et)-phenyl | Me |
| 129 | 4-CN-phenyl | Me |
| 130 | 2-CN-phenyl | Me |
| 131 | 3-Me-phenyl | Me |
| 132 | 2-Me-phenyl | Me |
| 133 | 3-OMe-phenyl | Me |
| 134 | 3-F-phenyl | Me |
| 135 | 3-CF₃-phenyl | Me |
| 136 | 3-SO₂Me-phenyl | Me |
| 137 | 3-Cl-phenyl | Me |
| 138 | 3,4,5-triF-phenyl | Me |
| 139 | 4-F-phenyl | Et |
| 140 | 2-CN-phenyl | Et |

TABLE 8

| Example | R⁶ | R⁴ |
|---|---|---|
| 141 | 2-methylpyridin-yl | Me |
| 142 | 3-methylpyridin-yl | Me |
| 143 | 1-Et,5-methyl-pyrazol-3-yl | Me |
| 144 | 2-methylthiazol-yl | Me |
| 145 | 1,3-dimethyl-5-methyl-pyrazol-yl | Me |
| 146 | 3-Buᵗ,1-Me,5-methyl-pyrazol-yl | Me |
| 147 | 2-CN,5-methyl-pyridin-yl | Me |
| 148 | 1,3,4,5-tetramethyl-pyrazol-yl | Me |
| 149 | 2-OMe,5-methyl-pyridin-yl | Me |
| 150 | 5-F,2-methyl-pyridin-yl | Me |
| 151 | 1-Et,5-methyl-pyrazol-3-yl | Et |
| 152 | 3-methylpyridin-yl | Et |
| 153 | 1,3,4,5-tetramethyl-pyrazol-yl | Et |

TABLE 9
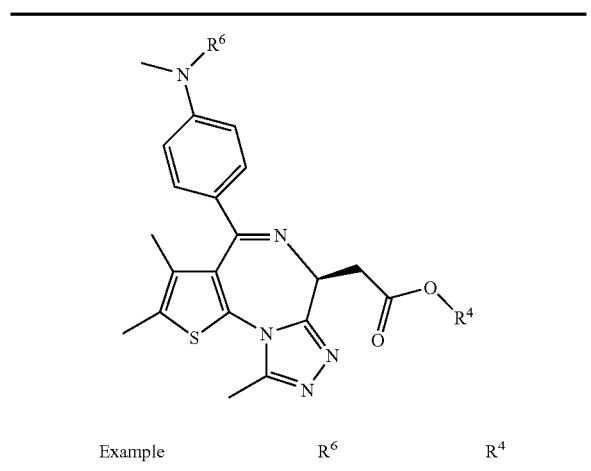
| Example | R6 | R4 |
|---|---|---|
| 154 | 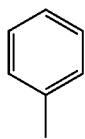 | Me |
| 155 | 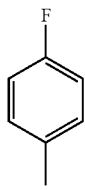 | Me |
| 156 | 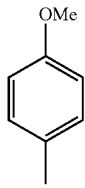 | Me |
| 157 | 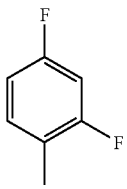 | Me |
| 158 | 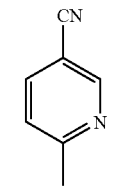 | Me |
| 159 | 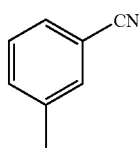 | Me |
TABLE 9-continued
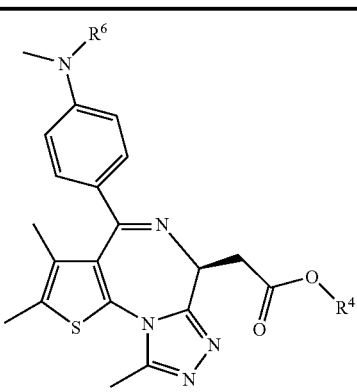
| Example | R6 | R4 |
|---|---|---|
| 160 | 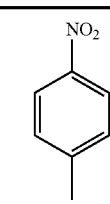 | Me |
| 161 | 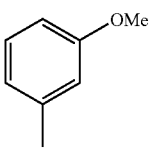 | Me |
| 162 | 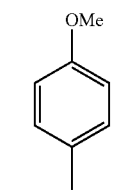 | Et |
| 163 | 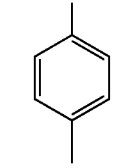 | Et |
| 164 | 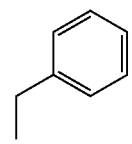 | Me |
| 165 | 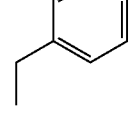 | Et |
| 166 | 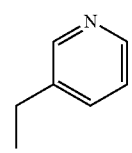 | Me |

TABLE 9-continued
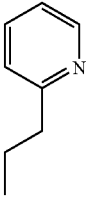
| Example | R6 | R4 |
|---|---|---|
| 194 | (2-pyridyl) | Me |
TABLE 10
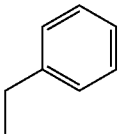
| Example | —(CH2)n—R6 |
|---|---|
| 167 | benzyl |
| 168 | (3-pyridyl)methyl |
| 169 | (4-pyridyl)methyl |
| 170 | 4-CF3-benzyl |
| 171 | 3-phenylpropyl |
| 172 | 4-OMe-benzyl |
| 173 | (2-thienyl)methyl |
| 174 | 3-OMe-benzyl |
| 175 | 3,4-diOMe-benzyl |
| 176 | 2-Me-benzyl |

TABLE 10-continued

| Example | —(CH$_2$)$_n$—R$_6$ |
|---|---|
| 177 | 4-fluorobenzyl |
| 178 | 4-(methoxycarbonyl)benzyl |
| 179 | 2,4-difluorobenzyl |
| 180 | 4-methylbenzyl |
| 181 | 2-methoxybenzyl |
| 182 | 2,3-dimethoxybenzyl |
| 183 | 4-methoxyphenylpropyl |
| 184 | 4-fluorophenylpropyl |
| 185 | benzo[1,3]dioxol-5-ylethyl |
| 186 | naphthalen-1-ylethyl |
| 187 | 1-(4-fluorophenyl)-1-oxopropyl |
| 188 | 4-phenylbutyl |
| 190 | furan-2-ylethyl |

TABLE 10-continued
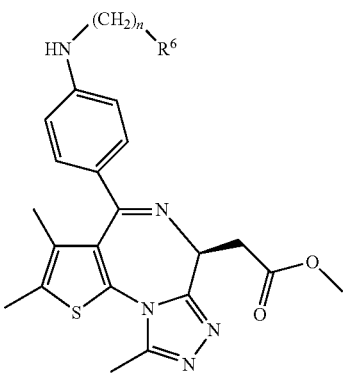
| Example | —(CH$_2$)$_n$—R$_6$ |
|---|---|
| 191 | 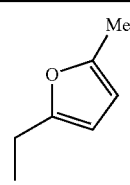 |
| 195 | 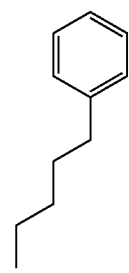 |
TABLE 11
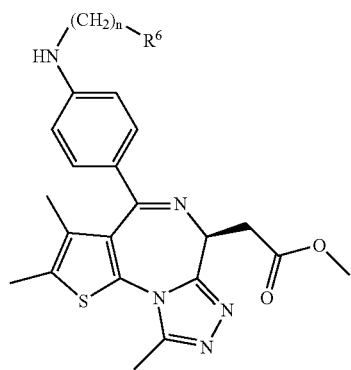
| Example | —(CH$_2$)$_n$—R$_6$ |
|---|---|
| 192 | 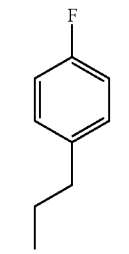 |
TABLE 11-continued
| Example | —(CH$_2$)$_n$—R$_6$ |
|---|---|
| 193 | 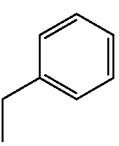 |
| 196 | 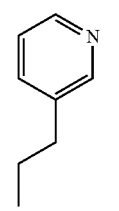 |
| 197 | 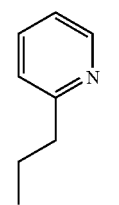 |
| 198 | 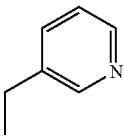 |
| 199 | 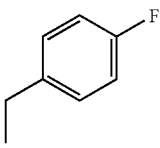 |
| 200 | 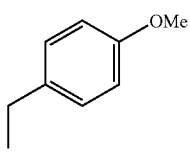 |
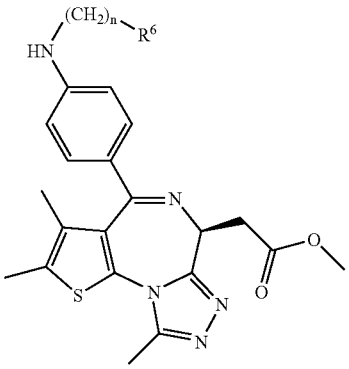

TABLE 11-continued

[Structure: thienotriazolodiazepine with 4-(HN-(CH₂)ₙ-R⁶)phenyl substituent and methyl ester]

| Example | —(CH₂)ₙ—R₆ |
|---------|------------|
| 201 | [3-phenoxypropyl] |
| 202 | [2-(pyridin-4-yl)ethyl] |
| 203 | [3-phenylpropyl] |
| 204 | [4-(imidazol-1-yl)butyl] |

TABLE 12

[Structure: thienotriazolodiazepine with 4-R³-phenyl substituent and -C(O)-O-R⁴ ester]

| Example | R³ | R⁴ |
|---------|-----|-----|
| 205 | [2-methyl-1,2,3,4-tetrahydroisoquinolin-6-yl] | Me |
| 206 | [2-methylisoindolin-5-yl] | Me |
| 207 | [1-methylindolin-5-yl] | e |
| 208 | [6,7-dimethoxy-2-methyl-1,2,3,4-tetrahydroisoquinolin-? -yl] | Me |
| 209 | [2-methylisoindolin-5-yl] | Et |

TABLE 12-continued
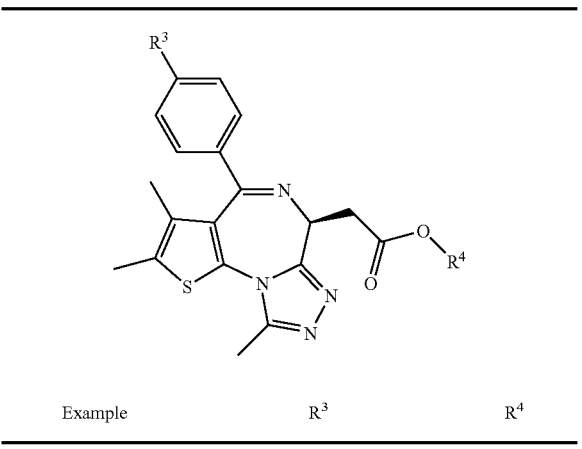
| Example | R³ | R⁴ |
|---|---|---|
| 210 | 4-(4-methylpiperazin-1-yl)phenyl | Me |
| 211 | 4-cyano-1-methylpiperidin-4-yl-phenyl | Me |
| 212 | (1-methylpiperidin-4-yl)(diphenyl)methanol | Me |
| 213 | 4-(pyridin-2-yl)-1-methylpiperazin-1-yl | Me |
TABLE 12-continued
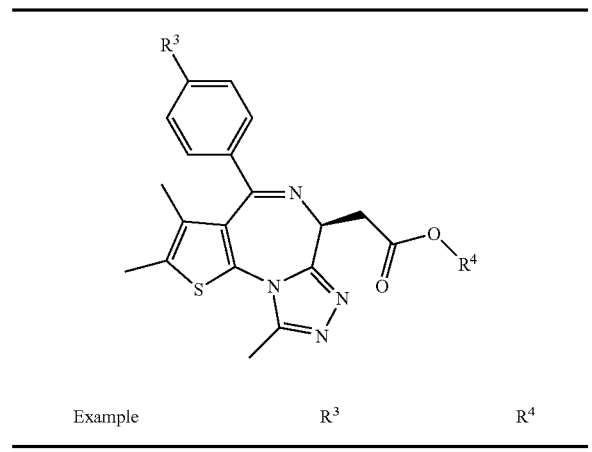
| Example | R³ | R⁴ |
|---|---|---|
| 214 | 4-(benzyl)-1-methylpiperazin-1-yl | Me |
| 215 | 4-hydroxy-1-methyl-4-phenylpiperidin-4-yl | Me |
| 216 | 4-(2-methoxyphenyl)-1-methylpiperazin-1-yl | Me |
| 217 | 4-benzyl-4-hydroxy-1-methylpiperidin-4-yl | Me |

TABLE 12-continued

[Structure with R³ and R⁴ substituents on thieno-triazolo-diazepine core]

| Example | R³ | R⁴ |
|---|---|---|
| 218 | 4-(4-methylpiperazin-1-ylcarbonyl)pyridin-4-yl (N-methylpiperazinyl carbonyl pyridinyl) | Me |

TABLE 13

[Structure with R³ and R⁴ substituents on thieno-triazolo-diazepine core]

| Example | R³ | R⁴ |
|---|---|---|
| 219 | (E)-propenyl-phenyl | Me |
| 220 | 4-F, (E)-propenyl-phenyl | Me |

TABLE 13-continued

[Structure with R³ and R⁴ substituents on thieno-triazolo-diazepine core]

| Example | R³ | R⁴ |
|---|---|---|
| 221 | 4-OMe, (E)-propenyl-phenyl | Me |
| 223 | 3-(hydroxymethyl), (E)-propenyl-phenyl | Me |
| 222 | 4-methylthiazol-5-yl, (E)-propenyl | Me |
| 224 | (E)-N-phenyl-but-2-enamide | Me |
| 225 | 4-OH, (E)-propenyl-phenyl | Me |

TABLE 13-continued
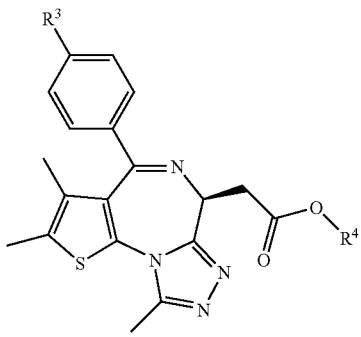
| Example | R³ | R⁴ |
|---|---|---|
| 226 | 3-cyanocinnamyl (3-CN-C6H4-CH=CH-CH3) | Me |
| 227 | N-(3-cyanophenyl)but-2-enamide | Me |
| 228 | 4-methyl-5-(prop-1-enyl)thiazole | Et |
| 229 | 1-phenylbutan-1-one | Me |
| 230 | 1-(4-methoxyphenyl)propan-1-one | Me |
TABLE 13-continued
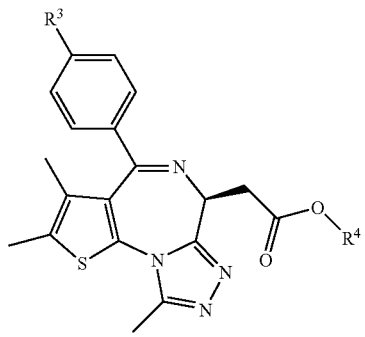
| Example | R³ | R⁴ |
|---|---|---|
| 189 | 1-(pyridin-4-yl)propan-1-one | Et |
TABLE 14
| Example | R³ | R⁴ |
|---|---|---|
| 232 | N-methylaniline | Me |
| 233 | 4-fluoro-N-methylaniline | Me |
| 235 | 3-cyano-methylbenzene | Me |

TABLE 14-continued
| Example | R³ | R⁴ |
|---|---|---|
| 234 | 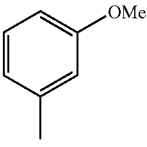 | Me |
| 236 | 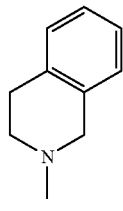 | Me |
| 237 | 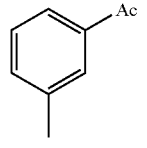 | Me |
| 238 | 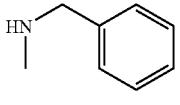 | Me |
| 239 |  | Me |
| 240 | 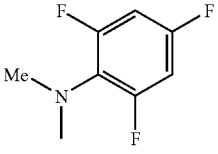 | Me |
TABLE 14-continued
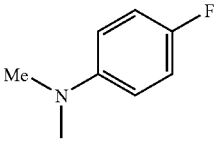
| Example | R³ | R⁴ |
|---|---|---|
| 241 | 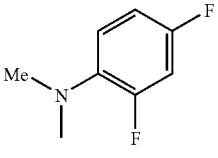 | Me |
| 242 | 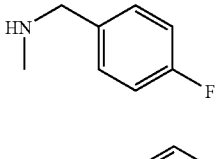 | Me |
| 243 | 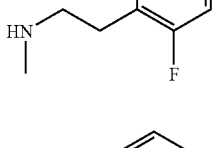 | Me |
| 244 | 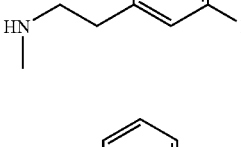 | Me |
| 245 | 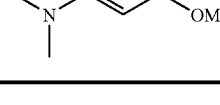 | Me |
| 246 |  | Me |
| 247 |  | Me |

TABLE 15
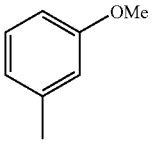
| Example | R¹ | R⁴ | R³ |
|---|---|---|---|
| 248 | —CH₂OMe | Me | 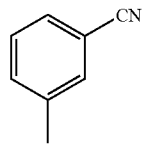 3-OMe-phenyl |
| 249 | —CH₂OMe | Me | 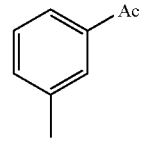 3-CN-phenyl |
| 250 | —CH₂OMe | Me | 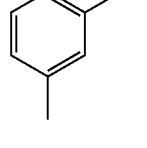 3-Ac-phenyl |
| 251 | —CH₂OEt | Et | 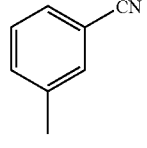 3-CN-phenyl |
| 252 | —CH₂OEt | Me | 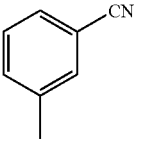 3-CN-phenyl |
TABLE 16
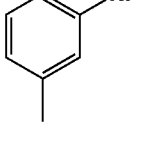
| Example | R³ |
|---|---|
| 253 | 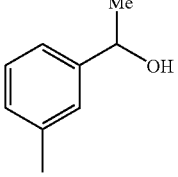 |
| 254 | 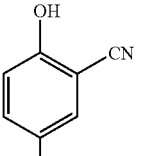 |
| 255 |  |
| 256 | |
| 257 | |
| 258 | 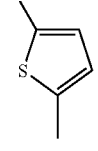 |
| 259 | 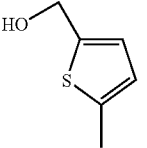 |

TABLE 16-continued

| Example | R³ |
|---------|-----|
| 260 | 1-hydroxy-1-(5-methylthiophen-2-yl)ethyl |
| 261 | 2-methylthiazol-?-yl |
| 262 | 2-methyl-4-cyanopyridin-?-yl |
| 263 | 5-methyl-3-cyanopyridin-?-yl |
| 264 | 3-amino-6-methylpyridazin-?-yl |
| 265 | 5-methylpyrimidin-?-yl |
| 266 | 3-methylpyridin-?-yl |
| 267 | 6-methyl-2-cyanopyridin-?-yl |
| 268 | 1,4-dimethylpyrazol-?-yl |
| 269 | 5-bromo-2-methylthiazol-?-yl |
| 270 | 2-methylpyrimidin-?-yl |
| 271 | 4-chloro-6-methylpyrimidin-?-yl |

TABLE 17
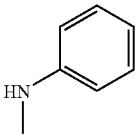
| Example | R³ |
|---|---|
| 273 | 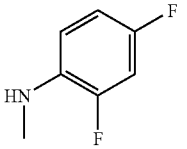 |
| 274 | 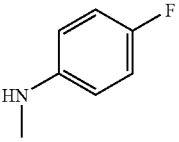 |
| 275 | 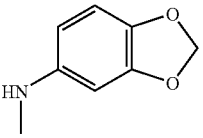 |
| 276 | 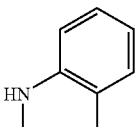 |
| 277 | 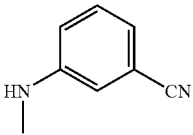 |
| 278 | 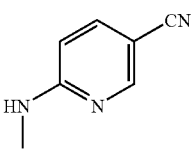 |
| 335 | 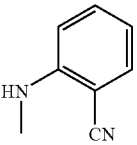 |
| 279 | 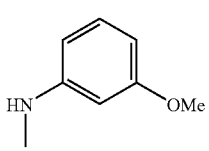 |
TABLE 17-continued
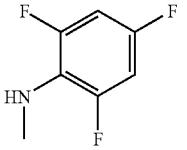
| Example | R³ |
|---|---|
| 280 | 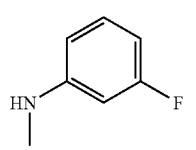 |
| 281 | 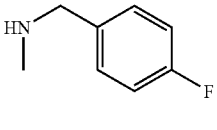 |
| 282 | 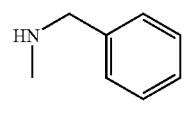 |
| 283 | 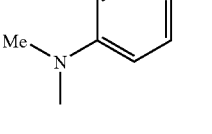 |
| 284 | 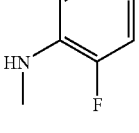 |
| 336 | 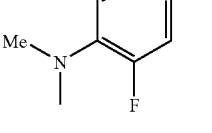 |
| 272 | 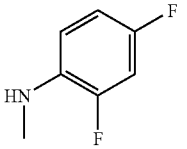 |
| 285 | 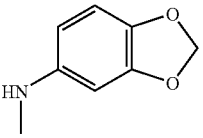 |

TABLE 17-continued

| Example | R³ |
|---|---|
| 286 | 3-(N-methyl-N-methylamino)benzonitrile |
| 287 | 4-(N-methyl-N-methylamino)benzonitrile |
| 288 | N-methyl-N-methyl-(pyridin-3-ylmethyl)amine |
| 289 | N-methyl-5-(trifluoromethyl)pyridin-2-amine |
| 337 | N-methyl-(3,4-difluorobenzyl)amine |
| 290 | N-methyl-5-fluoropyridin-2-amine |
| 291 | N-methyl-6-methoxypyridin-2-amine |
| 292 | N-methyl-5-chloropyridin-2-amine |
| 293 | N-methyl-6-fluoropyridin-3-amine |
| 294 | N-methyl-pyridin-3-amine |
| 295 | N-methyl-(pyridin-4-ylmethyl)amine |
| 296 | N-methyl-2-(pyridin-4-yl)ethylamine |
| 338 | N-methyl-(3,5-difluorobenzyl)amine |
| 339 | N-methyl-(2,5-difluorobenzyl)amine |

TABLE 18
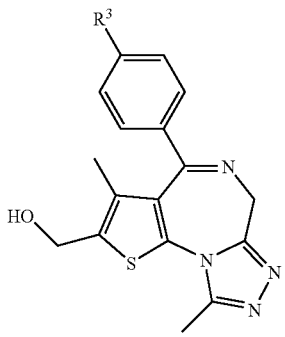
| Example | R³ |
|---|---|
| 297 | 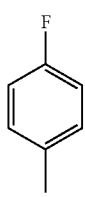 |
| 298 | 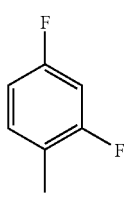 |
| 299 | 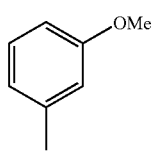 |
TABLE 19
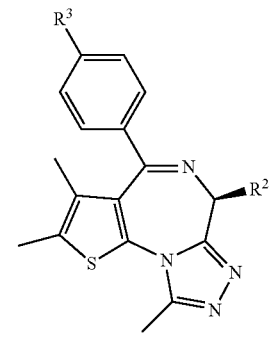
| Example | R² | R³ |
|---|---|---|
| 300 | 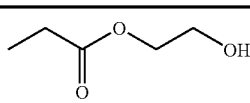 | 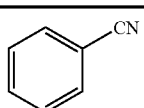 |
TABLE 19-continued
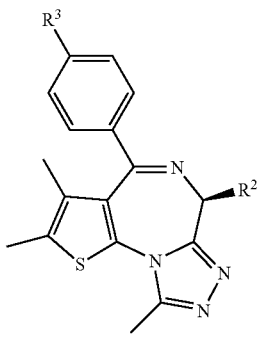
| Example | R² | R³ |
|---|---|---|
| 301 | 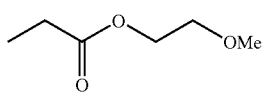 | 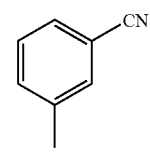 |
| 302 | 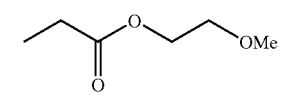 | 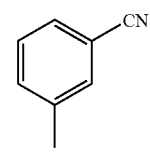 |
| 303 | 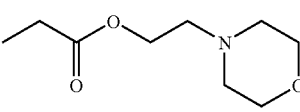 | 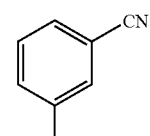 |
| 304 | 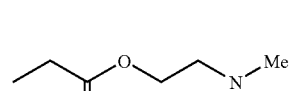 | 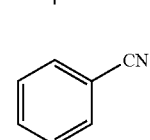 |
| 305 | 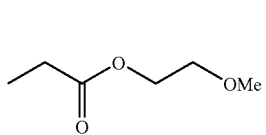 | 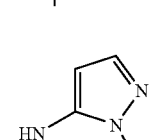 |
| 306 | 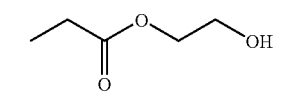 | 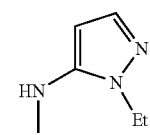 |
| 307 | 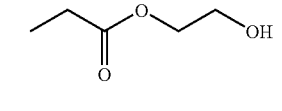 | 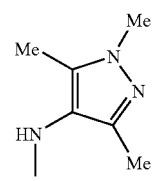 |

TABLE 20

| Example | R³ |
|---|---|
| 308 | N-methyl-4-(trifluoromethyl)benzamide |
| 309 | N-methyl-3-cyanobenzamide |
| 310 | 2-acetoxy-N-methylbenzamide |
| 311 | N-methyl-3-phenylpropanamide |
| 312 | N-methyl-3-(4-methoxyphenyl)propanamide |
| 313 | N-methyl-2-(4-methoxyphenyl)acetamide |
| 314 | N-methyl-2-(4-fluorophenyl)acetamide |

TABLE 20-continued

| Example | R³ |
|---|---|
| 315 | N-methyl-2-(4-fluorophenyl)acetamide |
| 316 | N-methyl-2-phenylacetamide |
| 317 | N-methyl-4-methoxybenzamide |
| 318 | N-methyl-4-fluorobenzamide |
| 319 | N-methylcinnamamide |
| 320 | N,N-dimethylcinnamamide |
| 321 | N-methyl-5-bromonicotinamide |

TABLE 20-continued
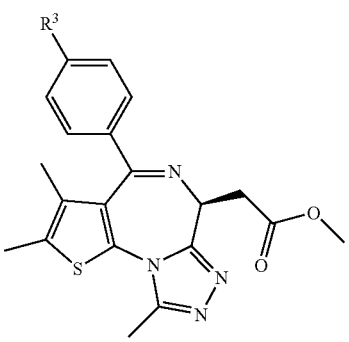
| Example | R³ |
|---|---|
| 322 | 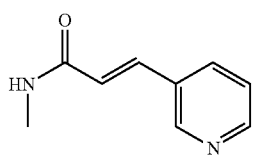 |
| 323 | 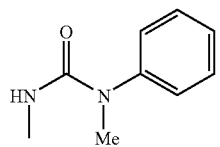 |
| 324 | 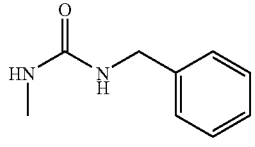 |
| 325 | 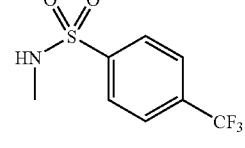 |
| 326 | 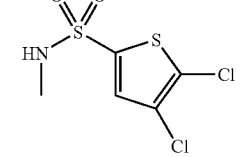 |
| 327 | 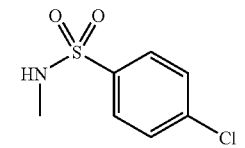 |
| 328 | 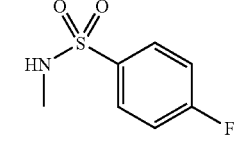 |
TABLE 20-continued
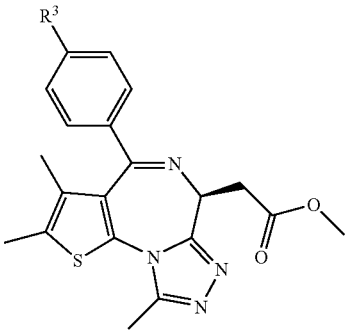
| Example | R³ |
|---|---|
| 329 | 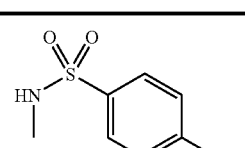 |
| 330 | 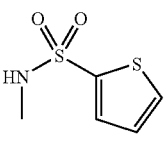 |
| 330 | 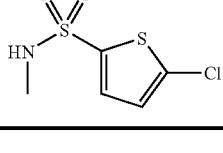 |
TABLE 21
| Example | |
|---|---|
| 1 | 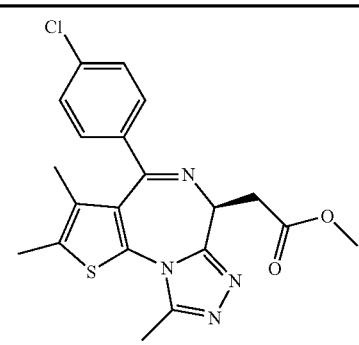 |
| 62 | 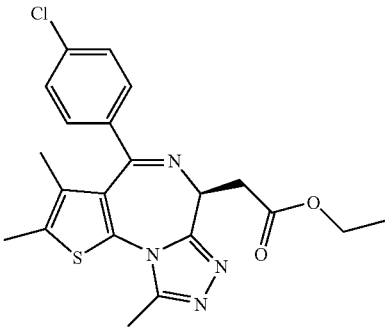 |

TABLE 21-continued
| Example | |
|---|---|
| 231 | 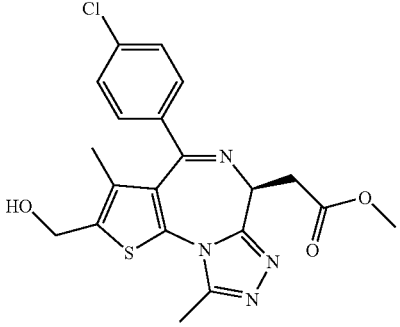 |
| 332 | 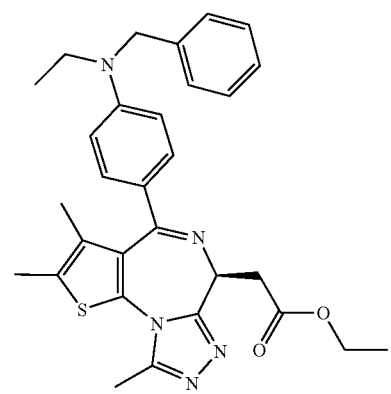 |
TABLE 22
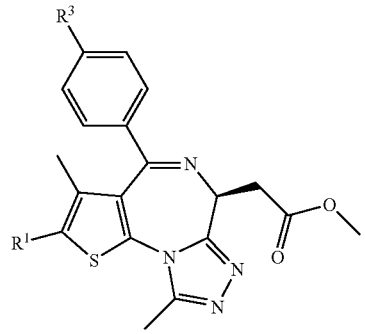
| Example | R³ |
|---|---|
| 340 | 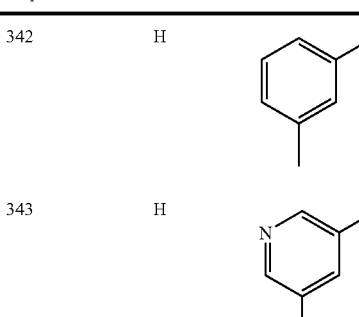 |
| 341 | 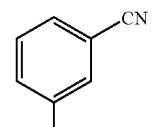 |
TABLE 23
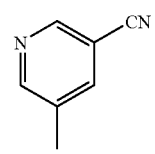
| Example | R¹ | R³ |
|---|---|---|
| 342 | H | 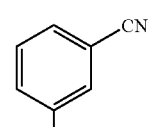 |
| 343 | H | 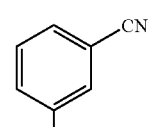 |
| 344 | Cl | 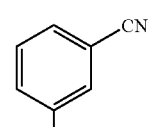 |
| 345 | Br | 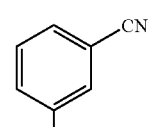 |
TABLE 24
| Example | |
|---|---|
| 346 | 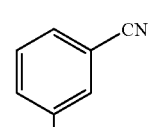 |

TABLE 25

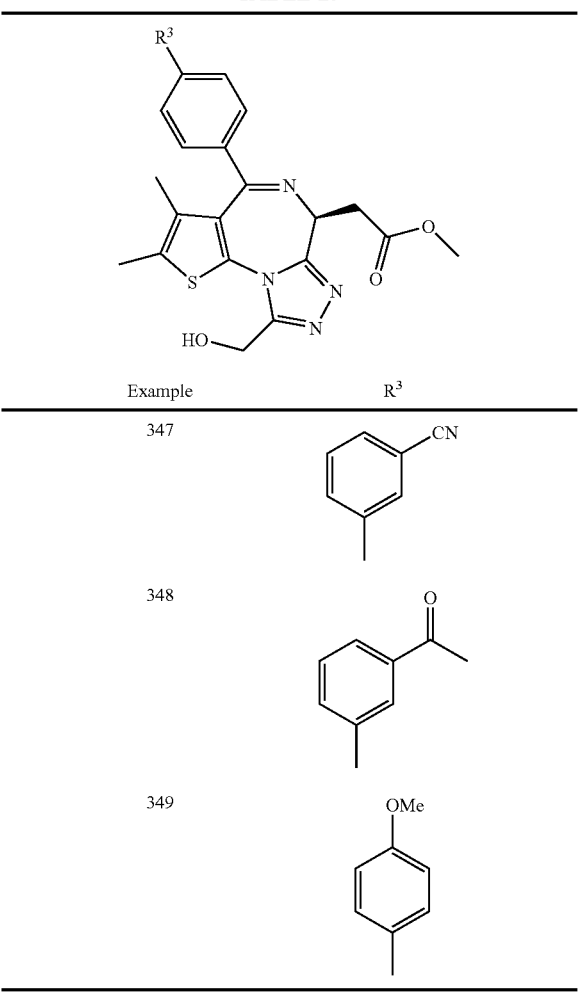

| Example | R³ |
|---|---|
| 347 | 3-CN-phenyl |
| 348 | 3-acetyl-phenyl |
| 349 | 4-OMe-phenyl |

Experimental Example 1

Effect on Mouse T Cell Proliferation Stimulated with Anti-CD28 Antibody and Phorbol 12-Myristate 13-Acetate (PMA)

The spleen was aseptically isolated from 6-7-week-old male BALB/c mice (CHARLES RIVER LABORATORIES JAPAN, INC.), and splenocyte suspension was prepared using RPMI1640 medium (manufactured by Sigma-Aldrich Ltd.). After hemolysis by a hypotonic treatment using a mixed solution of 0.83% aqueous ammonium chloride and Tris-HCl buffer (pH 7.65) at 9:1, a T cell concentrated fraction was obtained using a T cell concentrated column (manufactured by R&D systems). A cell suspension prepared using RPMI1640 medium containing 10% fetal calf serum (FCS, manufactured by Sigma-Aldrich Ltd.) was added to a flat-bottomed 96 well microtest plate (manufactured by Becton, Dickinson and Company) at $5 \times 10^5$ cells/well. Furthermore, a test compound diluted with a medium to the final concentration of 1-10000 nmol/L, 10 ng/mL PMA (manufactured by Sigma-Aldrich Ltd.) and 250 ng/mL anti-CD28 antibody (manufactured by BD pharmingen) were added, and the mixture was cultured under the conditions of 37° C., 5% carbon dioxide, 95% air for 20 hr. After the completion of culture, tritiumthymidine (specific activity: 18.5 kBq/mmol, manufactured by MP Biochemicals) was added at 18.5 kBq/well, and the mixture was further cultured for 4 hr. Then, the cells were recovered in a glass fiber filter using a cell harvester (manufactured by Molecular Devices Corp.), the radioactivity taken into the cells was measured using a plate scintillation counter (microbeta 1460, manufactured by PerkinElmer), based on which the mouse T cell growth induced by stimulation with PMA and anti-CD28 antibody was measured. To be specific, suppressing rate (%)=(1−(radioactivity (cpm) of well added with test compound)/(radioactivity (cpm) of well without addition of test compound))×100 was calculated from the average amount of tritiumthymidine uptake (cpm) of T cells in each well added with various concentrations of test compound. In addition, based on the dose response curve obtained by plotting the average tritiumthymidine uptake amount (cpm) or suppressing rate on the vertical axis and the concentration on the transverse axis, the concentration of the compound ($IC_{50}$) suppressing the value to 50% of that of the control group was determined by nonlinear regression.

TABLE 26 suppressive action on CD28-dependent T cell growth

| compound | CD28-dependent T cell growth suppressive action ($IC_{50}$, μM) |
|---|---|
| Example 1 | 0.038 |
| Example 8 | 0.026 |
| Example 61 | 0.055 |
| Example 120 | 0.0011 |
| Example 163 | 0.070 |
| Example 167 | 0.029 |
| Example 234 | 0.097 |
| Example 253 | 0.10 |
| Example 311 | 0.025 |
| Example 335 | 0.19 |
| comparison compound A | >1 |
| comparison compound B | >1 |
| Ciclosporin | >1 |
| Tacrolimus | >1 |

In the Table, comparison compound A is JP-A-3-215489, Example 15 (the following formula A), and comparison compound B is WO97/47622, Reference Example 100 (the following formula B).

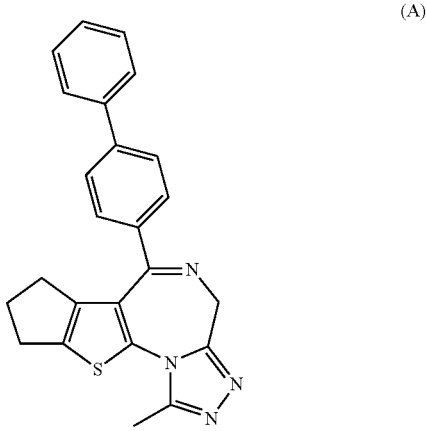

(A)

-continued (B)

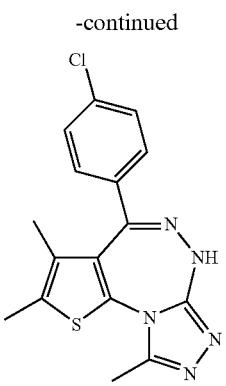

From the above results, it has been clarified that Examples 1, 8, 61, 120, 163, 167, 234, 253, 311 and 335 have a CD28-dependent T cell growth suppressive action, showing extremely strong CD28 dependency T cell growth suppressive action as compared to that of compounds A and B. In addition, since a calcineurin inhibitor (ciclosporin and tacrolimus) that signals from T cell receptor hardly inhibits the growth even at 1 μM in this evaluation system, it has been shown that this evaluation system is suitable for evaluating an inhibitory action on costimulatory signal from CD28.

Experimental Example 2

Effect on TYPE II Collagen-Induced Arthritis in DBA/1J Mouse

Bovine Type II collagen (purchased from collagen technical workshop) (100-200 μg) was mixed with complete Freund's adjuvant (manufactured by Sigma-Aldrich Ltd.) containing killed tuberculosis H37Ra. Using the resulting emulsion, 6 to 7-week-old male DBA/1J mice (CHARLES RIVER LABORATORIES JAPAN, INC.) were subcutaneously immunized at the tail root twice at 3 week intervals, whereby arthritis was developed. A test compound was suspended or dissolved in 0.5% carboxymethylcellulose (manufactured by Sigma-Aldrich Ltd.), and repetitively administered orally at a dose of 0.1-30 mg/kg body weight using an oral gavage needle for 2 weeks from the day of booster. As to this model, the symptoms of arthritis of four limbs were evaluated based on the following judgment criteria using the scores of from 0 to 4. The arthritis score of each mouse was shown by the total of the scores of four limbs (maximum: 16 points).

TABLE 27

| score | symptom |
| --- | --- |
| 0 | No change |
| 1 | edema only in one joints |
| 2 | edema only in two or more joints (mild edema of whole leg) |
| 3 | severe edema of whole leg |
| 4 | severe edema of whole leg and ankylosis |

As regards the arthritis score, each group (n=5-6) was evaluated using an average value and mean error, with a group administered only with a vehicle being control, and Mann-Whitney U test was used for statistical analysis, wherein p value of 0.05 or below was determined to be significant. In the following, the suppressive action of the compound of the present invention on mouse collagen induced arthritis is shown by the suppressing rate (%) (1−(average arthritis score of compound administration group)/(average arthritis score of control group)×100) calculated from the average arthritis score at 35 days after the primary immunization.

It has been confirmed that the compound of the present invention significantly suppresses the onset of arthritis in DBA/1J mouse with collagen induced arthritis. From the results, the compound is considered effective for rheumatoid arthritis and the like.

TABLE 28

Effect on mouse collagen-induced arthritis

| Example no. | dose (mg/kg) | suppressing rate (%) | P value |
| --- | --- | --- | --- |
| 1 | 3 | 66.1 | <0.05 |
| 8 | 3 | 50.0 | <0.05 |
| 120 | 3 | 53.1 | <0.05 |
| 163 | 3 | 57.4 | <0.05 |
| 167 | 3 | 61.4 | <0.05 |
| 234 | 3 | 53.6 | <0.05 |
| 253 | 10 | 46.4 | <0.05 |
| 311 | 3 | 85.2 | <0.05 |
| 335 | 10 | 65.5 | <0.05 |

Experimental Example 3

Effect on Experimental Autoimmune Encephalomyelitis in SJL/J Mouse

The 139th-151st peptides (50 μg) of rat-derived proteolipid protein (manufactured by Bachem) was mixed with complete Freund's adjuvant containing killed tuberculosis H37Ra. Using the resulting emulsion, 10-week-old female SJL/J mice (CHARLES RIVER LABORATORIES JAPAN, INC.) were subcutaneously immunized on the back, whereby experimental autoimmune encephalomyelitis (EAE) was developed. The compound of the present invention or a pharmaceutically acceptable salt thereof was suspended or dissolved in 0.5% carboxymethylcellulose (manufactured by Sigma-Aldrich Ltd.), and repetitively administered orally at a dose of 3-30 mg/kg body weight using an oral gavage needle for 3 weeks from the day of immunization. As to this model, the symptoms of EAE were evaluated based on the following judgment criteria using the scores of from 0 to 5.

TABLE 29

| score | symptom |
| --- | --- |
| 0 | no symptom |
| 0.5 | paralysis of tail tip |
| 1 | paralysis of tail tip and root |
| 1.5 | complete weakness of tail |
| 2 | partial paralysis of one hindpaw |
| 2.5 | partial paralysis of both hindpaws |
| 3 | partial paralysis of both hindpaws and paralysis of lower body |
| 3.5 | complete paralysis of both hindpaws and paralysis of lower body |
| 4 | moribund |
| 5 | death |

As regards the EAE score, each group (n=10) was evaluated using an average value and mean error, with a group administered only with a vehicle being control, and Mann-Whitney U test was used for statistical analysis, wherein p value of 0.05 or below was determined to be significant. In the following, the suppressive action of the compound of the present invention on EAE is shown by the suppressing rate (%) calculated from the average EAE score at 14 days after the immunization. It has been confirmed that the compound of the present invention significantly suppresses the onset of EAE in SJL/J mouse. From the results, the compound is considered effective for encephalomyelitis, multiple sclerosis and the like.

TABLE 30

Effect on mouse EAE

| Example No. | dose (mg/kg) | suppressing rate (%) | P value |
|---|---|---|---|
| 8 | 10 | 98 | <0.05 |
| 163 | 30 | 60 | <0.05 |
| 167 | 3 | 62 | <0.05 |
| 335 | 30 | 53 | <0.05 |

Experimental Example 4

Effect on Lupus Nephritis in Spontaneous Systemic Lupus Erythematosus Model MRL/MpJ-lpr/lpr Mouse The compound of the present invention or a pharmaceutically acceptable salt thereof was suspended or dissolved in 0.5% carboxymethylcellulose, and repetitively administered orally to male MRL/MpJ-lpr/lpr mice at 16 weeks after birth (CHARLES RIVER LABORATORIES JAPAN, INC.), that had developed lupus nephritis, at a dose of 1 and 3 mg/kg body weight for 4 weeks using an oral gavage needle. During the dosing period, urine-protein level was scored once a week using Ames urine test paper (Albustix (registered trademark), Bayer, Ltd.•Sankyo Corp.). As regards the urine protein levels, each group (n=10) was evaluated using an average value and mean error, with a group administered only with a vehicle being control, and Dunnett's test was used for statistical analysis, wherein p value of 0.05 or below was determined to be significant.

The urine protein levels after repetitive oral administration of the compound of Example 1 for 4 weeks are shown below. Example 1 significantly decreased the urine protein score at not less than 1 mg/kg as compared to the control group. From the results, the compound of the present invention is considered effective for systemic lupus erythematosus, lupus nephritis and the like.

TABLE 31

Effect on lupus nephritis in MRL/MpJ-lpr/lpr mouse (4 weeks after administration of compound)

| Example No. | dose (mg/kg) | urine protein score (mean ± SE) | P value |
|---|---|---|---|
| medium | | 2.8 ± 0.2 | |
| 1 | 1 | 1.8 ± 0.3 | <0.05 |
| 1 | 3 | 1.6 ± 0.2 | <0.05 |

Experimental Example 5

Effect on Biphasic Auricular Edema in Egg Albumin-Induced Mouse

Using saline (0.5 ml) containing egg albumin (10 μg, manufactured by Sigma-Aldrich Ltd.) and 1 mg of aluminum hydroxide gel, 6 to 7-week-old male BALB/c mice (CHARLES RIVER LABORATORIES JAPAN, INC.) were intraperitoneally immunized. Two weeks later, egg albumin (1.25 μg) was intradermally injected into the auricle of the mice for challenge, whereby biphasic auricular edema was induced 1 hr and 24 hr after the challenge. The compound of the present invention or a pharmaceutically acceptable salt thereof was suspended or dissolved in 0.5% carboxymethylcellulose, and repetitively administered orally at a dose of 0.01-30 mg/kg body weight for 3 days, from 2 days before the antigen challenge to the day of challenge, using an oral gavage needle. As for this model, the thickness of the auricle of the mouse was measured using a dial gauge (manufactured by Ozaki MFG. Co. Ltd.) and used as an index of auricular edema. As regards the thickness of the auricle, each group (n=8) was evaluated using an average value and mean error, with a group administered only with a vehicle being control, and t-test was used for statistical analysis, wherein p value of 0.05 or below was determined to be significant.

Example 8 (3 mg/kg), Example 163 (3 mg/kg), Example 167 (3 mg/kg), Example 234 (10 mg/kg) and Example 335 (10 mg/kg) showed a significant suppressive action on edema at 24 hr after induction with egg albumin. From the results, it is considered that the compound of the present invention is useful for atopic dermatitis, urticaria, contact dermatitis and the like.

From the above, the compound of the present invention is considered useful for atopic dermatitis, urticaria, contact dermatitis and the like.

TABLE 32

Effect on egg albumin-induced mouse biphasic auricular edema (24 hr later)

| Example No. | dose (mg/kg) | suppressing rate (%) | P value |
|---|---|---|---|
| 8 | 3 | 40.5 | <0.05 |
| 163 | 3 | 44.5 | <0.05 |
| 167 | 3 | 30.1 | <0.05 |
| 234 | 10 | 35.8 | <0.05 |
| 335 | 10 | 45.1 | <0.05 |

Experimental Example 6

Effect on Mouse Graft-Versus-Host Reaction (GvHR)

Cyclophosphamide (manufactured by Shionogi & Co., Ltd.) is administered to male BDF1 recipient mouse (8-week-old, CHARLES RIVER LABORATORIES JAPAN, INC.) at a dose of 300 mg/kg from the tail vein as a pretreatment at 24 hr prior to injection of spleen cells. The spleen was aseptically isolated from male C57BL/6 donor mouse (8-week-old, CHARLES RIVER LABORATORIES JAPAN, INC.), minced in RPMI1640 medium (manufactured by Sigma-Aldrich Ltd.), and passed through a stainless mesh to give a splenocyte single cell suspension. After removal of red blood cells by a hypotonic treatment using a mixed solution of 0.83% aqueous ammonium chloride and Tris-HCl buffer (pH 7.65) at 9:1, splenocytes were washed and suspended in physiological saline to give a splenocyte suspension. The prepared cells were injected at $1 \times 10^8$ cells/mouse into the tail vein to induce acute GvHR. The compound of the present invention or a pharmaceutically acceptable salt thereof was suspended or dissolved in 0.5% carboxymethylcellulose, and repetitively administered orally at a dose of 3-30 mg/kg body weight for 28 days from the day of splenocyte injection, and the influence on the survival time was evaluated. After induction of acute GvHR, the survival of each individual was determined every day, and the day of confirmed death was taken as the survival time of each individual. As for the survival time, log-rank test analysis was performed using the group administered with vehicle alone as a control, and the multiplicity was adjusted by the Holm's method, wherein p value of 0.05 or below was determined to be significant.

It has been confirmed that the compound of the present invention significantly prolongs the survival time in mouse acute GvHR. From the results, the compound of the present invention is considered useful for the prophylaxis or suppression of graft-versus-host disease (GvHD) due to bone marrow transplantation and the like.

TABLE 33

Effect on mouse GvHR

| Example No. | dose (mg/kg) | median survival time (shortest number of days-longest number of days) | P value |
|---|---|---|---|
| vehicle | | 22 (14-31) | |
| 8 | 3 | 56 (50-60<) | <0.05 |
| vehicle | | 15 (14-17) | |
| 163 | 10 | 19 (17-44) | <0.05 |
| vehicle | | 22 (14-28) | |
| 167 | 3 | 56 (11-120<) | <0.05 |
| vehicle | | 20 (17-25) | |
| 234 | 30 | 32 (17-55) | <0.05 |
| vehicle | | 15 (12-55) | |
| 335 | 30 | 36.5 (20-56) | <0.05 |

Experimental Example 7

Effect on Mouse Skin Allograft Survival

A tail skin graft (4×7 mm) of 5- to 7-week-old male AKR mouse (KYUDO Co. Ltd. was) was transplanted on the back of 5- to 7-week-old male C3H mouse (CHARLES RIVER LABORATORIES JAPAN, INC.), covered with aseptic gauze and bandaged. The bandage was removed at day 6 from the transplantation, and the graft was observed every day up to rejection. The rejection of the skin graft was determined to be the time point when 90% or more of the epithelium of the graft turned brown due to necrosis. The number of days from the transplantation to the rejection was taken as the survival time of the graft. The compound of the present invention or a pharmaceutically acceptable salt thereof was suspended or dissolved in 0.5% carboxymethylcellulose, and repetitively administered orally at a dose of 0.3-100 mg/kg body weight once a day for 14 days from the day of transplantation. As for the graft survival time, generalized Wilcoxon test analysis was performed using the group administered with vehicle alone as a control, and the multiplicity was adjusted by the Holm's method, wherein p value of 0.05 or below was determined to be significant.

In the mouse allogenic skin transplantation, Example 234 significantly prolonged the graft survival time at 100 mg/kg. From the results, it is considered that the compound of the present invention is useful for the prophylaxis or suppression of rejection reaction in transplantation and the like.

TABLE 34

Graft survival prolongation effect in mouse allogenic skin transplantation

| Example No. | dose (mg/kg) | median survival time (shortest number of days-longest number of days) | P value |
|---|---|---|---|
| vehicle | | 9.5 (8-14) | |
| 234 | 30 | 11 (8-20) | 0.13 |
| 234 | 100 | 14 (11-21) | <0.05 |

INDUSTRIAL APPLICABILITY

According to the present invention, a novel thienotriazolodiazepine compound having an inhibitory action on the costimulatory signal from CD28, a pharmaceutical agent comprising this as an active ingredient, and a production intermediate and a production method of the thienotriazolodiazepine compound can be provided.

This application is based on a patent application No. 2005-157825 filed in Japan, the contents of which are incorporated in full herein by this reference.

The invention claimed is:
1. A thienotriazolodiazepine compound represented by the formula (I)

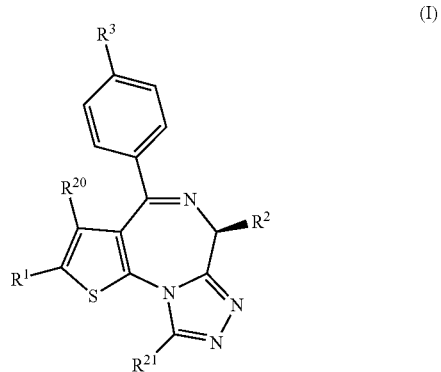

wherein
$R^1$ is hydrogen atom, halogen atom, $C_{1-6}$ alkyl optionally substituted by halogen atom or hydroxyl group, or —$(CH_2)_k OR^a$ (k is an integer of 1 to 4, and $R^a$ is $C_{1-6}$ alkyl optionally having substituent(s)),
$R^{20}$ is $C_{1-6}$ alkyl,
$R^2$ is hydrogen atom, or the following formula (a)

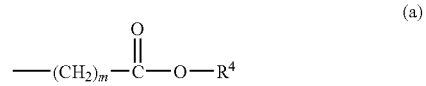

wherein $R^4$ is $C_{1-6}$ alkyl optionally having substituent(s), and m is an integer of 1 to 4,
$R^{21}$ is methyl or hydroxymethyl, and
$R^3$ is
when $R^2$ is a hydrogen atom, then $C_{6-12}$ aryl optionally having one or more substituents selected from halogen atom, cyano, acetyl, hydroxymethyl, hydroxyethyl, methoxy and hydroxyl group; pyridyl, thienyl, thiazolyl, pyrimidinyl, or pyrazolyl, each of which optionally has one or more substituents selected from acetyl, hydroxymethyl, hydroxyethyl, cyano, amino, methyl and halogen atom; or —NR$^5$—(CH$_2$)$_n$—R$^6$ (R$^5$ is hydrogen atom or methyl, n is an integer of 0 to 3, and R$^6$ is C$_{6\text{-}12}$ aryl optionally having one or more substituents selected from halogen atom, hydroxyl group, methoxy, methylenedioxy and cyano; or pyridyl, thiazolyl, isoxazolyl, pyrazolyl, tetrahydrofuranyl or tetrahydropyranyl, each of which optionally has substituents one or more selected from methyl optionally substituted by halogen atom, cyano, halogen atom and methoxy), and when R$^2$ is the formula (a), then C$_{6\text{-}12}$ aryl optionally having substituent(s), heteroaryl having 5 to 12 ring-constituting atoms and optionally having substituent(s), arylcarbonyl alkyl (the aryl moiety has 6 to 12 carbon atoms, and the alkyl moiety has 1 to 6 carbon atoms) optionally having substituent(s) on the ring, —NR$^{5a}$—(CH$_2$)$_o$—R$^{6a}$ (R$^{5a}$ is hydrogen atom or C$_{1\text{-}6}$ alkyl optionally having substituent(s), o is an integer of 0 to 4, and R$^{6a}$ is C$_{6\text{-}12}$ aryl optionally having substituent(s), C$_{7\text{-}13}$ arylcarbonyl optionally having substituent(s), C$_{6\text{-}12}$ aryloxy optionally having substituent(s) or heteroaryl having 5 to 12 ring-constituting atoms and optionally having substituent(s)), or a group selected by following

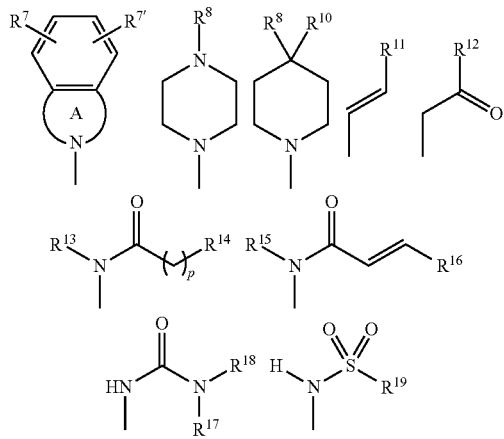

wherein
R$^7$ and R$^{7'}$ are the same or different and each is hydrogen atom, C$_{1\text{-}6}$ alkyl optionally having substituent(s) or C$_{1\text{-}6}$ alkoxy optionally having substituent(s),
ring A is cyclic amine having 4 or 5 carbon atoms, which is condensed with aromatic ring,
R$^8$ is C$_{6\text{-}12}$ aryl optionally having substituent(s), heteroaryl having 5 to 12 ring-constituting atoms and optionally having substituent(s), C$_{7\text{-}18}$ aralkyl optionally having substituent(s), C$_{7\text{-}13}$ arylcarbonyl optionally having substituent(s) or heteroarylcarbonyl having 5 to 12 ring-constituting atoms and optionally having substituent(s),
R$^9$ is hydrogen atom, hydroxyl group or cyano group,
R$^{10}$ is C$_{1\text{-}6}$ alkyl optionally having substituent(s), C$_{6\text{-}12}$ aryl optionally having substituent(s) or heteroaryl having 5 to 12 ring-constituting atoms and optionally having substituent(s),
R$^{11}$ is C$_{6\text{-}12}$ aryl optionally having substituent(s), heteroaryl having 5 to 12 ring-constituting atoms and optionally having substituent(s) or anilinocarbonyl optionally having substituent(s),
R$^{12}$ is heteroaryl having 5 to 12 ring-constituting atoms and optionally having substituent(s), R$^{13}$ is hydrogen atom or C$_{1\text{-}6}$ alkyl optionally having substituent(s),
p is an integer of 0 to 2,
R$^{14}$ is C$_{6\text{-}12}$ aryl optionally having substituent(s) or heteroaryl having 5 to 12 ring-constituting atoms and optionally having substituent(s),
R$^{15}$ is hydrogen atom or C$_{1\text{-}6}$ alkyl optionally having substituent(s),
R$^{16}$ is C$_{6\text{-}12}$ aryl optionally having substituent(s) or heteroaryl having 5 to 12 ring-constituting atoms and optionally having substituent(s),
R$^{17}$ is hydrogen atom or C$_{1\text{-}6}$ alkyl optionally having substituent(s),
R$^{18}$ is C$_{6\text{-}12}$ aryl optionally having substituent(s) or C$_{7\text{-}18}$ aralkyl, and
R$^{19}$ is C$_{6\text{-}12}$ aryl optionally having substituent(s) or heteroaryl having 5 to 12 ring-constituting atoms and optionally having substituent(s),
or a pharmaceutically acceptable salt thereof.

2. The compound of claim 1, wherein R$^{20}$ is methyl, or a pharmaceutically acceptable salt thereof.

3. The compound of claim 1, wherein R$^{21}$ is methyl, or a pharmaceutically acceptable salt thereof.

4. The compound of claim 1, wherein R$^1$ is hydrogen atom, halogen atom, methyl, hydroxymethyl, —CH$_2$OCH$_3$ or —CH$_2$OCH$_2$CH$_3$, or a pharmaceutically acceptable salt thereof.

5. The compound of claim 1, wherein R$^1$ is methyl, hydroxymethyl or —(CH$_2$)$_k$OR$^a$ (k is an integer of 1 to 4, and R$^a$ is C$_{1\text{-}6}$ alkyl optionally having substituent(s)), or a pharmaceutically acceptable salt thereof.

6. The compound of claim 1, wherein
R$^1$ is methyl, hydroxymethyl or —(CH$_2$)$_k$OR$^a$ (k is an integer of 1 to 4, and R$^a$ is C$_{1\text{-}6}$ alkyl optionally having substituent(s)), and
R$^{20}$ and R$^{21}$ are each methyl,
or a pharmaceutically acceptable salt thereof.

7. The compound of claim 1, wherein R$^1$ is methyl, hydroxymethyl, —CH$_2$OCH$_3$ or —CH$_2$OCH$_2$CH$_3$, or a pharmaceutically acceptable salt thereof.

8. The compound of claim 1, wherein R$^1$ is methyl, hydroxymethyl or —CH$_2$OCH$_3$, or a pharmaceutically acceptable salt thereof.

9. The compound of claim 1, wherein R$^1$ is methyl or hydroxymethyl, or a pharmaceutically acceptable salt thereof.

10. The compound of claim 1, wherein R$^2$ is hydrogen atom, or

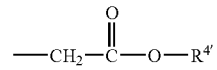

wherein
R$^{4'}$ is methyl, ethyl, hydroxyethyl, methoxyethyl, morpholinoethyl or dimethylaminoethyl,
or a pharmaceutically acceptable salt thereof.

11. The compound of claim 1, wherein R$^2$ is hydrogen atom, or

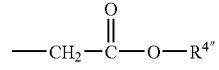

wherein

R⁴" methyl or ethyl, or a pharmaceutically acceptable salt thereof.

12. The compound of claim 1, wherein

R² is hydrogen atom, and

R³ is thiazolyl, phenyl substituted by cyano, pyridyl substituted by cyano, or —NH—(CH₂)ₙ—R⁶ (n is an integer of 0 to 2, and R⁶' is phenyl optionally having one or more substituents selected from halogen atom and cyano, or pyridyl optionally having one or more substituents selected from halogen atom and cyano), or a pharmaceutically acceptable salt thereof.

13. The compound of claim 1, wherein R² is hydrogen atom, and R³ is phenyl substituted by cyano, or a pharmaceutically acceptable salt thereof.

14. The compound of claim 1, wherein

R² is the formula (a), and

R³ is phenyl substituted by one or more selected from hydroxyl group, cyano, ethoxy substituted by morpholino, methylsulfonyl, piperazinyl substituted by methyl, methylcarbonyl, methylenedioxy, methoxy and morpholino; thienyl substituted by cyano; pyrazinyl; pyridyl substituted by cyano or methylcarbonyl; pyrimidinyl; —NR⁵ᵃ'—(CH₂)ₒ—R⁶ᵃ' (wherein R⁵ᵃ' is hydrogen atom or methyl, o is an integer of 0 to 2, and R⁶ᵃ' is phenyl optionally substituted by cyano or halogen atom, or pyrazolyl substituted by methyl or ethyl);

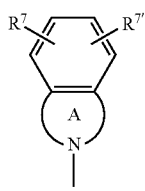

wherein R⁷ and R⁷' are each hydrogen atom, and ring A is piperidine or pyrrolidine, each of which is condensed with aromatic ring;

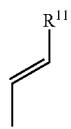

wherein R¹¹ is phenyl substituted by halogen atom; or

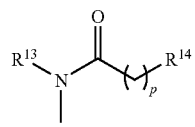

wherein R¹³ is hydrogen atom, p is 2, and R¹⁴ is phenyl, or a pharmaceutically acceptable salt thereof.

15. The compound of claim 1, wherein

R² is the formula (a),

R³ is phenyl substituted by cyano, phenyl substituted by methoxy, —NR⁵ᵃ"—(CH₂)ₒ—R⁶ᵃ" (R⁵ᵃ" is hydrogen atom or methyl, o is 0 or 1, and R⁶ᵃ" is phenyl optionally substituted by halogen atom), or

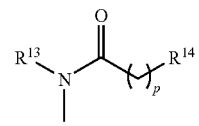

wherein R¹³ is hydrogen atom, p is 2, and R¹⁴ is phenyl, or a pharmaceutically acceptable salt thereof.

16. 4-(3'-Cyanobiphenyl-4-yl)-2,3,9-trimethyl-6H-thieno[3,2-f][1,2,4]triazolo[4,3-a][1,4]diazepine, Ethyl (S)-(4-{4-[(4-fluorophenyl)methylamino]phenyl}-2,3,9-trimethyl-6H-thieno[3,2-f][1,2,4]triazolo[4,3-a][1,4]diazepin-6-yl)acetate, Methyl (S)-{2-hydroxymethyl-4-(4'-methoxybiphenyl-4-yl)-3,9-dimethyl-6H-thieno[3,2-f][1,2,4]triazolo[4,3-a][1,4]diazepin-6-yl}acetate, Methyl (S)-{4-(3'-cyanobiphenyl-4-yl)-2,3,9-trimethyl-6H-thieno[3,2-f][1,2,4]triazolo[4,3-a][1,4]diazepin-6-yl}acetate, Methyl (S)-{2,3,9-trimethyl-4-(4-phenylaminophenyl)-6H-thieno[3,2-f][1,2,4]triazolo[4,3-a][1,4]diazepin-6-yl}acetate, Methyl (S)-{4-(4-benzylaminophenyl)-2,3,9-trimethyl-6H-thieno[3,2-f][1,2,4]triazolo[4,3-a][1,4]diazepin-6-yl}acetate, or Methyl (S)-{2,3,9-trimethyl-4-[4-(3-phenylpropionylamino)phenyl]-6H-thieno[3,2-f][1,2,4]triazolo[4,3-a][1,4]diazepin-6-yl}acetate, or a pharmaceutically acceptable salt thereof.

17. A pharmaceutical composition comprising the compound of claim 1 or a pharmaceutically acceptable salt thereof, and a pharmaceutically acceptable carrier.

18. A method of suppressing a rejection reaction in organ or bone marrow transplantation or treating an autoimmune disease or allergic disease, which method comprises administering the compound of claim 1 or a pharmaceutically acceptable salt thereof to a human, thereby suppressing a rejection reaction in organ or bone marrow transplantation or treating an autoimmune disease or allergic disease in the human.

19. The method of claim 18, wherein the rejection reaction in organ or bone marrow transplantation is a rejection reaction in organ or tissue transplantation or a graft-versus-host (GvH) reaction in bone marrow transplantation.

20. The method of claim 18, wherein the autoimmune disease is rheumatoid arthritis, systemic lupus erythematosus, multiple sclerosis, psoriasis, inflammatory bowel disease, Type I diabetes mellitus, lupus nephritis or encephalomyelitis, and the allergic disease is asthma, allergic rhinitis, pollinosis, atopic demiatitis, urticaria, contact dermatitis or allergic conjunctivitis.

21. A thienotriazolodiazepine compound represented by the formula (II)

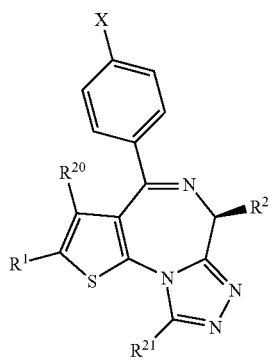

wherein X is fluorine atom, bromine atom, iodine atom, p-toluenesulfonyloxy, or methylsulfonyloxy optionally substituted by a halogen atom, $R^1$ is hydrogen atom, halogen atom, $C_{1-6}$ alkyl optionally substituted by halogen atom or hydroxyl group, or —$(CH_2)_kOR^a$ (k is an integer of 1 to 4, and $R^a$ is $C_{1-6}$ alkyl optionally having substituent(s)), $R^2$ is hydrogen atom, or the following formula (a)

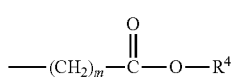

wherein $R^4$ is $C_{1-6}$ alkyl optionally having substituent(s), and m is an integer of 1 to 4, $R^{20}$ is $C_{1-6}$ alkyl, and $R^{21}$ is methyl or hydroxymethyl, or a salt thereof.

22. The compound of claim 21, wherein $R^1$ is methyl, hydroxymethyl or —$(CH_2)_kOR^a$ (k is an integer of 1 to 4, and $R^a$ is $C_{1-6}$ alkyl optionally having substituent(s)), and $R^{20}$ and $R^{21}$ are each methyl, or a salt thereof.

23. A production method of the compound of claim 1, which is represented by the formula (I), comprising reacting a thienotriazolodiazepine compound represented by the formula (II)

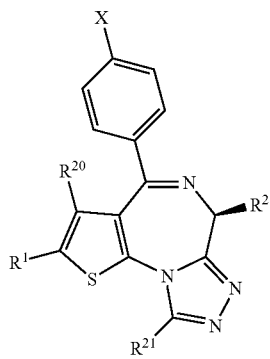

wherein X is halogen atom, p-toluenesulfonyloxy, or methylsulfonyloxy optionally substituted by a halogen atom, $R^1$ is hydrogen atom, halogen atom, $C_{1-6}$ alkyl optionally substituted by halogen atom or hydroxyl group, or —$(CH_2)_kOR^a$ (k is an integer of 1 to 4, and $R^a$ is $C_{1-6}$ alkyl optionally having substituent(s)), $R^2$ is hydrogen atom, or the following formula (a)

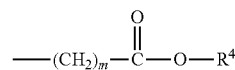

wherein $R^4$ is $C_{1-6}$ alkyl optionally having substituent(s), and m is an integer of 1 to 4, $R^{20}$ is $C_{1-6}$ alkyl, and $R^{21}$ is methyl or hydroxymethyl, or a salt thereof with a compound represented by $R^{3'}$—H wherein $R^{3'}$ is when $R^2$ is hydrogen, then —$NR^5$—$(CH_2)_n$—$R^6$ ($R^5$ is hydrogen atom or methyl, n is an integer of 0 to 3, and $R^6$ is $C_{6-12}$ aryl optionally having one or more substituents selected from halogen atom, hydroxyl group, methoxy, methylenedioxy and cyano; or pyridyl, thiazolyl, isoxazolyl, pyrazolyl, tetrahydrofuranyl or tetrahydropyranyl, each of which optionally has one or more substituents selected from methyl optionally substituted by halogen atom, cyano, halogen atom and methoxy, and when $R^2$ is the formula (a), then —$NR^{5a}$—$(CH_2)_o$—$R^{6a}$ (wherein $R^{5a}$ is hydrogen atom or $C_{1-6}$ alkyl optionally having substituent(s), o is an integer of 0 to 4, and $R^{6a}$ is $C_{6-12}$ aryl optionally having substituent(s), $C_{7-13}$ arylcarbonyl optionally having substituent(s), $C_{6-12}$ aryloxy optionally having substituent(s) or heteroaryl having 5 to 12 ring-constituting atoms and optionally having substituent(s)), or a group selected by following

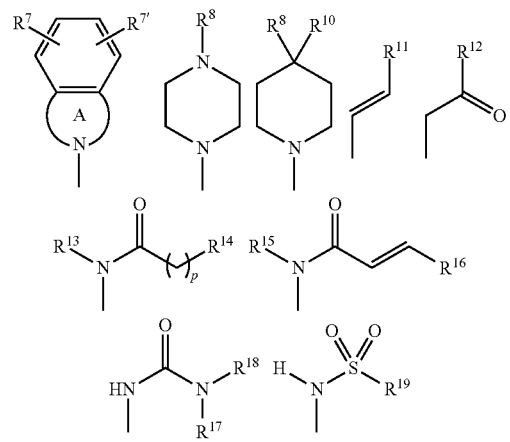

wherein $R^7$ and $R^{7'}$ are the same or different and each is hydrogen atom, $C_{1-6}$ alkyl optionally having substituent(s) or $C_{1-6}$ alkoxy optionally having substituent(s), ring A is cyclic amine having 4 or 5 carbon atoms, which is condensed with aromatic ring, $R^8$ is $C_{6-12}$ aryl optionally having substituent(s), heteroaryl having 5 to 12 ring-constituting atoms and optionally having substituent(s), $C_{7-18}$ aralkyl optionally having substituent(s), $C_{7-13}$ arylcarbonyl optionally having substituent(s) or heteroarylcarbonyl having 5 to 12 ring-constituting atoms and optionally having substituent(s), $R^9$ is hydrogen atom, hydroxyl group or cyano group, $R^{10}$ is $C_{1-6}$ alkyl optionally having substituent(s), $C_{6-12}$ aryl optionally having substituent(s) or heteroaryl having 5 to 12 ring-constituting atoms and optionally having substituent(s), $R^{11}$ is $C_{6-12}$ aryl optionally having substituent(s), heteroaryl having 5 to 12 ring-constituting atoms and optionally having substituent(s) or anilinocarbonyl optionally having substituent(s), $R^{12}$ is heteroaryl having 5 to 12 ring-constituting atoms and optionally having substituent(s), $R^{13}$ is hydrogen atom or $C_{1-6}$ alkyl optionally having substituent(s), p is an integer of 0 to 2, $R^{14}$ is $C_{6-12}$ aryl optionally having substituent(s) or heteroaryl having 5 to 12 ring-constituting atoms and optionally having substituent(s), $R^{15}$ is hydrogen atom or $C_{1-6}$ alkyl optionally having substituent(s), $R^{16}$ is $C_{6-12}$ aryl optionally having substituent(s) or heteroaryl having 5 to 12 ring-constituting atoms and optionally having substituent(s), $R^{17}$ is hydrogen atom or $C_{1-6}$ alkyl optionally having substituent(s), $R^{18}$ is $C_{6-12}$ aryl optionally having substituent(s) or $C_{7-18}$ aralkyl, and $R^{19}$ is $C_{6-12}$ aryl optionally having substituent(s) or heteroaryl having 5 to 12 ring-constituting atoms and optionally having substituent(s), or a boronic acid represented by $R^{3''}$—$B(OH)_2$ or an ester thereof, wherein $R^{3''}$ is when $R^2$ is hydrogen, then $C_{6-12}$ aryl optionally having one or more substituents selected from halogen atom, cyano, acetyl, hydroxymethyl, hydroxyethyl, methoxy and hydroxyl group; or pyridyl, thienyl, thiazolyl, pyrimidinyl or pyrazolyl, each of which optionally has one or more substituents selected from acetyl, hydroxymethyl, hydroxyethyl, cyano, amino, methyl and halogen atom, when $R^2$ is the formula (a), then $C_{6-12}$ aryl optionally having substituent(s), heteroaryl having 5 to 12 ring-constituting atoms and optionally having substituent(s), or arylcarbonylalkyl (wherein the aryl moiety has 6 to 12 carbon atoms, and the alkyl moiety has 1 to 6 carbon atoms) optionally having substituent(s) on the ring.

24. The production method of claim 23, wherein, in the compound represented by formula (I), $R^1$ is methyl, hydroxymethyl or —$(CH_2)_kOR^a$ (wherein k is an integer of 1 to 4, and $R^a$ is $C_{1-6}$ alkyl optionally having substituent(s)), and $R^{20}$ and $R^{21}$ are each methyl.

25. The production method of claim 23, wherein the reaction is carried out using a palladium catalyst.

26. A production method of a compound represented by the following formula (II')

(II')

wherein

X is a halogen atom, p-toluenesulfonyloxy, or methylsulfonyloxy optionally substituted by a halogen atom, $R^2$ is hydrogen atom, or the following formula (a)

$$—(CH_2)_m—\overset{O}{\underset{\|}{C}}—O—R^4$$ (a)

wherein $R^4$ is $C_{1-6}$ alkyl optionally having substituent(s), and m is an integer of 1 to 4, $R^{20'}$ is $C_{1-6}$ alkyl, and $R^{21}$ is methyl or hydroxymethyl, which comprises reacting a compound represented by the following formula (III)

(III)

wherein

X is a halogen atom, p-toluenesulfonyloxy, or methylsulfonyloxy optionally substituted by a halogen atom, $R^2$ is hydrogen atom, or the following formula (a)

$$—(CH_2)_m—\overset{O}{\underset{\|}{C}}—O—R^4$$ (a)

wherein $R^4$ is $C_{1-6}$ alkyl optionally having substituent(s), and m is an integer of 1 to 4, $R^{20'}$ is $C_{1-6}$ alkyl, and $R^{21}$ is methyl or hydroxymethyl, with a mixture of acetic acid, acetic anhydride and concentrated sulfuric acid in the presence of manganese acetate (III), and subjecting the resulting compound to hydrolysis.

27. The production method of claim 26, wherein $R^{20'}$ and $R^{21}$ are each methyl.

28. The production method of claim 26, wherein the hydrolysis is carried out using a base.

29. The production method of claim 28, wherein the base is potassium carbonate, sodium carbonate, potassium hydroxide and/or sodium hydroxide.

30. The production method of claim 26, which further comprises reduction after the hydrolysis.

31. The production method of claim 30, wherein the reduction is carried out using sodium borohydride as a reducing agent.

* * * * *

UNITED STATES PATENT AND TRADEMARK OFFICE
CERTIFICATE OF CORRECTION

PATENT NO. : 8,044,042 B2
APPLICATION NO. : 11/916015
DATED : October 25, 2011
INVENTOR(S) : Adachi et al.

It is certified that error appears in the above-identified patent and that said Letters Patent is hereby corrected as shown below:

In the claims:

Claim 1, at column 225, lines 27-33, the structure of the third depicted group should be:

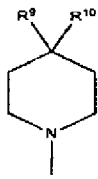

Claim 12, at column 227, line 8, the formula "-NH-$(CH_2)_n$-$R^6$" should read "-NH-$(CH_2)_n$-$R^{6'}$"

Claim 23, at column 230, lines 42-48, the structure of the third depicted group should be:

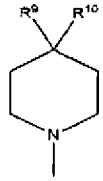

Signed and Sealed this
Twenty-seventh Day of March, 2012

David J. Kappos
*Director of the United States Patent and Trademark Office*